United States Patent
Bories et al.

(10) Patent No.: US 11,827,637 B2
(45) Date of Patent: Nov. 28, 2023

(54) AZAINDOLE DERIVATIVES AND THEIR USE AS ERK KINASE INHIBITORS

(71) Applicants: AGV Discovery, Montpellier (FR); Institut National de la Sante et de la Recherche Medicale (INSERM), Paris (FR); CENTRE NATIONAL DE LA RECHERCHE SCIENTIFIQUE (CNRS), Paris (FR); Universite De Montpellier, Montpellier (FR)

(72) Inventors: Cédric Bories, Jacou (FR); Loïc Mathieu, Lyons (FR); Jean-François Guichou, Torreilles (FR); Muriel Gelin, Clapiers (FR); Aurélien Biechy, Boulogne-Billancourt (FR)

(73) Assignees: AGV Discovery, Montpellier (FR); Institut National de la Sante et de la Recherche Medicale (INSERM), Paris (FR); CENTRE NATIONAL DE LA RECHERCHE SCIENTIFIQUE (CNRS), Montpellier (FR); Université De Montpellier, Montpellier (FR)

( * ) Notice: Subject to any disclaimer, the term of this patent is extended or adjusted under 35 U.S.C. 154(b) by 0 days.

(21) Appl. No.: 18/096,996

(22) Filed: Jan. 13, 2023

(65) Prior Publication Data

US 2023/0227451 A1    Jul. 20, 2023

(30) Foreign Application Priority Data

Jan. 14, 2022    (EP) ................................ 22305031

(51) Int. Cl.
| | |
|---|---|
| *C07D 413/14* | (2006.01) |
| *A61K 31/5377* | (2006.01) |
| *C07D 471/04* | (2006.01) |
| *C07D 213/643* | (2006.01) |
| *C07F 5/02* | (2006.01) |

(52) U.S. Cl.
CPC ....... *C07D 471/04* (2013.01); *C07D 213/643* (2013.01); *C07F 5/027* (2013.01)

(58) Field of Classification Search
CPC ... C07D 413/14; A61K 31/5377; A61P 35/00; A12Q 1/00
USPC .......... 544/127; 514/234.5; 435/184
See application file for complete search history.

(56) References Cited

U.S. PATENT DOCUMENTS

| | | | |
|---|---|---|---|
| 8,697,697 B2 | 4/2014 | Fairfax et al. | |
| 9,695,200 B2 | 7/2017 | Jacobsen et al. | |
| 10,995,089 B2 | 5/2021 | Guichou et al. | |
| 2006/0106041 A1 | 5/2006 | Kuo et al. | |
| 2006/0106069 A1 | 5/2006 | Martinez-Botella et al. | |
| 2007/0043068 A1 | 2/2007 | Arnold et al. | |
| 2014/0011806 A1 | 1/2014 | Fairfax et al. | |
| 2020/0283432 A1 | 9/2020 | Guichou et al. | |
| 2021/0221809 A1 | 7/2021 | Guichou et al. | |

FOREIGN PATENT DOCUMENTS

| | | | |
|---|---|---|---|
| EP | | 3170822 A1 | 5/2017 |
| EP | | 3377491 A1 | 9/2018 |
| GB | | 2515785 A | 1/2015 |
| WO | WO-2005/028475 A2 | | 3/2005 |
| WO | WO-2008/005457 A2 | | 1/2008 |
| WO | WO-2008/011557 A2 | | 1/2008 |
| WO | WO-2008/076805 A2 | | 6/2008 |
| WO | WO-2012/094313 A1 | | 7/2012 |
| WO | WO-2013/022766 A1 | | 2/2013 |
| WO | WO-2014/023367 A1 | | 2/2014 |
| WO | WO-2014/060395 A1 | | 4/2014 |
| WO | WO-2020/102686 A1 | | 5/2020 |

OTHER PUBLICATIONS

Bodai et al., "A novel target for Huntington's disease: ERK at the crossroads of signaling. The ERK signaling pathway is implicated in Huntington's disease and its upregulation ameliorates pathology," Bioessays 34(2):142-8 (Feb. 2012).
Caunt et al., "MEK1 and MEK2 inhibitors and cancer therapy: the long and winding road," Nat Rev Cancer. 15(10):577-92 (Oct. 2015).

(Continued)

*Primary Examiner* — Charanjit Aulakh
(74) *Attorney, Agent, or Firm* — Clark & Elbing LLP

(57) ABSTRACT

The present invention concerns a compound of formula (I):

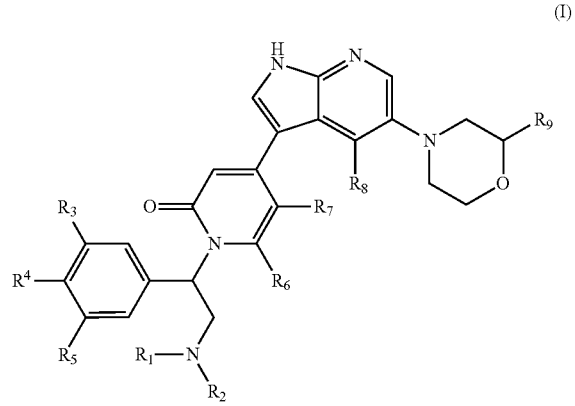

or one of its pharmaceutically acceptable salts, especially for use as inhibitors of the ERK kinase activity, in particular ERK2 activity.

18 Claims, No Drawings

(56) References Cited

OTHER PUBLICATIONS

Cheung et al., "Emerging Role for ERK as a Key Regulator of Neuronal Apoptosis," Science's STKE, 2004. (5 pages).
Davies et al., "Mutations of the BRAF gene in human cancer," Nature. 417(6892):949-54 (2002).
Downward, "Targeting RAS signalling pathways in cancer therapy," Nat Rev Cancer. 3(1):11-22 (2003).
Extended European Search Report for European Application No. 22305031.1, dated Aug. 12, 2022 (10 pages).
Garnett et al., "Guilty as charged: B-RAF is a human oncogene," Cancer Cell. 6(4):313-9 (2004).
Golub et al., "Molecular classification of cancer: class discovery and class prediction by gene expression monitoring," Science. 286(5439):531-7 (1999) (8 pages).
Lito et al., "Tumor adaptation and resistance to RAF inhibitors," Nat Med. 19(11):1401-9 (Nov. 2013).
Little et al., "Mechanisms of Acquired Resistance to ERK1/2 Pathway Inhibitors," Oncogene. 32(10):1207-15 (2013).
Sureshbabu et al., Chapter 1: Protection Reactions. *Amino Acids, Peptides and Proteins in Organic Chemistry. vol. 4—Protection Reactions, Medicinal Chemistry, Combinatorial Synthesis.* ed. Hughes, Wiley-VCH Verlag GmbH & Co. KGaA, Weinheim, Germany, 2011 (97 pages).
Thalhamer et al., "MAPKs and their relevance to arthritis and inflammation," Rheumatology (Oxford). 47(4):409-414 (2008).

AZAINDOLE DERIVATIVES AND THEIR USE AS ERK KINASE INHIBITORS

FIELD OF THE INVENTION

The present invention relates to azaindole derivatives which are inhibitors of ERK kinases (ERK1 and ERK2), to the process for the preparation thereof and to the therapeutic use thereof.

BACKGROUND OF THE INVENTION

ERK proteins belongs to the RAS/RAF/MEK/ERK pathway which plays a major role in the cell cycle including proliferation, growth, and survival. The RAS/RAF/MEK/ERK pathway is activated by growth factors through their receptor tyrosine kinase that allows activation of GTPases RAS. In turn, RAS activates RAF proteins. Then, RAF activates MEK, which activates ERK.

Finally, this enables phosphorylation of many substrates that have key roles in metabolism, protein synthesis, cell proliferation and survival.

RAF mutations lead specifically to an over-activation of this RAS/RAF/MEK/ERK pathway and are responsible for 7% of all human cancers (Davies et al., *Nature*. 2002; Garnett et al., *Cancer Cell*. 2004).

Indeed, RAF mutations are frequently observed in melanomas (27-70%), thyroid cancers (36-53%), colorectal cancers (5-22%) and ovarian cancers (30%). Likewise, RAS mutations occur in almost 30% of cancers and are present in pancreatic (90%), lung (35%), colorectal (45%) and liver (30%) cancers (Downward, *Nat. Rev. Cancer*. 2003).

Thus, proteins of RAS/RAF/MEK/ERK pathway represent targets of interest for cancers treatment. Indeed, pharmaceutical companies focused on upstream kinases (RAF, MEK).

However, resistances ultimately appear after current treatment with RAF and MEK inhibitors (Lito et al., *Nat. Med.* 2013; Caunt et al., *Nat. Rev. Cancer*, 2015).

Moreover, most resistances to MEK or RAF inhibitors induce ERK reactivation, through different mechanisms such as MEK mutation, B-RAF amplification, C-RAF mutation . . . (Little et al., *Oncogene*. 2013).

Furthermore, RAF or MEK inhibition suppresses ERK negative feedback that restores upward signaling and finally ERK activity (Lito et al., *Nat. Med.*, 2013).

Considering the resistance phenomena that emerged after current treatment with RAF and MEK inhibitors, it is essential to develop new therapeutic options.

Except for its key role in hyperproliferative diseases, ERK signaling has also been described as implied in neurodegenerative disorders such as in Parkinson's, Alzheimer's and Huntington's diseases (Cheung et al., *Sci. STKE*. 2004; Bodai et al., *Bioessays.*, 2012) and in inflammation such as in the pathogenesis of Rheumatoid Arthritis (Thalhamer et al., *Rheumatology*. 2008).

Thus, the present invention relates to ERK inhibitors development to treat a broad spectrum of diseases.

Some ERK inhibitors are already described in the prior art. Thus, U.S. Pat. No. 8,697,697 B2 describes substituted pyrazole derivatives as inhibitors of ERK2 kinase activity.

Pyrrolo[2,3-b]pyrazine derivatives are also reported as ERK inhibitors in the international patent application WO 2014/060395 A1, and azaindole derivatives are reported as ERK inhibitors in the international patent application WO 2017/085230 A1.

However, there remains a need for efficient compounds able to selectively inhibit ERK1 and/or ERK2 kinases.

The present invention is precisely directed to novel compounds and their use as inhibitors of the ERK kinases activity.

The compounds of the present invention are novel azaindole derivatives with at least an enhanced anti-proliferative activity.

The compounds according to the invention are also characterized by their low toxicity, high permeability, and kinase inhibition selectivity.

Overall, the compounds according to the invention are remarkable for their drug-like properties.

A first subject of the invention concerns the compounds corresponding to the general formula (I):

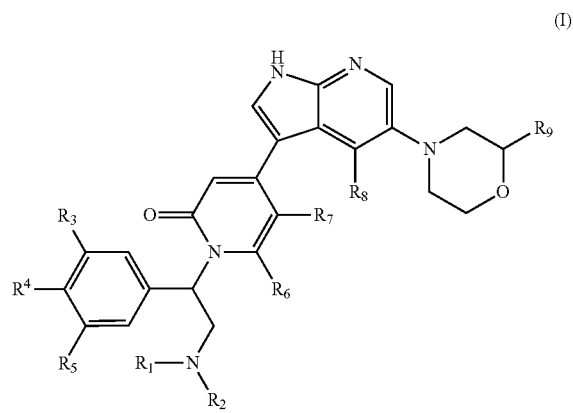

(I)

wherein:
R$_1$ represents a (C$_1$-C$_5$)alkyl group;
R$_2$ represents a (C$_1$-C$_5$)alkyl group, a (C$_3$-C$_5$)cycloalkyl group, or a (C$_1$-C$_5$)alkyl group substituted by one or more radicals selected from halogen atoms, cyano group, (C$_1$-C$_5$)alkoxy group and (C$_3$-C$_5$)cycloalkyl group;
or R$_1$ and R$_2$ form together with the nitrogen atom a 3- to 6-membered heterocyclic group;
R$_3$, R$_4$, R$_5$, R$_6$, R$_7$, R$_8$ and R$_9$ represent, independently of each other, a hydrogen atom, a halogen atom, a (C$_1$-C$_5$)alkyl group, a trifluoromethyl group or a cyano group, wherein said (C$_1$-C$_5$)alkyl is itself optionally substituted with a (C$_1$-C$_5$)alkoxy group;
or one of its pharmaceutically acceptable salts.

After extensive searching of the ERK crystalline structure and structural screening tests, the inventors have identified that these new azaindole derivatives of formula (I) selectively target the active sites of the ERK kinases, and act as effective inhibitors of ERK kinases activity as demonstrated in the following examples.

In the meaning of the present invention, a "kinase inhibitor" is intended to mean a compound that reduces or suppresses the activity of the targeted kinase, as compared with said activity determined without said inhibitor.

Within the meaning of the invention, the term "prevent" or "prevention" with respect to an event is intended to mean the decrease of a risk of occurrence of said event.

As will be seen below, these compounds have utility in the treatment of conditions or diseases in which modification of the activity of ERK would have a positive therapeutic outcome, in particular cancers.

Another subject concerns processes for preparing the compounds of general formula (I).

Another subject concerns the compounds of general formula (I) for their use especially in medicaments or in pharmaceutical compositions.

A further subject concerns the compounds according to the invention for use as inhibitors of the ERK kinases activity, particularly for use as inhibitors of the ERK1 and/or ERK2 kinases activity.

Abbreviations and Definitions

In the context of the present invention, the following abbreviations and empirical formulae are used:

| | |
|---|---|
| ATP | adenosine 5'-triphosphate |
| Brij-35 | Polyoxyethyleneglycol dodecyl ether |
| Boc | tert-butyloxycarbonyl |
| Bs | Brosyl |
| C18 column | Reversed-phase C18 column |
| CMC | Carboxymethylcellulose |
| $Cs_2CO_3$ | Cesium carbonate |
| DABCO | 1,4-Diazabicyclo[2.2.2]octane |
| DIEA | N,N-Diisopropylethylamine |
| DMF | Dimethylformamide |
| DMEM | Dulbecco's Modified Eagle Medium |
| DMSO | Dimethylsulfoxide |
| ° C. | Degree Celsius |
| DCM | Dichloromethane |
| ee | Enantiomeric excess |
| EGTA | Egtazic acid |
| Eq | Equivalent |
| $Et_3N$ | Triethylamine |
| $Et_2O$ | Diethyl ether |
| EtOAc | Ethyl acetate |
| EtOH | Ethanol |
| FBS | Fetal bovine serum |
| g | gram(s) |
| h | hour(s) |
| HBSS | Hanks' Balanced Salt Solution |
| HCl | Hydrochloric acid |
| $H_2CO_2$ | Formic acid |
| HEPES | (4-(2-hydroxyethyl)-1-piperazineethanesulfonic acid |
| hERG | Human Ether-à-go-go-Related gene |
| HPLC | High performance liquid chromatography |
| IPA | Isopropanol |
| $K_2CO_3$ | Potassium carbonate |
| LC/MS | Liquid chromatography/mass spectrometry |
| $LiAlH_4$ | Lithium aluminium hydride |
| LiHMDS | Lithium bis(trimethylsilyl)amide |
| M | Mole(s) per liter |
| MeCN | Acetonitrile |
| MeOH | Methanol |
| MeTHF | 2-Methyltetrahydrofuran |
| mg | Milligram(s) |
| MH+ | Pseudo-molecular ion (positive ion mode in mass spectrometry) |
| MHz | Megahertz |
| Ms | Mesyl |
| μl | Microliter(s) |
| ml | Milliliter(s) |
| mmol | Millimole(s) |
| mol | Mole(s) |
| $Na_2CO_3$ | Sodium carbonate |
| $NaHCO_3$ | Sodium hydrogen carbonate |
| $NaH_2PO_2$ | Sodium hypophosphite |
| NaOH | Sodium hydroxide |
| $Na_2SO_4$ | Sodium sulfate |
| $NH_4Cl$ | Ammonium chloride |
| Ni Raney | Raney nickel |
| NMR | Nuclear Magnetic Resonance |
| Ns | Nosyl |
| $PdCl_2(PPh_3)_2$ | Bis(triphenylphosphine)palladium(II) dichloride |
| PG | Protecting group |
| RuPhos | 2-Dicyclohexylphosphino-2',6'-diisopropoxybiphenyl |
| RuPhos Pd G2 | Chloro(2-dicyclohexylphosphino-2',6'-diisopropoxy-1,1'-bi-phenyl)[2- |

-continued

| | |
|---|---|
| | (2'-amino-1,1'-biphenyl)]palladium(II) |
| SDS | Sodium dodecyl sulfate |
| TBAF | Tetrabutylammonium fluoride |
| tBuONa | Sodium tert-butoxide |
| TEA | Triethylamine |
| Tf | Triflyl |
| THF | Tetrahydrofuran |
| TIPS | Triisopropylsilyl |
| TMS | Trimethylsilyl |
| Ts | Tosyl |

In the context of the present invention, the following definitions apply:

a halogen atom: a fluorine, a chlorine, a bromine, or an iodine atom. The halogen atoms may be more particularly chosen among chlorine and fluorine atoms.

$C_t$-$C_z$: a carbon-based chain possibly containing from t to z carbon atoms in which t and z may take values from 1 to 10; for example, $C_1$-$C_3$ is a carbon-based chain possibly containing from 1 to 3 carbon atoms.

an alkyl: a linear or branched saturated aliphatic group, in particular comprising from 1 to 6 carbon atoms. Examples that may be mentioned include methyl, ethyl, n-propyl, isopropyl, butyl, isobutyl, tert-butyl, pentyl, etc. . . . .

an alkoxy: a radical —O-alkyl in which the alkyl group is as defined previously.

a cyano group: a radical —C≡N.

a trifluoromethyl group: a radical —$CF_3$.

a cycloalkyl group: a non-aromatic mono- or bicyclic saturated or partially saturated or unsaturated ring containing 3 to 8 carbon atoms. Examples of cycloalkyl group that may be mentioned include cyclopropane, cyclobutane, cyclopentane, cyclopentene, cyclohexane or cyclohexene.

3- to 6-membered heterocyclic group: a monocyclic saturated ring containing at least one heteroatom. Examples of 3- to 6-membered heterocyclic group that may be mentioned include aziridinyl, azetidinyl, pyrrolidinyl, piperidinyl, morpholinyl, thiomorpholinyl, piperazinyl, 2-oxa-6-azaspiro[3.3]heptanyl.

Other features, properties and advantages of the invention will emerge more clearly from the description and examples that follow.

COMPOUNDS OF THE INVENTION

As above-mentioned, the compounds according to the invention correspond to general formula (I):

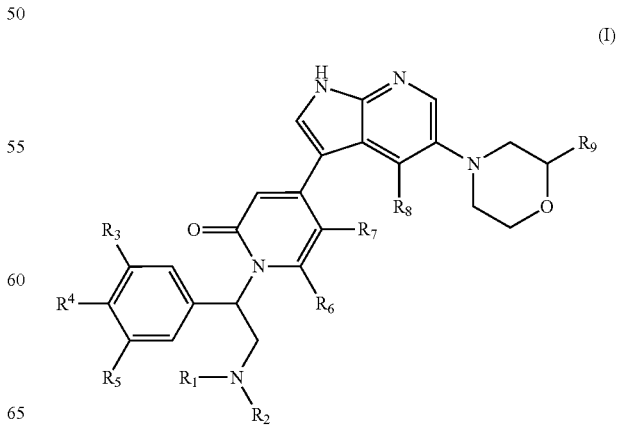

wherein:

$R_1$ represents a $(C_1$-$C_5)$alkyl group;

$R_2$ represents a $(C_1$-$C_5)$alkyl group, a $(C_3$-$C_5)$cycloalkyl group, or a $(C_1$-$C_5)$alkyl group substituted by one or more radicals selected from halogen atoms, cyano group, $(C_1$-$C_5)$alkoxy group and $(C_3$-$C_5)$cycloalkyl group;

or $R_1$ and $R_2$ form together with the nitrogen atom a 3- to 6-membered heterocyclic group;

$R_3$, $R_4$, $R_5$, $R_6$, $R_7$, $R_8$ and $R_9$ represent, independently of each other, a hydrogen atom, a halogen atom, a $(C_1$-$C_5)$alkyl group, a trifluoromethyl group or a cyano group, wherein said $(C_1$-$C_5)$alkyl is itself optionally substituted with a $(C_1$-$C_5)$alkoxy group;

or one of its pharmaceutically acceptable salts.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

According to a preferred embodiment, the asymmetric carbon bearing the group —$CH_2NR_1R_2$ of the compounds of formula (I) is of S configuration.

The compounds of formula (I) may also exist in the form of free bases or of acid-addition salts. These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

According to an embodiment, $R_1$ represents a methyl group, an ethyl group, a propyl group, a butyl group, a pentyl group, or a hexyl group, in particular $R_1$ represents a methyl group, an ethyl group, or a propyl group, and preferably $R_1$ represents a methyl group or an ethyl group.

According to a preferred embodiment, $R_1$ represents a methyl group.

According to a preferred embodiment, $R_2$ represents a $(C_1$-$C_5)$alkyl group.

According to an embodiment, $R_2$ represents a methyl group, an ethyl group, a propyl group, a butyl group, a pentyl group, or a hexyl group, in particular $R_2$ represents a methyl group, an ethyl group or a propyl group, and preferably $R_2$ represents a methyl group or an ethyl group.

Preferably, $R_2$ represents a methyl group.

According to another embodiment, $R_2$ represents a $(C_3$-$C_6)$cycloalkyl group, and preferably a cyclopropyl group.

According to another embodiment, $R_2$ represents a $(C_1$-$C_6)$alkyl group substituted by one or more radicals selected from halogen atoms, cyano group, $(C_1$-$C_5)$alkoxy group and $(C_3$-$C_6)$cycloalkyl group.

Preferably, $R_2$ represents a $(C_1$-$C_6)$alkyl group, in particular a methyl group or an ethyl group, a cyclopropyl group, —$CH_2$—$CF_2$, —$CH_2$—$CN$, —$CH_2$—$CH_2$—$O$—$CH_3$ or —$CH_2$-cyclopropyl.

According to another embodiment, $R_1$ and $R_2$ form together with the nitrogen atom an aziridinyl group.

According to a preferred embodiment, both $R_1$ and $R_2$ represent a methyl group.

According to a preferred embodiment, $R_3$ represents a halogen atom, a $(C_1$-$C_6)$alkyl group, a trifluoromethyl group or a cyano group, wherein said $(C_1$-$C_6)$alkyl is itself optionally substituted with a $(C_1$-$C_6)$alkoxy group.

According to a preferred embodiment, $R_3$ represents a halogen atom, a $(C_1$-$C_6)$alkyl group, in particular a methyl group or an ethyl group, a —$CH_2$—$O$—$CH_3$ group, a trifluoromethyl group or a cyano group.

In particular, $R_3$ represents a halogen atom, in particular a chlorine atom, a fluorine atom, a bromine atom or an iodine atom.

Preferably, $R_3$ represents a chlorine atom or a fluorine atom.

According to a preferred embodiment, $R_3$ represents a chlorine atom.

According to another preferred embodiment, $R_3$ represents a fluorine atom.

According to a preferred embodiment, $R_4$ represents a hydrogen atom or a halogen atom, in particular a chlorine atom, a fluorine atom, a bromine atom, or an iodine atom.

More particularly, $R_4$ represents a hydrogen atom, a chlorine atom, or a fluorine atom.

Preferably, $R_4$ represents a hydrogen atom or a chlorine atom.

According to a preferred embodiment, $R_4$ represents a chlorine atom.

According to another preferred embodiment, $R_4$ represents a fluorine atom.

According to another preferred embodiment, $R_4$ represents a hydrogen atom.

According to another preferred embodiment, $R_5$ represents a hydrogen atom or a halogen atom, in particular a chlorine atom, a fluorine atom, a bromine atom, or an iodine atom.

More particularly, $R_5$ represents a hydrogen atom, a chlorine atom, or a fluorine atom.

According to a preferred embodiment, $R_5$ represents a chlorine atom.

According to another preferred embodiment, $R_5$ represents a fluorine atom.

According to another preferred embodiment, $R_5$ represents an iodine atom.

According to another preferred embodiment, $R_5$ represents a hydrogen atom.

According to a preferred embodiment, at least one of $R_3$, $R_4$ and $R_5$ does not represent a hydrogen atom.

According to a preferred embodiment, at least one of $R_3$, $R_4$ and $R_5$ is a halogen atom, and the two others represent independently a hydrogen atom or a halogen atom.

According to a preferred embodiment, one of $R_3$, $R_4$ and $R_5$ represents a chlorine atom, and the two others represent independently a hydrogen atom or a halogen atom.

According to a preferred embodiment, at least one of $R_3$, $R_4$ and $R_5$ is a fluorine atom, and the two others represent independently a hydrogen atom or a halogen atom.

According to a preferred embodiment, two of $R_3$, $R_4$ and $R_5$ represent a chlorine atom, and the other represents a hydrogen atom.

According to a preferred embodiment, $R_6$ represents a hydrogen atom or a $(C_1$-$C_6)$alkyl group.

More particularly, $R_6$ represents a hydrogen atom or a methyl group.

According to a preferred embodiment, $R_6$ represents a hydrogen atom.

According to another preferred embodiment, $R_6$ represents a $(C_1$-$C_6)$alkyl group, in particular a methyl group or an ethyl group, and preferably a methyl group.

According to a preferred embodiment, $R_7$ represents a hydrogen atom or a halogen atom, in particular a chlorine atom, a fluorine atom, a bromine atom, or an iodine atom.

More particularly, $R_7$ represents a hydrogen atom, a chlorine atom, or a fluorine atom.

According to a preferred embodiment, $R_7$ represents a hydrogen atom.

According to another preferred embodiment, $R_7$ represents a halogen atom, in particular a chlorine atom, a fluorine atom, a bromine atom, or an iodine atom, and preferably a fluorine atom.

According to a preferred embodiment, both $R_6$ and $R_7$ represent a hydrogen atom.

According to a preferred embodiment, $R_5$ represents a hydrogen atom or a halogen atom, in particular a chlorine atom, a fluorine atom, a bromine atom, or an iodine atom.

More particularly, $R_5$ represents a hydrogen atom, a chlorine atom, or a fluorine atom.

According to a preferred embodiment, $R_5$ represents a hydrogen atom.

According to another preferred embodiment, $R_5$ represents a halogen atom, in particular a chlorine atom, a fluorine atom, a bromine atom, or an iodine atom, and preferably a fluorine atom.

According to a preferred embodiment, $R_5$ represents a hydrogen atom, a halogen atom or a trifluoromethyl group.

More particularly, $R_5$ represents a hydrogen atom or a trifluoromethyl group.

According to a preferred embodiment, $R_5$ represents a hydrogen atom.

According to another preferred embodiment, $R_5$ represents a trifluoromethyl group.

According to a preferred embodiment, all of $R_6$, $R_7$, $R_8$ and $R_9$ represent a hydrogen atom.

According to a preferred embodiment, both $R_1$ and $R_2$ represent a methyl group, and all of $R_6$, $R_7$, $R_8$ and $R_9$ represent a hydrogen atom.

According to a preferred embodiment, both $R_1$ and $R_2$ represent a methyl group, all of $R_6$, $R_7$, $R_8$ and $R_9$ represent a hydrogen atom, and $R_3$ represents a halogen atom, preferably a chlorine atom.

According to another preferred embodiment, both $R_1$ and $R_2$ represent a methyl group, all of $R_6$, $R_7$, $R_8$ and $R_9$ represent a hydrogen atom, $R_3$ represents a halogen atom, preferably a chlorine atom, and $R_4$ and $R_5$ represent independently a hydrogen atom or a halogen atom.

According to another preferred embodiment, both $R_1$ and $R_2$ represent a methyl group, all of $R_6$, $R_7$, $R_8$ and $R_9$ represent a hydrogen atom, $R_3$ represents a halogen atom, preferably a chlorine atom, $R_4$ and $R_5$ represent independently a hydrogen atom or a halogen atom, and the asymmetric carbon bearing the group —$CH_2NR_1R_2$ is of S configuration.

It is clear that features of the above-mentioned embodiments may be combined with each other, unless specifically noted otherwise.

Among the compounds of formula (I) mention may be made especially of the following compounds:

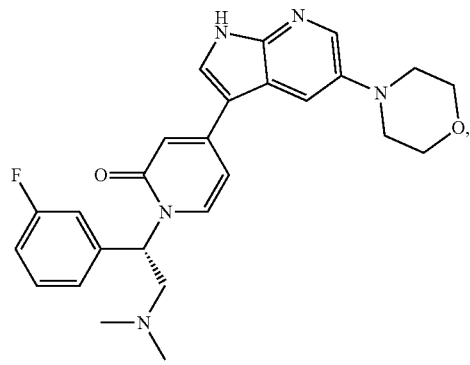

(1)

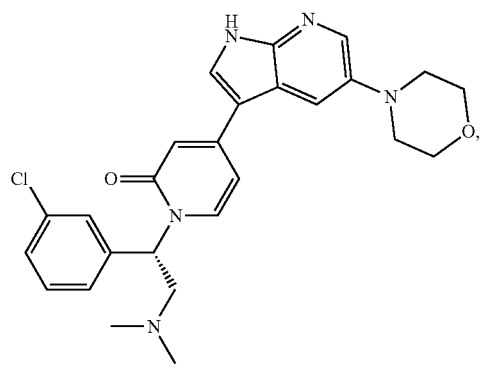

(2)

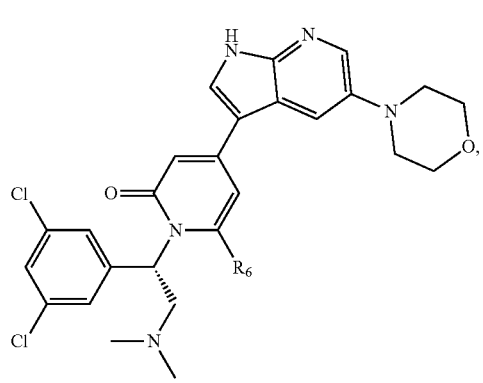

(3)

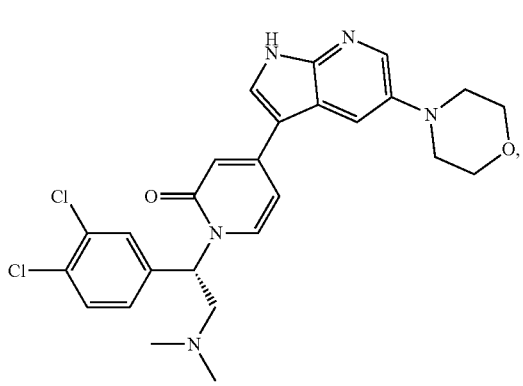

(4)

-continued
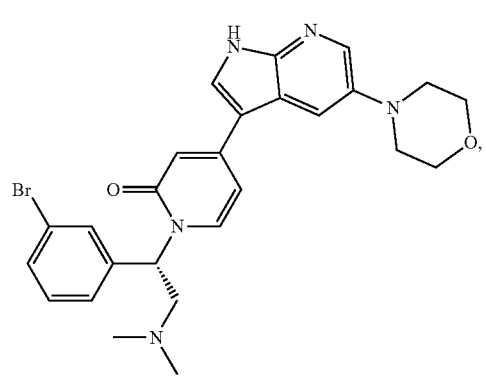
(5)
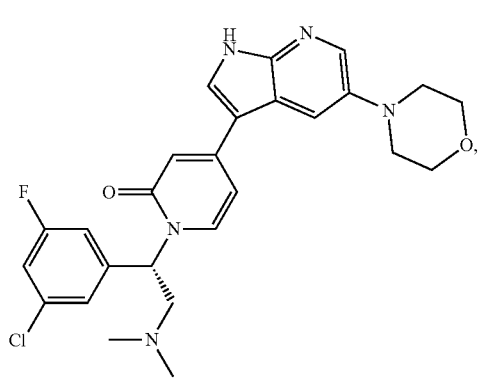
(9)
(6)
(10)
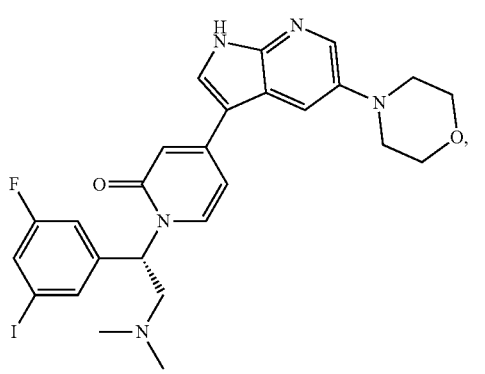
(7)
(11)
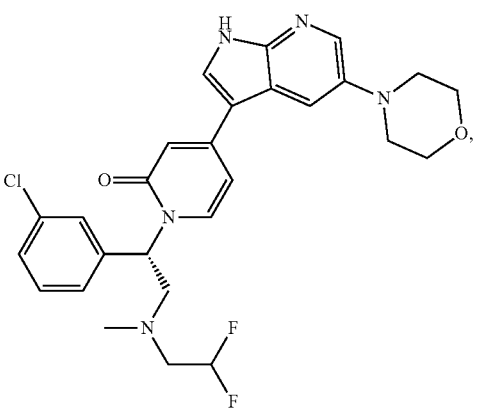
(8)
(12)
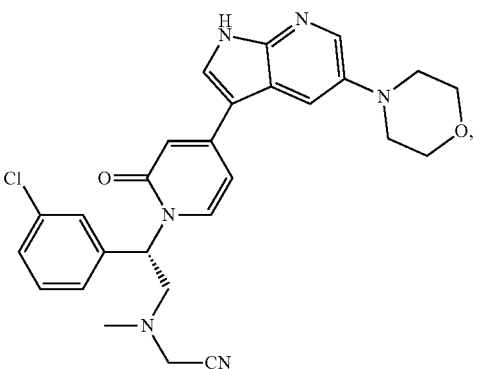

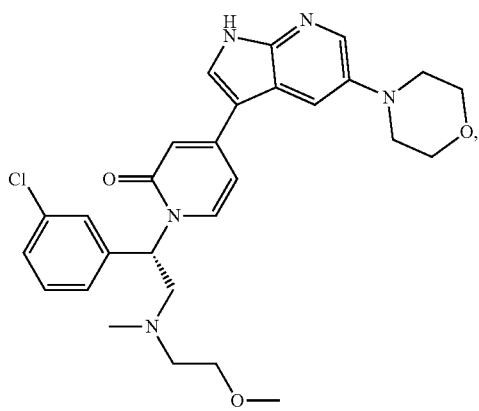 (13)
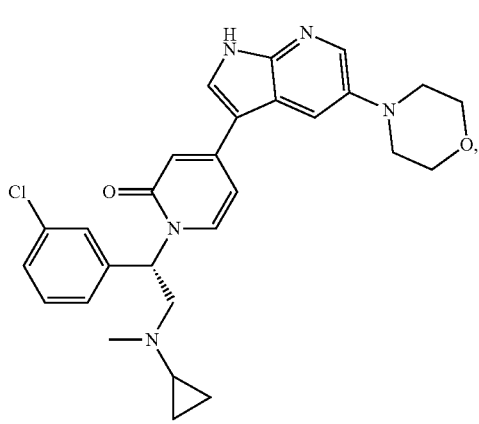 (14)
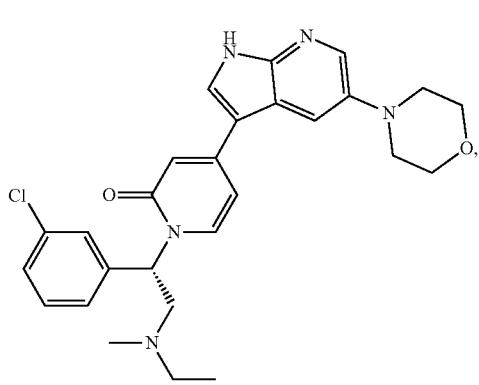 (15)
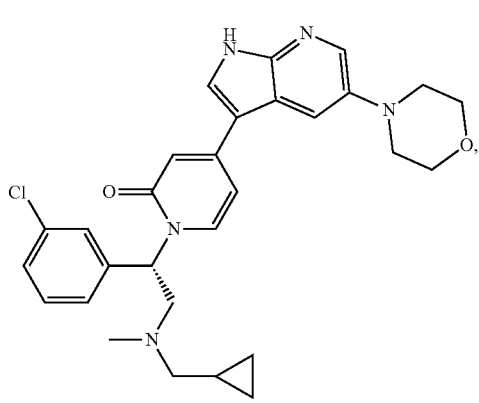 (16)
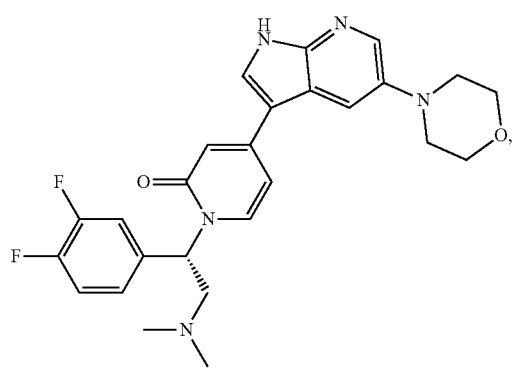 (17)
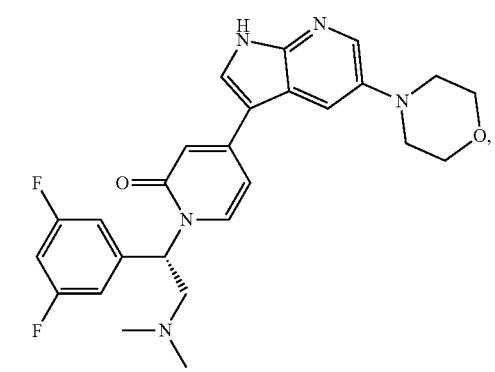 (18)
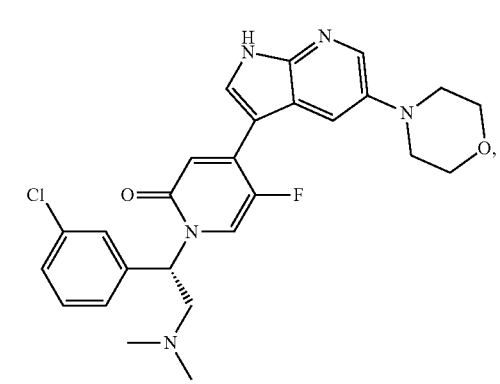 (19)
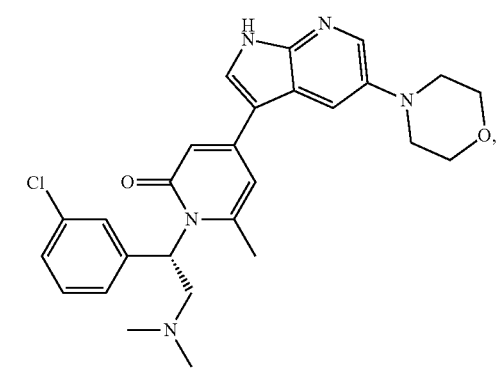 (20)

(21) 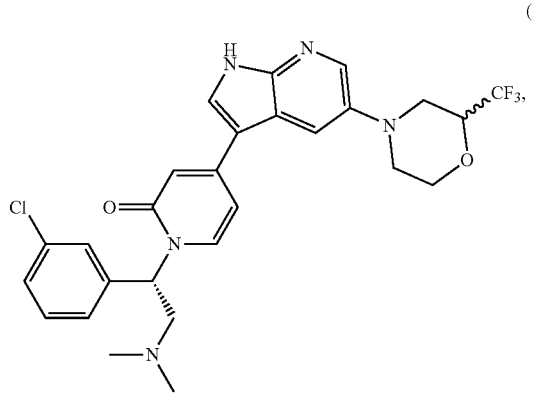
(22) 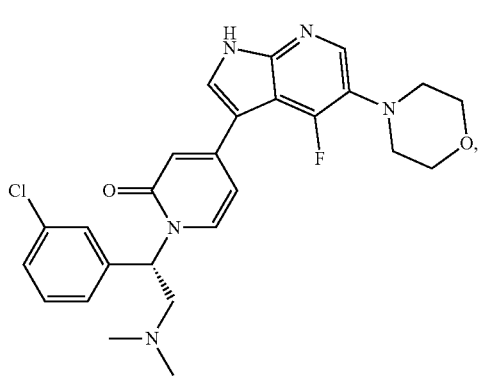
(23) 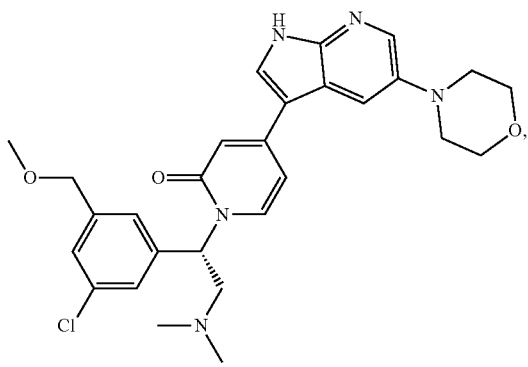
(24) 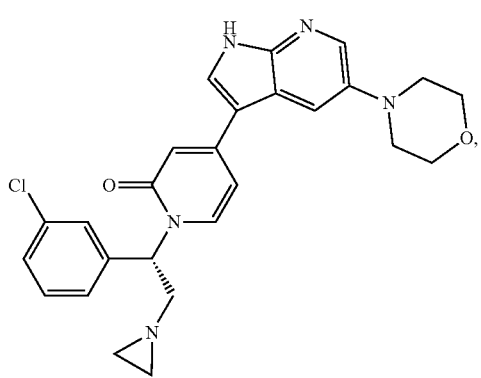
(25) 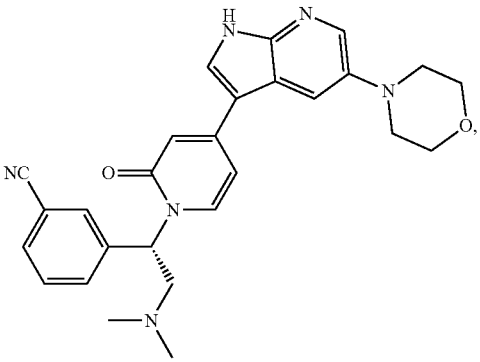
(26) 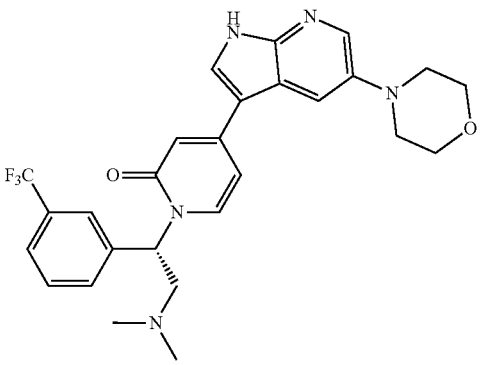
or one of their pharmaceutically acceptable salts.
Preferably, among the compounds of formula (I) mention may be made especially of the following compounds:
(1) 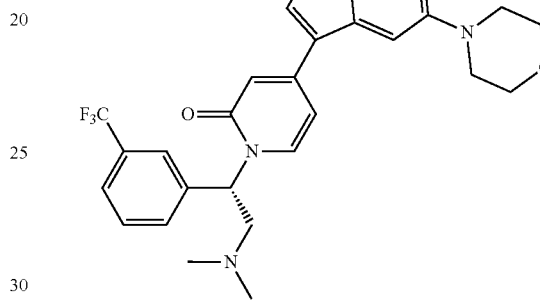
(2) 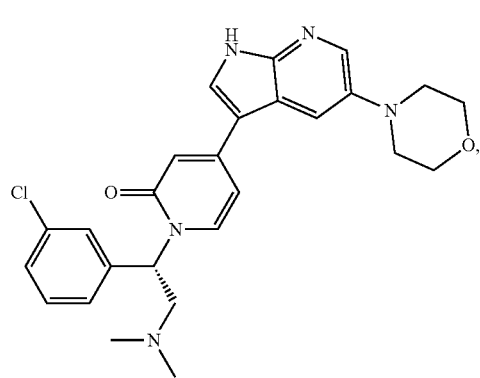

-continued
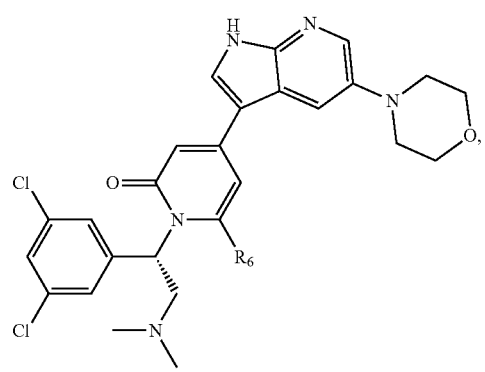
(3)
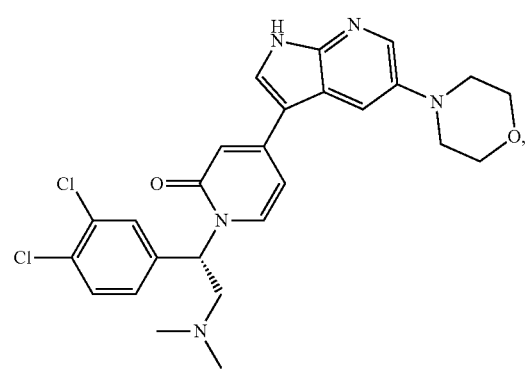
(4)
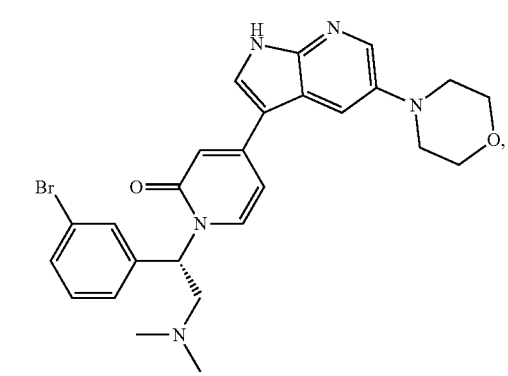
(5)
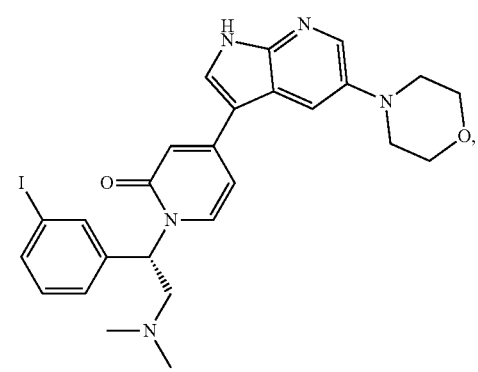
(6)
-continued
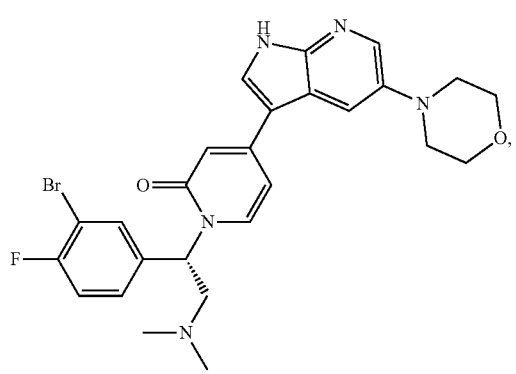
(7)
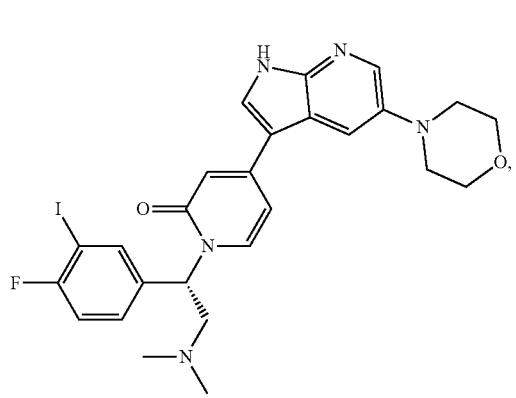
(8)
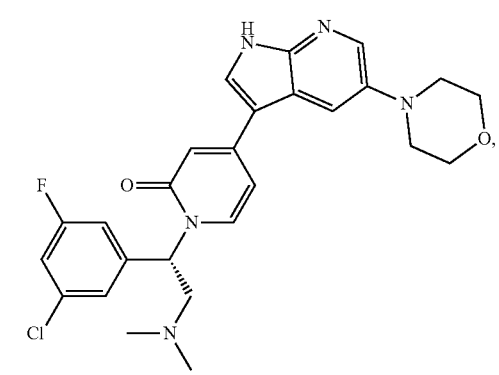
(9)
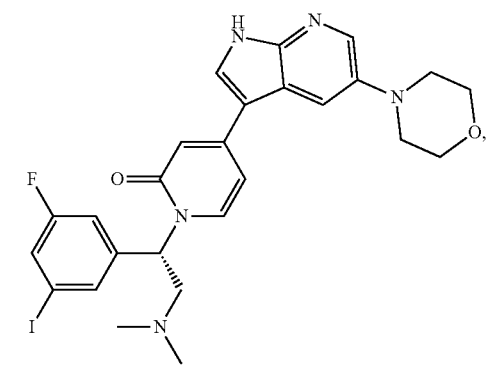
(10)

-continued

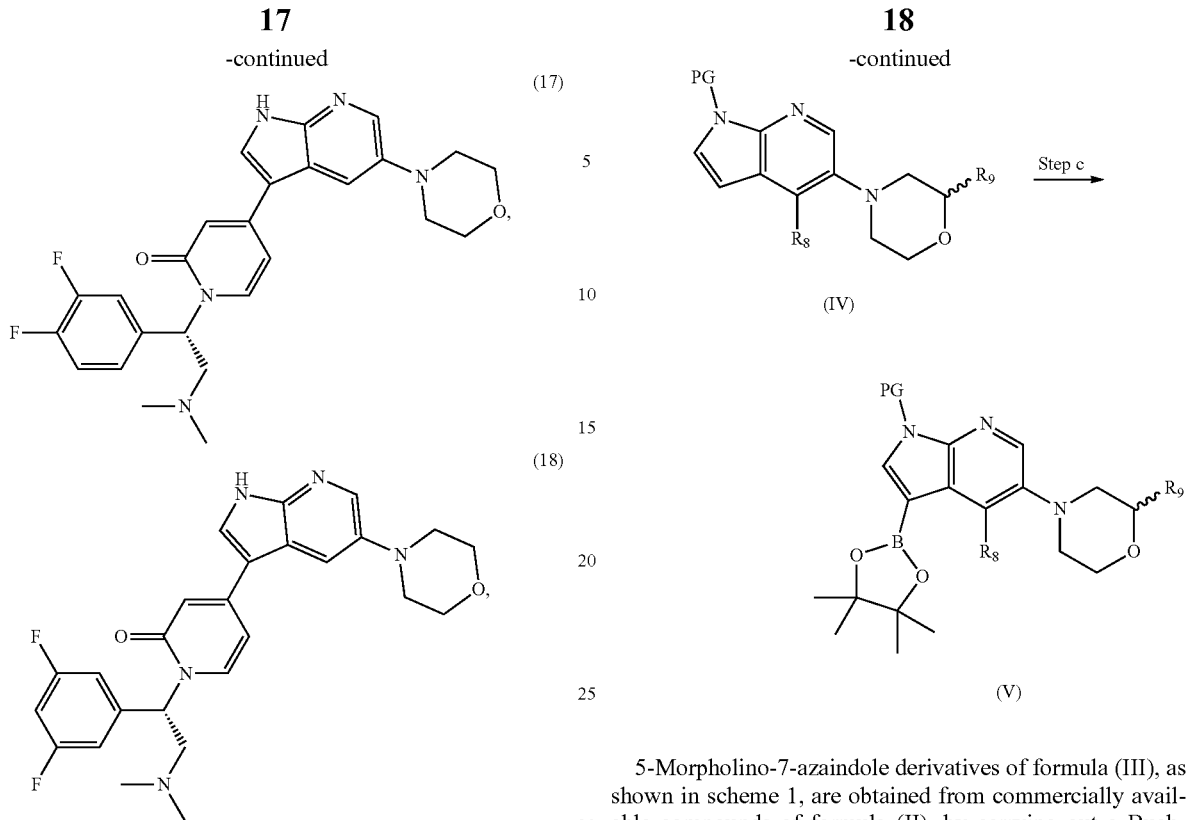

or one of their pharmaceutically acceptable salts.

Preparation of the Compounds of the Invention

Compounds of the invention may be prepared according to well-known methods by the skilled artisan, as illustrated in the examples that follow.

According to a first embodiment, the synthesis of synthetic intermediates of compounds of the present invention may be accomplished according to the Schemes 1 and 2 below.

More precisely, synthetic intermediates of formula (V) may be prepared according to Scheme 1, wherein $R_8$ and $R_9$ are as defined above in formula (I) and PG is a protecting group as defined below.

Scheme 1

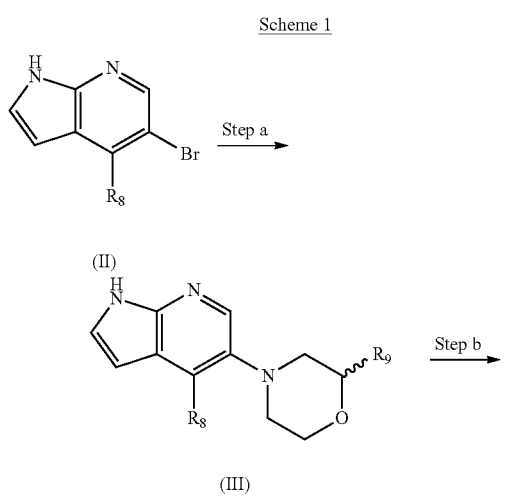

5-Morpholino-7-azaindole derivatives of formula (III), as shown in scheme 1, are obtained from commercially available compounds of formula (II), by carrying out a Buchwald-Hartwig coupling reaction, with a base such as LiHMDS, a catalyst like RuPhos and a RuPhos ligand such as RuPhos Pd G2 (Step a). Other RuPhos ligands such as RuPhos Pd G3 or RuPhos Pd G4 could also be used to obtain compounds of formula (III). This reaction is generally performed in anhydrous solvent such as THF and at a temperature of 60-70° C.

Then, compounds of formula (IV) are obtained by performing a protection of the pyrrolyl moiety of the 7-azaindole core with a protecting group, such as Ts or another sulfonyl group, and using a base, such as NaH or $K_2CO_3$, in an anhydrous solvent, such as DMF, DCM or THF (Step b). This reaction could also be performed with another protecting group such as Boc, trimethylsilylethoxymethyl, TMS or TIPS.

Finally, compounds of formula (V) are obtained by a selective borylation of the azaindole core in position 3 (Step c), using (1,5-cyclooctadiene)(methoxy)iridium(I), in presence of a ligand, such as 4,4'-di-ted-butylbiphenyl, and a source of boron, such as bis(pinacolato)diboron. This reaction is generally performed in methyl-THF at reflux for 30 min to several hours under argon.

Thus, the present invention also concerns a process for preparing compounds of general formula (V) wherein $R_8$ and $R_9$ are as defined in formula (I) and PG is a protecting group as defined below, wherein the following steps are carried out in that order, starting from compounds of formula (II):
a) a Buchwald-Hartwig coupling reaction to obtain 5-morpholino-7-azaindoles of formula (III),
b) a protection of the pyrrolyl moiety of the 7-azindole core to obtain compounds of formula (IV),
c) a selective borylation of the azaindole core in position 3 to finally obtain compounds of formula (V).

Synthetic intermediates of formula (XI) may be prepared according to Scheme 2, wherein $R_1$, $R_2$, $R_3$, $R_4$, $R_5$, $R_6$, and $R_7$ are as defined above, X is Cl, Br or OMs, and Y is a halogen atom as defined below.

Scheme 2

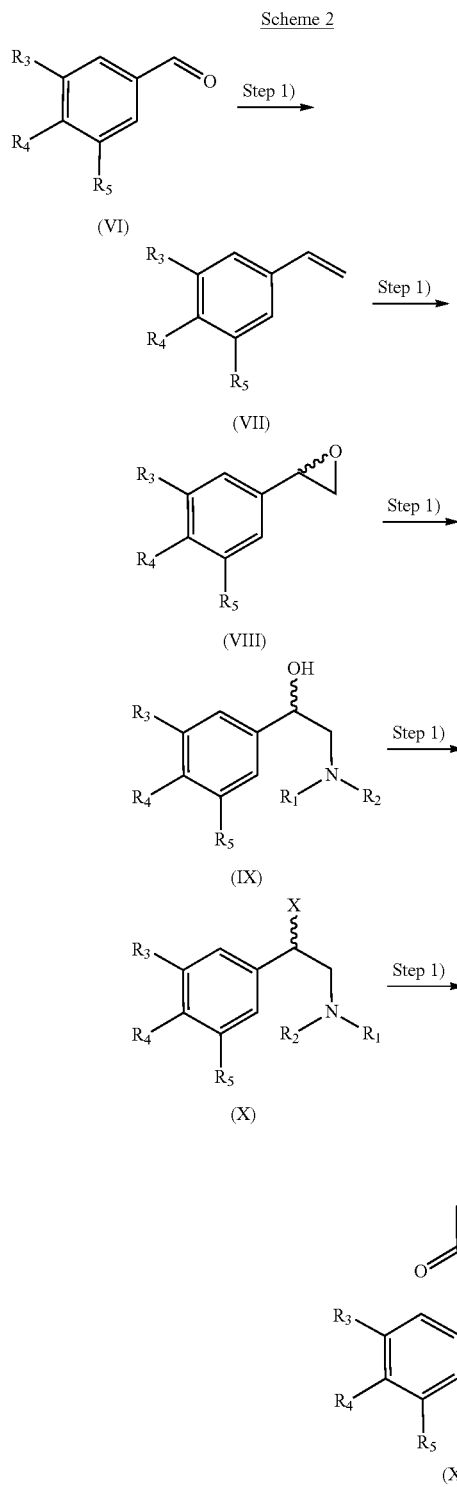

Compounds of formula (VII) are obtained by direct olefination of commercially available aldehydes of formula (VI). The reaction is generally performed with methyltriphenylphosphonium bromide in presence of a base such as NaH, and in an anhydrous solvent such as $Et_2O$, DCM or THF (Step 1).

Then, alkenes of formula (VII) are converted to the corresponding epoxides of formula (VIII) typically using the couple NBS/AcOH at 0° C. followed by a NaOH solution (Step 2). Epoxide formation could also be performed with other reageants such as peroxides or NaOCl.

Selective epoxide opening of compounds of formula (VIII) is then carrying out with commercially available disubstituted amines $HNR_1R_2$ (Step 3). The reaction is preferably performed in EtOH 96% at room temperature for 24 h to obtain the best regioselectivity but could also be done in an EtOH/water mixture, and/or heating for few hours.

Benzylalcohol derivatives of formula (IX) are then converted to the corresponding benzylchlorides or mesylate derivatives of formula (X) using MsCl at 0° C. in an anhydrous solvent such as DCM (Step 4). Benzylbromides of formula (X) could also be prepared with thionyl bromide instead of MsCl in DCM at 0° C.

Compounds of formula (XI) are finally obtained by a substitution of the halogen or the OMs moiety, using commercially available 4-halogenopyridin-2-ones in the presence of a base such as $K_2CO_3$ or $Na_2CO_3$, in DMF or DMA. The reaction could also be done in another solvent such as THF, $Et_2O$, DCM or acetone and with other bases like NaOH or tBuOK, but a higher presence of O-alkylated by-product formation could be observed (Step 5).

The present invention also concerns a process for preparing compounds of general formula (XI) wherein $R_1$, $R_2$, $R_3$, $R_4$, $R_5$, $R_6$, and $R_7$ are as defined in formula (I), and Y is a halogen atom as defined below, wherein the following steps are carried out in that order, starting from commercially available compounds of formula (VI):
1) an olefination of the aldehydes to give the corresponding alkenes of formula (VII),
2) an epoxidation of the olefins to obtain the compounds of formula (VIII),
3) a regioselective ring opening to conduct to the benzylalcohols of formula (IX),
4) a conversion of the alcohols into their corresponding halogeno- or mesylate derivatives to give compounds of formula (X), directly followed by,
5) a N-alkylation of commercially available 4-halogenopyridin-2-ones to finally give the compounds of formula (XI).

Finally, compounds of formula (I) may be prepared according to Scheme 3, wherein $R_1$, $R_2$, $R_3$, $R_4$, $R_5$, $R_6$, $R_7$, $R_8$ and $R_9$ are as defined above in formula (I), Y is a halogen atom as defined below, and PG is a protecting group as defined below.

Scheme 3

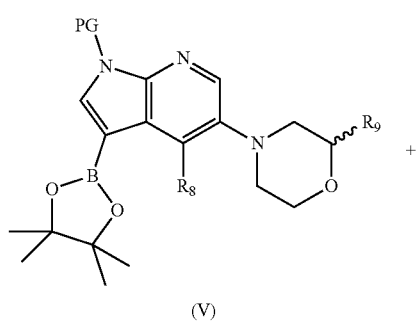

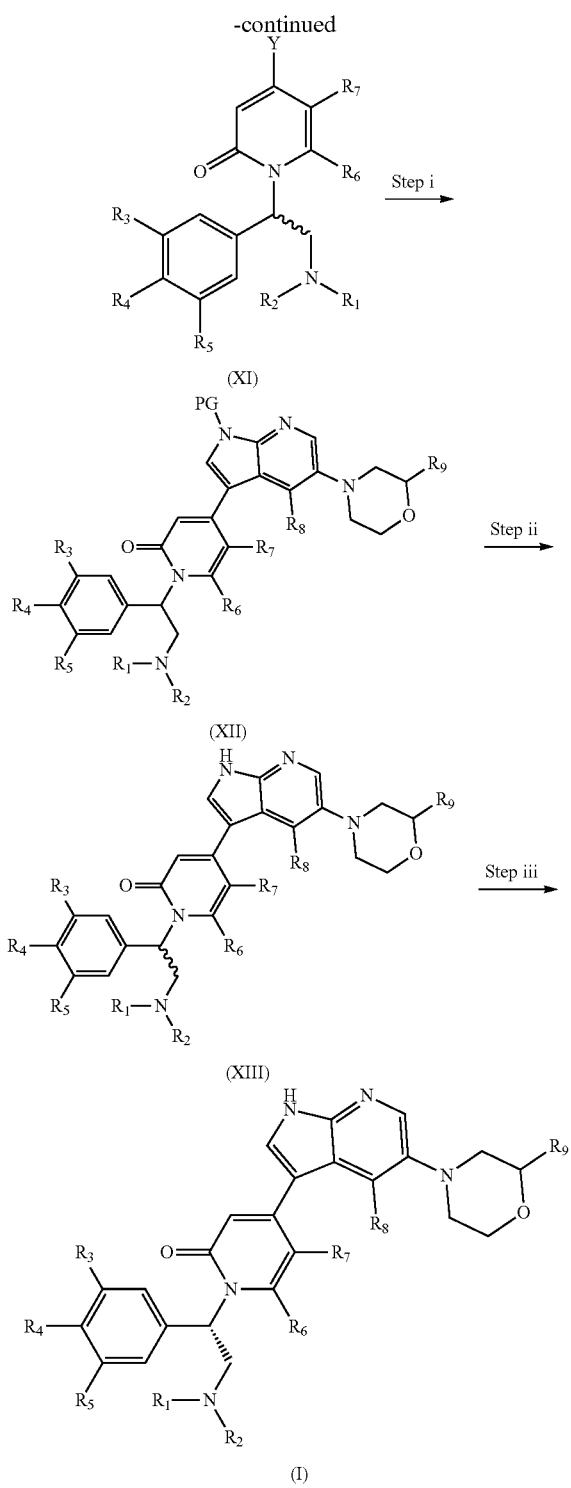

lysts, such as palladium chloride or tris(dibenzylideneacetone)dipalladium, or other bases, such as NaOH or $Cs_2CO_3$.

Compounds of formula (XII) are then deprotected to give the azaindole derivatives of formula (XIII) by using NaOH in DMSO at room temperature or $Na_2CO_3$ solution at 110° C. (Step ii). This step could also be performed with other conditions like TBAF in THF at 66° C., or MeONa in MeOH at room temperature.

Compounds of formula (I) are finally obtained by chiral separation of the racemate of formula (XIII) (Step iii), typically using a Daicel chiralflash IG. (−,R)-enantiomers are first eluted, followed by the (+,S)-enantiomers.

The present invention also concerns a process for preparing compounds of general formula (I), wherein the following steps are carried out in that order, starting from synthetic intermediates of formula (V) and (XI):

i. a Suzuki coupling reaction performed at a temperature comprised between 60° C. and 110° C., to give compounds of formula (XII), ii. a deprotection of the protecting groups to give azaindoles of formula (XIII), iii. a separation of the racemates by chiral chromatography.

Synthetic Intermediates

The present invention also concerns synthetic intermediates of formula (V):

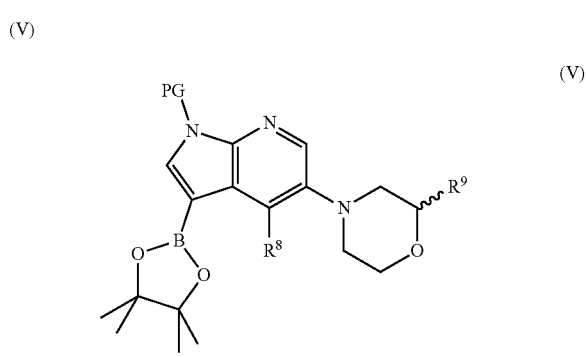

wherein $R_8$ and $R_9$ are as defined in formula (I) and PG is a protecting group chosen from -Tosyl, -Mesyl, -Brosyl, -Nosyl, -Trifyl, -tert-butyloxycarbonyl, -trimethylsilylethoxymethyl, -Trimethylsilyl, -Triisopropylsilyl, preferably a group -Tosyl.

Among the compounds of formula (V) mention may be made especially of the following compound (Va):

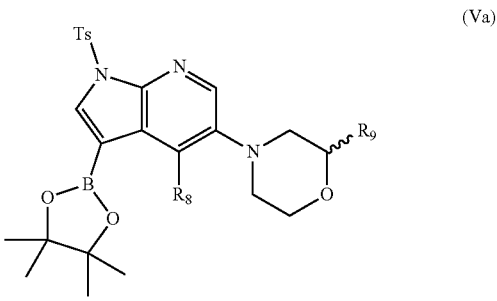

Compounds of formula (XII) are prepared by coupling synthetic intermediates of formula (V) and (XI) previously described in scheme 1 and 2 (Step i). The Suzuki coupling reaction is typically performed in the presence of a base like $K_2CO_3$ or $Na_2CO_3$ (in powder or in aqueous solution), a palladium II catalyst such as bis(triphenylphosphine)palladium dichloride in MeCN, at a temperature comprised between 60° C. and 110° C. Other conditions can be used for this step, for example other solvents, such as 1,4-dioxane, DMSO, 1,2-dimethoxyethane, EtOH or DMF, other cata- The present invention also concerns synthetic intermediates of formula (XI):

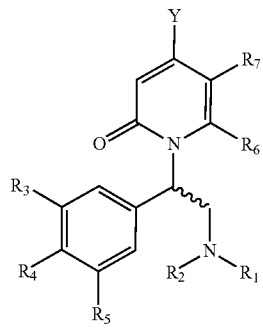
(XI)

wherein $R_1$, $R_2$, $R_3$, $R_4$, $R_5$, $R_6$, and $R_7$ are as defined in formula (I), and Y is a halogen atom.

According to a preferred embodiment, at least one of $R_3$, $R_4$ and $R_5$ is a halogen atom, and the two others represent independently a hydrogen atom or a halogen atom.

According to a preferred embodiment, one of $R_3$, $R_4$ and $R_5$ represents a chlorine atom, and the two others represent independently a hydrogen atom or a halogen atom.

According to a preferred embodiment, at least one of $R_3$, $R_4$ and $R_5$ is a fluorine atom, and the two others represent independently a hydrogen atom or a halogen atom.

According to a preferred embodiment, two of $R_3$, $R_4$ and $R_5$ represent a chlorine atom, and the other represents a hydrogen atom.

According to a preferred embodiment, Y is a bromine atom or an iodine atom.

According to a preferred embodiment, when any of $R_3$, $R_4$ and $R_5$ is an iodine atom, Y is an iodine atom.

According to a preferred embodiment, when none of $R_3$, $R_4$ and $R_5$ is an iodine atom, Y is a bromine atom.

Among the compounds of formula (XI) mention may be made especially of the following compounds:

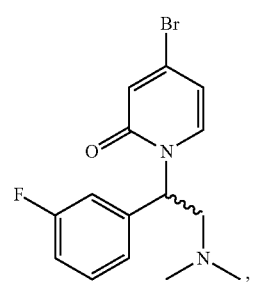
(XIa)

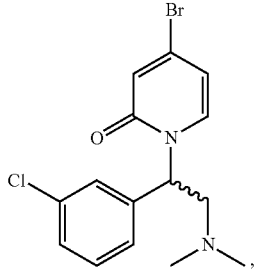
(XIb)

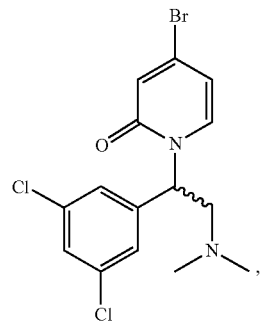
(XIc)

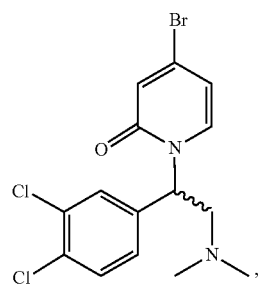
(XId)

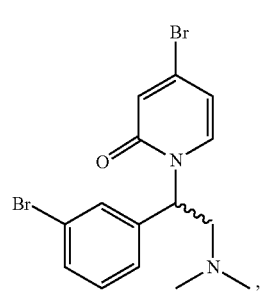
(XIe)

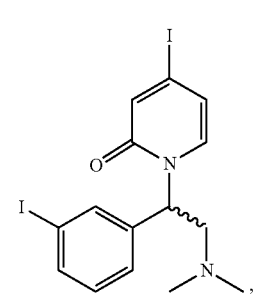
(XIf)

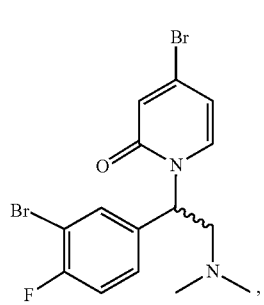
(XIg)

(XIh)
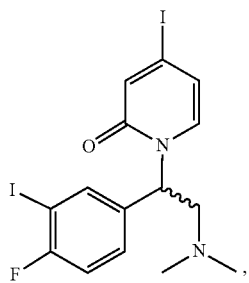
(XIi)
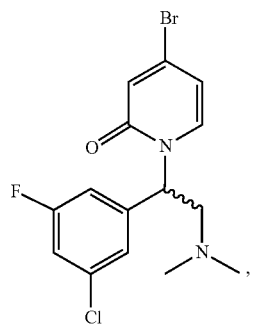
(XIj)
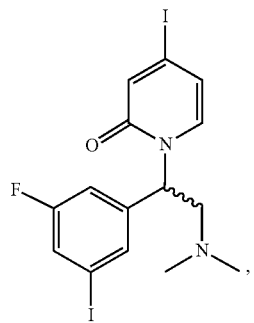
(XIk)
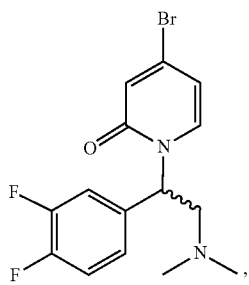
(XI-l)
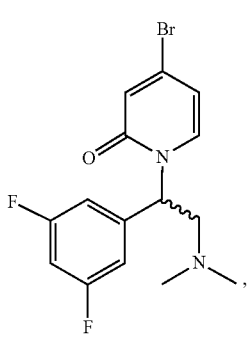
The present invention also concerns synthetic intermediates of formula (XII):
(XII)
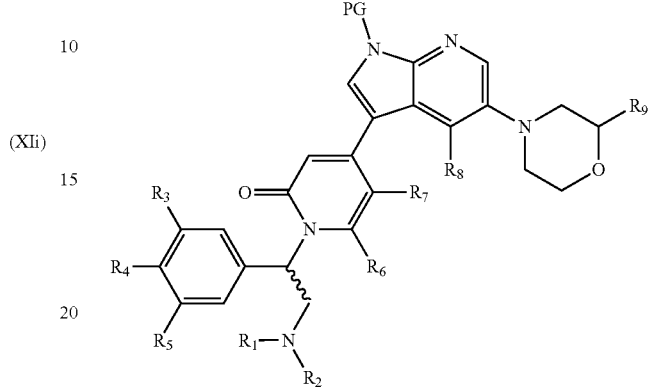
wherein $R_1$, $R_2$, $R_3$, $R_4$, $R_5$, $R_6$, $R_7$, $R_8$ and $R_9$ are as defined in formula (I), and PG is as defined in formula (V).
Among the compounds of formula (XII) mention may be made especially of the following compounds:
(XIIa)
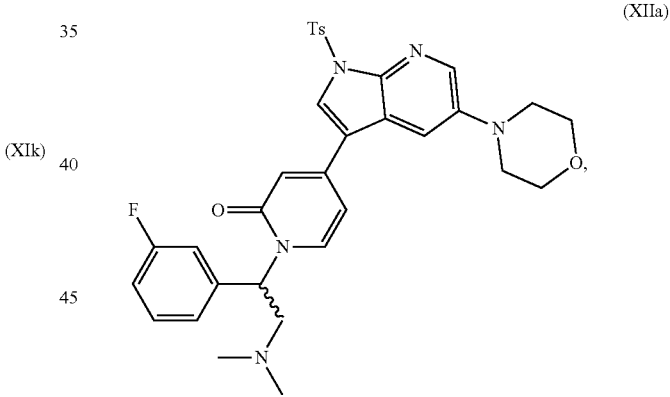
(XIIb)
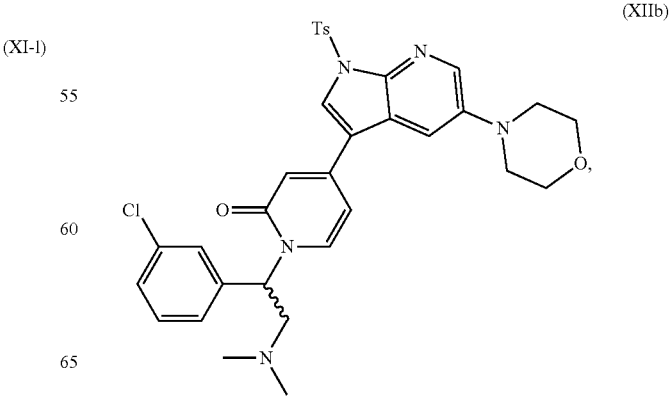

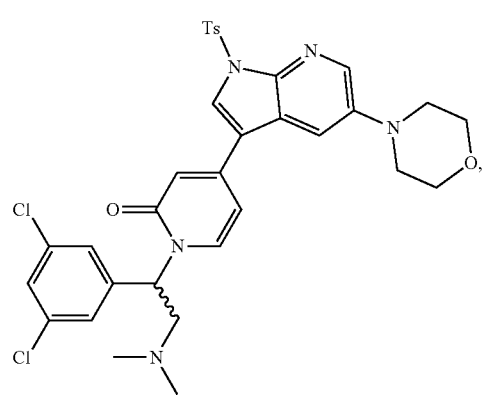
(XIIc)
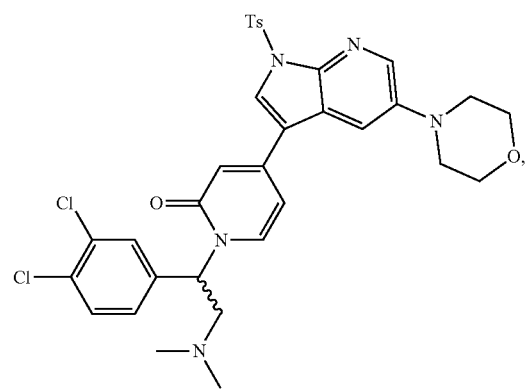
(XIId)
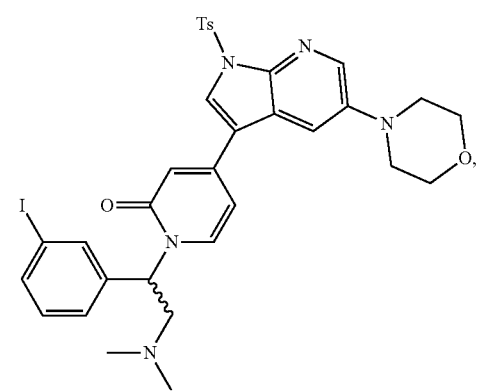
(XIIe)
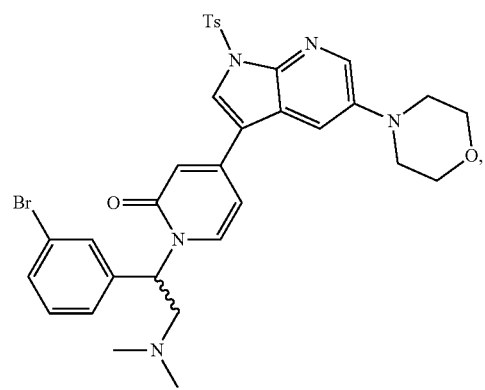
(XIIf)
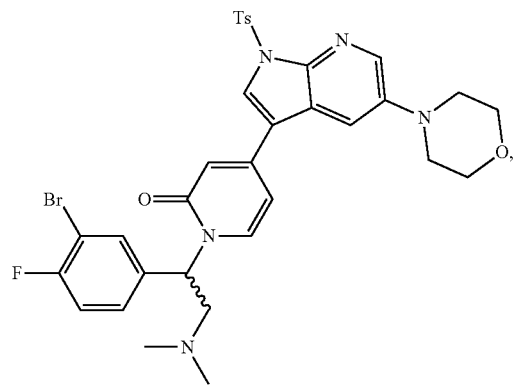
(XIIg)
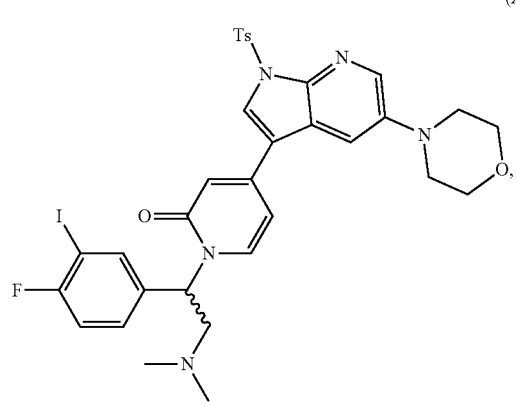
(XIIh)
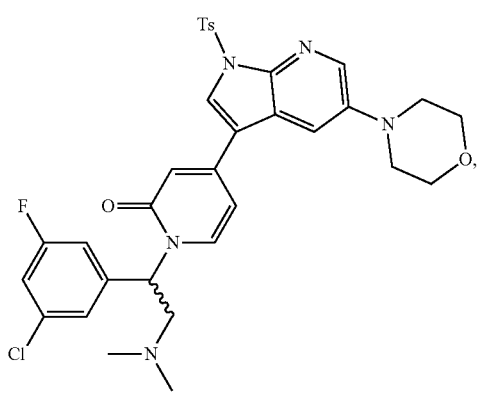
(XIIi)
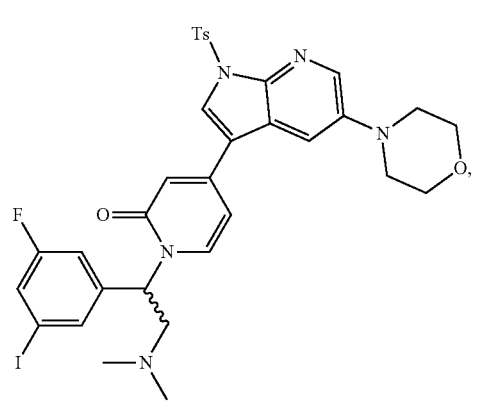
(XIIj)

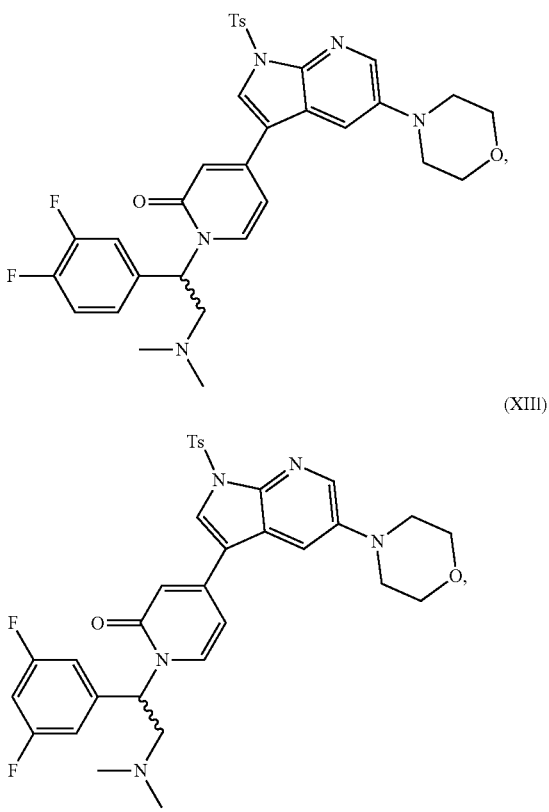

Thus, another subject of the invention concerns compounds of formula (V), (XI) and (XII) wherein:
$R_1$ represents a $(C_1-C_5)$alkyl group;
$R_2$ represents a $(C_1-C_5)$alkyl group, a $(C_3-C_5)$cycloalkyl group, or a $(C_1-C_5)$alkyl group substituted by one or more radicals selected from halogen atoms, cyano group, $(C_1-C_5)$alkoxy group and $(C_3-C_5)$cycloalkyl group;
or $R_1$ and $R_2$ form together with the nitrogen atom a 3- to 6-membered heterocyclic group;
$R_3$, $R_4$, $R_5$, $R_6$, $R_7$, $R_8$ and $R_9$ represent, independently of each other, a hydrogen atom, a halogen atom, a $(C_1-C_5)$alkyl group, a trifluoromethyl group or a cyano group, wherein said $(C_1-C_5)$alkyl is itself optionally substituted with a $(C_1-C_5)$alkoxy group;
Y is a halogen atom; and
PG is a protecting group chosen from -Tosyl, -Mesyl, -Brosyl, -Nosyl, -Triflyl, -tert-butyloxycarbonyl, -trimethylsilylethoxymethyl, -Trimethylsilyl, -Triisopropylsilyl, preferably a group -Tosyl.

Another subject of the invention concerns compounds (Va), (XIa), (XIb), (XIc), (XId), (XIe), (XIf), (XIg), (XIh), (XIi), (XIj), (XIk), (XII), (XIIa), (XIIb), (XIIc), (XIId), (XIIe), (XIIf), (XIIg), (XIIh), (XIIi), (XIIj), (XIIk) and (XIII).

Applications

As specified previously and clearly illustrated by the following examples, the compounds according to the present invention are useful as inhibitors of the ERK kinases activity.

According to a first aspect, the compounds of the invention are used as inhibitors of the ERK2 kinase activity, preferably as selective inhibitors of the ERK2 kinase activity.

More specifically, the compounds of the invention are used for preventing and/or inhibiting and/or treating a disease or a condition mediated by ERK kinases activity, in particular by ERK2 kinase activity.

The present invention therefore provides a method for preventing and/or treating a disease or a condition mediated by ERK kinases activity, comprising at least a step of administering to an individual in need thereof at least an effective amount of at least one compound in accordance with the invention.

The present invention also provides the compounds of the invention for their use for preventing and/or inhibiting and/or treating, preferably for preventing and/or treating, more preferably for treating, a disease or a condition mediated by ERK kinases activity, preferably ERK2 kinases activity.

The present invention also provides the use of compounds of the invention for preventing and/or inhibiting and/or treating, preferably for preventing and/or treating, more preferably for treating, a disease or a condition mediated by ERK kinases activity, preferably ERK2 kinases activity.

The invention features a method of inhibiting ERK kinase activity in a cell, the method including the step of contacting the cell with a compound selected from:
(S)-1-(2-(dimethylamino)-1-(3-fluorophenyl)ethyl)-4-(5-morpholino-1H-pyrrolo[2,3-b]pyridin-3-yl)pyridin-2(1H)-one;
(S)-1-(1-(3-chlorophenyl)-2-(dimethylamino)ethyl)-4-(5-morpholino-1H-pyrrolo[2,3-b]pyridin-3-yl)pyridin-2(1H)-one;
(S)-1-(1-(3,5-dichlorophenyl)-2-(dimethylamino)ethyl)-4-(5-morpholino-1H-pyrrolo[2,3-b]pyridin-3-yl)pyridin-2(1H)-one;
(S)-1-(1-(3,4-dichlorophenyl)-2-(dimethylamino)ethyl)-4-(5-morpholino-1H-pyrrolo[2,3-b]pyridin-3-yl)pyridin-2(1H)-one;
(S)-1-(1-(3-bromophenyl)-2-(dimethylamino)ethyl)-4-(5-morpholino-1H-pyrrolo[2,3-b]pyridin-3-yl)pyridin-2(1H)-one;
(S)-1-(2-(dimethylamino)-1-(3-iodophenyl)ethyl)-4-(5-morpholino-1H-pyrrolo[2,3-b]pyridin-3-yl)pyridin-2(1H)-one;
(S)-1-(1-(3-bromo-4-fluorophenyl)-2-(dimethylamino)ethyl)-4-(5-morpholino-1H-pyrrolo[2,3-b]pyridin-3-yl)pyridin-2(1H)-one;
(S)-1-(2-(dimethylamino)-1-(4-fluoro-3-iodophenyl)ethyl)-4-(5-morpholino-1H-pyrrolo[2,3-b]pyridin-3-yl)pyridin-2(1H)-one;
(S)-1-(1-(3-chloro-5-fluorophenyl)-2-(dimethylamino)ethyl)-4-(5-morpholino-1H-pyrrolo[2,3-b]pyridin-3-yl)pyridin-2(1H)-one;
(S)-1-(2-(dimethylamino)-1-(3-fluoro-5-iodophenyl)ethyl)-4-(5-morpholino-1H-pyrrolo[2,3-b]pyridin-3-yl)pyridin-2(1H)-one;
(S)-1-(1-(3-chlorophenyl)-2-((2,2-difluoroethyl)(methyl)amino)ethyl)-4-(5-morpholino-1H-pyrrolo[2,3-b]pyridin-3-yl)pyridin-2(1H)-one;
(S)-2-((2-(3-chlorophenyl)-2-(4-(5-morpholino-1H-pyrrolo[2,3-b]pyridin-3-yl)-2-oxopyridin-1(2H)-yl)ethyl)(methyl)amino)acetonitrile;
(S)-1-(1-(3-chlorophenyl)-2-((2-methoxyethyl)(methyl)amino)ethyl)-4-(5-morpholino-1H-pyrrolo[2,3-b]pyridin-3-yl)pyridin-2(1H)-one;

(S)-1-(1-(3-chlorophenyl)-2-(cyclopropyl(methyl)amino)
   ethyl)-4-(5-morpholino-1H-pyrrolo[2,3-b]pyridin-3-yl)
   pyridin-2(1H)-one;
(S)-1-(1-(3-chlorophenyl)-2-(ethyl(methyl)amino)ethyl)-4-
   (5-morpholino-1H-pyrrolo[2,3-b]pyridin-3-yl)pyridin-2
   (1H)-one;
(S)-1-(1-(3-chlorophenyl)-2-((cyclopropylmethyl)(methyl)
   amino)ethyl)-4-(5-morpholino-1H-pyrrolo[2,3-b]pyridin-
   3-yl)pyridin-2(1H)-one;
(S)-1-(1-(3,4-difluorophenyl)-2-(dimethylamino)ethyl)-4-
   (5-morpholino-1H-pyrrolo[2,3-b]pyridin-3-yl)pyridin-2
   (1H)-one;
(S)-1-(1-(3,5-difluorophenyl)-2-(dimethylamino)ethyl)-4-
   (5-morpholino-1H-pyrrolo[2,3-b]pyridin-3-yl)pyridin-2
   (1H)-one;
(S)-1-(1-(3-chlorophenyl)-2-(dimethylamino)ethyl)-5-
   fluoro-4-(5-morpholino-1H-pyrrolo[2,3-b]pyridin-3-yl)
   pyridin-2(1H)-one;
(S)-1-(1-(3-chlorophenyl)-2-(dimethylamino)ethyl)-6-
   methyl-4-(5-morpholino-1H-pyrrolo[2,3-b]pyridin-3-yl)
   pyridin-2(1H)-one;
1-((S)-1-(3-chlorophenyl)-2-(dimethylamino)ethyl)-4-(5-
   (2-(trifluoromethyl)morpholino)-1H-pyrrolo[2,3-b]pyri-
   din-3-yl)pyridin-2(1H)-one;
(S)-1-(1-(3-chlorophenyl)-2-(dimethylamino)ethyl)-4-(4-
   fluoro-5-morpholino-1H-pyrrolo[2,3-b]pyridin-3-yl)pyri-
   din-2(1H)-one;
(S)-1-(1-(3-chloro-5-(methoxymethyl)phenyl)-2-(dimethyl-
   amino)ethyl)-4-(5-morpholino-1H-pyrrolo[2,3-b]pyridin-
   3-yl)pyridin-2(1H)-one;
(S)-1-(2-(aziridin-1-yl)-1-(3-chlorophenyl)ethyl)-4-(5-mor-
   pholino-1H-pyrrolo[2,3-b]pyridin-3-yl)pyridin-2(1H)-
   one;
(S)-3-(2-(dimethylamino)-1-(4-(5-morpholino-1H-pyrrolo
   [2,3-b]pyridin-3-yl)-2-oxopyridin-1(2H)-yl)ethyl)benzo-
   nitrile; or
(S)-1-(2-(dimethylamino)-1-(3-(trifluoromethyl)phenyl)
   ethyl)-4-(5-morpholino-1H-pyrrolo[2,3-b]pyridin-3-yl)
   pyridin-2(1H)-one,
or a pharmaceutically acceptable salt thereof, in an amount sufficient to inhibit the ERK kinase activity. The method can include inhibiting inhibit the ERK kinase inside the cell (e.g., in the cytoplasm or nucleus of the cell). In some embodiments the cell is a human cell. In particular embodiments, the cell is a human cancer cell.

According to one embodiment, the disease or the condition may be chosen among cancers, metastases, and the Human Immunodeficiency Virus (HIV), and preferably chosen among cancers and metastases.

More specifically, the disease or the condition may be chosen among glioblastomas, multiple myelomas, carcinomas, leukemia, in particular myeloid (AML), lymphocytic, myelocytic, myelogenous (CML) or lymphoblastic leukemias, myelodysplastic syndromes, Kaposi's sarcomas, cutaneous angiosarcomas, solid tumours, lymphomas, in particular non-hodgkin's lymphomas, melanomas, in particular malignant melanomas, bladder cancers, breast cancers, gastric cancers, colon cancers, colorectal cancers, endometrial cancers, lung cancers, including non-small-cell cancers, pancreatic cancers, prostate cancers, rectal cancers, kidney cancers, head and neck cancers, liver cancers, ovarian cancers, in particular serous ovarian cancers, seminoma cancers, cancers of the respiratory tract and chest, thyroid cancers, in particular papillary or follicular thyroid cancers, or other tumours expressing ERK. In some embodiments, the disease mediated by ERK kinase activity is cancer. In some embodiments, the ERK kinase activity is inhibited in a cell. In some embodiments, the cancer cell is in a human.

According to another embodiment, the disease or condition may be chosen among a neoplastic disorder, an allergy disorder, an inflammatory disorder, an autoimmune disorder, a Plasmodium related disease, a mast cell associated disease, a graft-versus-host disease, a metabolic syndrome, a CNS related disorder, a neurodegenerative disorder, a pain condition, a substance abuse disorder, a prion disease, a heart disease, a fibrotic disease, idiopathic arterial hypertension (IPAH), or primary pulmonary hypertension (PPH).

According to yet another embodiment, the compounds of the invention may be used for preventing and/or inhibiting and/or treating the Human Immunodeficiency Virus (HIV).

The compounds of the present invention may be used alone or combined with chemotherapeutic agents or radiotherapeutic regimen.

Thus, according to one embodiment, a method of the invention may comprise the step of administering a compound of formula (I) in accordance with the invention, separately, sequentially, or simultaneously with a chemotherapeutic agent.

As examples of chemotherapeutic agents that may be suitable for the invention, one may mention chemotherapeutic agents chosen from alkylating agents, intercalating agents, antimicrotubule agents, antimitotics, antimetabolites, antiproliferative agents, antibiotics, immunomodulatory agents, anti-inflammatories, kinases inhibitors, anti-angiogenic agents, antivascular agents, oestrogenic and androgenic hormones.

A radiotherapeutic regimen may be administrated by exposing an individual in need thereof to a source of ionizing radiation such as X-ray, gamma-ray or beta-ray.

According to another of its aspects, the present invention relates to a pharmaceutical composition comprising at least one compound according to the invention or a pharmaceutically acceptable salt thereof, and at least one pharmaceutically acceptable excipient.

The compounds according to the invention may be used for the preparation of medicaments, in particular of medicaments for inhibiting the activity of ERK kinases preferably ERK2 kinases activity.

Thus, according to yet another of its aspects, the present invention relates to a medicament comprising at least one compound according to the invention, or a pharmaceutically acceptable salt thereof.

The term "pharmaceutically acceptable" means that which is useful in preparing a pharmaceutical composition that is generally safe, non-toxic, and neither biologically nor otherwise undesirable and includes what is acceptable for veterinary as well as human pharmaceutical use.

The pharmaceutical compositions may contain more particularly an effective dose of at least one compound according to the invention.

An "effective dose" means an amount sufficient to induce a positive modification in the condition to be regulated or treated, but low enough to avoid serious side effects. An effective amount may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound of formula (I) according to the invention may be administered in an effective dose by any of the accepted modes of administration in the art.

In one embodiment, a compound of the invention may be used in a composition intended to be administrated by oral, nasal, sublingual, aural, ophthalmic, topical, rectal, vaginal, urethral, or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

According to one embodiment, a pharmaceutical composition of the invention may be intended to be administered separately, sequentially, or simultaneously with an agent useful for the prevention and/or the treatment of a disease condition, in particular a cancer condition, said agent being different from the compound of formula (I) of the invention.

The exact amount of the compound of formula (I) needed for therapeutic benefit can vary from subject to subject, depending on the species, age, weight, and general condition of the subject, the severity of the disease being treated, the particular formulation, and its route of administration. For the treatment of disease, compounds of formula (I) can be dosed in the range of 0.2-20 mg/kg per day. However, the efficacious regimen utilized will generally be decided by an attending physician within the scope of sound medical judgment.

The applications also include a novel kit-of-parts that is suitable for use in the treatment of cancers. A kit-of-part according to the invention may comprise (i) a compound of formula (I) according to the invention, and (ii) at least one agent useful for the prevention and/or the treatment of a cancer condition, said agent being different from said compound of formula (I). An agent useful for the prevention and/or treatment of a cancer condition may be a chemotherapeutic agent or a radiotherapeutic agent.

The present invention will be better understood by referring to the following examples which are provided for illustrative purpose only and should not be interpreted as limiting in any manner the instant invention.

EXAMPLES

Equipment and Analytical Methods Used for the Syntheses of Examples
    Microwaves irradiation:
    Apparatus: CEM Discover with Synergy Software.
    Method: 10 mL or 30 mL sealed tube, power up to 50 W, high stirring.
Flash chromatography:
    Apparatus: Biotage SP with auto-collector and UV detection (2 wavelengths).
        Normal phase columns: 10, 25 or 120 g Biotage external dry load cartridge kit, packed with Sigma-Aldrich 40-63 µm silica gel.
    Reverse phase column: 30 g Biotage SNAP Cartridges, KP-C18-HS.
    Chiral column: Daicel ChiralFlash IG 100×30 mm 20 µM.
Liquid Chromatography:
    Apparatus: Waters alliance 2695 HPLC system with autosampler and Waters 2996 diode array detector.
    Reverse phase conditions:
        Column: Macherey-Nagel Nucleoshell RP18 plus (5 µm, 4 mm×100 mm).
        Column temperature: 40° C.
        Solvents: A ($H_2O$ 99.9%, $H_2CO_2$ 0.1%); B (MeCN 99.9%, $H_2CO_2$ 0.1%).
        Flow rate: 1 mL/min.
        Gradient (A/B v/v): 95/5 (t=0 min), 95/5 (t=1 min), 0/100 (t=7 min), 0/100 (t=10 min).
    Chiral phase conditions:
        Column: Daicel ChiralPak IG (Amylose-based) 20 µm, 4.6 mm×100 mm.
        Column temperature: 25° C.
        Solvents: Heptane 50%/EtOH containing 0.1% TEA 40%/DCM 10%.
        Flow rate: 1 mL/min.
Mass Spectrometer:
Apparatus: Waters Micromass ZQ (simple quad).
Mass detection method: Electrospray positive mode (ESI+), mass range: 50-800 uma.
Detection: 210-400 nm range.
NMR Spectrometer:
Apparatus: Bruker 400 MHz.
Methods: $^1$H NMR spectra performed in DMSO-d6 using DMSO-d5 as internal reference, chemical shifts expressed in parts per million (ppm), signals expressed as follows:
s=singlet, d=doublet, t=triplet, q=quadruplet, sept=septuplet, dd=double doublet, dt=double triplet, m=multiplet or large singlet, br=broad, H=proton.

Example 1: Synthesis of (S)-1-(2-(dimethylamino)-1-(3-fluorophenyl)ethyl)-4-(5-morpholino-1H-pyrrolo[2,3-b]pyridin-3-yl)pyridin-2(1H)-one

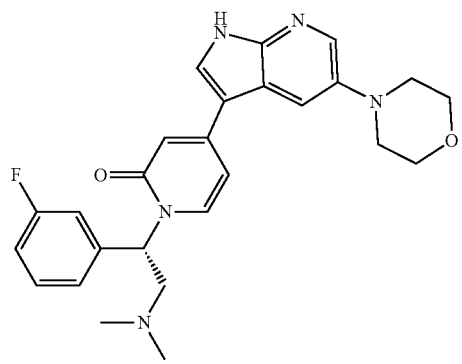 [SMILES: CN(C)C[C@H](c1cccc(F)c1)n1ccc(-c2c[nH]c3ncc(N4CCOCC4)cc23)cc1=O]

Step 1: 4-(1H-Pyrrolo[2,3-b]pyridin-5-yl)morpholine

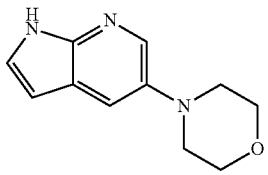 [SMILES: c1cc2cc(N3CCOCC3)cnc2[nH]1]

In 487 ml of LiHMDS (1 M in THF, 487 mmol, 2.4 eq) are dissolved 947 mg (2.03 mmol, 0.01 eq) of RuPhos and 1.58 g (2.03 mmol, 0.01 eq) of RuPhos Pd G2. Then are added under argon 40 g (203 mmol, 1 eq) of 5-bromo-1H-pyrrolo[2,3-b]pyridine and 21.1 ml (244 mmol, 1.2 eq) of morpholine and the solution is heated at 66° C. for 1 h 30. The reaction mixture is then cooled to room temperature and dropped into 1.2 l of a saturated NH$_4$Cl solution maintaining the temperature under 10° C. with an ice water bath. The mixture is stirred for 10 min at this temperature and decanted. Aqueous layer is extracted 3 times with DCM. Combined organic layers are dried over Na$_2$SO$_4$, filtered, and evaporated under reduced pressure to give 44.4 g of a brown solid. Crude is triturated in 200 ml of a mixture of EtOAc and hexane (3/7) for 1 h. The solid is filtrated, rinsed with 200 ml of a mixture of EtOAc and hexane (1/9) and dried under vacuum to give 38.98 g of a slightly brown powder.

Yield: 94%.
MH+: 204.3 (M+1).

Step 2: 4-(1-Tosyl-1H-pyrrolo[2,3-b]pyridin-5-yl)morpholine

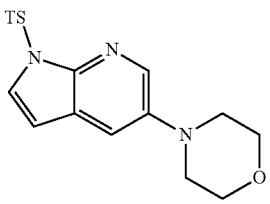

38.98 g (192 mmol, 1 eq) of 4-(1H-pyrrolo[2,3-b]pyridin-5-yl)morpholine (described in the previous step) are dissolved in 390 ml of dry DMF, under argon. The solution is cooled to 0° C., and 11.5 g (288 mmol, 1.5 eq) of sodium hydride (60% in paraffin oil) are slowly added. The mixture is stirred for 10 min at this temperature and then 40 min at room temperature. The mixture is cooled again to 0° C., 47.5 g (249 mmol, 1.3 eq) of tosyl chloride are slowly added under argon and the reaction mixture is stirred at 0° C. for 1 h followed by 1 h at room temperature. The mixture is dropped into 800 g of ice/water and stirred for 1 h. A precipitate is obtained, which is filtrated and rinsed several times with cold water. The precipitate is then dissolved with 1.2 l of DCM, and the solution is washed 2 times with a saturated NaHCO$_3$ solution, 2 times with water and once with brine. The organic layer is dried over Na$_2$SO$_4$, filtered, and evaporated under reduced pressure. Crude compound is triturated in 500 ml of a mixture of EtOAc and hexane (5/95) for 3 h. The solid is filtrated, rinsed with hexane and dried under vacuum to give 62.56 g of an off-white solid.

Yield: 91%.
MH+: 358.6 (M+1).
$^1$H NMR (DMSO-d6, 400 MHz): δ 8.18 (d, J=2.7 Hz, 1H); 7.92 (d, J=8.3 Hz, 2H); 7.78 (d, J=4.0 Hz, 1H); 7.52 (d, J=2.7 Hz, 1H); 7.39 (d, J=8.3 Hz, 2H); 6.68 (d, J=4.0 Hz, 1H); 3.76-3.71 (m, 4H); 3.12-3.07 (m, 4H); 2.33 (s, 3H).

Step 3: 4-(3-(4,4,5,5-tetramethyl-1,3,2-dioxaborolan-2-yl)-1-tosyl-1H-pyrrolo[2,3-b]pyridin-5yl)morpholine

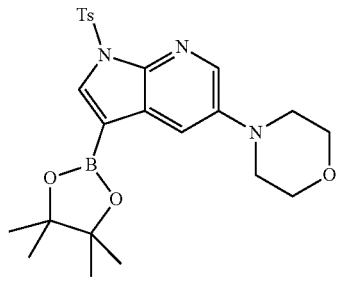 [SMILES: Cc1ccc(S(=O)(=O)n2cc(B3OC(C)(C)C(C)(C)O3)c3cc(N4CCOCC4)cnc32)cc1]

62.56 g (175 mmol, 1 eq) of 4-(1-tosyl-1H-pyrrolo[2,3-b]pyridin-5-yl)morpholine (described in the previous step) are suspended in 512 ml of Me-THF under argon. Then 48.9 g of bis(pinacolato)diboron (193 mmol, 1.1 eq), 1.88 g of 4,4'-di-tert-butylbiphenyl (7 mmol, 0.036 eq) and 2.32 g of (1,5-cyclooctadiene)(methoxy)iridium(I) dimer (3.5 mmol, 0.018 eq) are added. The reaction is heated to reflux for 45 min under argon. The reaction mixture is then cooled to −10° C. with an ice/acetone bath and quenched carefully with MeOH (350 ml). The solution is stirred at room temperature for 15 min and evaporated under vacuum to give a brown oil. Dark oil is then dissolved in 1 l of DCM, washed 3 times with water and once with brine. Organic layer is evaporated under reduced pressure to give a black paste. 2 l of Et$_2$O are added and the mixture is stirred for 15 min at room temperature, filtrated on Celite and evaporated under reduced pressure to give 95 g of a brown solid foam. Crude mixture is finally purified by flash chromatography using a silica gel column and an EtOAc/hexane mixture as eluent. 75.5 g of the title compound are obtained.

Yield: 89%.
MH+: 484.6 (M+1).
$^1$H NMR (DMSO-d6, 400 MHz): δ 8.21 (d, J=2.5 Hz, 1H); 8.01 (d, J=8.3 Hz, 2H); 7.94 (s, 1H); 7.50 (d, J=2.4 Hz, 1H); 7.41 (d, J=8.0 Hz, 2H); 3.78-3.72 (m, 4H); 3.12-3.07 (m, 4H); 2.33 (s, 3H); 1.30 (s, 12H).

Step 4: 1-Fluoro-3-vinylbenzene

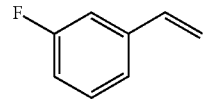

5 g (40.3 mmol, 1 eq) of 3-fluorobenzaldehyde are dissolved in 50 ml of dry THF and the solution is cooled to −10° C. with an ice/acetone bath. 17.3 g (48.4 mmol, 1.2 eq)

of methyltriphenylphosphonium bromide are added followed by 2.1 g (52.4 mmol, 1.3 eq) of sodium hydride (60% in paraffin oil). The suspension is then stirred at room temperature overnight under argon. The mixture is diluted with 100 ml of Et₂O and the precipitate is filtrated on Celite. The filtrate is evaporated under reduced pressure to give an orange residue. Crude mixture is finally purified by flash chromatography using a silica gel column and an Et₂O/pentane mixture as eluent (3/97). 1.25 g of the title compound are obtained.

Yield: 25%.

MH+: Non ionizable.

Step 5: 2-(3-Fluorophenyl)oxirane

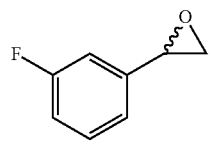

1.25 g (10.2 mmol, 1 eq) of 1-fluoro-3-vinylbenzene (described in the previous step) are dissolved in 6 ml of 1,4-dioxane and 18 ml of water. The solution is cooled to 0° C. and 584 µl (10.2 mmol, 1 eq) of acetic acid are added, followed by 1.99 g (11.2 mmol, 1.1 eq) of N-bromosuccinimide. Reaction mixture is stirred at 0° C. for 5 min then at room temperature for 2 h. Mixture is then cooled again to 0° C. and a solution of NaOH 2N in water (35.7 mmol, 3.5 eq) is slowly added. The solution is allowed to stir at room temperature for 1 h. Reaction mixture is concentrated under reduced pressure and aqueous resulting phase is extracted 3 times with DCM. Combined organic layers are dried over Na₂SO₄, filtrated and evaporated under reduced pressure. Crude mixture is purified by flash chromatography using a silica gel column and a DCM/hexane mixture as eluent (2/98). 1.02 g of the title compound are obtained.

Yield: 72%.

MH+: Non ionizable.

Step 6:
2-(Dimethylamino)-1-(3-fluorophenyl)ethan-1-ol

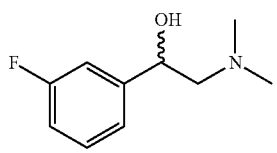

To a solution of 1.02 g (7.38 mmol, 1 eq) of 2-(3-fluorophenyl)oxirane (described in the previous step) in 14 ml of EtOH 96%, are added 7.38 ml (14.76 mmol, 2 eq) of a solution of dimethylamine (2M in THF). The clear resulting solution is heated under microwave irradiation at for 30 min. Reaction mixture is then concentrated under vacuum and diluted with water. The solution is extracted 3 times with DCM. Combined organic layers are dried over Na₂SO₄, filtrated and evaporated under reduced pressure. Crude mixture is purified by flash chromatography using a silica gel column and a DCM/MeOH mixture as eluent. 0.927 g of the title compound are obtained.

Yield: 69%.

MH+: 322.6 (M+1).

Step 7: 2-Chloro-2-(3-fluorophenyl)-N,N-dimethylethan-1-amine

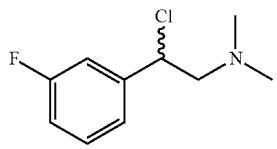

0.927 g (5.03 mmol, 1 eq) of 2-(dimethylamino)-1-(3-fluorophenyl)ethan-1-ol (described in the previous step) are dissolved in 15 ml of DCM and placed at 0° C. 2.1 ml (15.1 mmol, 3 eq) of triethylamine are added, followed by 0.781 ml (10.1 mmol, 2 eq) of mesyl chloride. The reaction is stirred at 0° C. under argon for 2 h. Water is then added and the mixture is decanted. Aqueous layer is extracted 2 times with DCM. Combined organic layers are dried over Na₂SO₄, filtrated and evaporated under reduced pressure. Crude compound is directly used in the next step without further purification.

Yield: Quantitative.

MH+: 202.3; 204.3 (M; M+2).

Step 8: 4-Bromo-1-(2-(dimethylamino)-1-(3-fluorophenyl)ethyl)pyridin-2(1H)-one

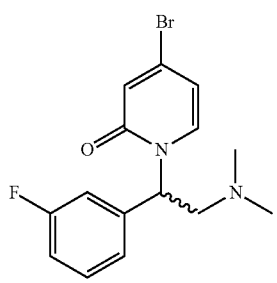

To a mixture of 0.744 g (4.28 mmol, 1 eq) of 4-bromopyridin-2-(1H)-one and 1.39 g (4.28 mmol, 1 eq) of cesium carbonate in 10 ml of dry DMF, is added at 0° C. a solution of 1.02 g (5.08 mmol, 1.18 eq) of 2-chloro-2-(3-fluorophenyl)-N,N-dimethylethan-1-amine (described in the previous step) in 5 ml of dry DMF. The solution is then stirred at room temperature for 2 h. EtOAc is added, and the mixture is washed 4 times with water and once with brine. Organic layer is dried over Na₂SO₄, filtrated and evaporated under reduced pressure. Crude mixture is purified by flash chromatography using a deactivated silica gel column and a Hexane/EtOAc mixture as eluent. 1.31 g of the title compound are obtained.

Yield: 76%.

MH+: 339.4; 341.5 (M; M+2).

Step 9: 1-(2-(Dimethylamino)-1-(3-fluorophenyl)ethyl)-4-(5-morpholino-1-tosyl-1H-pyrrolo[2,3-b]pyridin-3-yl)pyridin-2(1H)-one

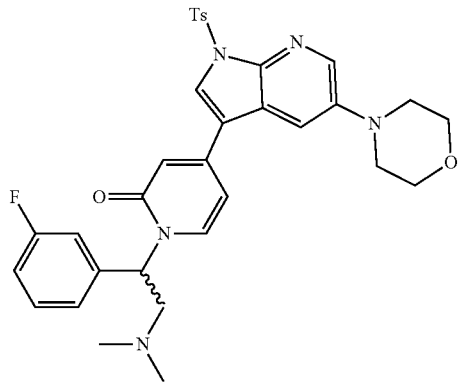 [SMILES: Cc1ccc(S(=O)(=O)n2cc(-c3ccn(C(CN(C)C)c4cccc(F)c4)c(=O)c3)c3cc(N4CCOCC4)cnc32)cc1]

1.31 g (3.86 mmol, 1 eq) of 4-bromo-1-(2-(dimethylamino)-1-(3-fluorophenyl)ethyl)pyridin-2(1H)-one (described in the previous step) and 2.45 g (5.01 mmol, 1.3 eq) of 4-(3-(4,4,5,5-tetramethyl-1,3,2-dioxaborolan-2-yl)-1-tosyl-1H-pyrrolo[2,3-b]pyridin-5-yl)morpholine (described in Step 3) are dissolved in 13 ml of MeCN under argon. Then 13 ml of a solution of $Na_2CO_3$ 2M are added to give a biphasic mixture which is bubbled with argon for 15 min. 135 mg (0.19 mmol, 0.05 eq) of bis(triphenylphosphine)palladium dichloride are added and the solution was bubbled with argon for another 15 min. The reaction is stirred at 70° C. for 2 h under argon. Reaction mixture is then diluted with water and EtOAc and then decanted. Aqueous layer is extracted 2 times with EtOAc. Combined organic layer are dried over $Na_2SO_4$, filtrated and evaporated under reduced pressure. Crude mixture is purified by flash chromatography using a silica gel column and a DCM/MeOH mixture as eluent. 2.05 g of the title compound are obtained.

Yield: 86%.

MH+: 616.6 (M+1).

Step 10: 1-(2-(Dimethylamino)-1-(3-fluorophenyl)ethyl)-4-(5-morpholino-1H-pyrrolo[2,3-b]pyridin-3-yl)pyridin-2(1H)-one

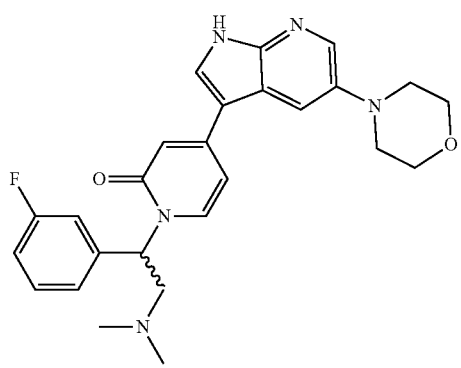 [SMILES: CN(C)CC(c1cccc(F)c1)n1ccc(-c2c[nH]c3ncc(N4CCOCC4)cc23)cc1=O]

2.05 g (3.33 mmol, 1 eq) of 1-(2-(dimethylamino)-1-(3-fluorophenyl)ethyl)-4-(5-morpholino-1-tosyl-1H-pyrrolo[2,3-b]pyridin-3-yl)pyridin-2(1H)-one (described in the previous step) are dissolved in 15 ml of dry THF under argon. Then 10 ml (10 mmol, 3 eq) of a solution of TBAF (1M in THF) are added and the reaction is stirred at 66° C. for 1 h under argon. Solvent is removed under reduced pressure and 100 ml of a saturated $NaHCO_3$ solution are added. Mixture is extracted 3 times with EtOAc. Combined organic layer are dried over $Na_2SO_4$, filtrated and evaporated under reduced pressure. Crude mixture is purified by flash chromatography using a silica gel column and a DCM/MeOH mixture as eluent. 1.49 g of a yellow solid are obtained.

Yield: 96%.

MH+: 462.7 (M+1).

$^1$H NMR (DMSO-d6, 400 MHz): δ 12.04 (br s, 1H); 8.16 (d, J=2.4 Hz, 1H); 8.09 (d, J=1.8 Hz, 1H); 7.74 (d, J=8.0 Hz, 1H); 7.70 (d, J=2.5 Hz, 1H); 7.45-7.36 (m, 1H); 7.30-7.18 (m, 2H); 7.18-7.10 (m, 1H); 6.72-6.64 (m, 2H); 6.27-6.16 (m, 1H); 3.84-3.73 (m, 4H); 3.32-3.22 (m, 1H); 3.20-3.08 (m, 4H); 2.80-2.69 (m, 1H); 2.21 (s, 6H).

Step 11: (S)-1-(2-(Dimethylamino)-1-(3-fluorophenyl)ethyl)-4-(5-morpholino-1H-pyrrolo[2,3-b]pyridin-3-yl)pyridin-2(1H)-one

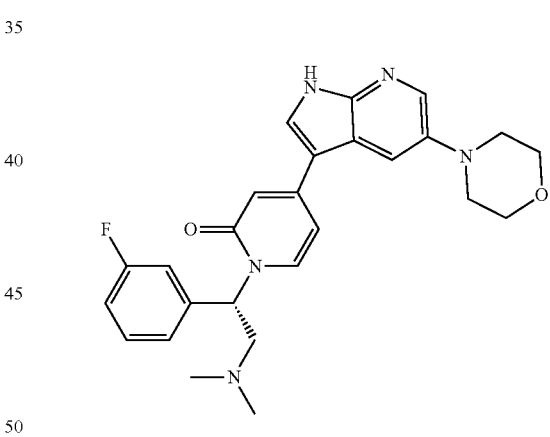

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 275 mg of the title compound are obtained starting from 1.49 g of racemate.

MH+: 462.7 (M+1).

$^1$H NMR (DMSO-d6, 400 MHz): δ 12.04 (br s, 1H); 8.16 (d, J=2.4 Hz, 1H); 8.09 (d, J=1.8 Hz, 1H); 7.74 (d, J=8.0 Hz, 1H); 7.70 (d, J=2.5 Hz, 1H); 7.45-7.36 (m, 1H); 7.30-7.18 (m, 2H); 7.18-7.10 (m, 1H); 6.72-6.64 (m, 2H); 6.27-6.16 (m, 1H); 3.84-3.73 (m, 4H); 3.32-3.22 (m, 1H); 3.20-3.08 (m, 4H); 2.80-2.69 (m, 1H); 2.21 (s, 6H).

Example 2: Synthesis of (S)-1-(1-(3-chlorophenyl)-2-(dimethylamino)ethyl)-4-(5-morpholino-1H-pyrrolo[2,3-b]pyridin-3-yl)pyridin-2(1H)-one

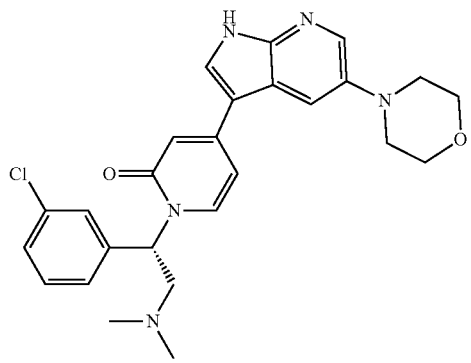 [SMILES: CN(C)C[C@H](c1cccc(Cl)c1)n1ccc(-c2c[nH]c3ncc(N4CCOCC4)cc23)cc1=O]

Step 1: 1-Chloro-3-vinylbenzene

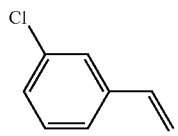

The compound is obtained by the procedure described in Example 1, Step 4, starting from 10 g (71.1 mmol) of 3-chlorobenzaldehyde instead of 3-fluorobenzaldehyde. 4.05 g of the title compound are obtained.
Yield: 41%.
MH+: Non ionizable.

Step 2: 2-(3-Chlorophenyl)oxirane

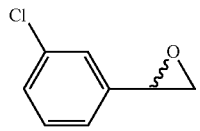

The compound is obtained by the procedure described in Example 1, Step 5, starting from 4.05 g (29.2 mmol) of 1-chloro-3-vinylbenzene (described in the previous step) instead of 1-fluoro-3-vinylbenzene. 3.85 g of the title compound are obtained.
Yield: 85%.
MH+: Non ionizable.

Step 3: 1-(3-Chlorophenyl)-2-(dimethylamino)ethan-1-ol

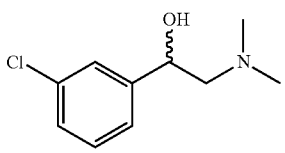

The compound is obtained by the procedure described in Example 1, Step 6, starting from 4.15 g (26.9 mmol) of 2-(3-chlorophenyl)oxirane (described in the previous step) instead of 2-(3-fluorophenyl)oxirane. 4.06 g of the title compound are obtained.
Yield: 76%.
MH+: 200.2; 202.3 (M; M+2).

Step 4: 2-Chloro-2-(3-chlorophenyl)-N,N-dimethylethan-1-amine

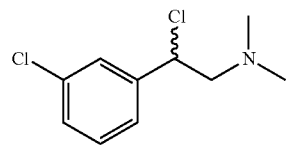

The compound is obtained by the procedure described in Example 1, Step 7, starting from 4.06 g (20.3 mmol) of 1-(3-chlorophenyl)-2-(dimethylamino)ethan-1-ol (described in the previous step) instead of 2-(dimethylamino)-1-(3-fluorophenyl)ethan-1-ol. 4.41 g of the title compound are obtained.
Yield: 99%.
MH+: 218.4; 220.4 (M; M+2).

Step 5: 4-Bromo-1-(1-(3-chlorophenyl)-2-(dimethylamino)ethyl)pyridin-2(1H)-one

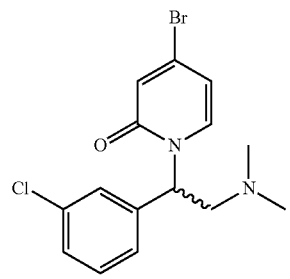 [SMILES: CN(C)CC(c1cccc(Cl)c1)n1ccc(Br)cc1=O]

The compound is obtained by the procedure described in Example 1, Step 8, starting from 4.41 g (20.3 mmol) of 2-chloro-2-(3-chlorophenyl)-N,N-dimethylethan-1-amine (described in the previous step) instead of 2-chloro-2-(3-fluorophenyl)-N,N-dimethylethan-1-amine. 5.02 g of the title compound are obtained.
Yield: 70%.
MH+: 355.2; 357.2 (M; M+2).

Step 6: 1-(1-(3-Chlorophenyl)-2-(dimethylamino)ethyl)-4-(5-morpholino-1-tosyl-1H-pyrrolo[2,3-b]pyridin-3-yl)pyridin-2(1H)-one

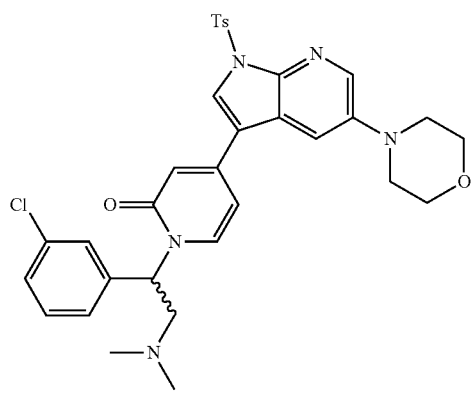 [SMILES: Cc1ccc(S(=O)(=O)n2cc(-c3ccn(C(CN(C)C)c4cccc(Cl)c4)c(=O)c3)c3cc(N4CCOCC4)cnc32)cc1]

The compound is obtained by the procedure described in Example 1, Step 9, starting from 2 g (5.6 mmol) of 4-bromo-1-(1-(3-chlorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 2.68 g of the title compound are obtained.

Yield: 75%.
MH+: 632.8; 634.8 (M; M+2).

Step 7: 1-(1-(3-Chlorophenyl)-2-(dimethylamino)ethyl)-4-(5-morpholino-1H-pyrrolo[2,3-b]pyridin-3-yl)pyridin-2(1H)-one

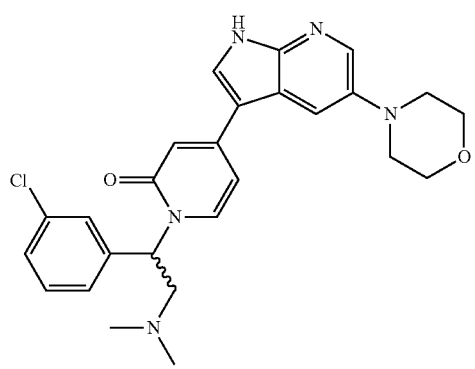 [SMILES: CN(C)CC(c1cccc(Cl)c1)n1ccc(-c2c[nH]c3ncc(N4CCOCC4)cc23)cc1=O]

The compound is obtained by the procedure described in Example 1, Step 10, starting from 2.68 g (4.2 mmol) of 1-(1-(3-chlorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(2-(dimethylamino)-1-(3-fluorophenyl)ethyl)-4-(5-morpholino-1-tosyl-1H-pyrrolo[2,3-b]pyridin-3-yl)pyridin-2(1H)-one. 617 mg of racemate are obtained.

Yield: 30%.
MH+: 478.5; 480.6 (M; M+2).
¹H NMR (DMSO-d6, 400 MHz): δ 12.06 (br s, 1H); 8.17 (d, J=2.4 Hz, 1H); 8.10 (d, J=2.3 Hz, 1H); 7.76 (d, J=8.0 Hz, 1H); 7.70 (d, J=2.4 Hz, 1H); 7.47 (s, 1H); 7.44-7.32 (m, 3H); 6.72-6.65 (m, 2H); 6.23-6.13 (m, 1H); 3.84-3.73 (m, 4H); 3.34-3.23 (m, 1H); 3.20-3.08 (m, 4H); 2.78-2.67 (m, 1H); 2.21 (s, 6H).

Step 8: (S)-1-(1-(3-Chlorophenyl)-2-(dimethylamino)ethyl)-4-(5-morpholino-1H-pyrrolo[2,3-b]pyridin-3-yl)pyridin-2(1H)-one

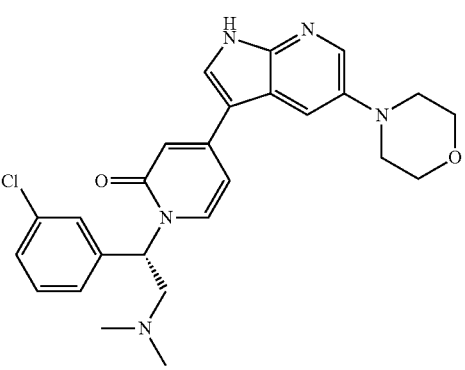 [SMILES: CN(C)C[C@H](c1cccc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 227 mg of the title compound are obtained starting from 617 mg of racemate.

MH+: 478.5; 480.6 (M; M+2).
¹H NMR (DMSO-d6, 400 MHz): δ 12.06 (br s, 1H); 8.17 (d, J=2.4 Hz, 1H); 8.10 (d, J=2.3 Hz, 1H); 7.76 (d, J=8.0 Hz, 1H); 7.70 (d, J=2.4 Hz, 1H); 7.47 (s, 1H); 7.44-7.32 (m, 3H); 6.72-6.65 (m, 2H); 6.23-6.13 (m, 1H); 3.84-3.73 (m, 4H); 3.34-3.23 (m, 1H); 3.20-3.08 (m, 4H); 2.78-2.67 (m, 1H); 2.21 (s, 6H).

Example 3: Synthesis of (S)-1-(1-(3,5-dichlorophenyl)-2-(dimethylamino)ethyl)-4-(5-morpholino-1H-pyrrolo[2,3-b]pyridin-3-yl)pyridin-2(1H)-one

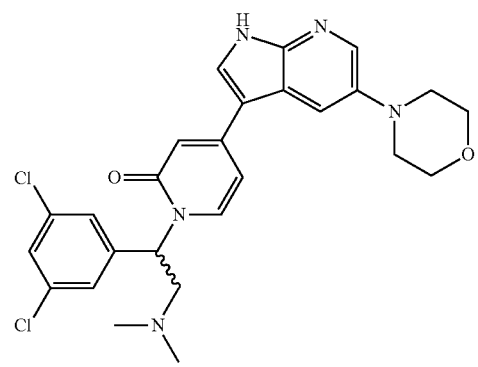 [SMILES: CN(C)CC(c1cc(Cl)cc(Cl)c1)n1ccc(-c2c[nH]c3ncc(N4CCOCC4)cc23)cc1=O]

Step 1: 1,3-Dichloro-5-vinylbenzene

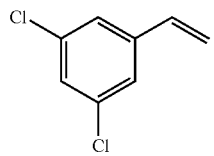

The compound is obtained by the procedure described in Example 1, Step 4, starting from 2.00 g (11.4 mmol) of 3,5-dichlorobenzaldehyde instead of 3-fluorobenzaldehyde. 495 mg of the title compound are obtained.

Yield: 25%.

MH+: Non ionizable.

Step 2: 2-(3,5-Dichlorophenyl)oxirane

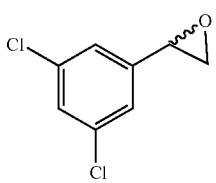 [SMILES: Clc1cc(Cl)cc(C2CO2)c1]

The compound is obtained by the procedure described in Example 1, Step 5, starting from 495 mg (2.86 mmol) of 1,3-dichloro-5-vinylbenzene (described in the previous step) instead of 1-fluoro-3-vinylbenzene. 433 mg of the title compound are obtained.

Yield: 80%.

MH+: Non ionizable.

Step 3: 1-(3,5-Dichlorophenyl)-2-(dimethylamino)ethan-1-ol

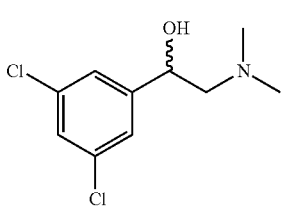

The compound is obtained by the procedure described in Example 1, Step 6, starting from 433 mg (2.29 mmol) of 2-(3,5-dichlorophenyl)oxirane (described in the previous step) instead of 2-(3-fluorophenyl)oxirane. 455 mg of the title compound are obtained.

Yield: 85%.

MH+: 234.3; 236.3 (M; M+2).

Step 4: 2-Chloro-2-(3,5-dichlorophenyl)-N,N-dimethylethan-1-amine

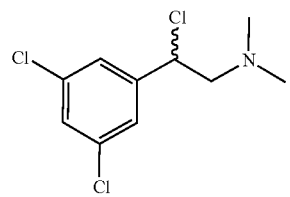

The compound is obtained by the procedure described in Example 1, Step 7, starting from 455 mg (1.94 mmol) of 1-(3,5-dichlorophenyl)-2-(dimethylamino)ethan-1-ol (described in the previous step) instead of 2-(dimethylamino)-1-(3-fluorophenyl)ethan-1-ol. 521 mg of the title compound are obtained.

Yield: Quantitative.

MH+: 252.3; 254.4 (M; M+2).

Step 5: 4-Bromo-1-(1-(3,5-dichlorophenyl)-2-(dimethylamino)ethyl)pyridin-2(1H)-one

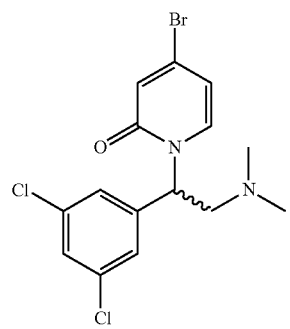 [SMILES: CN(C)CC(c1cc(Cl)cc(Cl)c1)n1ccc(Br)cc1=O]

The compound is obtained by the procedure described in Example 1, Step 8, starting from 521 mg (2.06 mmol) of 2-chloro-2-(3,5-dichlorophenyl)-N,N-dimethylethan-1-amine (described in the previous step) instead of 2-chloro-2-(3-fluorophenyl)-N,N-dimethylethan-1-amine. 276 mg of the title compound are obtained.

Yield: 36%.

MH+: 389.5; 391.5; 393.5 (M; M+2; M+4).

Step 6: 1-(1-(3,5-Dichlorophenyl)-2-(dimethyl-amino)ethyl)-4-(5-morpholino-1-tosyl-1H-pyrrolo[2,3-b]pyridin-3-yl)pyridin-2(1H)-one

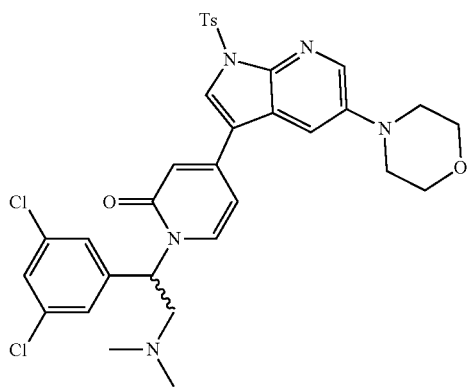 [SMILES: Cc1ccc(S(=O)(=O)n2cc(-c3ccn(C(CN(C)C)c4cc(Cl)cc(Cl)c4)c(=O)c3)c3cc(N4CCOCC4)cnc32)cc1]

The compound is obtained by the procedure described in Example 1, Step 9, starting from 276 mg (0.71 mmol) of 4-bromo-1-(1-(3,5-dichlorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 365 mg of the title compound are obtained.

Yield: 77%.

MH+: 666.9; 668.8 (M; M+2).

Step 7: 1-(1-(3,5-dichlorophenyl)-2-(dimethyl-amino)ethyl)-4-(5-morpholino-1H-pyrrolo[2,3-b]pyridin-3-yl)pyridin-2(1H)-one

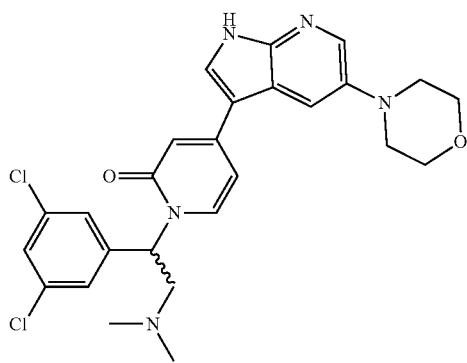 [SMILES: CN(C)CC(c1cc(Cl)cc(Cl)c1)n1ccc(-c2c[nH]c3ncc(N4CCOCC4)cc23)cc1=O]

365 mg (0.55 mmol) of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one (described in the previous step) are suspended in 10 ml of DMSO and 1.37 ml (2.74 mmol, 5 eq) of a solution of NaOH 2N are slowly added. The mixture is stirred at room temperature for 2 h then cooled to 0° C. with an ice/water bath and quenched carefully with a saturated NH$_4$Cl solution. Cold water is added and a white precipitate crashes out, which is filtrated, rinsed several times with water and dried under vacuum. Crude mixture is finally purified by flash chromatography using a silica gel column and a DCM/MeOH mixture as eluent. 226 mg of a slightly yellow solid are obtained.

Yield: 80%.

MH+: 512.7; 514.6 (M; M+2).

$^1$H NMR (DMSO-d6, 400 MHz): δ 12.06 (br s, 1H); 8.17 (d, J=2.5 Hz, 1H); 8.11 (d, J=2.8 Hz, 1H); 7.79 (d, J=7.3 Hz, 1H); 7.71 (d, J=2.5 Hz, 1H); 7.59-7.55 (m, 1H); 7.46 (d, J=1.8 Hz, 2H); 6.74-6.66 (m, 2H); 6.17-6.08 (m, 1H); 3.83-3.73 (m, 4H); 3.34-3.23 (m, 1H); 3.20-3.09 (m, 4H); 2.80-2.70 (m, 1H); 2.21 (s, 6H).

Step 8: (S)-1-(1-(3,5-dichlorophenyl)-2-(dimethyl-amino)ethyl)-4-(5-morpholino-1H-pyrrolo[2,3-b]pyridin-3-yl)pyridin-2(1H)-one

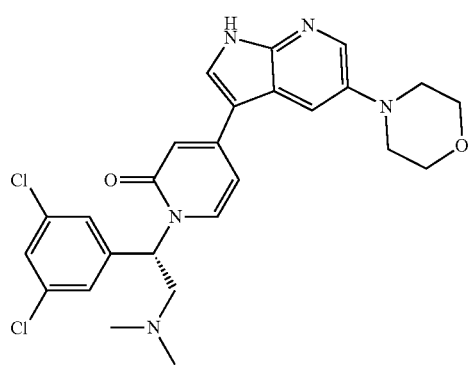 [SMILES: CN(C)C[C@H](c1cc(Cl)cc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 25 mg of the title compound are obtained.

MH+: 512.7; 514.6 (M; M+2).

$^1$H NMR (DMSO-d6, 400 MHz): δ 12.06 (br s, 1H); 8.17 (d, J=2.5 Hz, 1H); 8.11 (d, J=2.8 Hz, 1H); 7.79 (d, J=7.3 Hz, 1H); 7.71 (d, J=2.5 Hz, 1H); 7.59-7.55 (m, 1H); 7.46 (d, J=1.8 Hz, 2H); 6.74-6.66 (m, 2H); 6.17-6.08 (m, 1H); 3.83-3.73 (m, 4H); 3.34-3.23 (m, 1H); 3.20-3.09 (m, 4H); 2.80-2.70 (m, 1H); 2.21 (s, 6H).

Example 4: Synthesis of (S)-1-(1-(3,4-dichlorophenyl)-2-(dimethylamino)ethyl)-4-(5-morpholino-1H-pyrrolo[2,3-b]pyridin-3-yl)pyridin-2(1H)-one

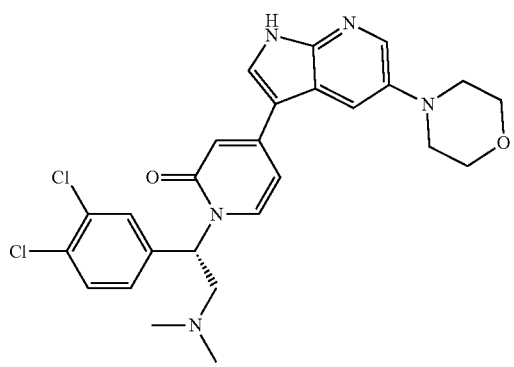 [SMILES: CN(C)C[C@H](c1ccc(Cl)c(Cl)c1)n1ccc(-c2c[nH]c3ncc(N4CCOCC4)cc23)cc1=O]

Step 1: 1,2-Dichloro-4-vinylbenzene

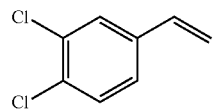

The compound is obtained by the procedure described in Example 1, Step 4, starting from 2.00 g (11.4 mmol) of 3,4-dichlorobenzaldehyde instead of 3-fluorobenzaldehyde. 850 mg of the title compound are obtained.
Yield: 43%.
MH+: Non ionizable.

Step 2: 2-(3,4-Dichlorophenyl)oxirane

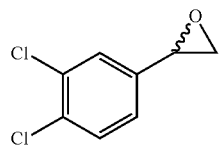 [SMILES: Clc1ccc(C2CO2)cc1Cl]

The compound is obtained by the procedure described in Example 1, Step 5, starting from 850 mg (4.91 mmol) of 1,2-dichloro-4-vinylbenzene (described in the previous step) instead of 1-fluoro-3-vinylbenzene. 630 mg of the title compound are obtained.
Yield: 68%.
MH+: Non ionizable.

Step 3: 1-(3,4-Dichlorophenyl)-2-(dimethylamino)ethan-1-ol

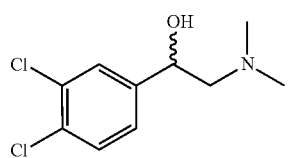

The compound is obtained by the procedure described in Example 1, Step 6, starting from 630 mg (3.33 mmol) of 2-(3,4-dichlorophenyl)oxirane (described in the previous step) instead of 2-(3-fluorophenyl)oxirane. 692 mg of the title compound are obtained.
Yield: 89%.
MH+: 234.3; 236.2 (M; M+2).

Step 4: 2-Chloro-2-(3,4-dichlorophenyl)-N,N-dimethylethan-1-amine

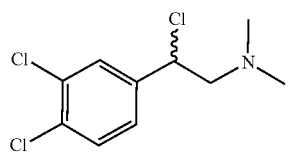

The compound is obtained by the procedure described in Example 1, Step 7, starting from 692 mg (2.96 mmol) of 1-(3,4-dichlorophenyl)-2-(dimethylamino)ethan-1-ol (described in the previous step) instead of 2-(dimethylamino)-1-(3-fluorophenyl)ethan-1-ol. 760 mg of the title compound are obtained.
Yield: Quantitative.
MH+: 252.2; 254.2 (M; M+2).

Step 5: 4-Bromo-1-(1-(3,4-dichlorophenyl)-2-(dimethylamino)ethyl)pyridin-2(1H)-one

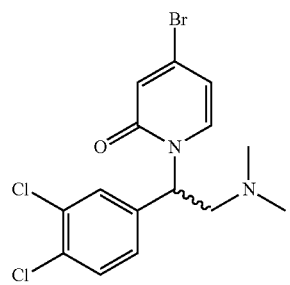 [SMILES: CN(C)CC(c1ccc(Cl)c(Cl)c1)n1ccc(Br)cc1=O]

The compound is obtained by the procedure described in Example 1, Step 8, starting from 760 mg (3.01 mmol) of 2-chloro-2-(3,4-dichlorophenyl)-N,N-dimethylethan-1-amine (described in the previous step) instead of 2-chloro-2-(3-fluorophenyl)-N,N-dimethylethan-1-amine. 553 mg of the title compound are obtained.
Yield: 47%.
MH+: 389.4; 391.3 (M; M+2).

Step 6: 1-(1-(3,4-Dichlorophenyl)-2-(dimethylamino)ethyl)-4-(5-morpholino-1-tosyl-1H-pyrrolo[2,3-b]pyridin-3-yl)pyridin-2(1H)-one

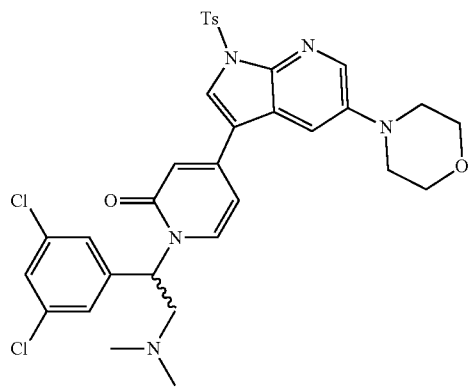 [SMILES: Cc1ccc(S(=O)(=O)n2cc(-c3ccn(C(CN(C)C)c4cc(Cl)cc(Cl)c4)c(=O)c3)c3cc(N4CCOCC4)cnc32)cc1]

The compound is obtained by the procedure described in Example 1, Step 9, starting from 276 mg (0.71 mmol) of 4-bromo-1-(1-(3,4-dichlorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 334 mg of the title compound are obtained.
Yield: 71%.
MH+: 666.6; 668.4 (M; M+2).

Step 7: 1-(1-(3,4-dichlorophenyl)-2-(dimethylamino)ethyl)-4-(5-morpholino-1H-pyrrolo[2,3-b]pyridin-3-yl)pyridin-2(1H)-one

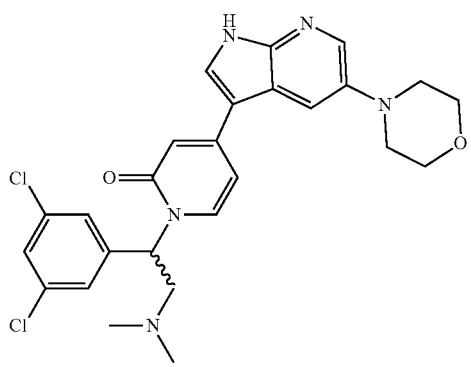 [SMILES: CN(C)CC(c1cc(Cl)cc(Cl)c1)n1ccc(-c2c[nH]c3ncc(N4CCOCC4)cc23)cc1=O]

The compound is obtained by the procedure described in Example 3, Step 7, starting from 334 mg (0.50 mmol) of 1-(1-(3,4-dichlorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 199 mg of racemate are obtained.

Yield: 77%.

MH+: 512.5; 514.5 (M; M+2).

$^1$H NMR (DMSO-d6, 400 MHz): δ 12.08 (br s, 1H); 8.17 (d, J=2.5 Hz, 1H); 8.11 (d, J=2.9 Hz, 1H); 7.76 (d, J=7.2 Hz, 1H); 7.69 (d, J=2.1 Hz, 2H); 7.64 (d, J=8.4 Hz, 1H); 7.39-7.33 (m, 1H); 6.73-6.66 (m, 2H); 6.20-6.10 (m, 1H); 3.82-3.73 (m, 4H); 3.33-3.23 (m, 1H); 3.18-3.09 (m, 4H); 2.79-2.69 (m, 1H); 2.20 (s, 6H).

Step 8: (S)-1-(1-(3,4-dichlorophenyl)-2-(dimethylamino)ethyl)-4-(5-morpholino-1H-pyrrolo[2,3-b]pyridin-3-yl)pyridin-2(1H)-one

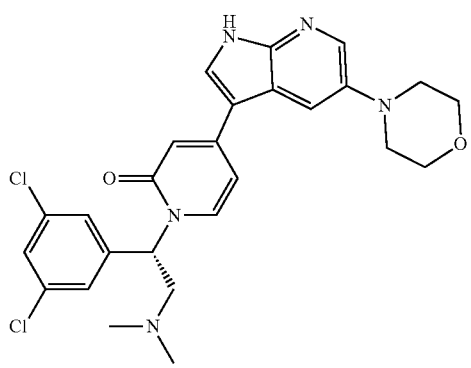 [SMILES: CN(C)C[C@H](c1cc(Cl)cc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 39 mg of the title compound are obtained starting from 199 mg of the racemate.

MH+: 512.5; 514.5 (M; M+2).

$^1$H NMR (DMSO-d6, 400 MHz): δ 12.08 (br s, 1H); 8.17 (d, J=2.5 Hz, 1H); 8.11 (d, J=2.9 Hz, 1H); 7.76 (d, J=7.2 Hz, 1H); 7.69 (d, J=2.1 Hz, 2H); 7.64 (d, J=8.4 Hz, 1H); 7.39-7.33 (m, 1H); 6.73-6.66 (m, 2H); 6.20-6.10 (m, 1H); 3.82-3.73 (m, 4H); 3.33-3.23 (m, 1H); 3.18-3.09 (m, 4H); 2.79-2.69 (m, 1H); 2.20 (s, 6H).

Example 5: Synthesis of (S)-1-(1-(3-bromophenyl)-2-(dimethylamino)ethyl)-4-(5-morpholino-1H-pyrrolo[2,3-b]pyridin-3-yl)pyridin-2(1H)-one

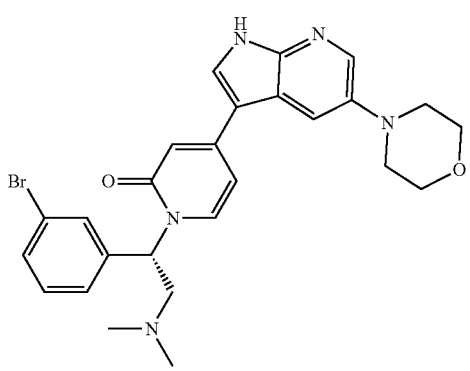

Step 1: 2-(3-Bromophenyl)oxirane

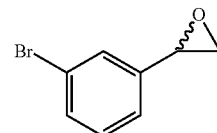

The compound is obtained by the procedure described in Example 1, Step 5, starting from 2 g (11 mmol) of 1-bromo-3-vinylbenzene instead of 1-fluoro-3-vinylbenzene. 2.12 g of the title compound are obtained.

Yield: 98%.

MH+: Non ionizable.

Step 2: 1-(3-Bromophenyl)-2-(dimethylamino)ethan-1-ol

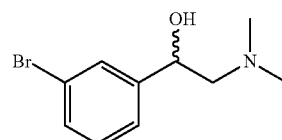

The compound is obtained by the procedure described in Example 1, Step 6, starting from 2.12 g (10.7 mmol) of 2-(3-bromophenyl)oxirane (described in the previous step) instead of 2-(3-fluorophenyl)oxirane. 2.11 g of the title compound are obtained.

Yield: 97%.

MH+: 244.3; 246.4 (M; M+2).

Step 3: 2-(3-Bromophenyl)-2-chloro-N,N-dimethylethan-1-amine

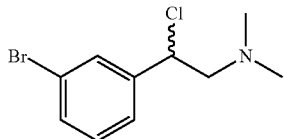

The compound is obtained by the procedure described in Example 1, Step 7, starting from 2.11 g (8.6 mmol) of 1-(3-bromophenyl)-2-(dimethylamino)ethan-1-ol (described in the previous step) instead of 2-(dimethylamino)-1-(3-fluorophenyl)ethan-1-ol. 2.30 g of the title compound are obtained.
Yield: Quantitative.
MH+: 262.4; 264.3 (M; M+2).

Step 4: 4-Bromo-1-(1-(3-bromophenyl)-2-(dimethylamino)ethyl)pyridin-2(1H)-one

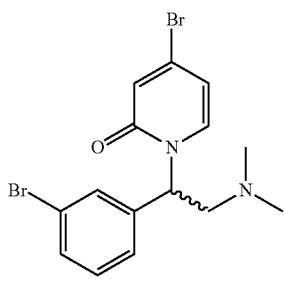

The compound is obtained by the procedure described in Example 1, Step 8, starting from 2.30 g (20.3 mmol) of 2-(3-bromophenyl)-2-chloro-N,N-dimethylethan-1-amine (described in the previous step) instead of 2-chloro-2-(3-fluorophenyl)-N,N-dimethylethan-1-amine. 1.85 g of the title compound are obtained.
Yield: 52%.
MH+: 399.3; 401.4 (M; M+2).

Step 5: 1-(1-(3-Bromophenyl)-2-(dimethylamino)ethyl)-4-(5-morpholino-1-tosyl-1H-pyrrolo[2,3-b]pyridin-3-yl)pyridin-2(1H)-one

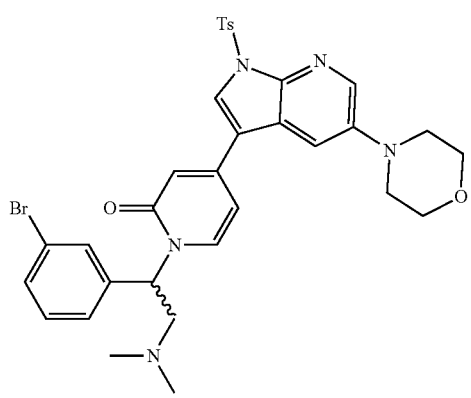 [SMILES: Cc1ccc(S(=O)(=O)n2cc(-c3ccn(C(CN(C)C)c4cccc(Br)c4)c(=O)c3)c3cc(N4CCOCC4)cnc32)cc1]

The compound is obtained by the procedure described in Example 1, Step 9, starting from 1.85 g (4.6 mmol) of 4-bromo-1-(1-(3-bromophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 2.72 g of the title compound are obtained.
Yield: 88%.
MH+: 676.8; 678.8 (M; M+2).

Step 6: 1-(1-(3-bromophenyl)-2-(dimethylamino)ethyl)-4-(5-morpholino-1H-pyrrolo[2,3-b]pyridin-3-yl)pyridin-2(1H)-one

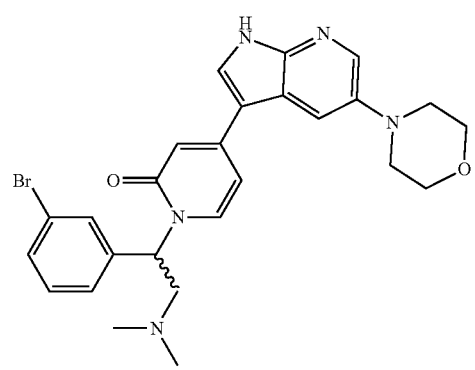 [SMILES: CN(C)CC(c1cccc(Br)c1)n1ccc(-c2c[nH]c3ncc(N4CCOCC4)cc23)cc1=O]

The compound is obtained by the procedure described in Example 3, Step 7, starting from 1.04 g (1.54 mmol) of 1-(1-(3-bromophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 681 mg of racemate are obtained.
Yield: 85%.
MH+: 522.6; 524.5 (M; M+2).
$^1$H NMR (DMSO-d6, 400 MHz): δ 12.04 (br s, 1H); 8.17 (d, J=2.5 Hz, 1H); 8.09 (s, 1H); 7.75 (d, J=8.0 Hz, 1H); 7.70 (d, J=2.5 Hz, 1H); 7.62-7.57 (m, 1H); 7.53-7.47 (m, 1H); 7.42-7.37 (m, 1H); 7.33 (t, J=7.8 Hz, 1H); 6.72-6.65 (m, 2H); 6.20-6.12 (m, 1H); 3.83-3.73 (m, 4H); 3.34-3.24 (m, 1H); 3.20-3.08 (m, 4H); 2.78-2.68 (m, 1H); 2.21 (s, 6H).

Step 7: (S)-1-(1-(3-bromophenyl)-2-(dimethylamino)ethyl)-4-(5-morpholino-1H-pyrrolo[2,3-b]pyridin-3-yl)pyridin-2(1H)-one

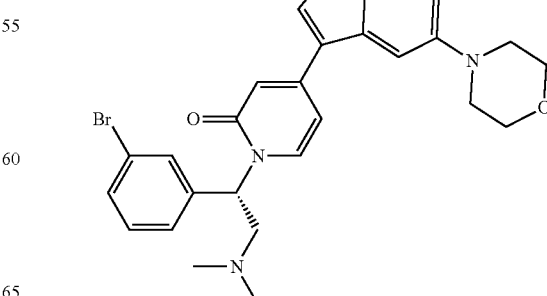

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 292 mg of the title compound are obtained starting from 681 mg of the racemate.

MH+: 522.6; 524.5 (M; M+2).

¹H NMR (DMSO-d6, 400 MHz): δ 12.04 (br s, 1H); 8.17 (d, J=2.5 Hz, 1H); 8.09 (s, 1H); 7.75 (d, J=8.0 Hz, 1H); 7.70 (d, J=2.5 Hz, 1H); 7.62-7.57 (m, 1H); 7.53-7.47 (m, 1H); 7.42-7.37 (m, 1H); 7.33 (t, J=7.8 Hz, 1H); 6.72-6.65 (m, 2H); 6.20-6.12 (m, 1H); 3.83-3.73 (m, 4H); 3.34-3.24 (m, 1H); 3.20-3.08 (m, 4H); 2.78-2.68 (m, 1H); 2.21 (s, 6H).

Example 6: Synthesis of (S)-1-(2-(dimethylamino)-1-(3-iodophenyl)ethyl)-4-(5-morpholino-1H-pyrrolo[2,3-b]pyridin-3-yl)pyridin-2(1H)-one

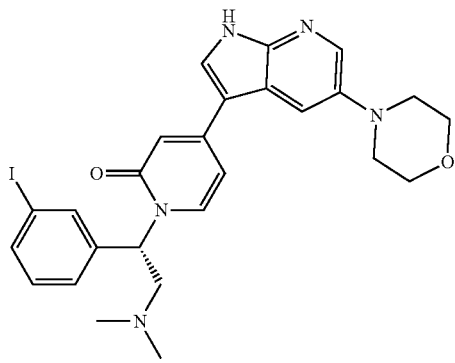 [SMILES: CN(C)C[C@H](c1cccc(I)c1)n1ccc(-c2c[nH]c3ncc(N4CCOCC4)cc23)cc1=O]

Step 1: 1-Iodo-3-vinylbenzene

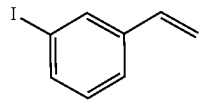

The compound is obtained by the procedure described in Example 1, Step 4, starting from 5 g (21.5 mmol) of 3-iodobenzaldehyde instead of 3-fluorobenzaldehyde.

3.20 g of the title compound are obtained.
Yield: 65%.
MH+: Non ionizable.

Step 2: 2-(3-Iodophenyl)oxirane

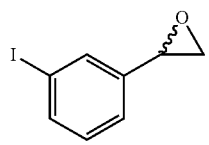

The compound is obtained by the procedure described in Example 1, Step 5, starting from 3.20 g (13.91 mmol) of 1-iodo-3-vinylbenzene (described in the previous step) instead of 1-fluoro-3-vinylbenzene. 2.78 g of the title compound are obtained.

Yield: 81%.
MH+: Non ionizable.

Step 3: 2-(Dimethylamino)-1-(3-iodophenyl)ethan-1-ol

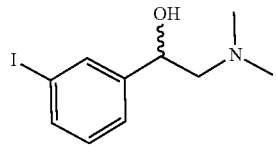

The compound is obtained by the procedure described in Example 1, Step 6, starting from 2.78 g (26.9 mmol) of 2-(3-iodophenyl)oxirane (described in the previous step) instead of 2-(3-fluorophenyl)oxirane. 2.54 g of the title compound are obtained.

Yield: 77%.
MH+: 292.2 (M+1).

Step 4: 2-Chloro-2-(3-iodophenyl)-N,N-dimethyl-ethan-1-amine

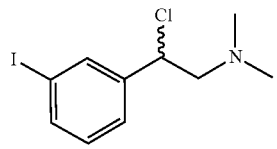

The compound is obtained by the procedure described in Example 1, Step 7, starting from 1.25 g (4.3 mmol) of 2-(dimethylamino)-1-(3-iodophenyl)ethan-1-ol (described in the previous step) instead of 2-(dimethylamino)-1-(3-fluorophenyl)ethan-1-ol. 1.59 g of the title compound are obtained.

Yield: Quantitative.
MH+: 310.3; 312.3 (M; M+2).

Step 5: 1-(2-(Dimethylamino)-1-(3-iodophenyl)ethyl)-4-iodopyridin-2(1H)-one

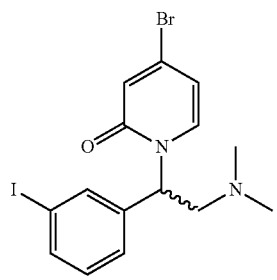 [SMILES: CN(C)CC(c1cccc(I)c1)n1ccc(Br)cc1=O]

To a mixture of 1.04 g (4.70 mmol, 1 eq) of 4-iodopyridin-2-(1H-1)-one and 1.68 g (5.20 mmol, 1.1 eq) of cesium carbonate in 10 ml of dry DMF, is added at 0° C. a solution of 1.59 g (5.14 mmol, 1 eq) of 2-chloro-2-(3-iodophenyl)-N,N-dimethylethan-1-amine (described in the previous step) in 5 ml of dry DMF. The solution is then stirred at room temperature for 1 h 30. EtOAc is added, and the mixture is washed 4 times with water and once with brine. Organic layer is dried over Na₂SO₄, filtrated and evaporated under reduced pressure. Crude mixture is purified by flash chromatography using a deactivated silica gel column and an Hexane/EtOAc mixture as eluent. 1.11 g of the title compound are obtained.

Yield: 52%.

MH+: 495.6 (M+1).

Step 6: 1-(2-(Dimethylamino)-1-(3-iodophenyl)ethyl)-4-(5-morpholino-1-tosyl-1H-pyrrolo[2,3-b]pyridin-3-yl)pyridin-2(1H)-one

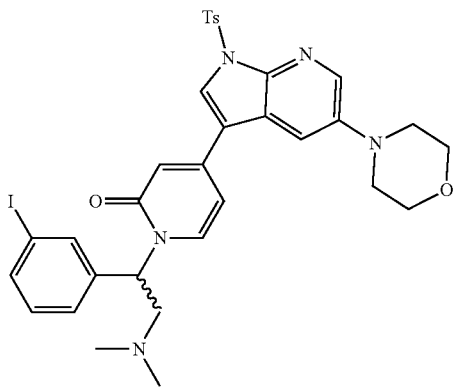 [SMILES: Cc1ccc(S(=O)(=O)n2cc(-c3ccn(C(CN(C)C)c4cccc(I)c4)c(=O)c3)c3cc(N4CCOCC4)cnc32)cc1]

The compound is obtained by the procedure described in Example 1, Step 9, starting from 1.11 g (22.5 mmol) of 1-(2-(dimethylamino)-1-(3-iodophenyl)ethyl)-4-iodopyridin-2(1H)-one (described in the previous step) instead of 4-bromo-1-(2-(dimethylamino)-1-(3-fluorophenyl)ethyl)pyridin-2(1H)-one. 589 mg of the title compound are obtained.

Yield: 80%.

MH+: 724.5 (M+1).

Step 7: 1-(2-(Dimethylamino)-1-(3-iodophenyl)ethyl)-4-(5-morpholino-1H-pyrrolo[2,3-b]pyridin-3-yl)pyridin-2(1H)-one

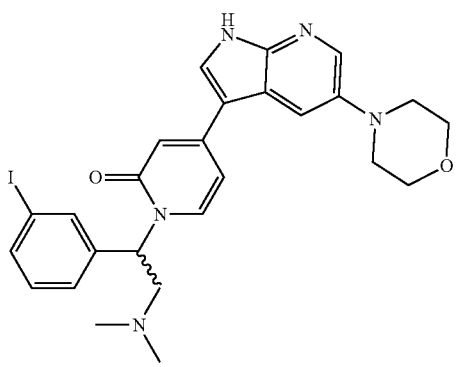 [SMILES: CN(C)CC(c1cccc(I)c1)n1ccc(-c2c[nH]c3ncc(N4CCOCC4)cc23)cc1=O]

The compound is obtained by the procedure described in Example 3, Step 7, starting from 875 mg (1.21 mmol) of 1-(2-(dimethylamino)-1-(3-iodophenyl)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 674 mg of racemate are obtained.

Yield: 97%.

MH+: 570.5 (M+1).

¹H NMR (DMSO-d6, 400 MHz): δ 12.06 (br s, 1H); 8.17 (d, J=2.5 Hz, 1H); 8.10 (d, J=2.9 Hz, 1H); 7.79-7.73 (m, 2H); 7.72-7.64 (m, 2H); 7.44-7.38 (m, 1H); 7.17 (t, J=7.8 Hz, 1H); 6.72-6.65 (m, 2H); 6.18-6.09 (m, 1H); 3.85-3.73 (m, 4H); 3.34-3.24 (m, 1H); 3.20-3.08 (m, 4H); 2.73-2.64 (m, 1H); 2.20 (s, 6H).

Step 8: (S)-1-(2-(Dimethylamino)-1-(3-iodophenyl)ethyl)-4-(5-morpholino-1H-pyrrolo[2,3-b]pyridin-3-yl)pyridin-2(1H)-one

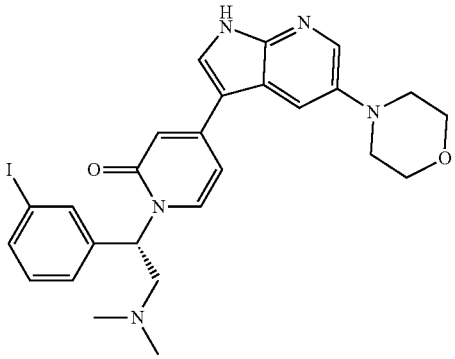 [SMILES: CN(C)C[C@H](c1cccc(I)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 262 mg of the title compound are obtained starting from 674 mg of the racemate.

MH+: 570.5 (M+1).

¹H NMR (DMSO-d6, 400 MHz): δ 12.06 (br s, 1H); 8.17 (d, J=2.5 Hz, 1H); 8.10 (d, J=2.9 Hz, 1H); 7.79-7.73 (m, 2H); 7.72-7.64 (m, 2H); 7.44-7.38 (m, 1H); 7.17 (t, J=7.8 Hz, 1H); 6.72-6.65 (m, 2H); 6.18-6.09 (m, 1H); 3.85-3.73 (m, 4H); 3.34-3.24 (m, 1H); 3.20-3.08 (m, 4H); 2.73-2.64 (m, 1H); 2.20 (s, 6H).

Example 7: Synthesis of (S)-1-(1-(3-bromo-4-fluorophenyl)-2-(dimethylamino)ethyl)-4-(5-morpholino-1H-pyrrolo[2,3-b]pyridin-3-yl)pyridin-2(1H)-one

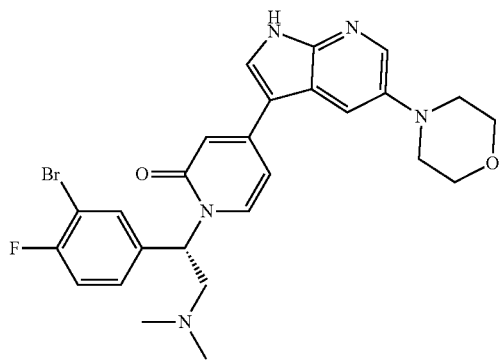 [SMILES: CN(C)C[C@H](c1ccc(F)c(Br)c1)n1ccc(-c2c[nH]c3ncc(N4CCOCC4)cc23)cc1=O]

Step 1: 2-Bromo-1-fluoro-4-vinylbenzene

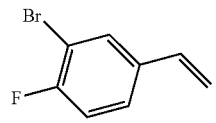

The compound is obtained by the procedure described in Example 1, Step 4, starting from 2.61 g (12.9 mmol) of 3-bromo-4-fluorobenzaldehyde instead of 3-fluorobenzaldehyde. 1.37 g of the title compound are obtained.
Yield: 53%.
MH+: Non ionizable.

Step 2: 2-(3-Bromo-4-fluorophenyl)oxirane

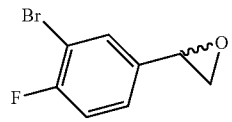

The compound is obtained by the procedure described in Example 1, Step 5, starting from 1.37 g (6.81 mmol) of 2-bromo-1-fluoro-4-vinylbenzene (described in the previous step) instead of 1-fluoro-3-vinylbenzene. 1.13 g of the title compound are obtained.
Yield: 76%.
MH+: Non ionizable.

Step 3: 1-(3-Bromo-4-fluorophenyl)-2-(dimethylamino)ethan-1-ol

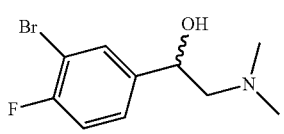

The compound is obtained by the procedure described in Example 1, Step 6, starting from 1.13 g (5.21 mmol) of 2-(3-bromo-4-fluorophenyl)oxirane (described in the previous step) instead of 2-(3-fluorophenyl)oxirane. 1.05 g of the title compound are obtained.
Yield: 77%.
MH+: 262.2; 264.3 (M; M+2).

Step 4: 2-(3-Bromo-4-fluorophenyl)-2-chloro-N,N-dimethylethan-1-amine

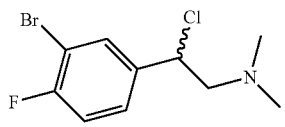

The compound is obtained by the procedure described in Example 1, Step 7, starting from 1.05 g (4.00 mmol) of 1-(3-bromo-4-fluorophenyl)-2-(dimethylamino)ethan-1-ol (described in the previous step) instead of 2-(dimethylamino)-1-(3-fluorophenyl)ethan-1-ol. 1.30 g of the title compound are obtained.
Yield: Quantitative.
MH+: 280.3; 282.3 (M; M+2).

Step 5: 4-Bromo-1-(1-(3-bromo-4-fluorophenyl)-2-(dimethylamino)ethyl)pyridin-2(1H)-one

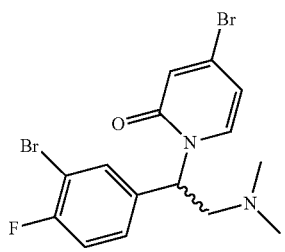 [SMILES: CN(C)CC(c1ccc(F)c(Br)c1)n1ccc(Br)cc1=O]

The compound is obtained by the procedure described in Example 1, Step 8, starting from 1.30 g (4.64 mmol) of 2-(3-bromo-4-fluorophenyl)-2-chloro-N,N-dimethylethan-1-amine (described in the previous step) instead of 2-chloro-2-(3-fluorophenyl)-N,N-dimethylethan-1-amine. 733 mg of the title compound are obtained.
Yield: 38%.
MH+: 417.3; 419.3; 421.2 (M; M+2; M+4).

Step 6: 1-(1-(3-Bromo-4-fluorophenyl)-2-(dimethylamino)ethyl)-4-(5-morpholino-1-tosyl-1H-pyrrolo[2,3-b]pyridin-3-yl)pyridin-2(1H)-one

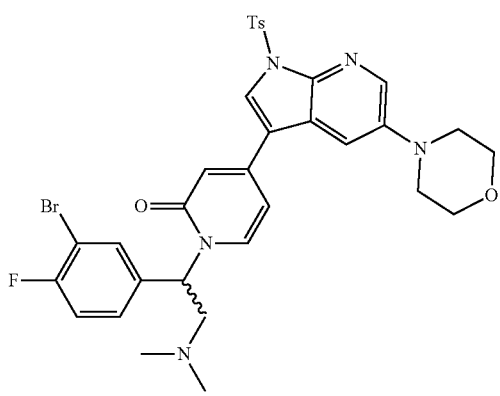 [SMILES: Cc1ccc(S(=O)(=O)n2cc(-c3ccn(C(CN(C)C)c4ccc(F)c(Br)c4)c(=O)c3)c3cc(N4CCOCC4)cnc32)cc1]

The compound is obtained by the procedure described in Example 1, Step 9, starting from 733 mg (1.74 mmol) of 4-bromo-1-(1-(3-bromo-4-fluorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 1.00 g of the title compound are obtained.

Yield: 82%.

MH+: 694.6; 696.5 (M; M+2).

Step 7: 1-(1-(3-bromo-4-fluorophenyl)-2-(dimethylamino)ethyl)-4-(5-morpholino-1H-pyrrolo[2,3-b]pyridin-3-yl)pyridin-2(1H)-one

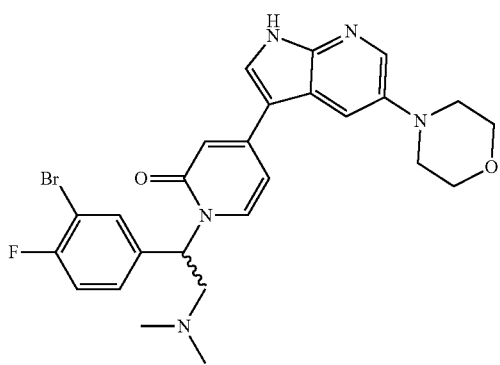 [SMILES: CN(C)CC(c1ccc(F)c(Br)c1)n1ccc(-c2c[nH]c3ncc(N4CCOCC4)cc23)cc1=O]

The compound is obtained by the procedure described in Example 3, Step 7, starting from 640 mg (0.92 mmol) of 1-(1-(3-bromo-4-fluorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 464 mg of racemate are obtained.

Yield: 93%.

MH+: 540.5; 542.4 (M; M+2).

$^1$H NMR (DMSO-d6, 400 MHz): δ 12.06 (br s, 1H); 8.17 (d, J=2.5 Hz, 1H); 8.10 (s, 1H); 7.80-7.73 (m, 2H); 7.69 (d, J=2.5 Hz, 1H); 7.48-7.41 (m, 1H); 7.38 (t, J=8.7 Hz, 1H); 6.72-6.66 (m, 2H); 6.21-6.12 (m, 1H); 3.83-3.74 (m, 4H); 3.34-3.24 (m, 1H); 3.18-3.08 (m, 4H); 2.77-2.67 (m, 1H); 2.20 (s, 6H).

Step 8: (S)-1-(1-(3-bromo-4-fluorophenyl)-2-(dimethylamino)ethyl)-4-(5-morpholino-1H-pyrrolo[2,3-b]pyridin-3-yl)pyridin-2(1H)-one

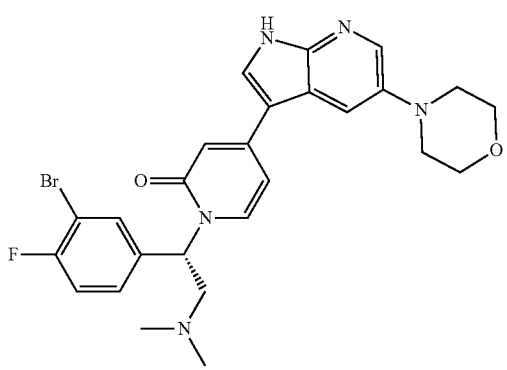 [SMILES: CN(C)C[C@H](c1ccc(F)c(Br)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 206 mg of the title compound are obtained starting from 464 mg of the racemate.

MH+: 540.5; 542.4 (M; M+2).

$^1$H NMR (DMSO-d6, 400 MHz): δ 12.06 (br s, 1H); 8.17 (d, J=2.5 Hz, 1H); 8.10 (s, 1H); 7.80-7.73 (m, 2H); 7.69 (d, J=2.5 Hz, 1H); 7.48-7.41 (m, 1H); 7.38 (t, J=8.7 Hz, 1H); 6.72-6.66 (m, 2H); 6.21-6.12 (m, 1H); 3.83-3.74 (m, 4H); 3.34-3.24 (m, 1H); 3.18-3.08 (m, 4H); 2.77-2.67 (m, 1H); 2.20 (s, 6H).

Example 8: Synthesis of (S)-1-(2-(dimethylamino)-1-(4-fluoro-3-iodophenyl)ethyl)-4-(5-morpholino-1H-pyrrolo[2,3-b]pyridin-3-yl)pyridin-2(1H)-one

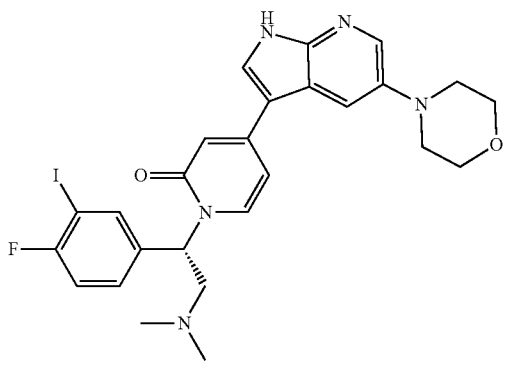 [SMILES: CN(C)C[C@H](c1ccc(F)c(I)c1)n1ccc(-c2c[nH]c3ncc(N4CCOCC4)cc23)cc1=O]

Step 1: 1-Fluoro-2-iodo-4-vinylbenzene

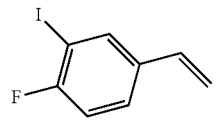

The compound is obtained by the procedure described in Example 1, Step 4, starting from 3.5 g (14.0 mmol) of 4-fluoro-3-iodobenzaldehyde instead of 3-fluorobenzaldehyde. 2.13 g of the title compound are obtained.
Yield: 61%.
MH+: Non ionizable.

Step 2: 2-(4-Fluoro-3-iodophenyl)oxirane

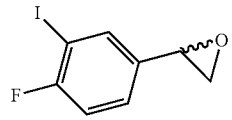

The compound is obtained by the procedure described in Example 1, Step 5, starting from 2.13 g (8.58 mmol) of 1-fluoro-2-iodo-4-vinylbenzene (described in the previous step) instead of 1-fluoro-3-vinylbenzene. 1.99 g of the title compound are obtained.
Yield: 88%.
MH+: Non ionizable.

Step 3: 2-(Dimethylamino)-1-(4-fluoro-3-iodophenyl)ethan-1-ol

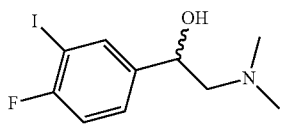

The compound is obtained by the procedure described in Example 1, Step 6, starting from 1.99 g (7.54 mmol) of 2-(4-fluoro-3-iodophenyl)oxirane (described in the previous step) instead of 2-(3-fluorophenyl)oxirane. 1.57 g of the title compound are obtained.
Yield: 67%.
MH+: 310.5 (M+1).

Step 4: 2-Chloro-2-(4-fluoro-3-iodophenyl)-N,N-dimethylethan-1-amine

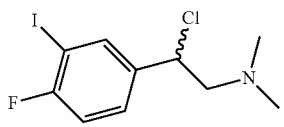

The compound is obtained by the procedure described in Example 1, Step 7, starting from 1.57 g (5.08 mmol) of 2-(dimethylamino)-1-(4-fluoro-3-iodophenyl)ethan-1-ol (described in the previous step) instead of 2-(dimethylamino)-1-(3-fluorophenyl)ethan-1-ol. 1.64 g of the title compound are obtained.
Yield: 98%.
MH+: 328.4 (M+1).

Step 5: 1-(2-(Dimethylamino)-1-(4-fluoro-3-iodophenyl)ethyl)-4-iodopyridin-2(1H)-one

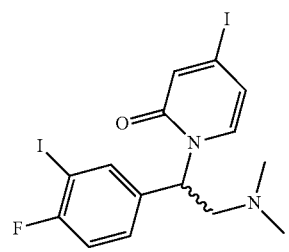 [SMILES: CN(C)CC(c1ccc(F)c(I)c1)n1ccc(I)cc1=O]

The compound is obtained by the procedure described in Example 6, Step 5, starting from 1.57 g (5.08 mmol) of 2-chloro-2-(4-fluoro-3-iodophenyl)-N,N-dimethylethan-1-amine (described in the previous step) instead of 2-chloro-2-(3-iodophenyl)-N,N-dimethylethan-1-amine. 555 mg of the title compound are obtained.
Yield: 22%.
MH+: 513.5 (M+1).

Step 6: 1-(2-(Dimethylamino)-1-(4-fluoro-3-iodophenyl)ethyl)-4-(5-morpholino-1-tosyl-1H-pyrrolo[2,3-b]pyridin-3-yl)pyridin-2(1H)-one

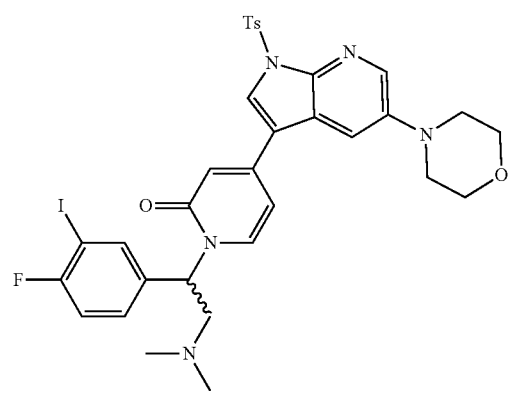 [SMILES: Cc1ccc(S(=O)(=O)n2cc(-c3ccn(C(CN(C)C)c4ccc(F)c(I)c4)c(=O)c3)c3cc(N4CCOCC4)cnc32)cc1]

The compound is obtained by the procedure described in Example 1, Step 9, starting from 555 mg (1.08 mmol) of 1-(2-(dimethylamino)-1-(4-fluoro-3-iodophenyl)ethyl)-4-iodopyridin-2(1H)-one (described in the previous step) instead of 4-bromo-1-(2-(dimethylamino)-1-(3-fluorophenyl)ethyl)pyridin-2(1H)-one. 780 mg of the title compound are obtained.
Yield: 97%.
MH+: 742.8 (M+1).

Step 7: 1-(2-(dimethylamino)-1-(4-fluoro-3-iodo-phenyl)ethyl)-4-(5-morpholino-1H-pyrrolo[2,3-b]pyridin-3-yl)pyridin-2(1H)-one

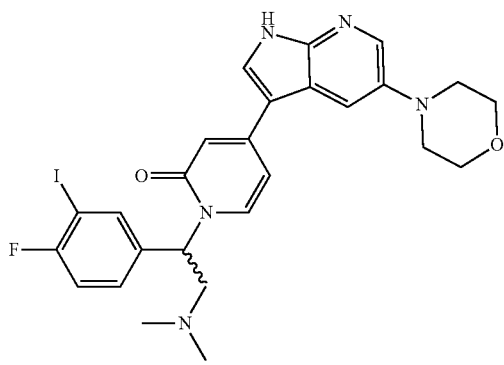 [SMILES: CN(C)CC(c1ccc(F)c(I)c1)n1ccc(-c2c[nH]c3ncc(N4CCOCC4)cc23)cc1=O]

The compound is obtained by the procedure described in Example 3, Step 7, starting from 760 mg (1.02 mmol) of 1-(2-(dimethylamino)-1-(4-fluoro-3-iodophenyl)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 240 mg of racemate are obtained followed by 87 mg of the title compound after chiral separation ((+) (S)-enantiomer).

Yield: 40%.
MH+: 588.4 (M+1).
¹H NMR (DMSO-d6, 400 MHz): δ 12.06 (br s, 1H); 8.16 (d, J=2.5 Hz, 1H); 8.10 (s, 1H); 7.91-7.85 (m, 1H); 7.75 (d, J=8.0 Hz, 1H); 7.69 (d, J=2.6 Hz, 1H); 7.49-7.41 (m, 1H); 7.26 (t, J=8.3 Hz, 1H); 6.72-6.64 (m, 2H); 6.19-6.08 (m, 1H); 3.84-3.72 (m, 4H); 3.34-3.24 (m, 1H); 3.18-3.08 (m, 4H); 2.73-2.65 (m, 1H); 2.20 (s, 6H).

Step 8: (S)-1-(2-(dimethylamino)-1-(4-fluoro-3-iodophenyl)ethyl)-4-(5-morpholino-1H-pyrrolo[2,3-b]pyridin-3-yl)pyridin-2(1H)-one

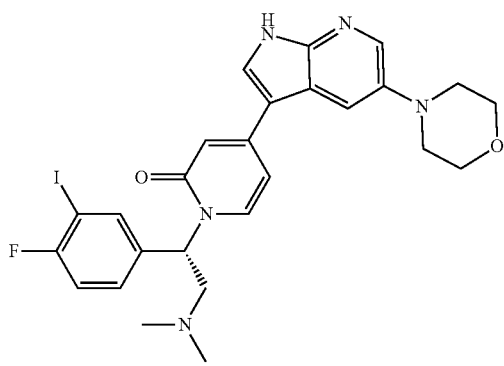

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 87 mg of the title compound are obtained starting from 240 mg of the racemate.

MH+: 588.4 (M+1).
¹H NMR (DMSO-d6, 400 MHz): δ 12.06 (br s, 1H); 8.16 (d, J=2.5 Hz, 1H); 8.10 (s, 1H); 7.91-7.85 (m, 1H); 7.75 (d, J=8.0 Hz, 1H); 7.69 (d, J=2.6 Hz, 1H); 7.49-7.41 (m, 1H); 7.26 (t, J=8.3 Hz, 1H); 6.72-6.64 (m, 2H); 6.19-6.08 (m, 1H); 3.84-3.72 (m, 4H); 3.34-3.24 (m, 1H); 3.18-3.08 (m, 4H); 2.73-2.65 (m, 1H); 2.20 (s, 6H).

Example 9: Synthesis of (S)-1-(1-(3-chloro-5-fluorophenyl)-2-(dimethylamino)ethyl)-4-(5-morpholino-1H-pyrrolo[2,3-b]pyridin-3-yl)pyridin-2(1H)-one

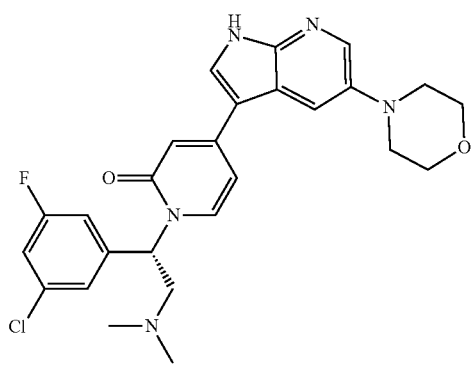 [SMILES: CN(C)C[C@H](c1cc(F)cc(Cl)c1)n1ccc(-c2c[nH]c3ncc(N4CCOCC4)cc23)cc1=O]

Step 1: 1-Chloro-3-fluoro-5-vinylbenzene

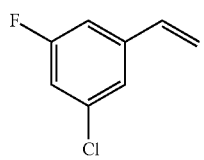

The compound is obtained by the procedure described in Example 1, Step 4, starting from g (31.5 mmol) of 3-chloro-5-fluorobenzaldehyde instead of 3-fluorobenzaldehyde. 3.07 g of the title compound are obtained.
Yield: 62%.
MH+: Non ionizable.

Step 2: 2-(3-Chloro-5-fluorophenyl)oxirane

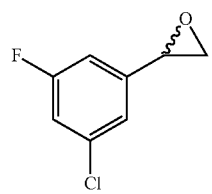 [SMILES: Fc1cc(Cl)cc(C2CO2)c1]

The compound is obtained by the procedure described in Example 1, Step 5, starting from 3.07 g (20 mmol) of 1-chloro-3-fluoro-5-vinylbenzene (described in the previous step) instead of 1-fluoro-3-vinylbenzene. 1.55 g of the title compound are obtained.
Yield: 46%.
MH+: Non ionizable.

Step 3: 1-(3-Chloro-5-fluorophenyl)-2-(dimethylamino)ethan-1-ol

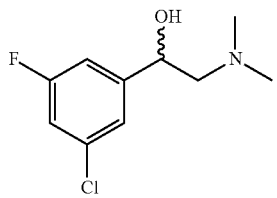

The compound is obtained by the procedure described in Example 1, Step 6, starting from 300 mg (1.74 mmol) of 2-(3-chloro-5-fluorophenyl)oxirane (described in the previous step) instead of 2-(3-fluorophenyl)oxirane. 136 mg of the title compound are obtained.

Yield: 36%.
MH+: 218.4; 220.4 (M; M+2).

Step 4: 2-Chloro-2-(3-chloro-5-fluorophenyl)-N,N-dimethylethan-1-amine

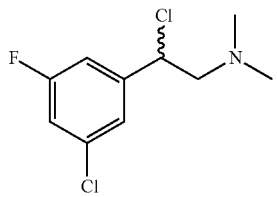

The compound is obtained by the procedure described in Example 1, Step 7, starting from 136 mg (0.62 mmol) of 1-(3-chloro-5-fluorophenyl)-2-(dimethylamino)ethan-1-ol (described in the previous step) instead of 2-(dimethylamino)-1-(3-fluorophenyl)ethan-1-ol. 145 mg of the title compound are obtained.

Yield: 98%.
MH+: 236.2; 238.2 (M; M+2).

Step 5: 4-Bromo-1-(1-(3-chloro-5-fluorophenyl)-2-(dimethylamino)ethyl)pyridin-2(1H)-one

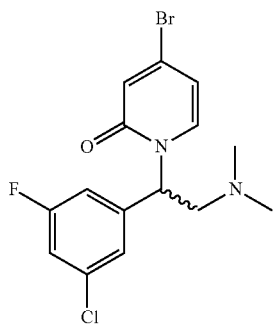

The compound is obtained by the procedure described in Example 1, Step 8, starting from 145 mg (0.61 mmol) of 2-chloro-2-(3-chloro-5-fluorophenyl)-N,N-dimethylethan-1-amine (described in the previous step) instead of 2-chloro-2-(3-fluorophenyl)-N,N-dimethylethan-1-amine. 90 mg of the title compound are obtained.

Yield: 39%.
MH+: 373.3; 375.5 (M; M+2).

Step 6: 1-(1-(3-Chloro-5-fluorophenyl)-2-(dimethylamino)ethyl)-4-(5-morpholino-1-tosyl-1H-pyrrolo[2,3-b]pyridin-3-yl)pyridin-2(1H)-one

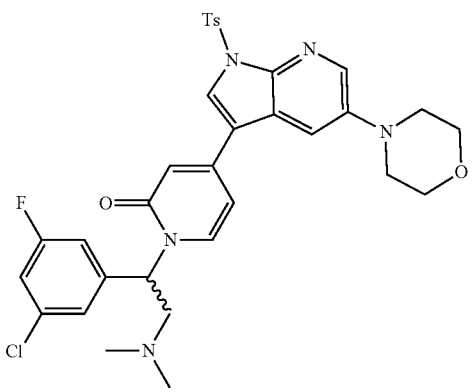 [SMILES: Cc1ccc(S(=O)(=O)n2cc(-c3ccn(C(CN(C)C)c4cc(F)cc(Cl)c4)c(=O)c3)c3cc(N4CCOCC4)cnc32)cc1]

The compound is obtained by the procedure described in Example 1, Step 9, starting from 90 mg (0.24 mmol) of 4-bromo-1-(1-(3-chloro-5-fluorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 94 mg of the title compound are obtained.

Yield: 60%.
MH+: 650.5; 652.6 (M; M+2).

Step 7: 1-(1-(3-Chloro-5-fluorophenyl)-2-(dimethylamino)ethyl)-4-(5-morpholino-1H-pyrrolo[2,3-b]pyridin-3-yl)pyridin-2(1H)-one

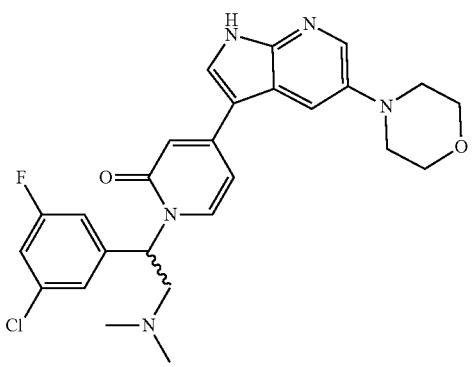 [SMILES: CN(C)CC(c1cc(F)cc(Cl)c1)n1ccc(-c2c[nH]c3ncc(N4CCOCC4)cc23)cc1=O]

94 mg (0.14 mmol) of 1-(1-(3-chloro-5-fluorophenyl)-2-(dimethylamino)ethyl)-4-(5-morpholino-1-tosyl-1H-pyrrolo[2,3-b]pyridin-3-yl)pyridin-2(1H)-one (described in the previous step) are suspended in 5 ml of MeCN and 2.5 ml of a Na$_2$CO$_3$ 2M solution. The mixture is stirred at 120° C. under microwave irradiation in a sealed tube (150 W) for 1 h. The mixture is cooled to room temperature, diluted with EtOAc and washed 3 times with water. Organic layer is dried over Na$_2$SO$_4$, filtrated and evaporated under reduced pressure. Crude product is finally purified by flash chromatography using a silica gel column and a DCM/MeOH mixture as eluent. 16 mg of a white solid are obtained.

Yield: 23%.

MH+: 588.7 (M+1).

$^1$H NMR (DMSO-d6, 400 MHz): δ 12.06 (br s, 1H); 8.17 (d, J=2.5 Hz, 1H); 8.11 (s, 1H); 7.77 (d, J=7.6 Hz, 1H); 7.70 (d, J=2.6 Hz, 1H); 7.43-7.36 (m, 1H); 7.34-7.24 (m, 2H); 6.74-6.67 (m, 2H); 6.20-6.11 (m, 1H); 3.83-3.73 (m, 4H); 3.34-3.23 (m, 1H); 3.19-3.09 (m, 4H); 2.81-2.71 (m, 1H); 2.21 (s, 6H).

Step 8: (S)-1-(1-(3-Chloro-5-fluorophenyl)-2-(dimethylamino)ethyl)-4-(5-morpholino-1H-pyrrolo[2,3-b]pyridin-3-yl)pyridin-2(1H)-one

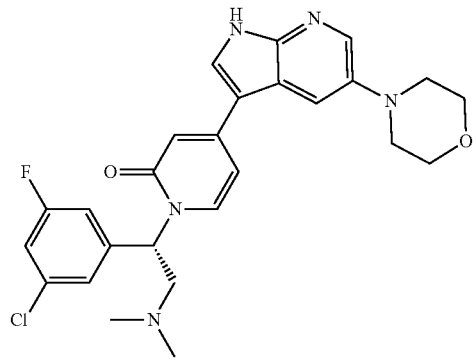 [SMILES: CN(C)C[C@H](c1cc(F)cc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 5 mg of the title compound are obtained starting from 16 mg of the racemate.

MH+: 588.7 (M+1).

$^1$H NMR (DMSO-d6, 400 MHz): δ 12.06 (br s, 1H); 8.17 (d, J=2.5 Hz, 1H); 8.11 (s, 1H); 7.77 (d, J=7.6 Hz, 1H); 7.70 (d, J=2.6 Hz, 1H); 7.43-7.36 (m, 1H); 7.34-7.24 (m, 2H); 6.74-6.67 (m, 2H); 6.20-6.11 (m, 1H); 3.83-3.73 (m, 4H); 3.34-3.23 (m, 1H); 3.19-3.09 (m, 4H); 2.81-2.71 (m, 1H); 2.21 (s, 6H).

Example 10: Synthesis of (S)-1-(2-(dimethylamino)-1-(3-fluoro-5-iodophenyl)ethyl)-4-(5-morpholino-1H-pyrrolo[2,3-b]pyridin-3-yl)pyridin-2(1H)-one

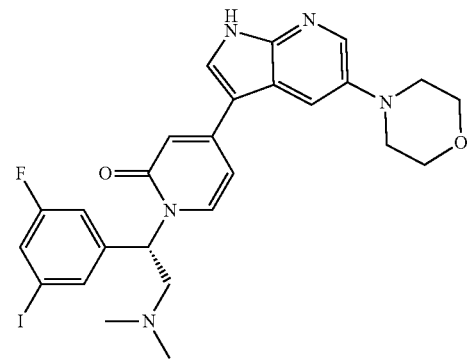

Step 1: 1-Fluoro-3-iodo-4-vinylbenzene

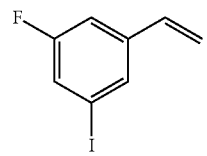

The compound is obtained by the procedure described in Example 1, Step 4, starting from 2 g (7.96 mmol) of 3-fluoro-5-iodobenzaldehyde instead of 3-fluorobenzaldehyde. 873 mg of the title compound are obtained.

Yield: 44%.

MH+: Non ionizable.

Step 2: 2-(3-Fluoro-5-iodophenyl)oxirane

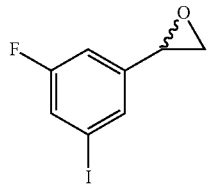

The compound is obtained by the procedure described in Example 1, Step 5, starting from 873 mg (3.5 mmol) of 1-fluoro-3-iodo-4-vinylbenzene (described in the previous step) instead of 1-fluoro-3-vinylbenzene. 432 mg of the title compound are obtained.

Yield: 47%.

MH+: Non ionizable.

Step 3: 2-(Dimethylamino)-1-(3-fluoro-5-iodophenyl)ethan-1-ol

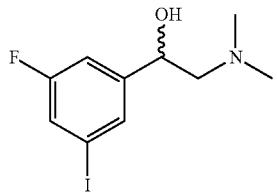

The compound is obtained by the procedure described in Example 1, Step 6, starting from 376 mg (1.40 mmol) of 2-(3-fluoro-5-iodophenyl)oxirane (described in the previous step) instead of 2-(3-fluorophenyl)oxirane. 295 mg of the title compound are obtained.

Yield: 67%.

MH+: 310.3 (M+1).

Step 4: 2-Chloro-2-(3-fluoro-5-iodophenyl)-N,N-dimethylethan-1-amine

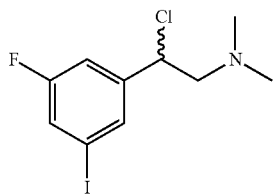

The compound is obtained by the procedure described in Example 1, Step 7, starting from 351 mg (1.14 mmol) of 2-(dimethylamino)-1-(3-fluoro-5-iodophenyl)ethan-1-ol (described in the previous step) instead of 2-(dimethylamino)-1-(3-fluorophenyl)ethan-1-ol. 328 mg of the title compound are obtained.
Yield: 88%.
MH+: 388.3 (M+1).

Step 5: 1-(2-(Dimethylamino)-1-(3-fluoro-5-iodophenyl)ethyl)-4-iodopyridin-2(1H)-one

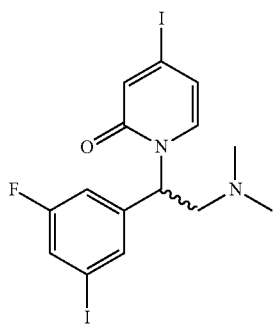

The compound is obtained by the procedure described in Example 6, Step 5, starting from 328 mg (0.85 mmol) of 2-chloro-2-(3-fluoro-5-iodophenyl)-N,N-dimethylethan-1-amine (described in the previous step) instead of 2-chloro-2-(3-iodophenyl)-N,N-dimethylethan-1-amine. 236 mg of the title compound are obtained.
Yield: 54%.
MH+: 513.2 (M+1).

Step 6: 1-(2-(Dimethylamino)-1-(3-fluoro-5-iodophenyl)ethyl)-4-(5-morpholino-1-tosyl-1H-pyrrolo[2,3-b]pyridin-3-yl)pyridin-2(1H)-one

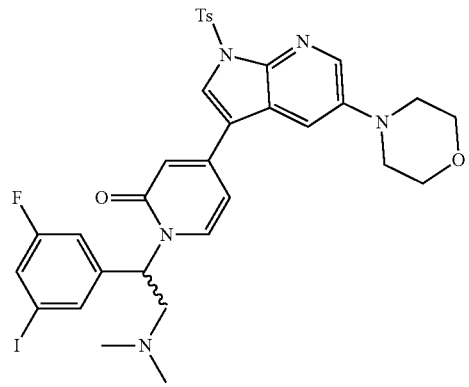 [SMILES: Cc1ccc(S(=O)(=O)n2cc(-c3ccn(C(CN(C)C)c4cc(F)cc(I)c4)c(=O)c3)c3cc(N4CCOCC4)cnc32)cc1]

The compound is obtained by the procedure described in Example 1, Step 9, starting from 236 mg (0.46 mmol) of 1-(2-(dimethylamino)-1-(3-fluoro-5-iodophenyl)ethyl)-4-iodopyridin-2(1H)-one (described in the previous step) instead of 4-bromo-1-(2-(dimethylamino)-1-(3-fluorophenyl)ethyl)pyridin-2(1H)-one. 340 mg of the title compound are obtained.
Yield: 99%.
MH+: 742.5 (M+1).

Step 7: 1-(2-(dimethylamino)-1-(3-fluoro-5-iodophenyl)ethyl)-4-(5-morpholino-1H-pyrrolo[2,3-b]pyridin-3-yl)pyridin-2(1H)-one

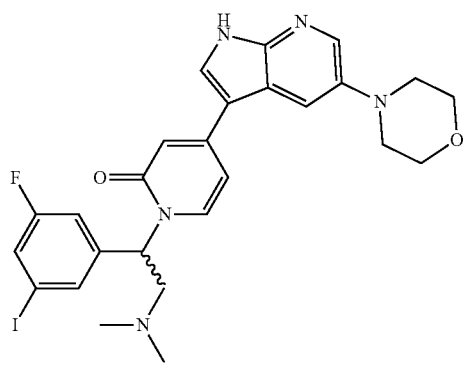 [SMILES: CN(C)CC(c1cc(F)cc(I)c1)n1ccc(-c2c[nH]c3ncc(N4CCOCC4)cc23)cc1=O]

The compound is obtained by the procedure described in Example 3, Step 7, starting from 207 mg (0.28 mmol) of 1-(2-(dimethylamino)-1-(3-fluoro-5-iodophenyl)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 97 mg of racemate are obtained.
Yield: 59%.
MH+: 588.6 (M+1).
$^1$H NMR (DMSO-d6, 400 MHz): δ 12.06 (br s, 1H); 8.17 (d, J=2.5 Hz, 1H); 8.10 (s, 1H); 7.77 (d, J=7.8 Hz, 1H); 7.71 (d, J=2.6 Hz, 1H); 7.64-7.57 (m, 2H); 7.35-7.28 (m, 1H); 6.74-6.67 (m, 2H); 6.17-6.08 (m, 1H); 3.83-3.74 (m, 4H); 3.34-3.22 (m, 1H); 3.19-3.08 (m, 4H); 2.78-2.68 (m, 1H); 2.20 (s, 6H).

Step 8: (S)-1-(2-(dimethylamino)-1-(3-fluoro-5-iodophenyl)ethyl)-4-(5-morpholino-1H-pyrrolo[2,3-b]pyridin-3-yl)pyridin-2(1H)-one

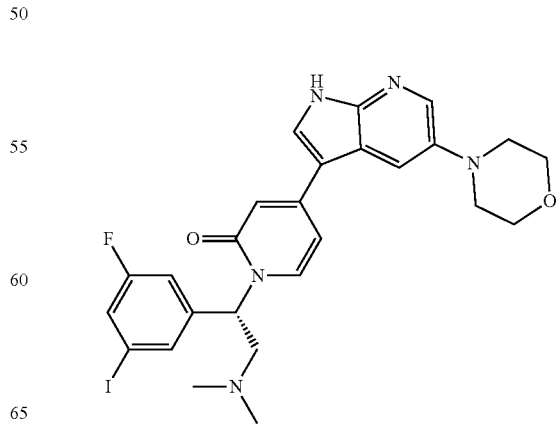

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 2.9 mg of the title compound are obtained.

MH+: 588.6 (M+1).

¹H NMR (DMSO-d6, 400 MHz): δ 12.06 (br s, 1H); 8.17 (d, J=2.5 Hz, 1H); 8.10 (s, 1H); 7.77 (d, J=7.8 Hz, 1H); 7.71 (d, J=2.6 Hz, 1H); 7.64-7.57 (m, 2H); 7.35-7.28 (m, 1H); 6.74-6.67 (m, 2H); 6.17-6.08 (m, 1H); 3.83-3.74 (m, 4H); 3.34-3.22 (m, 1H); 3.19-3.08 (m, 4H); 2.78-2.68 (m, 1H); 2.20 (s, 6H).

Example 11: Synthesis of (S)-1-(1-(3-chlorophenyl)-2-((2,2-difluoroethyl)(methyl)amino)ethyl)-4-(5-morpholino-1H-pyrrolo[2,3-b]pyridin-3-yl)pyridin-2(1H)-one

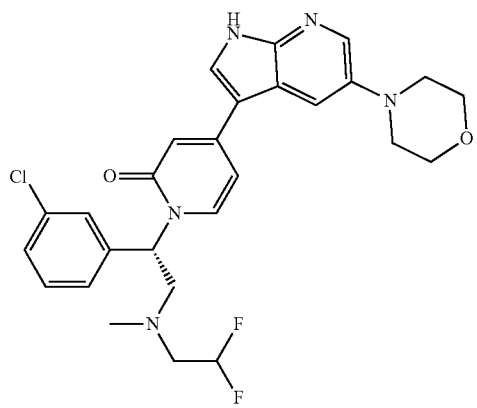 [SMILES: CN(CC(F)F)C[C@H](c1cccc(Cl)c1)n1ccc(-c2c[nH]c3ncc(N4CCOCC4)cc23)cc1=O]

Step 1: 1-(3-Chlorophenyl)-2-((2,2-difluoroethyl)(methyl)amino)ethan-1-ol

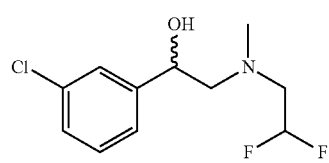 [SMILES: CN(CC(F)F)CC(Cl)c1cccc(Cl)c1]

The compound is obtained by the procedure described in Example 1, Step 6, starting from 500 mg (3.23 mmol) of 2-(3-chlorophenyl)oxirane (described in example 2 step 2) instead of 2-(3-fluorophenyl)oxirane, and 843 mg (6.46 mmol) of (2,2-difluoroethyl)(methyl)amine hydrochloride instead of dimethylamine. 277 mg of the title compound are obtained.

Yield: 34%.

MH+: 250.4; 252.3 (M; M+2).

Step 2: 2-Chloro-2-(3-chlorophenyl)-N-(2,2-difluoroethyl)-N-methylethan-1-amine

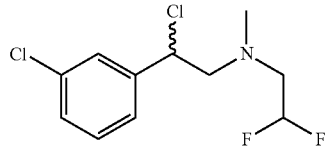

The compound is obtained by the procedure described in Example 1, Step 7, starting from 277 mg (1.10 mmol) of 1-(3-chlorophenyl)-2-((2,2-difluoroethyl)(methyl)amino)ethan-1-ol (described in the previous step) instead of 2-(dimethylamino)-1-(3-fluorophenyl)ethan-1-ol. 302 mg of the title compound are obtained.

Yield: Quantitative.

MH+: 268.4; 270.3 (M; M+2).

Step 3: 4-Bromo-1-(1-(3-chlorophenyl)-2-((2,2-difluoroethyl)(methyl)amino)ethyl)pyridin-2(1H)-one

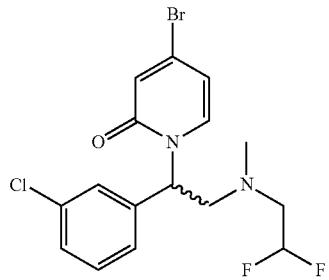 [SMILES: CN(CC(F)F)CC(c1cccc(Cl)c1)n1ccc(Br)cc1=O]

The compound is obtained by the procedure described in Example 1, Step 8, starting from 302 mg (1.10 mmol) of 2-chloro-2-(3-chlorophenyl)-N-(2,2-difluoroethyl)-N-methylethan-1-amine (described in the previous step) instead of 2-chloro-2-(3-fluorophenyl)-N,N-dimethylethan-1-amine. 197 mg of the title compound are obtained.

Yield: 44%.

MH+: 405.4; 407.4; 409.3 (M; M+2; M+4).

Step 4: 1-(1-(3-Chlorophenyl)-2-((2,2-difluoroethyl)(methyl)amino)ethyl)-4-(5-morpholino-1-tosyl-1H-pyrrolo[2,3-b]pyridin-3-yl)pyridin-2(1H)-one

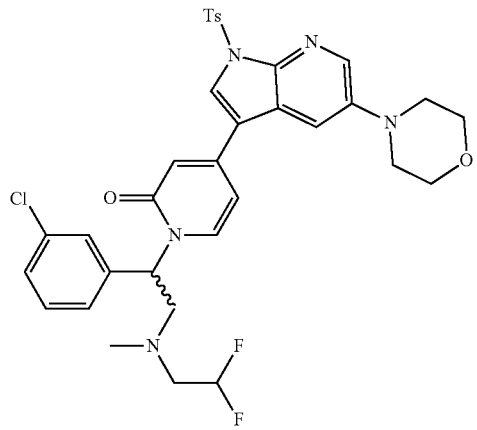 [SMILES: Cc1ccc(S(=O)(=O)n2cc(-c3ccn(C(CN(C)CC(F)F)c4cccc(Cl)c4)c(=O)c3)c3cc(N4CCOCC4)cnc32)cc1]

The compound is obtained by the procedure described in Example 1, Step 9, starting from 197 mg (0.49 mmol) of 4-bromo-1-(1-(3-chlorophenyl)-2-((2,2-difluoroethyl)(methyl)amino)ethyl)pyridin-2(1H)-one (described in the previous step) instead of 4-bromo-1-(2-(dimethylamino)-1-(3-fluorophenyl)ethyl)pyridin-2(1H)-one. 341 mg of the title compound are obtained.
Yield: Quantitative.
MH+: 682.6; 684.0 (M; M+2).

Step 5: 1-(1-(3-Chlorophenyl)-2-((2,2-difluoroethyl)(methyl)amino)ethyl)-4-(5-morpholino-1H-pyrrolo[2,3-b]pyridin-3-yl)pyridin-2(1H)-one

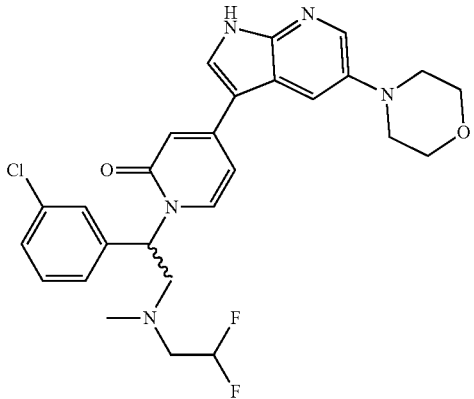 [SMILES: CN(CC(F)F)CC(c1cccc(Cl)c1)n1ccc(-c2c[nH]c3ncc(N4CCOCC4)cc23)cc1=O]

The compound is obtained by the procedure described in Example 3, Step 7, starting from 341 mg (0.49 mmol) of 1-(1-(3,4-difluorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 137 mg of racemate are obtained.
Yield: 51%.
MH+: 528.5; 530.5 (M; M+2).
¹H NMR (DMSO-d6, 400 MHz): δ 12.04 (br s, 1H); 8.17 (d, J=2.6 Hz, 1H); 8.11 (d, J=2.9 Hz, 1H); 7.73 (d, J=8.1 Hz, 1H); 7.70 (d, J=2.6 Hz, 1H); 7.50-7.46 (m, 1H); 7.43-7.33 (m, 3H); 6.73-6.67 (m, 2H); 6.24-6.17 (m, 1H); 6.06 (dt, J=55.8 and 4.3 Hz, 1H); 3.83-3.74 (m, 4H); 3.50-3.41 (m, 1H); 3.18-3.08 (m, 5H); 2.99-2.79 (m, 2H); 2.37 (s, 3H).

Step 6: (S)-1-(1-(3-Chlorophenyl)-2-((2,2-difluoroethyl)(methyl)amino)ethyl)-4-(5-morpholino-1H-pyrrolo[2,3-b]pyridin-3-yl)pyridin-2(1H)-one

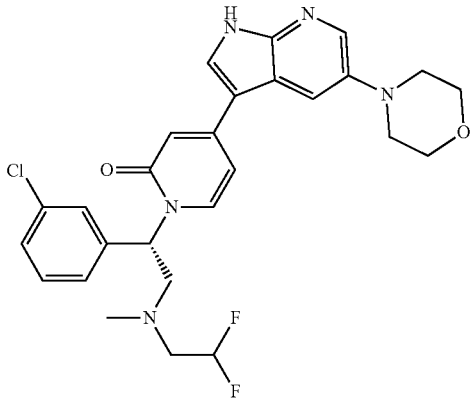 [SMILES: CN(CC(F)F)C[C@H](c1cccc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 19 mg of the title compound are obtained starting from 137 mg of the racemate.
MH+: 528.5; 530.5 (M; M+2).
¹H NMR (DMSO-d6, 400 MHz): δ 12.04 (br s, 1H); 8.17 (d, J=2.6 Hz, 1H); 8.11 (d, J=2.9 Hz, 1H); 7.73 (d, J=8.1 Hz, 1H); 7.70 (d, J=2.6 Hz, 1H); 7.50-7.46 (m, 1H); 7.43-7.33 (m, 3H); 6.73-6.67 (m, 2H); 6.24-6.17 (m, 1H); 6.06 (dt, J=55.8 and 4.3 Hz, 1H); 3.83-3.74 (m, 4H); 3.50-3.41 (m, 1H); 3.18-3.08 (m, 5H); 2.99-2.79 (m, 2H); 2.37 (s, 3H).

Example 12: Synthesis of (S)-2-((2-(3-chlorophenyl)-2-(4-(5-morpholino-1H-pyrrolo[2,3-b]pyridin-3-yl)-2-oxopyridin-1(2H)-yl)ethyl)(methyl)amino)acetonitrile

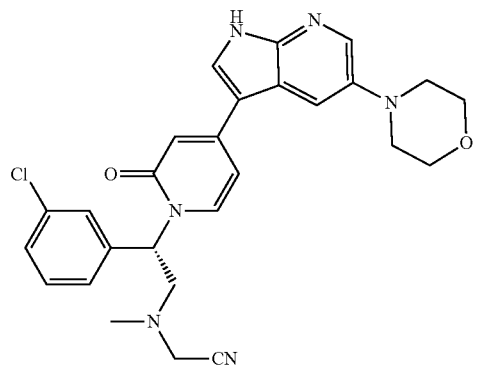 [SMILES: CN(CC#N)C[C@H](c1cccc(Cl)c1)n1ccc(-c2c[nH]c3ncc(N4CCOCC4)cc23)cc1=O]

Step 1: 2-((2-(3-Chlorophenyl)-2-hydroxyethyl)(methyl)amino)acetonitrile

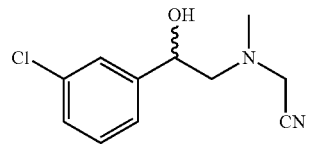

The compound is obtained by the procedure described in Example 1, Step 6, starting from 500 mg (3.23 mmol) of 2-(3-chlorophenyl)oxirane (described in example 2 step 2) instead of 2-(3-fluorophenyl)oxirane, and 688 mg (6.46 mmol) of 2-(methylamino)acetonitrile hydrochloride instead of dimethylamine. 398 mg of the title compound are obtained.
Yield: 55%.
MH+: 225.4; 227.1 (M; M+2).

Step 2: 2-((2-Chloro-2-(3-chlorophenyl)ethyl)(methyl)amino)acetonitrile

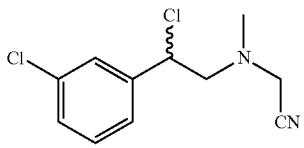

The compound is obtained by the procedure described in Example 1, Step 7, starting from 398 mg (1.77 mmol) of 2-((2-(3-chlorophenyl)-2-hydroxyethyl)(methyl)amino)acetonitrile (described in the previous step) instead of 2-(dimethylamino)-1-(3-fluorophenyl)ethan-1-ol. 430 mg of the title compound are obtained.
Yield: Quantitative.
MH+: 243.3; 245.2 (M; M+2).

Step 3: 2-((2-(4-Bromo-2-oxopyridin-1(2H)-yl)-2-(3-chlorophenyl)ethyl)(methyl)amino)acetonitrile

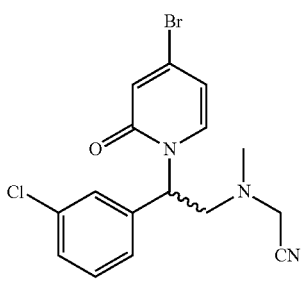 [SMILES: CN(CC#N)CC(c1cccc(Cl)c1)n1ccc(Br)cc1=O]

The compound is obtained by the procedure described in Example 1, Step 8, starting from 430 mg (1.77 mmol) of 2-((2-chloro-2-(3-chlorophenyl)ethyl)(methyl)amino)acetonitrile (described in the previous step) instead of 2-chloro-2-(3-fluorophenyl)-N,N-dimethylethan-1-amine. 205 mg of the title compound are obtained.
Yield: 30%.
MH+: 380.4; 382.3; 384.3 (M; M+2; M+4).

Step 4: 2-((2-(3-Chlorophenyl)-2-(4-(5-morpholino-1-tosyl-1H-pyrrolo[2,3-b]pyridin-3-yl)-2-oxopyridin-1(2H)-yl)ethyl)(methyl)amino)acetonitrile

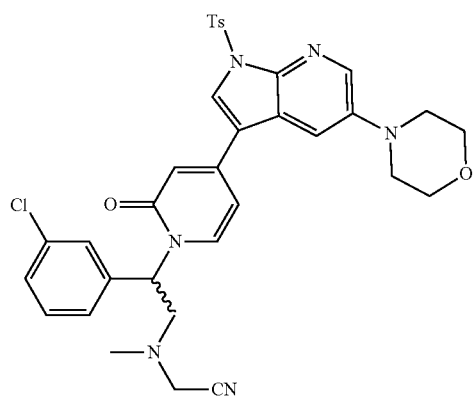 [SMILES: Cc1ccc(S(=O)(=O)n2cc(-c3ccn(C(CN(C)CC#N)c4cccc(Cl)c4)c(=O)c3)c3cc(N4CCOCC4)cnc32)cc1]

The compound is obtained by the procedure described in Example 1, Step 9, starting from 205 mg (0.54 mmol) of 2-((2-(4-bromo-2-oxopyridin-1(2H)-yl)-2-(3-chlorophenyl)ethyl)(methyl)amino)acetonitrile (described in the previous step) instead of 4-bromo-1-(2-(dimethylamino)-1-(3-fluorophenyl)ethyl)pyridin-2(1H)-one. 346 mg of the title compound are obtained.
Yield: 98%.
MH+: 657.6; 659.6 (M; M+2).

Step 5: 2-((2-(3-Chlorophenyl)-2-(4-(5-morpholino-1H-pyrrolo[2,3-b]pyridin-3-yl)-2-oxopyridin-1(2H)-yl)ethyl)(methyl)amino)acetonitrile

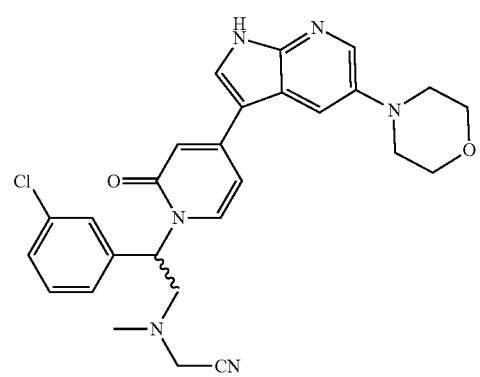 [SMILES: CN(CC#N)C[C@H](c1cccc(Cl)c1)n1ccc(-c2c[nH]c3ncc(N4CCOCC4)cc23)cc1=O]

The compound is obtained by the procedure described in Example 3, Step 7, starting from 346 mg (0.52 mmol) of 2-((2-(3-chlorophenyl)-2-(4-(5-morpholino-1-tosyl-1H-pyrrolo[2,3-b]pyridin-3-yl)-2-oxopyridin-1(2H)-yl)ethyl)(methyl)amino)acetonitrile (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 150 mg of racemate are obtained.
Yield: 56%.
MH+: 503.5; 505.5 (M; M+2).
$^1$H NMR (DMSO-d6, 400 MHz): δ 12.07 (br s, 1H); 8.17 (d, J=2.5 Hz, 1H); 8.11 (s, 1H); 7.73 (d, J=8.1 Hz, 1H); 7.70 (d, J=2.6 Hz, 1H); 7.51-7.47 (m, 1H); 7.46-7.34 (m, 3H); 6.74-6.68 (m, 2H); 6.26-6.17 (m, 1H); 3.84-3.73 (m, 6H); 3.52-3.41 (m, 1H); 3.18-3.09 (m, 4H); 3.00-2.90 (m, 1H); 2.33 (s, 3H).

Step 6: (S)-2-((2-(3-Chlorophenyl)-2-(4-(5-morpholino-1H-pyrrolo[2,3-b]pyridin-3-yl)-2-oxopyridin-1(2H)-yl)ethyl)(methyl)amino)acetonitrile

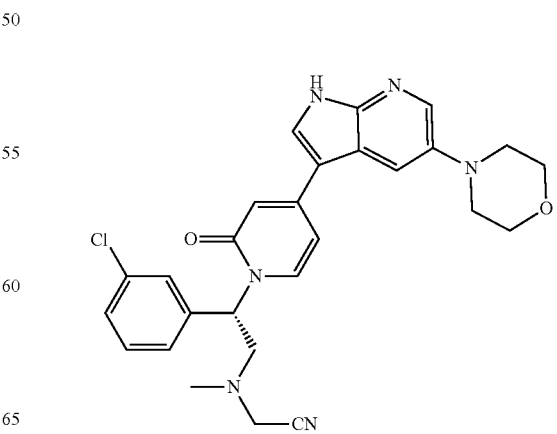

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 58 mg of the title compound are obtained starting from 150 mg of the racemate.

MH+: 503.5; 505.5 (M; M+2).

$^1$H NMR (DMSO-d6, 400 MHz): δ 12.07 (br s, 1H); 8.17 (d, J=2.5 Hz, 1H); 8.11 (s, 1H); 7.73 (d, J=8.1 Hz, 1H); 7.70 (d, J=2.6 Hz, 1H); 7.51-7.47 (m, 1H); 7.46-7.34 (m, 3H); 6.74-6.68 (m, 2H); 6.26-6.17 (m, 1H); 3.84-3.73 (m, 6H); 3.52-3.41 (m, 1H); 3.18-3.09 (m, 4H); 3.00-2.90 (m, 1H); 2.33 (s, 3H).

Example 13: Synthesis of (S)-1-(1-(3-chlorophenyl)-2-((2-methoxyethyl)(methyl)amino)ethyl)-4-(5-morpholino-1H-pyrrolo[2,3-b]pyridin-3-yl)pyridin-2(1H)-one

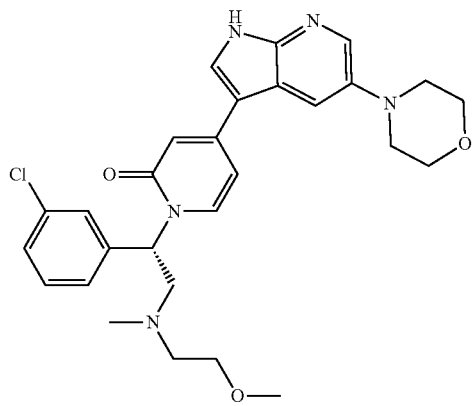

Step 1: 1-(3-Chlorophenyl)-2-((2-methoxyethyl)(methyl)amino)ethan-1-ol

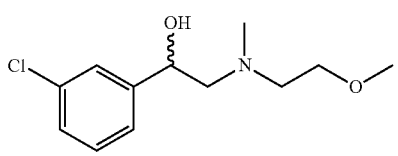 [SMILES: COCCN(C)CC(O)c1cccc(Cl)c1]

The compound is obtained by the procedure described in Example 1, Step 6, starting from 400 mg (2.59 mmol) of 2-(3-chlorophenyl)oxirane (described in example 2 step 2) instead of 2-(3-fluorophenyl)oxirane, and 462 mg (5.18 mmol) of N-(2-methoxyethyl)methylamine instead of dimethylamine. 470 mg of the title compound are obtained.

Yield: 74%.

MH+: 244.4; 246.2 (M; M+2).

Step 2: 2-Chloro-2-(3-chlorophenyl)-N-(2-methoxyethyl)-N-methylethan-1-amine

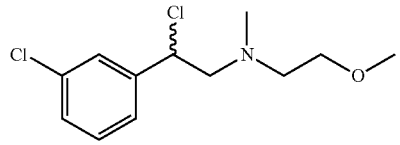 [SMILES: COCCN(C)CC(Cl)c1cccc(Cl)c1]

The compound is obtained by the procedure described in Example 1, Step 7, starting from 470 mg (1.93 mmol) of 1-(3-chlorophenyl)-2-((2-methoxyethyl)(methyl)amino)ethan-1-ol (described in the previous step) instead of 2-(dimethylamino)-1-(3-fluorophenyl)ethan-1-ol. 552 mg of the title compound are obtained.

Yield: Quantitative.

MH+: 262.4; 264.3 (M; M+2).

Step 3: 4-Bromo-1-(1-(3-chlorophenyl)-2-((2-methoxyethyl)(methyl)amino)ethyl)pyridin-2(1H)-one

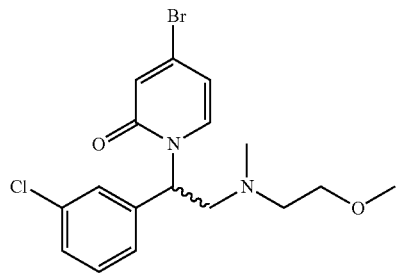 [SMILES: COCCN(C)CC(c1cccc(Cl)c1)n1ccc(Br)cc1=O]

The compound is obtained by the procedure described in Example 1, Step 8, starting from 506 mg (1.92 mmol) of 2-chloro-2-(3-chlorophenyl)-N-(2-methoxyethyl)-N-methylethan-1-amine (described in the previous step) instead of 2-chloro-2-(3-fluorophenyl)-N,N-dimethylethan-1-amine. 525 mg of the title compound are obtained.

Yield: 68%.

MH+: 399.3; 401.4; 403.2 (M; M+2; M+4).

Step 4: 1-(1-(3-Chlorophenyl)-2-((2-methoxyethyl)(methyl)amino)ethyl)-4-(5-morpholino-1-tosyl-1H-pyrrolo[2,3-b]pyridin-3-yl)pyridin-2(1H)-one

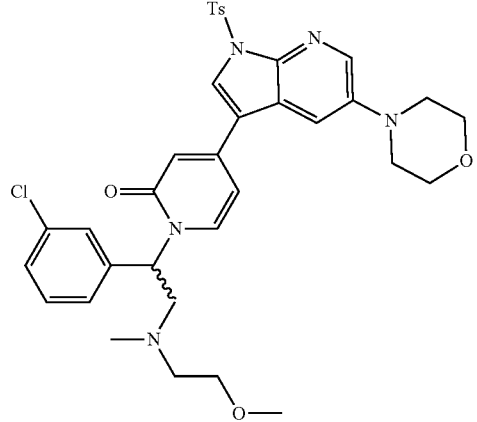 [SMILES: COCCN(C)CC(c1cccc(Cl)c1)n1ccc(-c2cn(S(=O)(=O)c3ccc(C)cc3)c3ncc(N4CCOCC4)cc23)cc1=O]

The compound is obtained by the procedure described in Example 1, Step 9, starting from 262 mg (0.66 mmol) of 4-bromo-1-(1-(3-chlorophenyl)-2-((2-methoxyethyl)(methyl)amino)ethyl)pyridin-2(1H)-one (described in the previous step) instead of 4-bromo-1-(2-(dimethylamino)-1-(3-fluorophenyl)ethyl)pyridin-2(1H)-one. 421 mg of the title compound are obtained.
Yield: 95%.
MH+: 676.7; 678.0 (M; M+2).

Step 5: 1-(1-(3-Chlorophenyl)-2-((2-methoxyethyl)(methyl)amino)ethyl)-4-(5-morpholino-1H-pyrrolo[2,3-b]pyridin-3-yl)pyridin-2(1H)-one

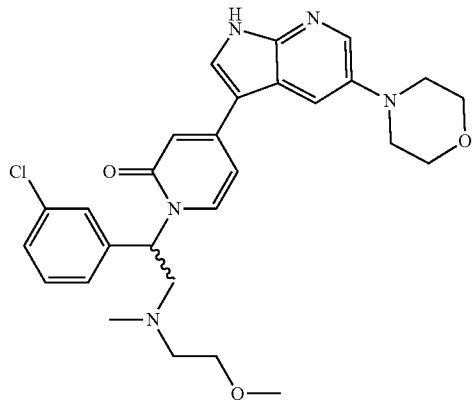 [SMILES: COCCN(C)CC(c1cccc(Cl)c1)n1ccc(-c2c[nH]c3ncc(N4CCOCC4)cc23)cc1=O]

The compound is obtained by the procedure described in Example 3, Step 7, starting from 421 mg (0.62 mmol) of 1-(1-(3-chlorophenyl)-2-((2-methoxyethyl)(methyl)amino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 240 mg of racemate are obtained.
Yield: 74%.
MH+: 522.6; 524.6 (M; M+2).
¹H NMR (DMSO-d6, 400 MHz): δ 12.08 (br s, 1H); 8.17 (d, J=2.5 Hz, 1H); 8.12 (s, 1H); 7.75 (d, J=7.8 Hz, 1H); 7.70 (d, J=2.5 Hz, 1H); 7.49-7.45 (m, 1H); 7.43-7.30 (m, 3H); 6.73-6.67 (m, 2H); 6.23-6.14 (m, 1H); 3.83-3.73 (m, 4H); 3.45-3.31 (m, 3H); 3.20 (s, 3H); 3.18-3.09 (m, 4H); 3.00-2.91 (m, 1H); 2.65-2.57 (m, 2H); 2.26 (s, 3H).

Step 6: (S)-1-(1-(3-Chlorophenyl)-2-((2-methoxyethyl)(methyl)amino)ethyl)-4-(5-morpholino-1H-pyrrolo[2,3-b]pyridin-3-yl)pyridin-2(1H)-one

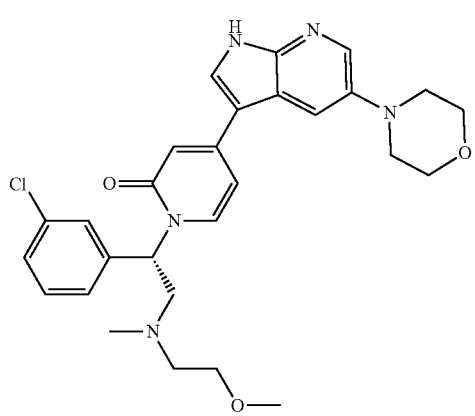 [SMILES: COCCN(C)C[C@H](c1cccc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 56 mg of the title compound are obtained starting from 240 mg of the racemate.
MH+: 522.6; 524.6 (M; M+2).
¹H NMR (DMSO-d6, 400 MHz): δ 12.08 (br s, 1H); 8.17 (d, J=2.5 Hz, 1H); 8.12 (s, 1H); 7.75 (d, J=7.8 Hz, 1H); 7.70 (d, J=2.5 Hz, 1H); 7.49-7.45 (m, 1H); 7.43-7.30 (m, 3H); 6.73-6.67 (m, 2H); 6.23-6.14 (m, 1H); 3.83-3.73 (m, 4H); 3.45-3.31 (m, 3H); 3.20 (s, 3H); 3.18-3.09 (m, 4H); 3.00-2.91 (m, 1H); 2.65-2.57 (m, 2H); 2.26 (s, 3H).

Example 14: Synthesis of (S)-1-(1-(3-chlorophenyl)-2-(cyclopropyl(methyl)amino)ethyl)-4-(5-morpholino-1H-pyrrolo[2,3-b]pyridin-3-yl)pyridin-2(1H)-one

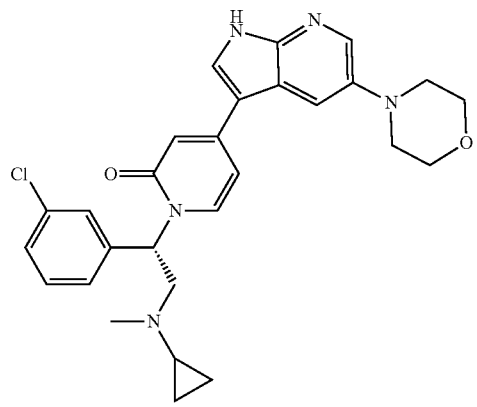 [SMILES: CN(C[C@H](c1cccc(Cl)c1)n1ccc(-c2c[nH]c3ncc(N4CCOCC4)cc23)cc1=O)C1CC1]

Step 1: 1-(3-Chlorophenyl)-2-(cyclopropyl(methyl)amino)ethan-1-ol

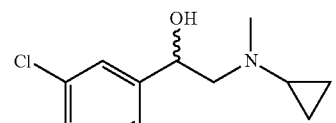

The compound is obtained by the procedure described in Example 1, Step 6, starting from 400 mg (2.59 mmol) of 2-(3-chlorophenyl)oxirane (described in example 2 step 2) instead of 2-(3-fluorophenyl)oxirane, and 557 mg (5.18 mmol) of N-cyclopropylmethylamine hydrochloride instead of dimethylamine. 412 mg of the title compound are obtained.
Yield: 70%.
MH+: 226.4; 228.3 (M; M+2).

Step 2: N-(2-Chloro-2-(3-chlorophenyl)ethyl)-N-methylcyclopropanamine

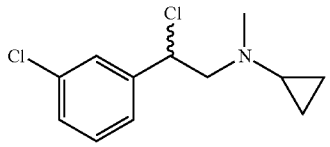

The compound is obtained by the procedure described in Example 1, Step 7, starting from 402 mg (1.78 mmol) of 1-(3-chlorophenyl)-2-(cyclopropyl(methyl)amino)ethan-1-ol (described in the previous step) instead of 2-(dimethylamino)-1-(3-fluorophenyl)ethan-1-ol. 505 mg of the title compound are obtained.
Yield: 58%.
MH+: 244.3; 246.3 (M; M+2).

Step 3: 4-Bromo-1-(1-(3-chlorophenyl)-2-(cyclopropyl(methyl)amino)ethyl)pyridin-2(1H)-one

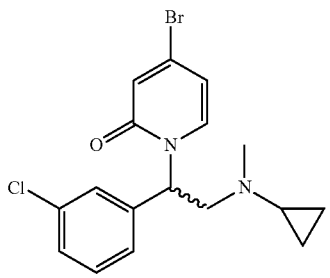 [SMILES: CN(CC(c1cccc(Cl)c1)n1ccc(Br)cc1=O)C1CC1]

The compound is obtained by the procedure described in Example 1, Step 8, starting from 505 mg (2.07 mmol) of N-(2-chloro-2-(3-chlorophenyl)ethyl)-N-methylcyclopropanamine (described in the previous step) instead of 2-chloro-2-(3-fluorophenyl)-N,N-dimethylethan-1-amine. 253 mg of the title compound are obtained.
Yield: 32%.
MH+: 381.3; 383.3; 385.3 (M; M+2; M+4).

Step 4: 1-(1-(3-Chlorophenyl)-2-(cyclopropyl(methyl)amino)ethyl)-4-(5-morpholino-1-tosyl-1H-pyrrolo[2,3-b]pyridin-3-yl)pyridin-2(1H)-one

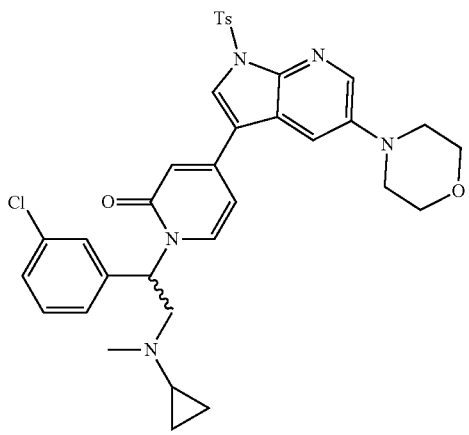 [SMILES: Cc1ccc(S(=O)(=O)n2cc(-c3ccn(C(CN(C)C4CC4)c4cccc(Cl)c4)c(=O)c3)c3cc(N4CCOCC4)cnc32)cc1]

The compound is obtained by the procedure described in Example 1, Step 9, starting from 253 mg (0.66 mmol) of 4-bromo-1-(1-(3-chlorophenyl)-2-(cyclopropyl(methyl)amino)ethyl)pyridin-2(1H)-one (described in the previous step) instead of 4-bromo-1-(2-(dimethylamino)-1-(3-fluorophenyl)ethyl)pyridin-2(1H)-one. 210 mg of the title compound are obtained.
Yield: 48%.
MH+: 658.4; 659.7; 660.6 (M; M+1; M+2).

Step 5: 1-(1-(3-Chlorophenyl)-2-(cyclopropyl(methyl)amino)ethyl)-4-(5-morpholino-1H-pyrrolo[2,3-b]pyridin-3-yl)pyridin-2(1H)-one

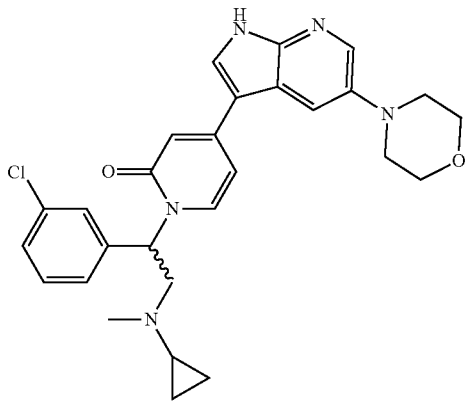 [SMILES: CN(CC(c1cccc(Cl)c1)n1ccc(-c2c[nH]c3ncc(N4CCOCC4)cc23)cc1=O)C1CC1]

The compound is obtained by the procedure described in Example 3, Step 7, starting from 210 mg (0.32 mmol) of 1-(1-(3-chlorophenyl)-2-(cyclopropyl(methyl)amino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 146 mg of racemate are obtained.
Yield: 91%.
MH+: 504.6; 506.5 (M; M+2).
$^1$H NMR (DMSO-d6, 400 MHz): δ 12.08 (br s, 1H); 8.17 (d, J=2.5 Hz, 1H); 8.12 (s, 1H); 7.77 (d, J=8.1 Hz, 1H); 7.69 (d, J=2.5 Hz, 1H); 7.50-7.46 (m, 1H); 7.43-7.33 (m, 3H); 6.72-6.65 (m, 2H); 6.30-6.20 (m, 1H); 3.83-3.74 (m, 4H); 3.53-3.41 (m, 1H); 3.18-3.10 (m, 4H); 3.08-2.99 (m, 1H); 2.32 (s, 3H); 1.78-1.69 (m, 1H); 0.45-0.36 (m, 2H); 0.25-0.14 (m, 2H).

Step 6: (S)-1-(1-(3-Chlorophenyl)-2-(cyclopropyl(methyl)amino)ethyl)-4-(5-morpholino-1H-pyrrolo[2,3-b]pyridin-3-yl)pyridin-2(1H)-one

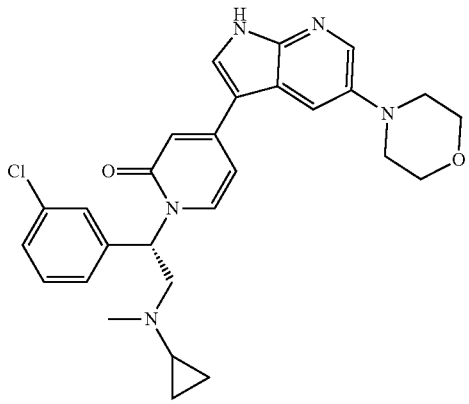 [SMILES: CN(C[C@H](c1cccc(Cl)c1)n1ccc(-c2c[nH]c3ncc(N4CCOCC4)cc23)cc1=O)C1CC1]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 38 mg of the title compound are obtained starting from 146 mg of the racemate.

MH+: 504.6; 506.5 (M; M+2).

$^{1}$H NMR (DMSO-d6, 400 MHz): δ 12.08 (br s, 1H); 8.17 (d, J=2.5 Hz, 1H); 8.12 (s, 1H); 7.77 (d, J=8.1 Hz, 1H); 7.69 (d, J=2.5 Hz, 1H); 7.50-7.46 (m, 1H); 7.43-7.33 (m, 3H); 6.72-6.65 (m, 2H); 6.30-6.20 (m, 1H); 3.83-3.74 (m, 4H); 3.53-3.41 (m, 1H); 3.18-3.10 (m, 4H); 3.08-2.99 (m, 1H); 2.32 (s, 3H); 1.78-1.69 (m, 1H); 0.45-0.36 (m, 2H); 0.25-0.14 (m, 2H).

Example 15: Synthesis of (S)-1-(1-(3-chlorophenyl)-2-(ethyl(methyl)amino)ethyl)-4-(5-morpholino-1H-pyrrolo[2,3-b]pyridin-3-yl)pyridin-2(1H)-one

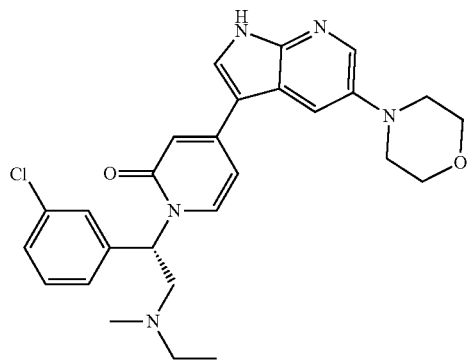 [SMILES: CCN(C)C[C@H](c1cccc(Cl)c1)n1ccc(-c2c[nH]c3ncc(N4CCOCC4)cc23)cc1=O]

Step 1: 1-(3-Chlorophenyl)-2-(ethyl(methyl)amino)ethan-1-ol

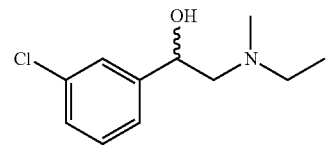

The compound is obtained by the procedure described in Example 1, Step 6, starting from 400 mg (2.59 mmol) of 2-(3-chlorophenyl)oxirane (described in example 2 step 2) instead of 2-(3-fluorophenyl)oxirane, and 495 mg (5.18 mmol) of N-methylethanamine hydrochloride instead of dimethylamine. 103 mg of the title compound are obtained.

Yield: 19%.

MH+: 214.3; 216.2 (M; M+2).

Step 2: 2-Chloro-2-(3-chlorophenyl)-N-ethyl-N-methylethan-1-amine

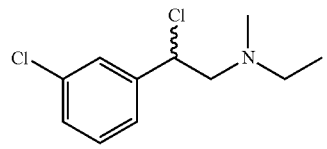

The compound is obtained by the procedure described in Example 1, Step 7, starting from 103 mg (0.48 mmol) of 1-(3-chlorophenyl)-2-(ethyl(methyl)amino)ethan-1-ol (described in the previous step) instead of 2-(dimethylamino)-1-(3-fluorophenyl)ethan-1-ol. 125 mg of the title compound are obtained.

Yield: Quantitative.

MH+: 232.3; 234.2 (M; M+2).

Step 3: 4-Bromo-1-(1-(3-chlorophenyl)-2-(ethyl(methyl)amino)ethyl)pyridin-2(1H)-one

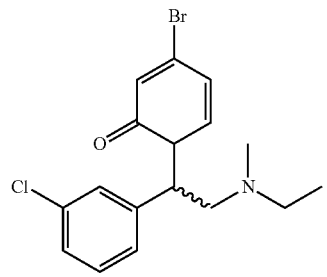 [SMILES: CCN(C)CC(c1cccc(Cl)c1)C1C=CC(Br)=CC1=O]

The compound is obtained by the procedure described in Example 1, Step 8, starting from 125 mg (0.54 mmol) of 2-chloro-2-(3-chlorophenyl)-N-ethyl-N-methylethan-1-amine (described in the previous step) instead of 2-chloro-2-(3-fluorophenyl)-N,N-dimethylethan-1-amine. 78 mg of the title compound are obtained.

Yield: 39%.

MH+: 369.4; 371.3; 373.3 (M; M+2; M+4).

Step 4: 1-(1-(3-Chlorophenyl)-2-(ethyl(methyl)amino)ethyl)-4-(5-morpholino-1-tosyl-1H-pyrrolo[2,3-b]pyridin-3-yl)pyridin-2(1H)-one

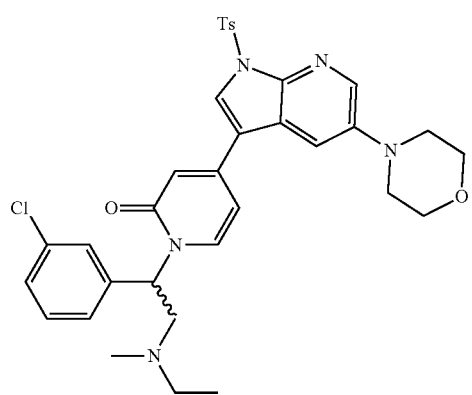 [SMILES: CCN(C)CC(c1cccc(Cl)c1)n1ccc(-c2cn(S(=O)(=O)c3ccc(C)cc3)c3ncc(N4CCOCC4)cc23)cc1=O]

The compound is obtained by the procedure described in Example 1, Step 9, starting from 78 mg (0.21 mmol) of 4-bromo-1-(1-(3-chlorophenyl)-2-(ethyl(methyl)amino)ethyl)pyridin-2(1H)-one (described in the previous step) instead of 4-bromo-1-(2-(dimethylamino)-1-(3-fluorophenyl)ethyl)pyridin-2(1H)-one. 128 mg of the title compound are obtained.

Yield: 94%.

MH+: 646.7; 648.6 (M; M+2).

Step 5: 1-(1-(3-Chlorophenyl)-2-(ethyl(methyl)amino)ethyl)-4-(5-morpholino-1H-pyrrolo[2,3-b]pyridin-3-yl)pyridin-2(1H)-one

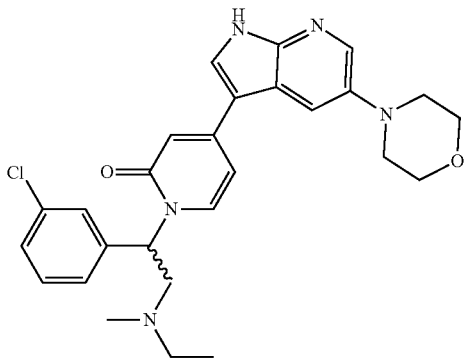 [SMILES: CCN(C)CC(c1cccc(Cl)c1)n1ccc(-c2c[nH]c3ncc(N4CCOCC4)cc23)cc1=O]

The compound is obtained by the procedure described in Example 3, Step 7, starting from 128 mg (0.20 mmol) of 1-(1-(3-chlorophenyl)-2-(ethyl(methyl)amino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 45 mg of racemate are obtained.

Yield: 46%.

MH+: 492.6; 494.6 (M; M+2).

$^1$H NMR (DMSO-d6, 400 MHz): δ 12.03 (br s, 1H); 8.16 (d, J=2.6 Hz, 1H); 8.09 (s, 1H); 7.74 (d, J=8.0 Hz, 1H); 7.70 (d, J=2.6 Hz, 1H); 7.49-7.45 (m, 1H); 7.43-7.34 (m, 3H); 6.71-6.66 (m, 2H); 6.22-6.15 (m, 1H); 3.82-3.74 (m, 4H); 3.34-3.24 (m, 1H); 3.17-3.10 (m, 4H); 2.91-2.83 (m, 1H); 2.51-2.40 (m, 2H); 2.21 (s, 3H); 0.95 (t, J=7.1 Hz, 3H).

Step 6: (S)-1-(1-(3-Chlorophenyl)-2-(ethyl(methyl)amino)ethyl)-4-(5-morpholino-1H-pyrrolo[2,3-b]pyridin-3-yl)pyridin-2(1H)-one

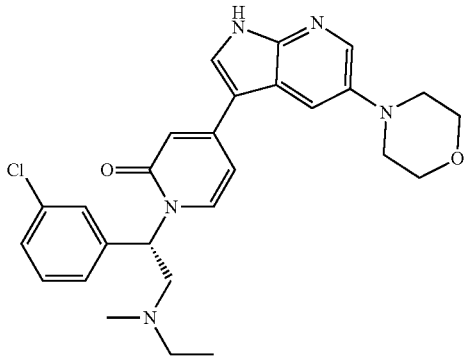 [SMILES: CCN(C)C[C@H](c1cccc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 16 mg of the title compound are obtained starting from 45 mg of the racemate.

MH+: 492.6; 494.6 (M; M+2).

$^1$H NMR (DMSO-d6, 400 MHz): δ 12.03 (br s, 1H); 8.16 (d, J=2.6 Hz, 1H); 8.09 (s, 1H); 7.74 (d, J=8.0 Hz, 1H); 7.70 (d, J=2.6 Hz, 1H); 7.49-7.45 (m, 1H); 7.43-7.34 (m, 3H); 6.71-6.66 (m, 2H); 6.22-6.15 (m, 1H); 3.82-3.74 (m, 4H); 3.34-3.24 (m, 1H); 3.17-3.10 (m, 4H); 2.91-2.83 (m, 1H); 2.51-2.40 (m, 2H); 2.21 (s, 3H); 0.95 (t, J=7.1 Hz, 3H).

Example 16: Synthesis of (S)-1-(1-(3-chlorophenyl)-2-((cyclopropylmethyl)(methyl)amino)ethyl)-4-(5-morpholino-1H-pyrrolo[2,3-b]pyridin-3-yl)pyridin-2(1H)-one

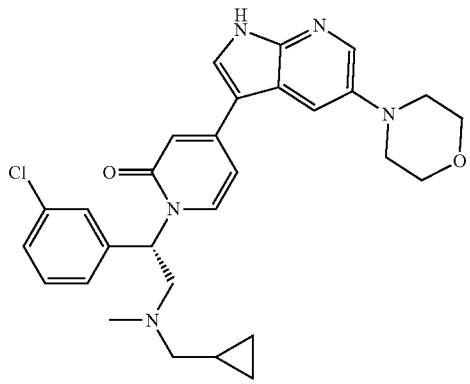 [SMILES: CN(CC1CC1)C[C@H](c1cccc(Cl)c1)n1ccc(-c2c[nH]c3ncc(N4CCOCC4)cc23)cc1=O]

Step 1: 1-(3-Chlorophenyl)-2-((cyclopropylmethyl)(methyl)amino)ethan-1-ol

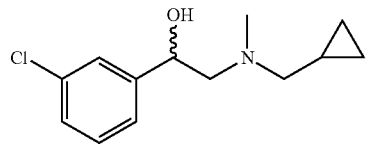 [SMILES: CN(CC1CC1)CC(O)c1cccc(Cl)c1]

The compound is obtained by the procedure described in Example 1, Step 6, starting from 400 mg (2.59 mmol) of 2-(3-chlorophenyl)oxirane (described in example 2 step 2) instead of 2-(3-fluorophenyl)oxirane, and 630 mg (5.18 mmol) of 1-cyclopropyl-N-methylmethanamine hydrochloride instead of dimethylamine. 183 mg of the title compound are obtained.

Yield: 29%.

MH+: 240.4; 242.2 (M; M+2).

Step 2: 2-Chloro-2-(3-chlorophenyl)-N-(cyclopropylmethyl)-N-methylethan-1-amine

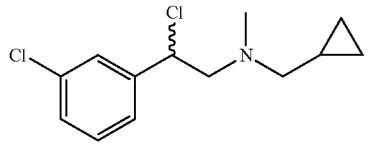 [SMILES: CN(CC1CC1)CC(Cl)c1cccc(Cl)c1]

The compound is obtained by the procedure described in Example 1, Step 7, starting from 183 mg (0.76 mmol) of 1-(3-chlorophenyl)-2-((cyclopropylmethyl)(methyl)amino)ethan-1-ol (described in the previous step) instead of 2-(dimethylamino)-1-(3-fluorophenyl)ethan-1-ol. 220 mg of the title compound are obtained.
Yield: Quantitative.
MH+: 258.4; 260.2 (M; M+2).

Step 3: 4-Bromo-1-(1-(3-chlorophenyl)-2-((cyclopropylmethyl)(methyl)amino)ethyl)pyridin-2(1H)-one

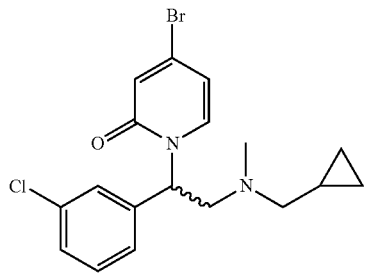 [SMILES: CN(CC1CC1)CC(c1cccc(Cl)c1)n1ccc(Br)cc1=O]

The compound is obtained by the procedure described in Example 1, Step 8, starting from 220 mg (0.85 mmol) of 2-chloro-2-(3-chlorophenyl)-N-(cyclopropylmethyl)-N-methylethan-1-amine (described in the previous step) instead of 2-chloro-2-(3-fluorophenyl)-N,N-dimethylethan-1-amine. 115 mg of the title compound are obtained.
Yield: 34%.
MH+: 395.4; 397.4; 399.3 (M; M+2; M+4).

Step 4: 1-(1-(3-Chlorophenyl)-2-((cyclopropylmethyl)(methyl)amino)ethyl)-4-(5-morpholino-1-tosyl-1H-pyrrolo[2,3-b]pyridin-3-yl)pyridin-2(1H)-one

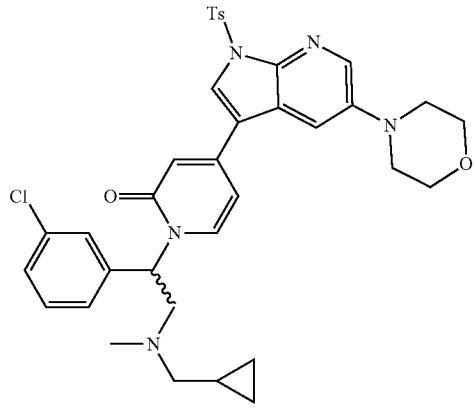 [SMILES: Cc1ccc(S(=O)(=O)n2cc(-c3ccn(C(CN(C)CC4CC4)c4cccc(Cl)c4)c(=O)c3)c3cc(N4CCOCC4)cnc32)cc1]

The compound is obtained by the procedure described in Example 1, Step 9, starting from 115 mg (0.29 mmol) of 4-bromo-1-(1-(3-chlorophenyl)-2-((cyclopropylmethyl)(methyl)amino)ethyl)pyridin-2(1H)-one (described in the previous step) instead of 4-bromo-1-(2-(dimethylamino)-1-(3-fluorophenyl)ethyl)pyridin-2(1H)-one. 144 mg of the title compound are obtained.
Yield: 73%.
MH+: 672.7; 674.7 (M; M+2).

Step 5: 1-(1-(3-Chlorophenyl)-2-((cyclopropylmethyl)(methyl)amino)ethyl)-4-(5-morpholino-1H-pyrrolo[2,3-b]pyridin-3-yl)pyridin-2(1H)-one

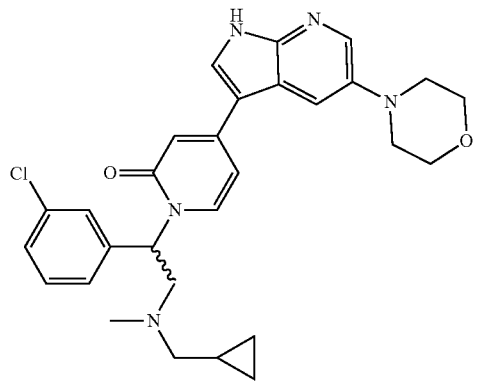 [SMILES: CN(CC1CC1)CC(c1cccc(Cl)c1)n1ccc(-c2c[nH]c3ncc(N4CCOCC4)cc23)cc1=O]

The compound is obtained by the procedure described in Example 3, Step 7, starting from 144 mg (0.21 mmol) of 1-(1-(3-chlorophenyl)-2-((cyclopropylmethyl)(methyl)amino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 68 mg of racemate are obtained.
Yield: 61%.
MH+: 518.7; 520.6 (M; M+2).
¹H NMR (DMSO-d6, 400 MHz): δ 12.03 (br s, 1H); 8.14 (d, J=2.5 Hz, 1H); 8.09 (s, 1H); 7.71 (d, J=7.3 Hz, 1H); 7.69 (d, J=2.6 Hz, 1H); 7.49-7.45 (m, 1H); 7.42-7.32 (m, 3H); 6.71-6.64 (m, 2H); 6.24-6.16 (m, 1H); 3.83-3.74 (m, 4H); 3.36-3.26 (m, 1H); 3.17-3.09 (m, 4H); 2.99-2.91 (m, 1H); 2.31 (d, J=6.6 Hz, 2H); 2.29 (s, 3H); 0.88-0.78 (m, 1H); 0.48-0.38 (m, 2H); 0.09-0.03 (m, 2H).

Step 6: (S)-1-(1-(3-Chlorophenyl)-2-((cyclopropylmethyl)(methyl)amino)ethyl)-4-(5-morpholino-1H-pyrrolo[2,3-b]pyridin-3-yl)pyridin-2(1H)-one

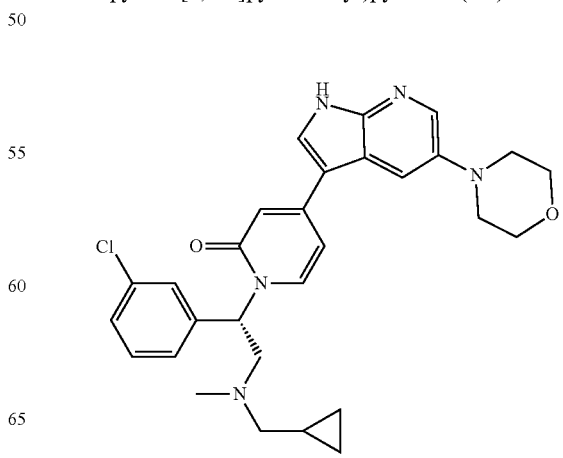

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 29 mg of the title compound are obtained starting from 68 mg of the racemate.

MH+: 518.7; 520.6 (M; M+2).

¹H NMR (DMSO-d6, 400 MHz): δ 12.03 (br s, 1H); 8.14 (d, J=2.5 Hz, 1H); 8.09 (s, 1H); 7.71 (d, J=7.3 Hz, 1H); 7.69 (d, J=2.6 Hz, 1H); 7.49-7.45 (m, 1H); 7.42-7.32 (m, 3H); 6.71-6.64 (m, 2H); 6.24-6.16 (m, 1H); 3.83-3.74 (m, 4H); 3.36-3.26 (m, 1H); 3.17-3.09 (m, 4H); 2.99-2.91 (m, 1H); 2.31 (d, J=6.6 Hz, 2H); 2.29 (s, 3H); 0.88-0.78 (m, 1H); 0.48-0.38 (m, 2H); 0.09-0.03 (m, 2H).

Example 17: Synthesis of (S)-1-(1-(3,4-difluorophenyl)-2-(dimethylamino)ethyl)-4-(5-morpholino-1H-pyrrolo[2,3-b]pyridin-3-yl)pyridin-2(1H)-one

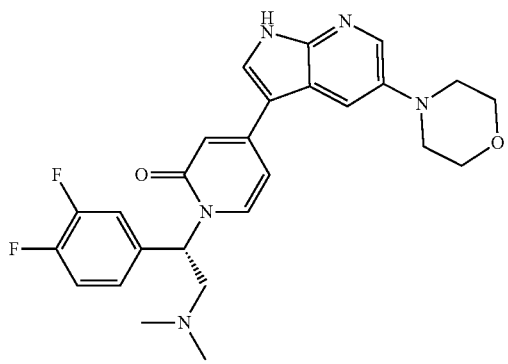 [SMILES: CN(C)C[C@H](c1ccc(F)c(F)c1)n1ccc(-c2c[nH]c3ncc(N4CCOCC4)cc23)cc1=O]

Step 1: 1,2-Difluoro-4-vinylbenzene

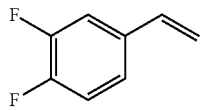

The compound is obtained by the procedure described in Example 1, Step 4, starting from 2.5 g (17.6 mmol) of 3,4-difluorobenzaldehyde instead of 3-fluorobenzaldehyde. 1.38 g of the title compound are obtained.

Yield: 56%.
MH+: Non ionizable.

Step 2: 2-(3,4-Difluorophenyl)oxirane

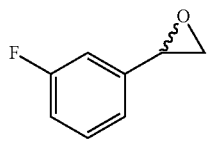

The compound is obtained by the procedure described in Example 1, Step 5, starting from 1.38 g (9.85 mmol) of 1,2-difluoro-4-vinylbenzene (described in the previous step) instead of 1-fluoro-3-vinylbenzene. 884 mg of the title compound are obtained.

Yield: 57%.
MH+: Non ionizable.

Step 3: 1-(3,4-Difluorophenyl)-2-(dimethylamino)ethan-1-ol

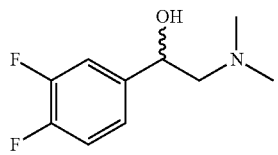

The compound is obtained by the procedure described in Example 1, Step 6, starting from 884 mg (5.66 mmol) of 2-(3,4-difluorophenyl)oxirane (described in the previous step) instead of 2-(3-fluorophenyl)oxirane. 784 mg of the title compound are obtained.

Yield: 69%.
MH+: 202.2 (M+1).

Step 4: 2-Chloro-2-(3,4-difluorophenyl)-N,N-dimethylethan-1-amine

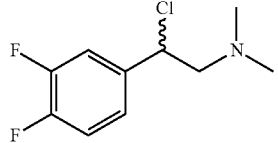

The compound is obtained by the procedure described in Example 1, Step 7, starting from 784 mg (3.90 mmol) of 1-(3,4-difluorophenyl)-2-(dimethylamino)ethan-1-ol (described in the previous step) instead of 2-(dimethylamino)-1-(3-fluorophenyl)ethan-1-ol. 770 mg of the title compound are obtained.

Yield: 90%.
MH+: 220.3; 222.1 (M; M+2).

Step 5: 4-Bromo-1-(1-(3,4-difluorophenyl)-2-(dimethylamino)ethyl)pyridin-2(1H)-one

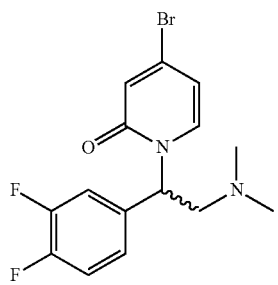

The compound is obtained by the procedure described in Example 1, Step 8, starting from 770 mg (3.51 mmol) of 2-chloro-2-(3,4-difluorophenyl)-N,N-dimethylethan-1- amine (described in the previous step) instead of 2-chloro-2-(3-fluorophenyl)-N,N-dimethylethan-1-amine. 560 mg of the title compound are obtained.

Yield: 45%.

MH+: 357.3; 359.3 (M; M+2).

Step 6: 1-(1-(3,4-Difluorophenyl)-2-(dimethylamino)ethyl)-4-(5-morpholino-1-tosyl-1H-pyrrolo[2,3-b]pyridin-3-yl)pyridin-2(1H)-one

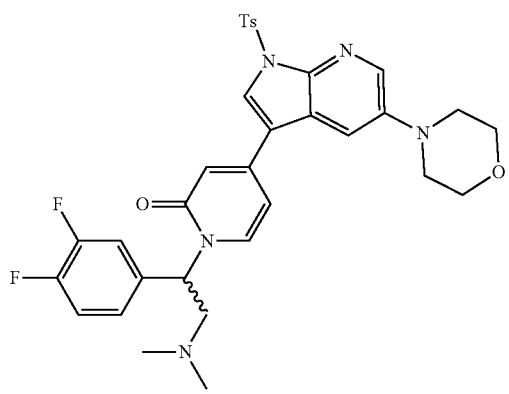

The compound is obtained by the procedure described in Example 1, Step 9, starting from 560 mg (1.57 mmol) of 4-bromo-1-(1-(3,4-difluorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 685 mg of the title compound are obtained.

Yield: 69%.

MH+: 634.5 (M+1).

Step 7: 1-(1-(3,4-Difluorophenyl)-2-(dimethylamino)ethyl)-4-(5-morpholino-1H-pyrrolo[2,3-b]pyridin-3-yl)pyridin-2(1H)-one

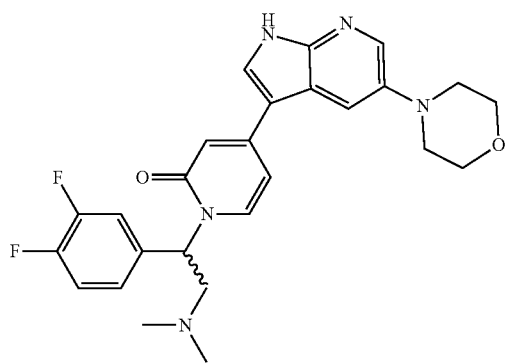 [SMILES: CN(C)CC(c1ccc(F)c(F)c1)n1ccc(-c2c[nH]c3ncc(N4CCOCC4)cc23)cc1=O]

The compound is obtained by the procedure described in Example 3, Step 7, starting from 685 mg (1.08 mmol) of 1-(1-(3,4-difluorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 400 mg of racemate are obtained.

Yield: 77%.

MH+: 480.6 (M+1).

$^1$H NMR (DMSO-d6, 400 MHz): δ 12.03 (br s, 1H); 8.17 (d, J=2.6 Hz, 1H); 8.08 (d, J=2.9 Hz, 1H); 7.73 (d, J=8.1 Hz, 1H); 7.69 (d, J=2.6 Hz, 1H); 7.56-7.50 (m, 1H); 7.46-7.39 (m, 1H); 7.25-7.20 (m, 1H); 6.70-6.65 (m, 2H); 6.20-6.14 (m, 1H); 3.81-3.74 (m, 4H); 3.28-3.21 (m, 1H); 3.17-3.09 (m, 4H); 2.79-2.70 (m, 1H); 2.21 (s, 6H).

Step 8: (S)-1-(1-(3,4-Difluorophenyl)-2-(dimethylamino)ethyl)-4-(5-morpholino-1H-pyrrolo[2,3-b]pyridin-3-yl)pyridin-2(1H)-one

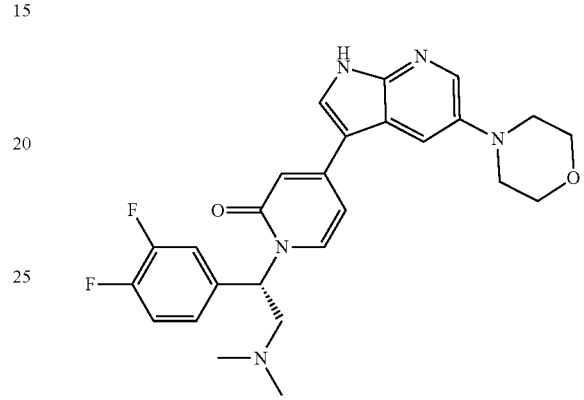

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 16 mg of the title compound are obtained.

MH+: 480.6 (M+1).

$^1$H NMR (DMSO-d6, 400 MHz): δ 12.03 (br s, 1H); 8.17 (d, J=2.6 Hz, 1H); 8.08 (d, J=2.9 Hz, 1H); 7.73 (d, J=8.1 Hz, 1H); 7.69 (d, J=2.6 Hz, 1H); 7.56-7.50 (m, 1H); 7.46-7.39 (m, 1H); 7.25-7.20 (m, 1H); 6.70-6.65 (m, 2H); 6.20-6.14 (m, 1H); 3.81-3.74 (m, 4H); 3.28-3.21 (m, 1H); 3.17-3.09 (m, 4H); 2.79-2.70 (m, 1H); 2.21 (s, 6H).

Example 18: Synthesis of (S)-1-(1-(3,5-difluorophenyl)-2-(dimethylamino)ethyl)-4-(5-morpholino-1H-pyrrolo[2,3-b]pyridin-3-yl)pyridin-2(1H)-one

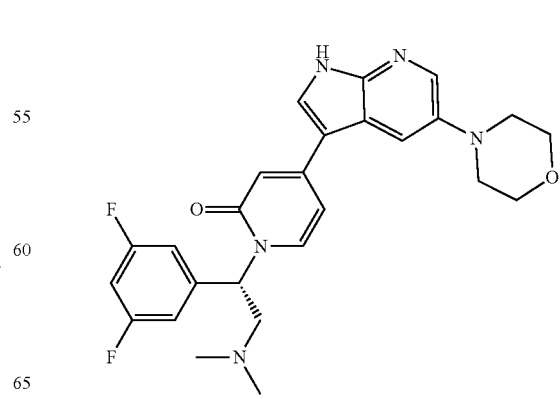

Step 1: 1,3-Difluoro-5-vinylbenzene

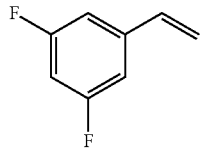

The compound is obtained by the procedure described in Example 1, Step 4, starting from 2.5 g (17.6 mmol) of 3,5-difluorobenzaldehyde instead of 3-fluorobenzaldehyde. 0.52 g of the title compound are obtained.

Yield: 21%.
MH+: Non ionizable.

Step 2: 2-(3,5-Difluorophenyl)oxirane

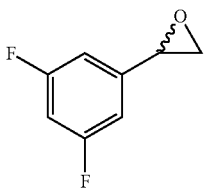 [SMILES: Fc1cc(F)cc(C2CO2)c1]

The compound is obtained by the procedure described in Example 1, Step 5, starting from g (3.71 mmol) of 1,3-difluoro-5-vinylbenzene (described in the previous step) instead of 1-fluoro-3-vinylbenzene. 226 mg of the title compound are obtained.

Yield: 39%.
MH+: Non ionizable.

Step 3: 1-(3,5-Difluorophenyl)-2-(dimethylamino)ethan-1-ol

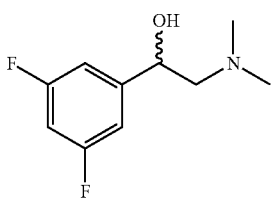

The compound is obtained by the procedure described in Example 1, Step 6, starting from 226 mg (1.45 mmol) of 2-(3,5-difluorophenyl)oxirane (described in the previous step) instead of 2-(3-fluorophenyl)oxirane. 120 mg of the title compound are obtained.

Yield: 41%.
MH+: 202.2 (M+1).

Step 4: 2-Chloro-2-(3,5-difluorophenyl)-N,N-dimethylethan-1-amine

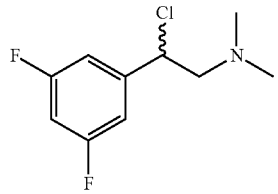

The compound is obtained by the procedure described in Example 1, Step 7, starting from 120 mg (0.60 mmol) of 1-(3,5-difluorophenyl)-2-(dimethylamino)ethan-1-ol (described in the previous step) instead of 2-(dimethylamino)-1-(3-fluorophenyl)ethan-1-ol. 105 mg of the title compound are obtained.

Yield: 80%.
MH+: 220.3; 221.1 (M; M+2).

Step 5: 4-Bromo-1-(1-(3,5-difluorophenyl)-2-(dimethylamino)ethyl)pyridin-2(1H)-one

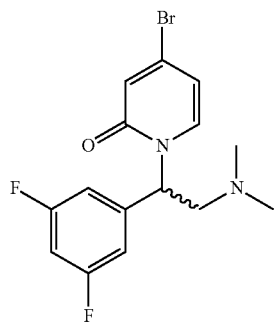 [SMILES: CN(C)CC(c1cc(F)cc(F)c1)n1ccc(Br)cc1=O]

The compound is obtained by the procedure described in Example 1, Step 8, starting from 105 mg (0.48 mmol) of 2-chloro-2-(3,5-difluorophenyl)-N,N-dimethylethan-1-amine (described in the previous step) instead of 2-chloro-2-(3-fluorophenyl)-N,N-dimethylethan-1-amine. 57 mg of the title compound are obtained.

Yield: 33%.
MH+: 3573; 359.3 (M; M+2).

Step 6: 1-(1-(3,5-Difluorophenyl)-2-(dimethylamino)ethyl)-4-(5-morpholino-1-tosyl-1H-pyrrolo[2,3-b]pyridin-3-yl)pyridin-2(1H)-one

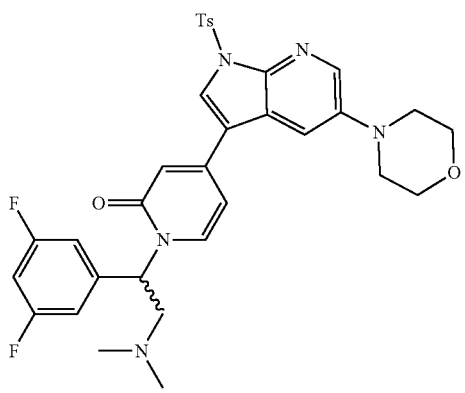 [SMILES: Cc1ccc(S(=O)(=O)n2cc(-c3ccn(C(CN(C)C)c4cc(F)cc(F)c4)c(=O)c3)c3cc(N4CCOCC4)cnc32)cc1]

The compound is obtained by the procedure described in Example 1, Step 9, starting from 57 mg (0.16 mmol) of 4-bromo-1-(1-(3,5-difluorophenyl)-2-(dimethylamino)ethyl)pyridin-2(1H)-one (described in the previous step) instead of 4-bromo-1-(2-(dimethylamino)-1-(3-fluorophenyl)ethyl)pyridin-2(1H)-one. 65 mg of the title compound are obtained.

Yield: 64%.

MH+: 634.5 (M+1).

Step 7: 1-(1-(3,5-Difluorophenyl)-2-(dimethylamino)ethyl)-4-(5-morpholino-1H-pyrrolo[2,3-b]pyridin-3-yl)pyridin-2(1H)-one

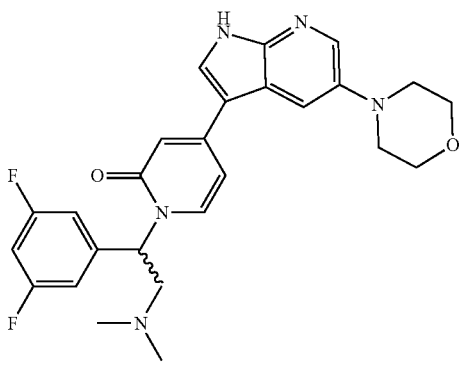 [SMILES: CN(C)CC(c1cc(F)cc(F)c1)n1ccc(-c2c[nH]c3ncc(N4CCOCC4)cc23)cc1=O]

The compound is obtained by the procedure described in Example 3, Step 7, starting from 65 mg (0.10 mmol) of 1-(1-(3,5-difluorophenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 12 mg of racemate are obtained.

Yield: 25%.

MH+: 480.5 (M+1).

$^1$H NMR (DMSO-d6, 400 MHz): δ 12.05 (br s, 1H); 8.16 (d, J=2.6 Hz, 1H); 8.10 (s, 1H); 7.75 (d, J=8.0 Hz, 1H); 7.70 (d, J=2.6 Hz, 1H); 7.22-7.16 (m, 1H); 7.16-7.10 (m, 2H); 6.73-6.66 (m, 2H); 6.21-6.14 (m, 1H); 3.84-3.74 (m, 4H); 3.31-3.22 (m, 1H); 3.17-3.10 (m, 4H); 2.81-2.72 (m, 1H); 2.21 (s, 6H).

Step 8: (S)-1-(1-(3,5-Difluorophenyl)-2-(dimethylamino)ethyl)-4-(5-morpholino-1H-pyrrolo[2,3-b]pyridin-3-yl)pyridin-2(1H)-one

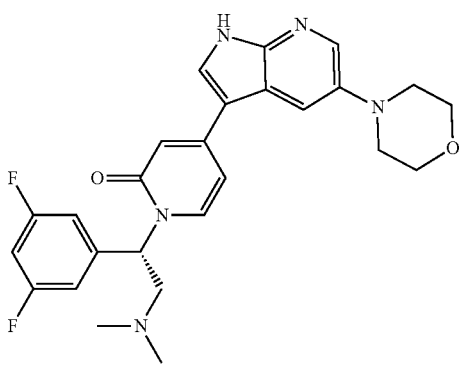 [SMILES: CN(C)C[C@H](c1cc(F)cc(F)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 3 mg of the title compound are obtained starting from 12 mg of the racemate.

MH+: 480.5 (M+1).

$^1$H NMR (DMSO-d6, 400 MHz): δ 12.05 (br s, 1H); 8.16 (d, J=2.6 Hz, 1H); 8.10 (s, 1H); 7.75 (d, J=8.0 Hz, 1H); 7.70 (d, J=2.6 Hz, 1H); 7.22-7.16 (m, 1H); 7.16-7.10 (m, 2H); 6.73-6.66 (m, 2H); 6.21-6.14 (m, 1H); 3.84-3.74 (m, 4H); 3.31-3.22 (m, 1H); 3.17-3.10 (m, 4H); 2.81-2.72 (m, 1H); 2.21 (s, 6H).

Example 19: Synthesis of (S)-1-(1-(3-chlorophenyl)-2-(dimethylamino)ethyl)-5-fluoro-4-(5-morpholino-1H-pyrrolo[2,3-b]pyridin-3-yl)pyridin-2(1H)-one

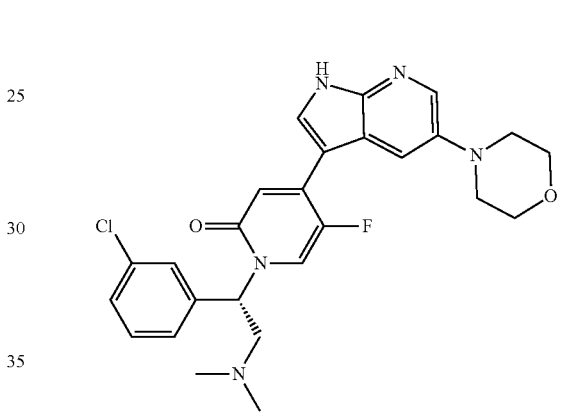

Step 1: 4-Bromo-1-(1-(3-chlorophenyl)-2-(dimethylamino)ethyl)-5-fluoropyridin-2(1H)-one

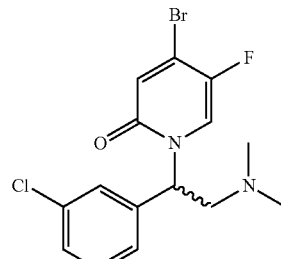

The compound is obtained by the procedure described in Example 1, Step 8, starting from 220 mg (1.15 mmol) of 4-bromo-5-fluoro-1H-pyridin-2-one instead of 4-bromopyridin-2-(1H)-one, and 250 mg (1.15 mmol) of 2-chloro-2-(3-chlorophenyl)-N,N-dimethylethan-1-amine (described in example 2 step 4) instead of 2-chloro-2-(3-fluorophenyl)-N,N-dimethylethan-1-amine. 145 mg of the title compound are obtained.

Yield: 34%.

MH+: 373.3; 375.3; 377.2 (M; M+2; M+4).

Step 2: 1-(1-(3-Chlorophenyl)-2-(dimethylamino)ethyl)-5-fluoro-4-(5-morpholino-1-tosyl-1H-pyrrolo[2,3-b]pyridin-3-yl)pyridin-2(1H)-one

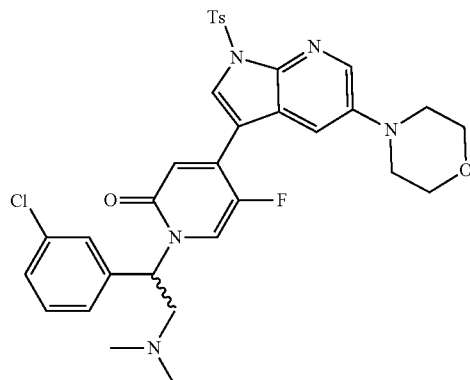

The compound is obtained by the procedure described in Example 1, Step 9, starting from 145 mg (0.39 mmol) of 4-bromo-1-(1-(3-chlorophenyl)-2-(dimethylamino)ethyl)-5-fluoropyridin-2(1H)-one (described in the previous step) instead of 4-bromo-1-(2-(dimethylamino)-1-(3-fluorophenyl)ethyl)pyridin-2(1H)-one. 211 mg of the title compound are obtained.

Yield: 84%.

MH+: 650.5; 651.9; 652.7 (M; M+1; M+2).

Step 3: 1-(1-(3-Chlorophenyl)-2-(dimethylamino)ethyl)-5-fluoro-4-(5-morpholino-1H-pyrrolo[2,3-b]pyridin-3-yl)pyridin-2(1H)-one

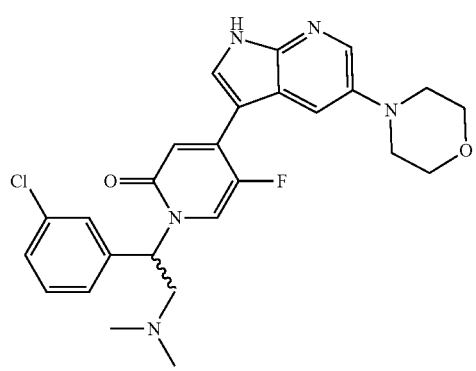 [SMILES: CN(C)CC(c1cccc(Cl)c1)n1cc(F)c(-c2c[nH]c3ncc(N4CCOCC4)cc23)cc1=O]

The compound is obtained by the procedure described in Example 3, Step 7, starting from 211 mg (0.32 mmol) of 1-(1-(3-chlorophenyl)-2-(dimethylamino)ethyl)-5-fluoro-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 95 mg of racemate are obtained.

Yield: 59%.

MH+: 496.5; 498.5 (M; M+2).

¹H NMR (DMSO-d6, 400 MHz): δ 12.16 (br s, 1H); 8.19 (d, J=2.6 Hz, 1H); 8.12 (d, J=7.7 Hz, 1H); 7.92 (d, J=2.8 Hz, 1H); 7.63-7.59 (m, 1H); 7.54-7.51 (m, 1H); 7.44-7.36 (m, 3H); 6.67 (d, J=7.7 Hz, 1H); 6.18-6.10 (m, 1H); 3.82-3.73 (m, 4H); 3.43-3.35 (m, 1H); 3.16-3.08 (m, 4H); 2.72-2.63 (m, 1H); 2.22 (s, 6H).

Step 4: (S)-1-(1-(3-Chlorophenyl)-2-(dimethylamino)ethyl)-5-fluoro-4-(5-morpholino-1H-pyrrolo[2,3-b]pyridin-3-yl)pyridin-2(1H)-one

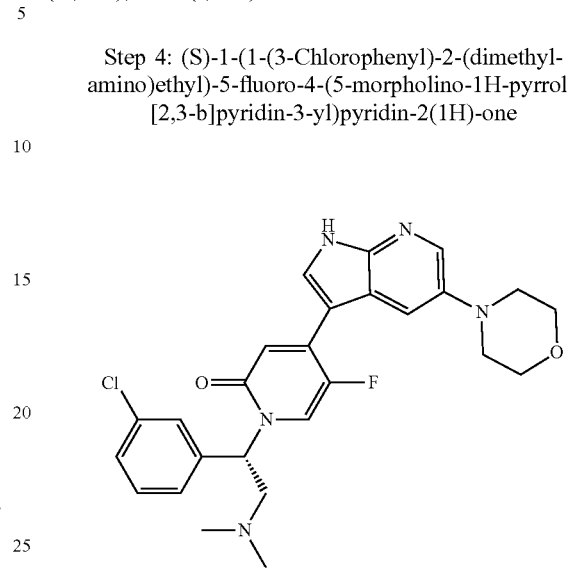

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 34 mg of the title compound are obtained starting from 95 mg of the racemate.

MH+: 496.5; 498.5 (M; M+2).

¹H NMR (DMSO-d6, 400 MHz): δ 12.16 (br s, 1H); 8.19 (d, J=2.6 Hz, 1H); 8.12 (d, J=7.7 Hz, 1H); 7.92 (d, J=2.8 Hz, 1H); 7.63-7.59 (m, 1H); 7.54-7.51 (m, 1H); 7.44-7.36 (m, 3H); 6.67 (d, J=7.7 Hz, 1H); 6.18-6.10 (m, 1H); 3.82-3.73 (m, 4H); 3.43-3.35 (m, 1H); 3.16-3.08 (m, 4H); 2.72-2.63 (m, 1H); 2.22 (s, 6H).

Example 20: Synthesis of (S)-1-(1-(3-chlorophenyl)-2-(dimethylamino)ethyl)-6-methyl-4-(5-morpholino-1H-pyrrolo[2,3-b]pyridin-3-yl)pyridin-2(1H)-one

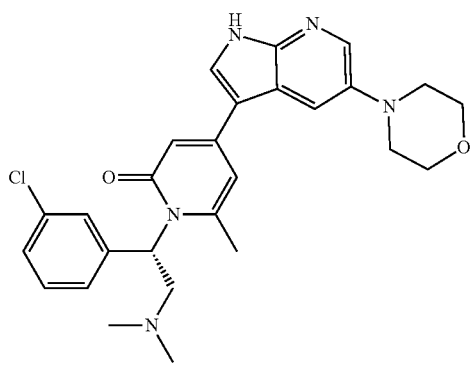 [SMILES: Cc1cc(-c2c[nH]c3ncc(N4CCOCC4)cc23)cc(=O)n1[C@H](CN(C)C)c1cccc(Cl)c1]

101

Step 1: 4-Bromo-1-(1-(3-chlorophenyl)-2-(dimethylamino)ethyl)-6-methylpyridin-2(1H)-one

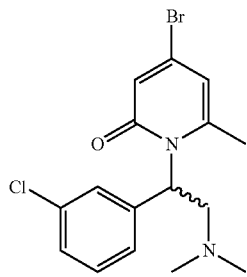 [SMILES: Cc1cc(Br)cc(=O)n1C(CN(C)C)c1cccc(Cl)c1]

The compound is obtained by the procedure described in Example 1, Step 8, starting from 216 mg (1.15 mmol) of 4-bromo-6-methylpyridin-2-(1H)-one instead of 4-bromopyridin-2-(1H)-one, and 250 mg (1.15 mmol) of 2-chloro-2-(3-chlorophenyl)-N,N-dimethylethan-1-amine (described in Example 2, Step 4) instead of 2-chloro-2-(3-fluorophenyl)-N,N-dimethylethan-1-amine. 40 mg of the title compound are obtained.

Yield: 9%.

MH+: 369.3; 371.3; 373.2 (M; M+2; M+4).

Step 2: 1-(1-(3-Chlorophenyl)-2-(dimethylamino)ethyl)-6-methyl-4-(5-morpholino-1-tosyl-1H-pyrrolo[2,3-b]pyridin-3-yl)pyridin-2(1H)-one

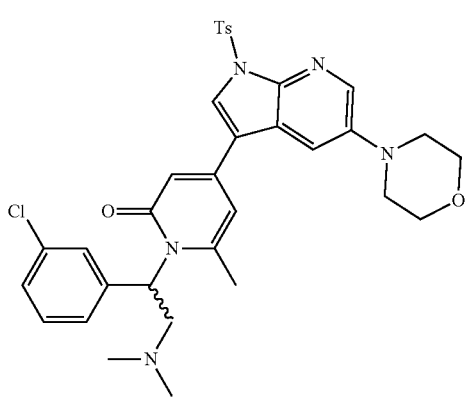 [SMILES: Cc1ccc(S(=O)(=O)n2cc(-c3cc(C)n(C(CN(C)C)c4cccc(Cl)c4)c(=O)c3)c3cc(N4CCOCC4)cnc32)cc1]

The compound is obtained by the procedure described in Example 1, Step 9, starting from 40 mg (0.39 mmol) of 4-bromo-1-(1-(3-chlorophenyl)-2-(dimethylamino)ethyl)-6-methylpyridin-2(1H)-one (described in the previous step) instead of 4-bromo-1-(2-(dimethylamino)-1-(3-fluorophenyl)ethyl)pyridin-2(1H)-one. 78 mg of the title compound are obtained.

Yield: Quantitative.

MH+: 646.6; 648.4 (M; M+2).

102

Step 3: 1-(1-(3-Chlorophenyl)-2-(dimethylamino)ethyl)-6-methyl-4-(5-morpholino-1H-pyrrolo[2,3-b]pyridin-3-yl)pyridin-2(1H)-one

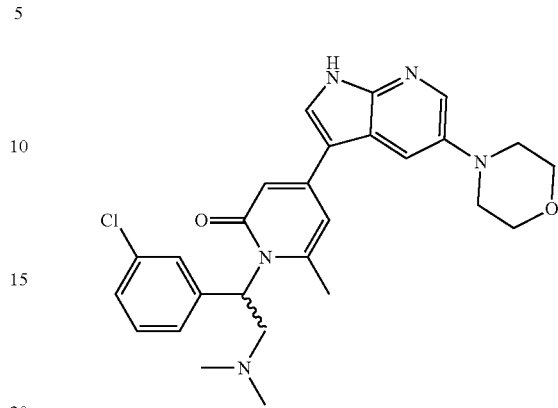

The compound is obtained by the procedure described in Example 3, Step 7, starting from 78 mg (0.12 mmol) of 1-(1-(3-chlorophenyl)-2-(dimethylamino)ethyl)-6-methyl-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 12 mg of racemate are obtained.

Yield: 20%.

MH+: 492.5; 494.5 (M; M+2).

$^1$H NMR (DMSO-d6, 400 MHz): δ 12.05 (br s, 1H); 8.17 (m, 1H); 8.06 (m, 1H); 7.80-7.64 (m, 1H); 7.47-7.18 (m, 4H); 6.77-6.53 (m, 1H); 6.50-6.40 (m, 1H); 5.40-5.30 (m, 1H); 3.87-3.71 (m, 4H); 3.33-3.21 (m, 1H); 3.21-3.07 (m, 4H); 2.90-2.78 (m, 1H); 2.54 (s, 3H); 2.26 (s, 6H).

Step 4: (S)-1-(1-(3-Chlorophenyl)-2-(dimethylamino)ethyl)-6-methyl-4-(5-morpholino-1H-pyrrolo[2,3-b]pyridin-3-yl)pyridin-2(1H)-one

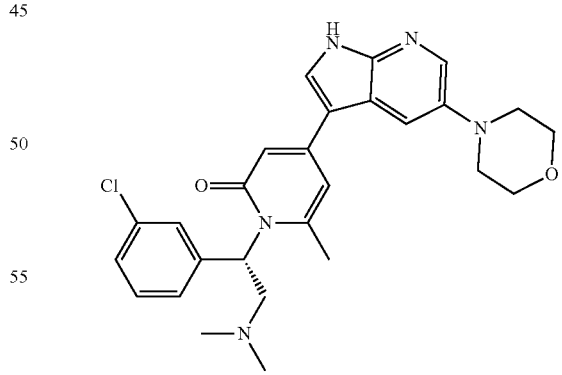

Enantiomers obtained in the previous step are separated by flash chromatography using a Chiralflash IG column and an Heptane/EtOH/DCM/0.1% TEA mixture as the mobile phase. First fraction to be eluted is the (−) (R)-enantiomer, followed by the (+) (S)-enantiomer with ee>98%. 4 mg of the title compound are obtained starting from 12 mg of the racemate.

MH+: 492.5; 494.5 (M; M+2).
¹H NMR (DMSO-d6, 400 MHz): δ 12.05 (br s, 1H); 8.17 (m, 1H); 8.06 (m, 1H); 7.80-7.64 (m, 1H); 7.47-7.18 (m, 4H); 6.77-6.53 (m, 1H); 6.50-6.40 (m, 1H); 5.40-5.30 (m, 1H); 3.87-3.71 (m, 4H); 3.33-3.21 (m, 1H); 3.21-3.07 (m, 4H); 2.90-2.78 (m, 1H); 2.54 (s, 3H); 2.26 (s, 6H).

Example 21: Synthesis of 1-((S)-1-(3-chlorophenyl)-2-(dimethylamino)ethyl)-4-(5-(2-(trifluoromethyl)morpholino)-1H-pyrrolo[2,3-b]pyridin-3-yl)pyridin-2(1H)-one

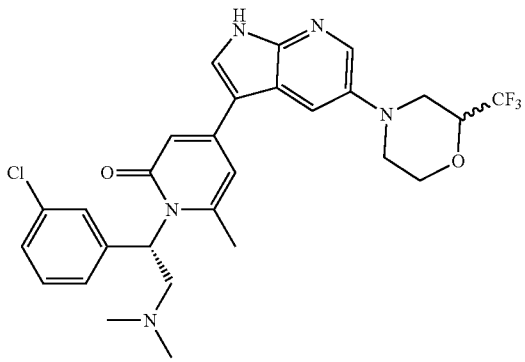 [SMILES: Cc1cc(-c2c[nH]c3ncc(N4CCOC(C(F)(F)F)C4)cc23)cc(=O)n1[C@H](CN(C)C)c1cccc(Cl)c1]

Step 1: 4-(1H-Pyrrolo[2,3-b]pyridin-5-yl)-2-(trifluoromethyl)morpholine

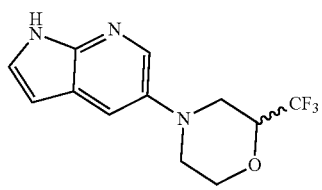 [SMILES: FC(F)(F)C1CN(c2cnc3[nH]ccc3c2)CCO1]

The compound is obtained by the procedure described in Example 1, Step 1, starting from 119 mg (0.62 mmol) of 2-(trifluoromethyl)morpholine hydrochloride instead of morpholine. 161 mg of the title compound are obtained.
Yield: Quantitative.
MH+: 272.4 (M+1).

Step 2: 4-(1-Tosyl-1H-pyrrolo[2,3-b]pyridin-5-yl)-2-(trifluoromethyl)morpholine

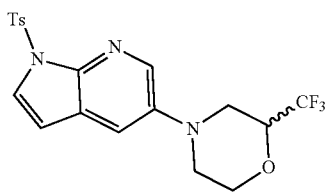 [SMILES: Cc1ccc(S(=O)(=O)n2ccc3cc(N4CCOC(C(F)(F)F)C4)cnc32)cc1]

The compound is obtained by the procedure described in Example 1, Step 2, starting from 161 mg (0.59 mmol) of 4-(1H-pyrrolo[2,3-b]pyridin-5-yl)-2-(trifluoromethyl)morpholine (described in the previous step) instead of 4-(1H-pyrrolo[2,3-b]pyridin-5-yl)morpholine. 305 mg of the title compound are obtained.

Yield: Quantitative.
MH+: 426.6 (M+1).

Step 3: 4-(3-(4,4,5,5-Tetramethyl-1,3,2-dioxaborolan-2-yl)-1-tosyl-1H-pyrrolo[2,3-b]pyridin-5-yl)-2-(trifluoromethyl)morpholine

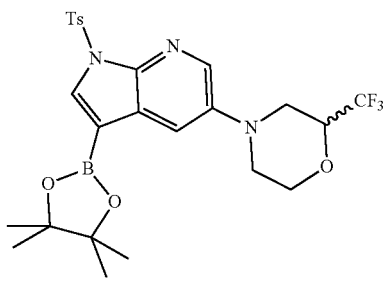 [SMILES: Cc1ccc(S(=O)(=O)n2cc(B3OC(C)(C)C(C)(C)O3)c3cc(N4CCOC(C(F)(F)F)C4)cnc32)cc1]

The compound is obtained by the procedure described in Example 1, Step 3, starting from 305 mg (0.72 mmol) of 4-(1-tosyl-1H-pyrrolo[2,3-b]pyridin-5-yl)-2-(trifluoromethyl)morpholine (described in the previous step) instead of 4-(1-tosyl-1H-pyrrolo[2,3-b]pyridin-5-yl)morpholine. 330 mg of the title compound are obtained.
Yield: 84%.
MH+: 552.5 (M+1).

Step 4: 1-(1-(3-Chlorophenyl)-2-(dimethylamino)ethyl)-4-(1-tosyl-5-(2-(trifluoromethyl)morpholino)-1H-pyrrolo[2,3-b]pyridin-3-yl)pyridin-2(1H)-one

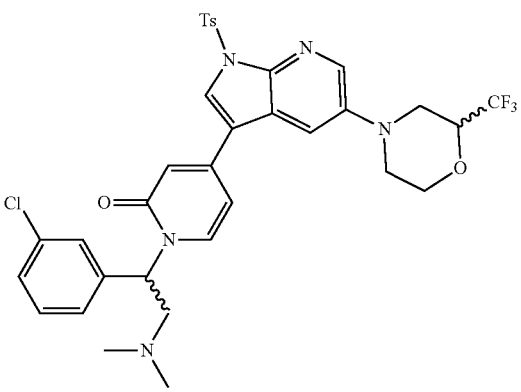 [SMILES: Cc1ccc(S(=O)(=O)n2cc(-c3ccn(C(CN(C)C)c4cccc(Cl)c4)c(=O)c3)c3cc(N4CCOC(C(F)(F)F)C4)cnc32)cc1]

The compound is obtained by the procedure described in Example 1, Step 9, starting from 160 mg (0.29 mmol) of 4-(3-(4,4,5,5-tetramethyl-1,3,2-dioxaborolan-2-yl)-1-tosyl-1H-pyrrolo[2,3-b]pyridin-5-yl)-2-(trifluoromethyl)morpholine (described in the previous step) instead of 4-(3-(4,4,5,5-tetramethyl-1,3,2-dioxaborolan-2-yl)-1-tosyl-1H-pyrrolo[2,3-b]pyridin-5-yl)morpholine, and 103 mg (0.29 mmol) of 4-bromo-1-(1-(3-chlorophenyl)-2-(dimethylamino)ethyl)pyridin-2(1H)-one (described in Example 2, Step 5) instead of 4-bromo-1-(2-(dimethylamino)-1-(3-fluorophenyl)ethyl)pyridin-2(1H)-one. 155 mg of the title compound are obtained.

Yield: 76%.
MH+: 700.6; 701.9; 702.7 (M; M+1; M+2).

Step 5: 1-(1-(3-Chlorophenyl)-2-(dimethylamino)ethyl)-4-(5-(2-(trifluoromethyl)morpholino)-1H-pyrrolo[2,3-b]pyridin-3-yl)pyridin-2(1H)-one

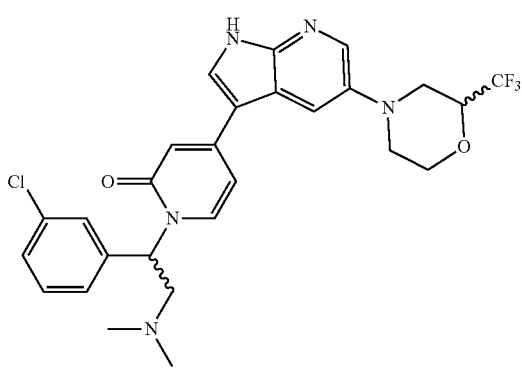 [SMILES: CN(C)CC(c1cccc(Cl)c1)n1ccc(-c2c[nH]c3ncc(N4CCOC(C(F)(F)F)C4)cc23)cc1=O]

The compound is obtained by the procedure described in Example 3, Step 7, starting from 155 mg (0.22 mmol) of 1-(1-(3-chlorophenyl)-2-(dimethylamino)ethyl)-4-(1-tosyl-5-(2-(trifluoromethyl)morpholino)-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 73 mg of racemate are obtained.
Yield: 60%.
MH+: 546.6; 548.6 (M; M+2).
$^1$H NMR (DMSO-d6, 400 MHz): δ 12.10 (br s, 1H); 8.21 (d, J=2.5 Hz, 1H); 8.12 (s, 1H); 7.83 (d, J=2.5 Hz, 1H); 7.76 (d, J=7.4 Hz, 1H); 7.49-7.44 (m, 1H); 7.44-7.33 (m, 3H); 6.76-6.66 (m, 2H); 6.23-6.13 (m, 1H); 4.46-4.33 (m, 1H); 4.15-4.05 (m, 1H); 3.91-3.78 (m, 1H); 3.78-3.63 (m, 1H); 3.54-3.44 (m, 1H); 3.32-3.23 (m, 1H); 2.96-2.79 (m, 2H); 2.79-2.69 (m, 1H); 2.21 (s, 6H).

Step 6: 1-((S)-1-(3-Chlorophenyl)-2-(dimethylamino)ethyl)-4-(5-(2-(trifluoromethyl)morpholino)-1H-pyrrolo[2,3-b]pyridin-3-yl)pyridin-2(1H)-one

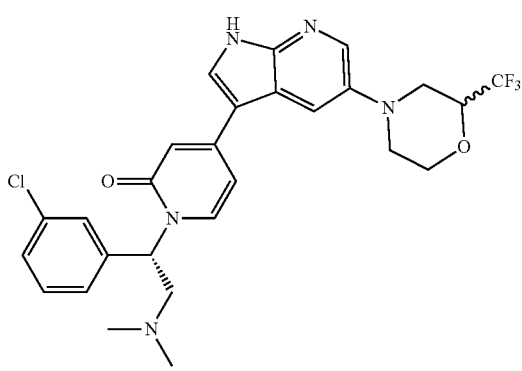 [SMILES: CN(C)C[C@H](c1cccc(Cl)c1)n1ccc(-c2c[nH]c3ncc(N4CCOC(C(F)(F)F)C4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 30 mg of the title compound are obtained starting from 73 mg of the racemate.

MH+: 546.6; 548.6 (M; M+2).
$^1$H NMR (DMSO-d6, 400 MHz): δ 12.10 (br s, 1H); 8.21 (d, J=2.5 Hz, 1H); 8.12 (s, 1H); 7.83 (d, J=2.5 Hz, 1H); 7.76 (d, J=7.4 Hz, 1H); 7.49-7.44 (m, 1H); 7.44-7.33 (m, 3H); 6.76-6.66 (m, 2H); 6.23-6.13 (m, 1H); 4.46-4.33 (m, 1H); 4.15-4.05 (m, 1H); 3.91-3.78 (m, 1H); 3.78-3.63 (m, 1H); 3.54-3.44 (m, 1H); 3.32-3.23 (m, 1H); 2.96-2.79 (m, 2H); 2.79-2.69 (m, 1H); 2.21 (s, 6H).

Example 22: Synthesis of (S)-1-(1-(3-chlorophenyl)-2-(dimethylamino)ethyl)-4-(4-fluoro-5-morpholino-1H-pyrrolo[2,3-b]pyridin-3-yl)pyridin-2(1H)-one

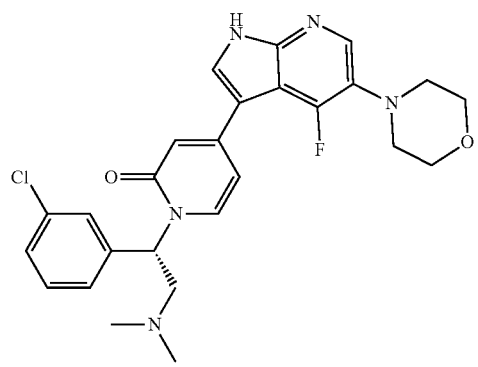 [SMILES: CN(C)C[C@H](c1cccc(Cl)c1)n1ccc(-c2c[nH]c3ncc(N4CCOCC4)c(F)c23)cc1=O]

Step 1: 4-(4-Fluoro-1H-pyrrolo[2,3-b]pyridin-5-yl)morpholine

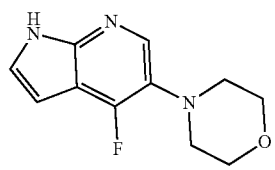 [SMILES: Fc1c(N2CCOCC2)cnc2[nH]ccc12]

The compound is obtained by the procedure described in Example 1, Step 1, starting from 145 mg (0.67 mmol) of 5-bromo-4-fluoro-1H-pyrrolo[2,3-b]pyridine instead of 5-bromo-1H-pyrrolo[2,3-b]pyridine. 35 mg of the title compound are obtained.
Yield: 23%.
MH+: 222.3 (M+1).

Step 2: 4-(4-Fluoro-1-tosyl-1H-pyrrolo[2,3-b]pyridin-5-yl)morpholine

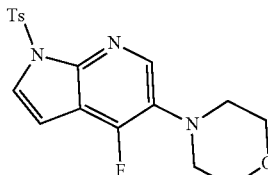

The compound is obtained by the procedure described in Example 1, Step 2, starting from 35 mg (0.16 mmol) of 4-(4-fluoro-1H-pyrrolo[2,3-b]pyridin-5-yl)morpholine (described in the previous step) instead of 4-(1H-pyrrolo[2,3-b]pyridin-5-yl)morpholine. 53 mg of the title compound are obtained.

Yield: 53%.
MH+: 376.4 (M+1).

Step 3: 4-(4-Fluoro-3-(4,4,5,5-tetramethyl-1,3,2-dioxaborolan-2-yl)-1-tosyl-1H-pyrrolo[2,3-b]pyridin-5yl)morpholine

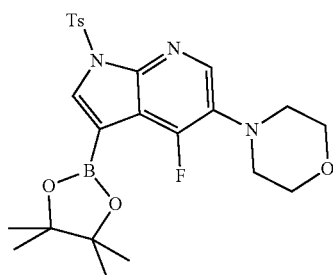

The compound is obtained by the procedure described in Example 1, Step 3, starting from 53 mg (0.14 mmol) of 4-(4-fluoro-1-tosyl-1H-pyrrolo[2,3-b]pyridin-5-yl)morpholine (described in the previous step) instead of 4-(1-tosyl-1H-pyrrolo[2,3-b]pyridin-5-yl)morpholine. 22 mg of the title compound are obtained.

Yield: 31%.
MH+: 502.5 (M+1).

Step 4: 1-(1-(3-Chlorophenyl)-2-(dimethylamino)ethyl)-4-(4-fluoro-5-morpholino-1-tosyl-1H-pyrrolo[2,3-b]pyridin-3-yl)pyridin-2(1H)-one

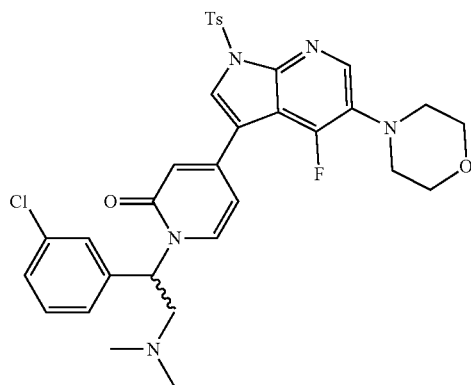 [SMILES: Cc1ccc(S(=O)(=O)n2cc(-c3ccn(C(CN(C)C)c4cccc(Cl)c4)c(=O)c3)c3c(F)c(N4CCOCC4)cnc32)cc1]

The compound is obtained by the procedure described in Example 1, Step 9, starting from 22 mg (0.044 mmol) of 1-(1-(3-chlorophenyl)-2-(dimethylamino)ethyl)-4-(4-fluoro-5-morpholino-1-tosyl-1H-pyrrolo[2,3-b]pyridin-3-yl)pyridin-2(1H)-one (described in the previous step) instead of 4-(3-(4,4,5,5-tetramethyl-1,3,2-dioxaborolan-2-yl)-1-tosyl-1H-pyrrolo[2,3-b]pyridin-5-yl)morpholine, and 16 mg (0.044 mmol) of 4-bromo-1-(1-(3-chlorophenyl)-2-(dimethylamino)ethyl)pyridin-2(1H)-one (described in Example 2, Step 5) instead of 4-bromo-1-(2-(dimethylamino)-1-(3-fluorophenyl)ethyl)pyridin-2(1H)-one. 17 mg of the title compound are obtained.

Yield: 61%.
MH+: 700.6; 701.9; 702.8 (M; M+1; M+2).

Step 5: 1-(1-(3-Chlorophenyl)-2-(dimethylamino)ethyl)-4-(4-fluoro-5-morpholino-1H-pyrrolo[2,3-b]pyridin-3-yl)pyridin-2(1H)-one

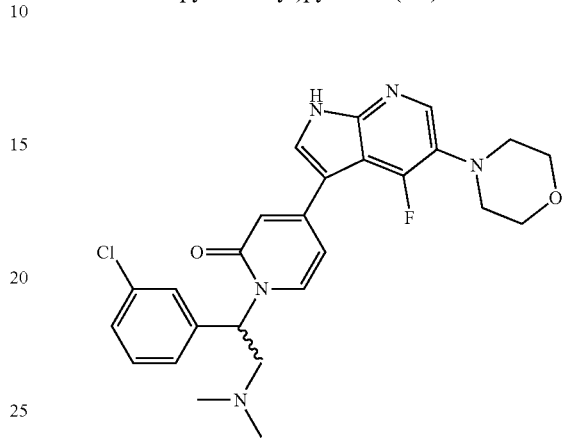

The compound is obtained by the procedure described in Example 3, Step 7, starting from 17 mg (0.026 mmol) of 1-(1-(3-chlorophenyl)-2-(dimethylamino)ethyl)-4-(4-fluoro-5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 5 mg of racemate are obtained.

Yield: 42%.
MH+: 496.6; 498.5 (M; M+2)

Step 6: (S)-1-(1-(3-Chlorophenyl)-2-(dimethylamino)ethyl)-4-(4-fluoro-5-morpholino-1H-pyrrolo[2,3-b]pyridin-3-yl)pyridin-2(1H)-one

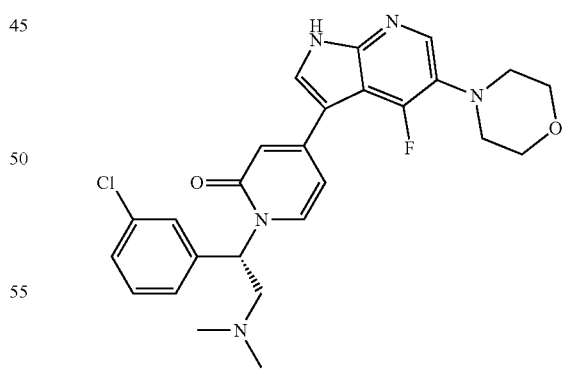

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 2 mg of the title compound are obtained starting from 5 mg of the racemate.
MH+: 496.6; 498.5 (M; M+2)

Example 23: Synthesis of (S)-1-(1-(3-chloro-5-(methoxymethyl)phenyl)-2-(dimethylamino)ethyl)-4-(5-morpholino-1H-pyrrolo[2,3-b]pyridin-3-yl)pyridin-2(1H)-one

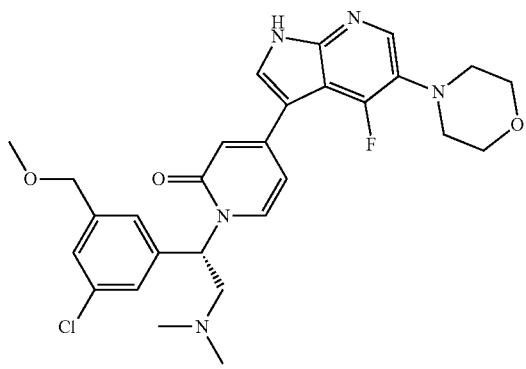 [SMILES: COCc1cc(Cl)cc([C@@H](CN(C)C)n2ccc(-c3c[nH]c4ncc(N5CCOCC5)c(F)c34)cc2=O)c1]

Step 1: 3-Chloro-5-(methoxymethyl)benzonitrile

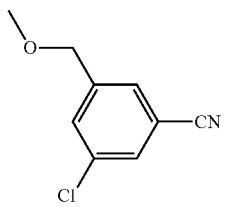

500 mg (2.98 mmol, 1 eq) of 3-chloro-5-cyanobenzyl alcohol are dissolved in 30 ml of dry DMF and the solution is cooled to 0° C. with an ice/water bath. 155 mg (3.88 mmol, 1.3 eq) of sodium hydride (60% in paraffin oil) are slowly added and the slurry is stirred for 15 min. Then, 441 µL (8.95 mmol) of methyl iodide are then added at 0° C. and the mixture is stirred for another 30 min. The mixture is diluted with 100 ml of Et$_2$O, washed 3 times with water and once with brine. Organic layer is dried over Na$_2$SO$_4$, filtered, and evaporated under reduced pressure to give 664 mg of the crude compound which is purified by flash chromatography using a silica gel column and an Et$_2$O/hexane mixture as eluent. 497 mg of the title compound are obtained.

Yield: 92%.

MH+: 182.2 (M+1).

Step 2: 3-Chloro-5-(methoxymethyl)benzaldehyde

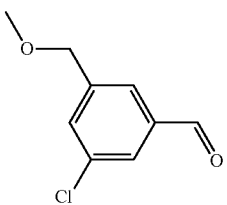

437 mg (2.40 mmol, 1 eq) of 3-chloro-5-(methoxymethyl)benzonitrile (described in the previous step) are dissolved in a mixture of 1.25 ml of pyridine, 1.25 mL of acetic acid and 1.25 mL of water. The solution is cooled to 0° C. and 2.04 g (19.25 mmol, 8 eq) of NaH$_2$PO$_2$ monohydrate are added, followed by a small amount of Ni Raney (50% in water). The reaction is stirred for 1 h at 0° C. and at room temperature for another 3 h. The mixture is filtrated on Celite and the precipitate is rinsed several times with EtOAc. Combined filtrates are washed with a saturated NaHCO$_3$ solution and the organic layer is dried over Na$_2$SO$_4$, filtered, and evaporated under reduced pressure. Crude compound is finally purified by flash chromatography using a silica gel column and an EtOAc/hexane mixture as eluent. 278 mg of the title compound are obtained.

Yield: 59%.

MH+: 185.2; 187.1 (M+1; M+3).

Step 3: 1-Chloro-3-(methoxymethyl)-5-vinylbenzene

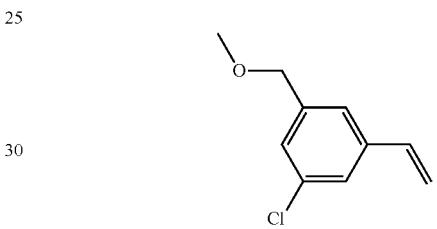

The compound is obtained by the procedure described in Example 1, Step 4, starting from 278 mg (1.50 mmol) of 3-chloro-5-(methoxymethyl)benzaldehyde (described in the previous step) instead of 3-fluorobenzaldehyde. 100 mg of the title compound are obtained.

Yield: 36%.

MH+: Non ionizable.

Step 4: 2-(3-Chloro-5-(methoxymethyl)phenyl)oxirane

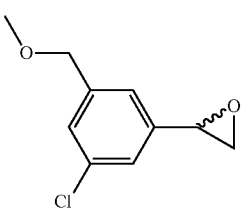

The compound is obtained by the procedure described in Example 1, Step 5, starting from 100 mg (0.55 mmol) of 1-chloro-3-(methoxymethyl)-5-vinylbenzene (described in the previous step) instead of 1-fluoro-3-vinylbenzene. 66 mg of the title compound are obtained.

Yield: 60%.

MH+: Non ionizable.

Step 5: 1-(3-Chloro-5-(methoxymethyl)phenyl)-2-(dimethylamino)ethan-1-ol

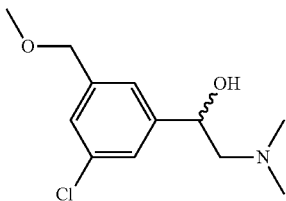

The compound is obtained by the procedure described in Example 1, Step 6, starting from 66 mg (0.33 mmol) of 2-(3-chloro-5-(methoxymethyl)phenyl)oxirane (described in the previous step) instead of 2-(3-fluorophenyl)oxirane. 58 mg of the title compound are obtained.
Yield: 71%.
MH+: 244.3; 246.2 (M; M+2).

Step 6: 2-Chloro-2-(3-chloro-5-(methoxymethyl)phenyl)-N,N-dimethylethan-1-amine

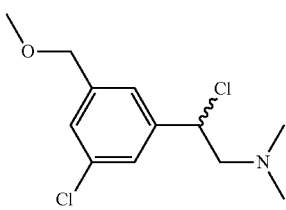

The compound is obtained by the procedure described in Example 1, Step 7, starting from 58 mg (0.24 mmol) of 1-(3-chloro-5-(methoxymethyl)phenyl)-2-(dimethylamino)ethan-1-ol (described in the previous step) instead of 2-(dimethylamino)-1-(3-fluorophenyl)ethan-1-ol. 70 mg of the title compound are obtained.
Yield: Quantitative.
MH+: 262.3; 264.3 (M; M+2).

Step 7: 1-(1-(3-Chloro-5-(methoxymethyl)phenyl)-2-(dimethylamino)ethyl)-4-iodopyridin-2(1H)-one

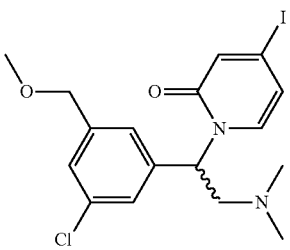

The compound is obtained by the procedure described in Example 6, Step 5, starting from 70 mg (0.27 mmol) of 2-chloro-2-(3-chloro-5-(methoxymethyl)phenyl)-N,N-dimethylethan-1-amine (described in the previous step) instead of 2-chloro-2-(3-iodophenyl)-N,N-dimethylethan-1-amine. mg of the title compound are obtained.

Yield: 33%.
MH+: 448.2; 450.3 (M; M+2).

Step 8: 1-(1-(3-Chloro-5-(methoxymethyl)phenyl)-2-(dimethylamino)ethyl)-4-(5-morpholino-1-tosyl-1H-pyrrolo[2,3-b]pyridin-3-yl)pyridin-2(1H)-one

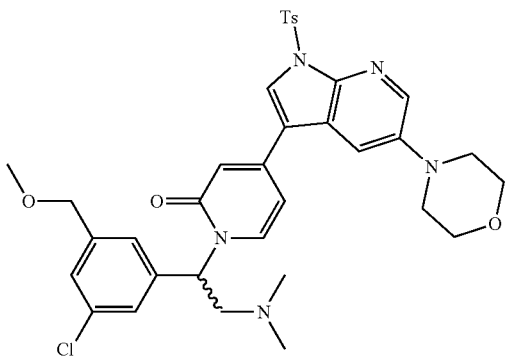 [SMILES: COCc1cc(Cl)cc(C(CN(C)C)n2ccc(-c3cn(S(=O)(=O)c4ccc(C)cc4)c4ncc(N5CCOCC5)cc34)cc2=O)c1]

The compound is obtained by the procedure described in Example 1, Step 9, starting from 136 mg (0.30 mmol) of 1-(1-(3-chloro-5-(methoxymethyl)phenyl)-2-(dimethylamino)ethyl)-4-iodopyridin-2(1H)-one (described in the previous step) instead of 4-bromo-1-(2-(dimethylamino)-1-(3-fluorophenyl)ethyl)pyridin-2(1H)-one. 168 mg of the title compound are obtained.
Yield: 81%.
MH+: 676.5; 678.5 (M; M+2).

Step 9: 1-(1-(3-Chloro-5-(methoxymethyl)phenyl)-2-(dimethylamino)ethyl)-4-(5-morpholino-1H-pyrrolo[2,3-b]pyridin-3-yl)pyridin-2(1H)-one

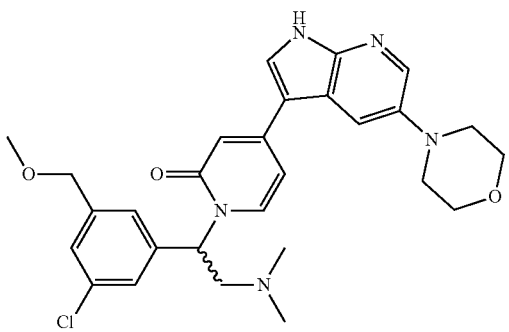 [SMILES: COCc1cc(Cl)cc(C(CN(C)C)n2ccc(-c3c[nH]c4ncc(N5CCOCC5)cc34)cc2=O)c1]

The compound is obtained by the procedure described in Example 3, Step 7, starting from 150 mg (0.22 mmol) of 1-(1-(3-chloro-5-(methoxymethyl)phenyl)-2-(dimethylamino)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 57 mg of racemate are obtained.
Yield: 49%.
MH+: 522.5; 524.7 (M; M+2).
$^1$H NMR (DMSO-d6, 400 MHz): δ 12.06 (br s, 1H); 8.17 (d, J=2.5 Hz, 1H); 8.10 (s, 1H); 7.76 (d, J=8.1 Hz, 1H); 7.70

(d, J=2.6 Hz, 1H); 7.42-7.37 (m, 1H); 7.33-7.27 (m, 2H); 6.73-6.65 (m, 2H); 6.22-6.12 (m, 1H); 4.40 (s, 2H); 3.83-3.73 (m, 4H); 3.43-3.35 (m, 1H); 3.29 (s, 3H); 3.18-3.08 (m, 4H); 2.75-2.64 (m, 1H); 2.20 (s, 6H).

Step 10: (S)-1-(1-(3-Chloro-5-(methoxymethyl)phenyl)-2-(dimethylamino)ethyl)-4-(5-morpholino-1H-pyrrolo[2,3-b]pyridin-3-yl)pyridin-2(1H)-one

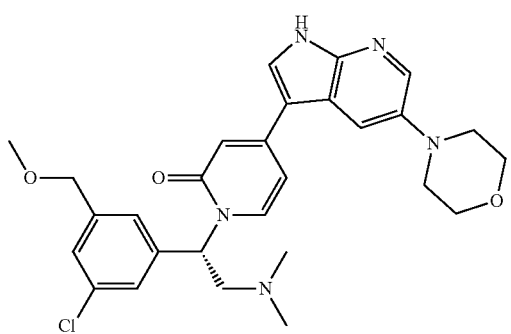 [SMILES: COCc1cc(Cl)cc([C@@H](CN(C)C)n2ccc(-c3c[nH]c4ncc(N5CCOCC5)cc34)cc2=O)c1]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 24 mg of the title compound are obtained starting from 57 mg of the racemate.

MH+: 522.5; 524.7 (M; M+2).

$^1$H NMR (DMSO-d6, 400 MHz): δ 12.06 (br s, 1H); 8.17 (d, J=2.5 Hz, 1H); 8.10 (s, 1H); 7.76 (d, J=8.1 Hz, 1H); 7.70 (d, J=2.6 Hz, 1H); 7.42-7.37 (m, 1H); 7.33-7.27 (m, 2H); 6.73-6.65 (m, 2H); 6.22-6.12 (m, 1H); 4.40 (s, 2H); 3.83-3.73 (m, 4H); 3.43-3.35 (m, 1H); 3.29 (s, 3H); 3.18-3.08 (m, 4H); 2.75-2.64 (m, 1H); 2.20 (s, 6H).

Example 24: Synthesis of (S)-1-(2-(aziridin-1-yl)-1-(3-chlorophenyl)ethyl)-4-(5-morpholino-1H-pyrrolo[2,3-b]pyridin-3-yl)pyridin-2(1H)-one

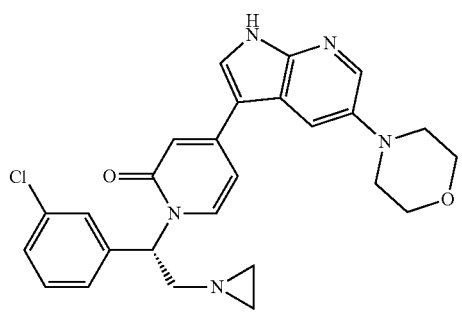 [SMILES: O=c1cc(-c2c[nH]c3ncc(N4CCOCC4)cc23)ccn1[C@H](CN1CC1)c1cccc(Cl)c1]

Step 1: 2-(Aziridin-1-yl)-1-(3-chlorophenyl)ethan-1-ol

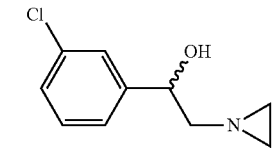

To a solution of 450 mg (3.88 mmol, 2 eq) of 2-chloroethanamine hydrochloride in 1 ml of water, is added a solution of 310 mg (7.76 mmol, 4 eq) of sodium hydroxide in 1 ml of water. The resulting mixture is stirred at 50° C. for 45 min. Then a solution of 300 mg (1.94 mmol, 1 eq) of 2-(3-chlorophenyl)oxirane (described in Example 2, Step 2) in 3 ml of 1,4-dioxane is added. The mixture is stirred at 50° C. for 4 h. Reaction is then diluted with water and extracted with DCM. Combined organic layers are washed 3 times with water, dried over Na$_2$SO$_4$, filtered, and evaporated under reduced pressure. Crude compound is used in the next step without further purification. 460 mg of the title compound are obtained.

Yield: Quantitative.
MH+: 198.1; 200.1 (M; M+2).

Step 2: 1-(2-Bromo-2-(3-chlorophenyl)ethyl)aziridine

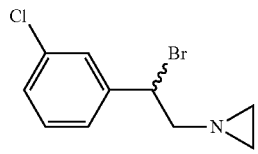 [SMILES: OC(CN1CC1)c1cccc(Cl)c1]

To a solution of 165 mg (0.83 mmol, 1 eq) of 2-(aziridin-1-yl)-1-(3-chlorophenyl)ethan-1-ol (described in the previous step) in 3 ml of dry DCM, placed at 0° C. with an ice/water bath, are added dropwise 129 µl (1.67 mmol, 2 eq) of thionyl bromide. The resulting mixture is allowed to reach room temperature over the night. Then reaction mixture is directly purified by flash chromatography using a silica gel column and an DCM/MeOH mixture as eluent. 176 mg of the title compound are obtained.

Yield: 76%.
MH+: 260.2; 262.2; 264.1 (M; M+2; M+4).

Step 3: 1-(2-(Aziridin-1-yl)-1-(3-chlorophenyl)ethyl)-4-bromopyridin-2(1H)-one

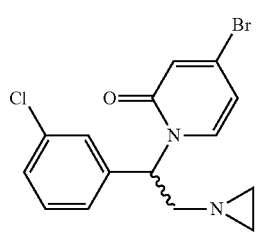 [SMILES: O=c1cc(Br)ccn1C(CN1CC1)c1cccc(Cl)c1]

The compound is obtained by the procedure described in Example 1, Step 8, starting from 166 mg (0.64 mmol) of 1-(2-bromo-2-(3-chlorophenyl)ethyl)aziridine (described in the previous step) instead of 2-chloro-2-(3-fluorophenyl)-N,N-dimethylethan-1-amine. 77 mg of the title compound are obtained.

Yield: 34%.
MH+: 353.3; 355.3; 357.2 (M; M+2; M+4).

Step 4: 1-(2-(Aziridin-1-yl)-1-(3-chlorophenyl)ethyl)-4-(5-morpholino-1-tosyl-1H-pyrrolo[2,3-b]pyridin-3-yl)pyridin-2(1H)-one

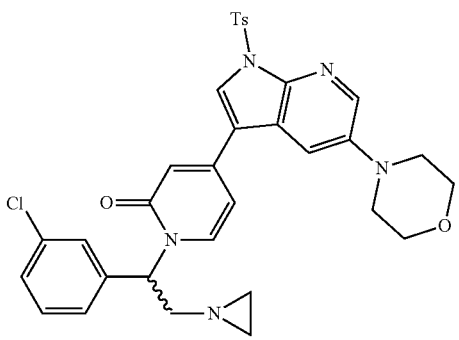 [SMILES: Cc1ccc(S(=O)(=O)n2cc(-c3ccn(C(CN4CC4)c4cccc(Cl)c4)c(=O)c3)c3cc(N4CCOCC4)cnc32)cc1]

The compound is obtained by the procedure described in Example 1, Step 9, starting from 77 mg (0.23 mmol) of 1-(2-(aziridin-1-yl)-1-(3-chlorophenyl)ethyl)-4-bromopyridin-2(1H)-one (described in the previous step) instead of 4-bromo-1-(2-(dimethylamino)-1-(3-fluorophenyl)ethyl)pyridin-2(1H)-one. 69 mg of the title compound are obtained.

Yield: 48%.
MH+: 630.6; 631.9; 632.7 (M; M+1; M+2).

Step 5: 1-(2-(Aziridin-1-yl)-1-(3-chlorophenyl)ethyl)-4-(5-morpholino-1H-pyrrolo[2,3-b]pyridin-3-yl)pyridin-2(1H)-one

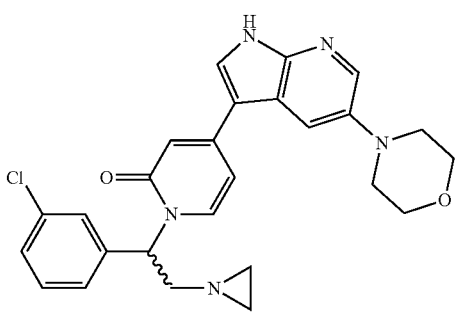 [SMILES: O=c1cc(-c2c[nH]c3ncc(N4CCOCC4)cc23)ccn1C(CN1CC1)c1cccc(Cl)c1]

The compound is obtained by the procedure described in Example 3, Step 7, starting from 69 mg (0.11 mmol) of 1-(2-(aziridin-1-yl)-1-(3-chlorophenyl)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 32 mg of racemate are obtained.

Yield: 61%.
MH+: 476.5; 478.5 (M; M+2).

¹H NMR (DMSO-d6, 400 MHz): δ 12.03 (br s, 1H); 8.17 (d, J=2.5 Hz, 1H); 8.03 (s, 1H); 7.67 (d, J=2.6 Hz, 1H); 7.52 (d, J=7.2 Hz, 1H); 7.30-7.22 (m, 2H); 7.21-7.12 (m, 2H); 6.67-6.63 (m, 1H); 6.55-6.50 (m, 1H); 4.11-4.00 (m, 2H); 3.84-3.74 (m, 4H); 3.19-3.10 (m, 4H); 2.77-2.58 (m, 3H); 1.83-1.74 (m, 2H).

Step 6: (S)-1-(2-(Aziridin-1-yl)-1-(3-chlorophenyl)ethyl)-4-(5-morpholino-1H-pyrrolo[2,3-b]pyridin-3-yl)pyridin-2(1H)-one

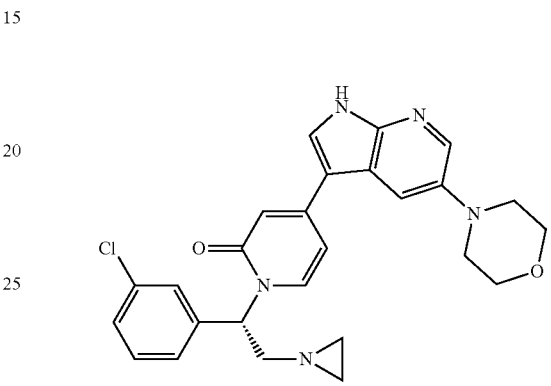

Enantiomers obtained in the previous step are separated by flash chromatography using a Chiralflash IG column and an Hexane/IPA/0.1% TEA mixture as the mobile phase. First fraction to be eluted is the (−) (R)-enantiomer, followed by the (+) (S)-enantiomer with ee>98%. 14 mg of the title compound are obtained starting from 32 mg of the racemate.

MH+: 476.5; 478.5 (M; M+2).

¹H NMR (DMSO-d6, 400 MHz): δ 12.03 (br s, 1H); 8.17 (d, J=2.5 Hz, 1H); 8.03 (s, 1H); 7.67 (d, J=2.6 Hz, 1H); 7.52 (d, J=7.2 Hz, 1H); 7.30-7.22 (m, 2H); 7.21-7.12 (m, 2H); 6.67-6.63 (m, 1H); 6.55-6.50 (m, 1H); 4.11-4.00 (m, 2H); 3.84-3.74 (m, 4H); 3.19-3.10 (m, 4H); 2.77-2.58 (m, 3H); 1.83-1.74 (m, 2H).

Example 25: Synthesis of (S)-3-(2-(dimethylamino)-1-(4-(5-morpholino-1H-pyrrolo[2,3-b]pyridin-3-yl)-2-oxopyridin-1(2H)-yl)ethyl)benzonitrile

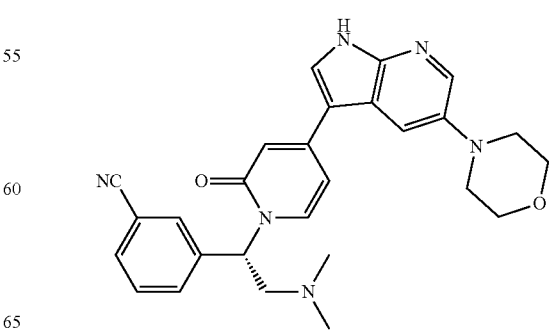

Step 1: 3-Vinylbenzonitrile

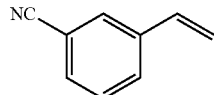

The compound is obtained by the procedure described in Example 1, Step 4, starting from g (3.8 mmol) of 3-cyanobenzaldehyde instead of 3-fluorobenzaldehyde. 180 mg of the title compound are obtained.
Yield: 37%.
MH+: Non ionizable.

Step 2: 3-(Oxiran-2-yl)benzonitrile

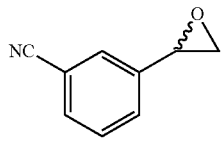 [SMILES: N#Cc1cccc(C2CO2)c1]

The compound is obtained by the procedure described in Example 1, Step 5, starting from 180 mg (1.39 mmol) of 3-vinylbenzonitrile (described in the previous step) instead of 1-fluoro-3-vinylbenzene. 136 mg of the title compound are obtained.
Yield: 67%.
MH+: Non ionizable.

Step 3: 3-(2-(Dimethylamino)-1-hydroxyethyl)benzonitrile

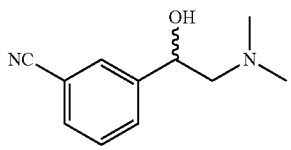

The compound is obtained by the procedure described in Example 1, Step 6, starting from 136 mg (0.94 mmol) of 3-(oxiran-2-yl)benzonitrile (described in the previous step) instead of 2-(3-fluorophenyl)oxirane. 156 mg of the title compound are obtained.
Yield: 88%.
MH+: 191.2 (M+1).

Step 4: 3-(1-Chloro-2-(dimethylamino)ethyl)benzonitrile

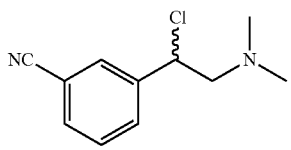

The compound is obtained by the procedure described in Example 1, Step 7, starting from 156 mg (0.82 mmol) of 3-(2-(dimethylamino)-1-hydroxyethyl)benzonitrile (described in the previous step) instead of 2-(dimethylamino)-1-(3-fluorophenyl)ethan-1-ol. 188 mg of the title compound are obtained.
Yield: Quantitative.
MH+: 209.2; 211.1 (M; M+2).

Step 5: 3-(1-(4-Bromo-2-oxopyridin-1(2H)-yl)-2-(dimethylamino)ethyl)benzonitrile

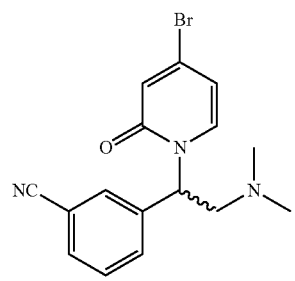 [SMILES: CN(C)CC(c1cccc(C#N)c1)n1ccc(Br)cc1=O]

The compound is obtained by the procedure described in Example 1, Step 8, starting from 171 mg (0.82 mmol) of 3-(1-chloro-2-(dimethylamino)ethyl)benzonitrile (described in the previous step) instead of 2-chloro-2-(3-fluorophenyl)-N,N-dimethylethan-1-amine. 109 mg of the title compound are obtained.
Yield: 38%.
MH+: 346.4; 348.4 (M; M+2).

Step 6: 3-(2-(Dimethylamino)-1-(4-(5-morpholino-1-tosyl-1H-pyrrolo[2,3-b]pyridin-3-yl)-2-oxopyridin-1(2H)-yl)ethyl)benzonitrile

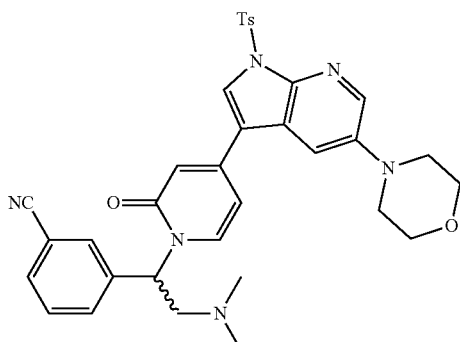

The compound is obtained by the procedure described in Example 1, Step 9, starting from 109 mg (0.31 mmol) of 3-(1-(4-bromo-2-oxopyridin-1(2H)-yl)-2-(dimethylamino)ethyl)benzonitrile (described in the previous step) instead of 4-bromo-1-(2-(dimethylamino)-1-(3-fluorophenyl)ethyl)pyridin-2(1H)-one. 138 mg of the title compound are obtained.
Yield: 70%.
MH+: 623.7 (M+1).

Step 7: 3-(2-(Dimethylamino)-1-(4-(5-morpholino-1H-pyrrolo[2,3-b]pyridin-3-yl)-2-oxopyridin-1(2H)-yl)ethyl)benzonitrile

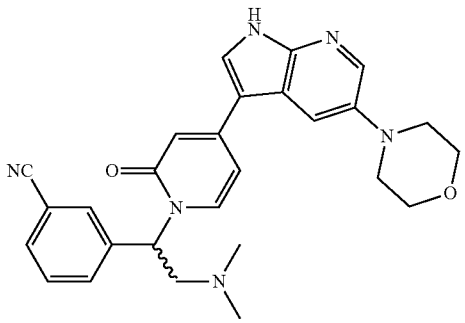 [SMILES: CN(C)CC(c1cccc(C#N)c1)n1ccc(-c2c[nH]c3ncc(N4CCOCC4)cc23)cc1=O]

The compound is obtained by the procedure described in Example 3, Step 7, starting from 138 mg (0.22 mmol) of 3-(2-(dimethylamino)-1-(4-(5-morpholino-1-tosyl-1H-pyrrolo[2,3-b]pyridin-3-yl)-2-oxopyridin-1(2H)-yl)ethyl)benzonitrile (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 32 mg of racemate are obtained.

Yield: 30%.
MH+: 469.7 (M+1).
$^1$H NMR (DMSO-d6, 400 MHz): δ 12.07 (br s, 1H); 8.17 (d, J=2.5 Hz, 1H); 8.10 (s, 1H); 7.93-7.88 (m, 1H); 7.82-7.74 (m, 2H); 7.73-7.67 (m, 2H); 7.58 (t, J=7.8 Hz, 1H); 6.74-6.66 (m, 2H); 6.25-6.15 (m, 1H); 3.84-3.73 (m, 4H); 3.34-3.24 (m, 1H); 3.18-3.08 (m, 4H); 2.83-2.72 (m, 1H); 2.21 (s, 6H).

Step 8: (S)-3-(2-(Dimethylamino)-1-(4-(5-morpholino-1H-pyrrolo[2,3-b]pyridin-3-yl)-2-oxopyridin-1(2H)-yl)ethyl)benzonitrile

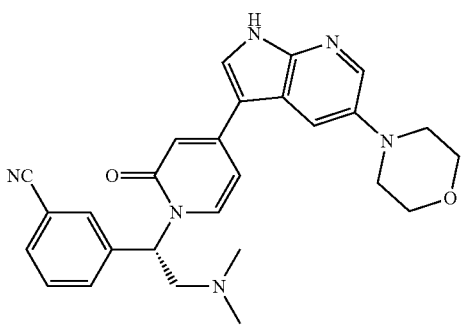

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 8 mg of the title compound are obtained starting from 32 mg of racemate.

MH+: 469.7 (M+1).
$^1$H NMR (DMSO-d6, 400 MHz): δ 12.07 (br s, 1H); 8.17 (d, J=2.5 Hz, 1H); 8.10 (s, 1H); 7.93-7.88 (m, 1H); 7.82-7.74 (m, 2H); 7.73-7.67 (m, 2H); 7.58 (t, J=7.8 Hz, 1H); 6.74-6.66 (m, 2H); 6.25-6.15 (m, 1H); 3.84-3.73 (m, 4H); 3.34-3.24 (m, 1H); 3.18-3.08 (m, 4H); 2.83-2.72 (m, 1H); 2.21 (s, 6H).

Example 26: Synthesis of (S)-1-(2-(dimethylamino)-1-(3-(trifluoromethyl)phenyl)ethyl)-4-(5-morpholino-1H-pyrrolo[2,3-b]pyridin-3-yl)pyridin-2(1H)-one

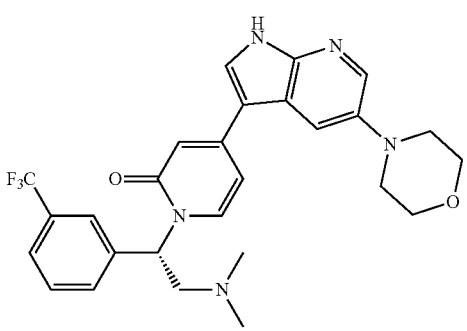

Step 1: 1-(Trifluoromethyl)-3-vinylbenzene

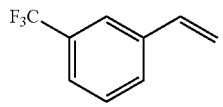

The compound is obtained by the procedure described in Example 1, Step 4, starting from 0.5 g (2.87 mmol) of 3-(trifluoromethyl)benzaldehyde instead of 3-fluorobenzaldehyde. 295 mg of the title compound are obtained.

Yield: 60%.
MH+: Non ionizable.

Step 2: 2-(3-(Trifluoromethyl)phenyl)oxirane

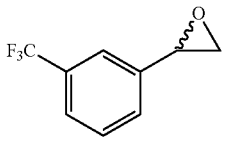

The compound is obtained by the procedure described in Example 1, Step 5, starting from 295 mg (1.71 mmol) of 1-(trifluoromethyl)-3-vinylbenzene (described in the previous step) instead of 1-fluoro-3-vinylbenzene. 176 mg of the title compound are obtained.

Yield: 55%.
MH+: Non ionizable.

Step 3: 2-(Dimethylamino)-1-(3-(trifluoromethyl)phenyl)ethan-1-ol

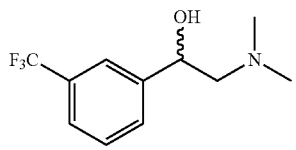 [SMILES: CN(C)CC(O)c1cccc(C(F)(F)F)c1]

The compound is obtained by the procedure described in Example 1, Step 6, starting from 176 mg (0.94 mmol) of 1-(trifluoromethyl)-3-vinylbenzene (described in the previous step) instead of 2-(3-fluorophenyl)oxirane. 183 mg of the title compound are obtained.

Yield: 84%.
MH+: 234.4 (M+1).

Step 4: 2-Chloro-N,N-dimethyl-2-(3-(trifluoromethyl)phenyl)ethan-1-amine

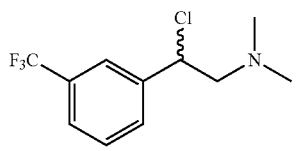 [SMILES: CN(C)CC(Cl)c1cccc(C(F)(F)F)c1]

The compound is obtained by the procedure described in Example 1, Step 7, starting from 183 mg (0.78 mmol) of 2-(dimethylamino)-1-(3-(trifluoromethyl)phenyl)ethan-1-ol (described in the previous step) instead of 2-(dimethylamino)-1-(3-fluorophenyl)ethan-1-ol. 203 mg of the title compound are obtained.

Yield: Quantitative.
MH+: 252.2; 254.2 (M; M+2).

Step 5: 4-Bromo-1-(2-(dimethylamino)-1-(3-(trifluoromethyl)phenyl)ethyl)pyridin-2(1H)-one

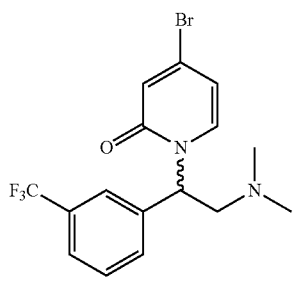 [SMILES: CN(C)CC(c1cccc(C(F)(F)F)c1)n1ccc(Br)cc1=O]

The compound is obtained by the procedure described in Example 1, Step 8, starting from 197 mg (0.78 mmol) of 2-chloro-N,N-dimethyl-2-(3-(trifluoromethyl)phenyl)ethan-1-amine (described in the previous step) instead of 2-chloro-2-(3-fluorophenyl)-N,N-dimethylethan-1-amine. 126 mg of the title compound are obtained.

Yield: 41%.
MH+: 389.4; 391.3 (M; M+2).

Step 6: 1-(2-(Dimethylamino)-1-(3-(trifluoromethyl)phenyl)ethyl)-4-(5-morpholino-1-tosyl-1H-pyrrolo[2,3-b]pyridin-3-yl)pyridin-2(1H)-one

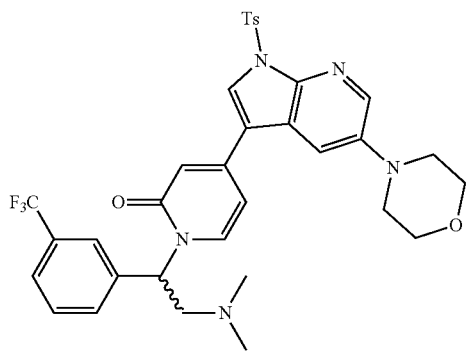 [SMILES: Cc1ccc(S(=O)(=O)n2cc(-c3ccn(C(CN(C)C)c4cccc(C(F)(F)F)c4)c(=O)c3)c3cc(N4CCOCC4)cnc32)cc1]

The compound is obtained by the procedure described in Example 1, Step 9, starting from 126 mg (0.32 mmol) of 4-bromo-1-(2-(dimethylamino)-1-(3-(trifluoromethyl)phenyl)ethyl)pyridin-2(1H)-one (described in the previous step) instead of 4-bromo-1-(2-(dimethylamino)-1-(3-fluorophenyl)ethyl)pyridin-2(1H)-one. 178 mg of the title compound are obtained.

Yield: 83%.
MH+: 666.7 (M+1).

Step 7: 1-(2-(Dimethylamino)-1-(3-(trifluoromethyl)phenyl)ethyl)-4-(5-morpholino-1H-pyrrolo[2,3-b]pyridin-3-yl)pyridin-2(1H)-one

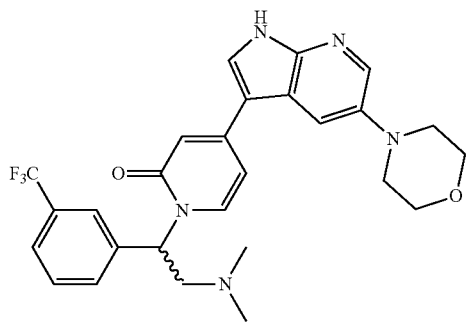 [SMILES: CN(C)CC(c1cccc(C(F)(F)F)c1)n1ccc(-c2c[nH]c3ncc(N4CCOCC4)cc23)cc1=O]

The compound is obtained by the procedure described in Example 3, Step 7, starting from 178 mg (0.26 mmol) of 1-(2-(dimethylamino)-1-(3-(trifluoromethyl)phenyl)ethyl)-4-(5-morpholino-1-tosyl-1H-pyrrolo[2,3-b]pyridin-3-yl)pyridin-2(1H)-one (described in the previous step) instead of 1-(1-(3,5-dichlorophenyl)-2-(dimethylamino)ethyl)-4-(5-morpholino-1-tosyl-1H-pyrrolo[2,3-b]pyridin-3-yl)pyridin-2(1H)-one. 106 mg of racemate are obtained.

Yield: 77%.
MH+: 512.6 (M+1).
$^1$H NMR (DMSO-d6, 400 MHz): δ 12.07 (br s, 1H); 8.17 (d, J=2.5 Hz, 1H); 8.11 (s, 1H); 7.83-7.78 (m, 1H); 7.78-7.74 (m, 1H); 7.73-7.65 (m, 3H); 7.61 (t, J=7.7 Hz, 1H); 6.74-

6.66 (m, 2H); 6.30-6.20 (m, 1H); 3.83-3.73 (m, 4H); 3.38-3.28 (m, 1H); 3.18-3.09 (m, 4H); 2.82-2.72 (m, 1H); 2.22 (s, 6H).

Step 8: (S)-1-(2-(Dimethylamino)-1-(3-(trifluoromethyl)phenyl)ethyl)-4-(5-morpholino-1H-pyrrolo[2,3-b]pyridin-3-yl)pyridin-2(1H)-one

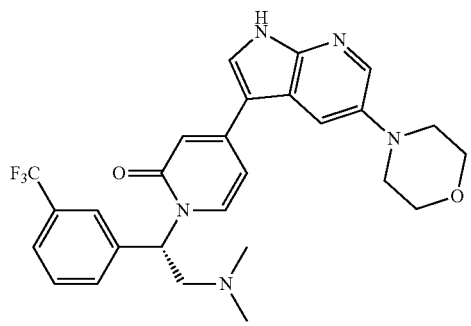 [SMILES: CN(C)C[C@H](c1cccc(C(F)(F)F)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 41 mg of the title compound are obtained starting from 106 mg of racemate.

MH+: 512.6 (M+1).

$^1$H NMR (DMSO-d6, 400 MHz): δ 12.07 (br s, 1H); 8.17 (d, J=2.5 Hz, 1H); 8.11 (s, 1H); 7.83-7.78 (m, 1H); 7.78-7.74 (m, 1H); 7.73-7.65 (m, 3H); 7.61 (t, J=7.7 Hz, 1H); 6.74-6.66 (m, 2H); 6.30-6.20 (m, 1H); 3.83-3.73 (m, 4H); 3.38-3.28 (m, 1H); 3.18-3.09 (m, 4H); 2.82-2.72 (m, 1H); 2.22 (s, 6H).

Example 27: Synthesis of comparative compound (S)-1-(2-amino-1-(3-chlorophenyl)ethyl)-4-(5-morpholino-1H-pyrrolo[2,3-b]pyridin-3-yl)pyridin-2(1H)-one (compound A)

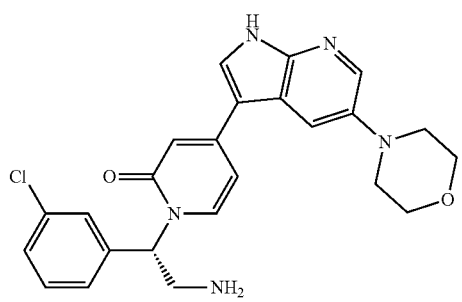 [SMILES: NC[C@H](c1cccc(Cl)c1)n1ccc(-c2c[nH]c3ncc(N4CCOCC4)cc23)cc1=O]

Step 1: 2-(3-Chlorophenyl)-2-((trimethylsilyl)oxy)acetonitrile

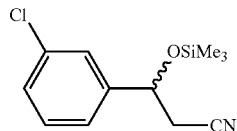

To a solution of 5 g (36 mmol, 1 eq) of 3-chlorobenzaldehyde in 50 ml of dry DCM under argon, are added 399 mg (36 mmol, 1 eq) of DABCO, followed by 4.45 ml (36 mmol, 1 eq) of trimethylsilyl cyanide and the resulting mixture is stirred at 40° C. for 2 h. Reaction mixture is then diluted with DCM and washed 2 times with water and once with brine. Organic layer is dried over Na$_2$SO$_4$, filtered, and evaporated under reduced pressure. Crude compound is used in the next step without further purification. 7.80 g of the title compound are obtained.

Yield: 91%.
MH+: Non ionizable.

Step 2: 2-Amino-1-(3-chlorophenyl)ethan-1-ol

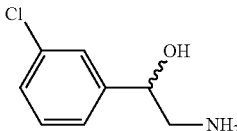

To a solution of 7.80 g (33 mmol, 1 eq) of 2-(3-chlorophenyl)-2-((trimethylsilyl)oxy)acetonitrile (described in the previous step) in 80 ml of dry Et$_2$O, placed at 0° C. with an ice/water bath, are added in portions 1.85 g (49 mmol, 1.5 eq) of LiAlH$_4$. The resulting mixture is stirred at 0° C. for 1 h. Then ice is slowly added into the reaction at 0° C. until no more gas is formed and finally 100 ml of water are added. The mixture is stirred at room temperature for 30 min, the precipitate is filtrated on Celite and washed 2 times with Et$_2$O. Filtrate is decanted and aqueous layer is extracted 2 times with Et$_2$O. Combined organic layers are dried over Na$_2$SO$_4$, filtered, and evaporated under reduced pressure. Crude compound is used in the next step without further purification. 5.95 g of the title compound are obtained.

Yield: Quantitative.
MH+: 172.3; 174.3 (M; M+2).

Step 3: Tert-butyl (2-(3-chlorophenyl)-2-hydroxyethyl)carbamate

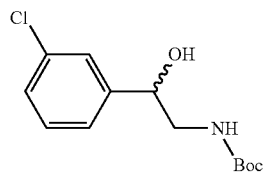 [SMILES: CC(C)(C)OC(=O)NCC(O)c1cccc(Cl)c1]

To a solution of 5.95 g (35 mmol, 1 eq) of 2-amino-1-(3-chlorophenyl)ethan-1-ol (described in the previous step)

in 60 ml of THF, are added 8.32 g (38 mmol, 1.1 eq) of di-tert-butyl dicarbonate and the resulting mixture is stirred at room temperature for 1 h. Solvent is then removed under reduced pressure and the mixture is diluted with 100 ml of EtOAc. Organic layer is washed 2 times with water and once with brine, dried over $Na_2SO_4$, filtered, and evaporated under reduced pressure. Crude mixture is purified by flash chromatography using a silica gel column and a DCM/MeOH mixture as eluent. 6.78 g of the title compound are obtained.

Yield: 72%.

MH+: 272.6; 274.7 (M; M+2).

Step 4: 2-((Tert-butoxycarbonyl)amino)-1-(3-chlorophenyl)ethyl methanesulfonate

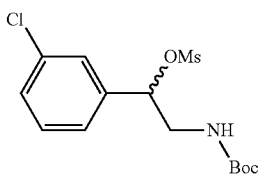 [SMILES: CC(C)(C)OC(=O)NCC(OS(C)(=O)=O)c1cccc(Cl)c1]

The compound is obtained by the procedure described in Example 1, Step 7, starting from 6.78 g (25 mmol) of tert-butyl (2-(3-chlorophenyl)-2-hydroxyethyl)carbamate (described in the previous step) instead of 2-(dimethylamino)-1-(3-fluorophenyl)ethan-1-ol. 9.28 g of the title compound are obtained.

Yield: Quantitative.

MH+(dimer): 700.2; 702.2 (M; M+2).

Step 5: Tert-butyl (2-(4-bromo-2-oxopyridin-1(2H)-yl)-2-(3-chlorophenyl)ethyl)carbamate

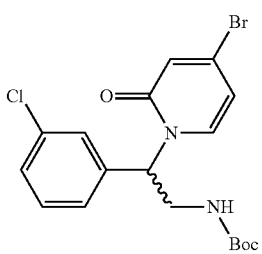 [SMILES: CC(C)(C)OC(=O)NCC(c1cccc(Cl)c1)n1ccc(Br)cc1=O]

The compound is obtained by the procedure described in Example 1, Step 8, starting from 8.73 g (25 mmol) of 2-((tert-butoxycarbonyl)amino)-1-(3-chlorophenyl)ethyl methanesulfonate (described in the previous step) instead of 2-chloro-2-(3-fluorophenyl)-N,N-dimethylethan-1-amine. 5.56 g of the title compound are obtained.

Yield: 52%.

MH+: 427.7; 429.7; 431.7 (M; M+2; M+4).

Step 6: Tert-butyl (2-(3-chlorophenyl)-2-(4-(5-morpholino-1-tosyl-1H-pyrrolo[2,3-b]pyridin-3-yl)-2-oxopyridin-1(2H)-yl)ethyl)carbamate

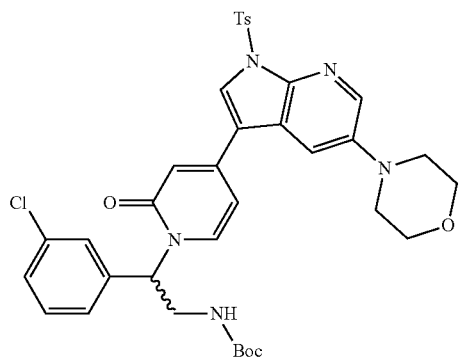 [SMILES: Cc1ccc(S(=O)(=O)n2cc(-c3ccn(C(CNC(=O)OC(C)(C)C)c4cccc(Cl)c4)c(=O)c3)c3cc(N4CCOCC4)cnc32)cc1]

2.8 g (6.50 mmol, 1 eq) of tert-butyl (2-(4-bromo-2-oxopyridin-1(2H)-yl)-2-(3-chlorophenyl)ethyl)carbamate (described in the previous step), 3.16 g (6.50 mmol, 1 eq) of 4-(3-(4,4,5,5-tetramethyl-1,3,2-dioxaborolan-2-yl)-1-tosyl-1H-pyrrolo[2,3-b]pyridin-5-yl)morpholine (described in Example 1, Step 3) and 905 mg (6.50 mmol, 1 eq) of $K_2CO_3$ are placed in 140 ml of MeCN under argon. The mixture is bubbled with argon for 15 min and 459 mg (0.65 mmol, 0.1 eq) of bis(triphenylphosphine)palladium dichloride are added. The mixture is bubbled for another 15 min and then the reaction is stirred at 80° C. for 1 h under argon. Reaction mixture is diluted with 140 ml of EtOAc and washed 3 times with water. Organic layer is dried over $Na_2SO_4$, filtrated and evaporated under reduced pressure. Crude mixture is purified by flash chromatography using a silica gel column and a DCM/MeOH mixture as eluent. 4.79 g of the title compound are obtained.

Yield: Quantitative.

Step 7: Tert-butyl (2-(3-chlorophenyl)-2-(4-(5-morpholino-1H-pyrrolo[2,3-b]pyridin-3-yl)-2-oxopyridin-1(2H)-yl)ethyl)carbamate

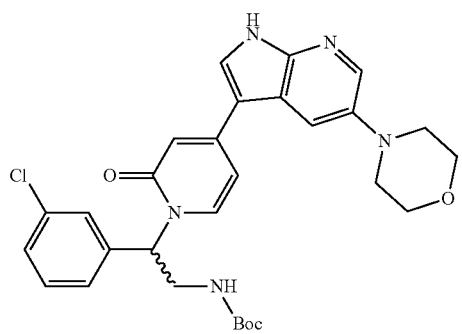 [SMILES: CC(C)(C)OC(=O)NCC(c1cccc(Cl)c1)n1ccc(-c2c[nH]c3ncc(N4CCOCC4)cc23)cc1=O]

The compound is obtained by the procedure described in Example 9, Step 7, starting from 1.0 g (1.4 mmol) of tert-butyl (2-(3-chlorophenyl)-2-(4-(5-morpholino-1-tosyl-1H-pyrrolo[2,3-b]pyridin-3-yl)-2-oxopyridin-1(2H)-yl)ethyl)carbamate (described in the previous step) instead of 1-(1-(3-chloro-5-fluorophenyl)-2-(dimethylamino)ethyl)-4-(5-morpholino-1-tosyl-1H-pyrrolo[2,3-b]pyridin-3-yl)pyridin-2(1H)-one. 644 mg of racemate are obtained.

Yield: 82%.
MH+: 550.6; 552.6 (M; M+2).

Step 8: 1-(2-Amino-1-(3-chlorophenyl)ethyl)-4-(5-morpholino-1H-pyrrolo[2,3-b]pyridin-3-yl)pyridin-2(1H)-one

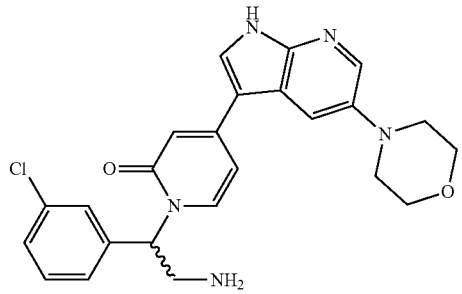 [SMILES: NCC(c1cccc(Cl)c1)n1ccc(-c2c[nH]c3ncc(N4CCOCC4)cc23)cc1=O]

To a solution of 644 mg (1.17 mmol, 1 eq) of tert-butyl (2-(3-chlorophenyl)-2-(4-(5-morpholino-1H-pyrrolo[2,3-b]pyridin-3-yl)-2-oxopyridin-1(2H)-yl)ethyl)carbamate (described in the previous step) in 6 ml of DCM, placed at 0° C. with an ice/water bath, are added 3 ml of trifluoroacetic acid. The solution is stirred at 0° C. for 1 h 30, then solvent is removed under reduced pressure and the mixture is diluted with 100 ml of a saturated NaHCO$_3$ solution. The solution is extracted 3 times with DCM. Combined organic layers are dried over Na$_2$SO$_4$, filtered, and evaporated under reduced pressure. Crude mixture is purified by flash chromatography using a C18 column and a water/MeOH mixture as eluent. 340 mg of the title compound are obtained.

Yield: 64%.
MH+: 450.7; 452.7 (M; M+2).
$^1$H NMR (DMSO-d6, 400 MHz): δ 12.06 (br s, 1H); 8.17 (d, J=2.5 Hz, 1H); 8.09 (s, 1H); 7.75 (d, J=8.1 Hz, 1H); 7.70 (d, J=2.6 Hz, 1H); 7.44-7.29 (m, 4H); 6.74-6.67 (m, 2H); 5.90 (t, J=7.5 Hz, 1H); 3.84-3.72 (m, 4H); 3.34-3.25 (m, 2H); 3.18-3.09 (m, 4H); 1.60 (br s, 2H).

Step 9: (S)-1-(2-Amino-1-(3-chlorophenyl)ethyl)-4-(5-morpholino-1H-pyrrolo[2,3-b]pyridin-3-yl)pyridin-2(1H)-one

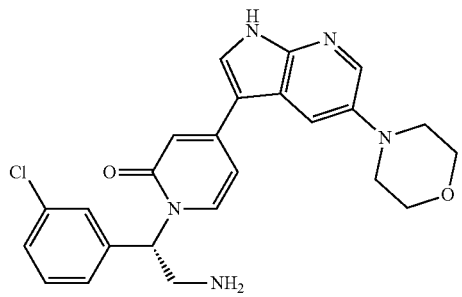 [SMILES: NC[C@H](c1cccc(Cl)c1)n1ccc(-c2c[nH]c3ncc(N4CCOCC4)cc23)cc1=O]

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 33 mg of the title compound are obtained starting from 120 mg of racemate.

MH+: 450.7; 452.7 (M; M+2).
$^1$H NMR (DMSO-d6, 400 MHz): δ 12.06 (br s, 1H); 8.17 (d, J=2.5 Hz, 1H); 8.09 (s, 1H); 7.75 (d, J=8.1 Hz, 1H); 7.70 (d, J=2.6 Hz, 1H); 7.44-7.29 (m, 4H); 6.74-6.67 (m, 2H); 5.90 (t, J=7.5 Hz, 1H); 3.84-3.72 (m, 4H); 3.34-3.25 (m, 2H); 3.18-3.09 (m, 4H); 1.60 (br s, 2H).

Example 28: Synthesis of comparative compound (S)-1-(1-(3,4-dichlorophenyl)-2-(methylamino)ethyl)-4-(5-morpholino-1H-pyrrolo[2,3-b]pyridin-3-yl)pyridin-2(1H)-one (compound B)

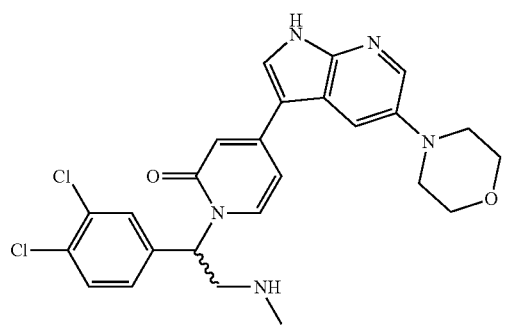

Step 1: 2-(3,4-Dichlorophenyl)-2-((trimethylsilyl)oxy)acetonitrile

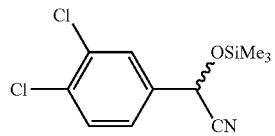

The compound is obtained by the procedure described in Example 27, Step 1, starting from 2.5 g (14.3 mmol) of 3,4-dichlorobenzaldehyde instead of 3-chlorobenzaldehyde. 3.70 g of the title compound are obtained.

Yield: 94%.
MH+: Non ionizable.

Step 2: 2-Amino-1-(3,4-dichlorophenyl)ethan-1-ol

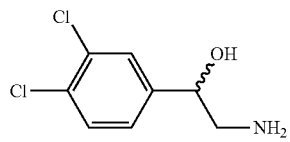 [SMILES: NCC(O)c1ccc(Cl)c(Cl)c1]

The compound is obtained by the procedure described in Example 27, Step 2, starting from 3.70 g (13.5 mmol) of 2-(3,4-dichlorophenyl)-2-((trimethylsilyl)oxy)acetonitrile (described in the previous step) instead of 2-(3-chlorophenyl)-2-((trimethylsilyl)oxy)acetonitrile. 1.66 g of the title compound are obtained.

Yield: 60%.
MH+: 206.1; 208.2; 210.1 (M; M+2; M+4).

Step 3: Tert-butyl (2-(3,4-dichlorophenyl)-2-hydroxyethyl)carbamate

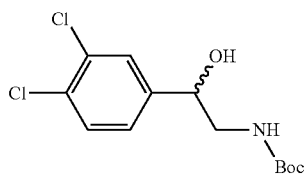 [SMILES: CC(C)(C)OC(=O)NCC(O)c1ccc(Cl)c(Cl)c1]

The compound is obtained by the procedure described in Example 27, Step 3, starting from 1.66 g (8.03 mmol) of 2-amino-1-(3,4-dichlorophenyl)ethan-1-ol (described in the previous step) instead of 2-amino-1-(3-chlorophenyl)ethan-1-ol. 2.55 g of the title compound are obtained.
Yield: Quantitative.
MH+: 306.3; 308.3 (M; M+2).

Step 4: 2-((Tert-butoxycarbonyl)amino)-1-(3,4-dichlorophenyl)ethyl methanesulfonate

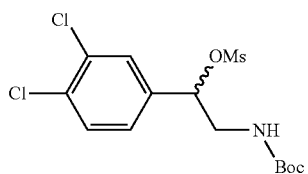 [SMILES: CC(C)(C)OC(=O)NCC(OS(C)(=O)=O)c1ccc(Cl)c(Cl)c1]

The compound is obtained by the procedure described in Example 1, Step 7, starting from 2.46 g (8.03 mmol) of tert-butyl (2-(3,4-dichlorophenyl)-2-hydroxyethyl)carbamate (described in the previous step) instead of 2-(dimethylamino)-1-(3-fluorophenyl)ethan-1-ol. 3.23 g of the title compound are obtained.
Yield: Quantitative.
MH+(dimer): 767.5; 769.4; 771.6 (M; M+2; M+4).

Step 5: Tert-butyl (2-(4-bromo-2-oxopyridin-1(2H)-yl)-2-(3,4-dichlorophenyl)ethyl)carbamate

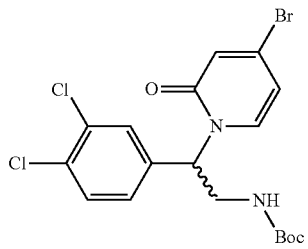 [SMILES: CC(C)(C)OC(=O)NCC(c1ccc(Cl)c(Cl)c1)n1ccc(Br)cc1=O]

The compound is obtained by the procedure described in Example 1, Step 8, starting from 3.09 g (8.03 mmol) of 2-((tert-butoxycarbonyl)amino)-1-(3,4-dichlorophenyl)ethyl methanesulfonate (described in the previous step) instead of 2-chloro-2-(3-fluorophenyl)-N,N-dimethylethan-1-amine. 1.74 g of the title compound are obtained.

Yield: 47%.
MH+: 461.3; 463.3; 465.2 (M; M+2; M+4).

Step 6: Tert-butyl (2-(4-bromo-2-oxopyridin-1(2H)-yl)-2-(3,4-dichlorophenyl)ethyl)(methyl)carbamate

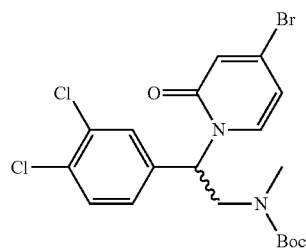 [SMILES: CN(CC(c1ccc(Cl)c(Cl)c1)n1ccc(Br)cc1=O)C(=O)OC(C)(C)C]

To a solution of 840 mg (1.82 mmol, 1 eq) of tert-butyl (2-(4-bromo-2-oxopyridin-1(2H)-yl)-2-(3,4-dichlorophenyl)ethyl)carbamate (described in the previous step) in 9 ml of dry DMF, placed at 0° C. with an ice/water bath, are added under argon 87 mg (2.18 mmol, 1.2 eq) of sodium hydride (60% in paraffin oil), followed by 170 µl (2.73 mmol, 1.5 eq) of methyl iodide. The solution is stirred at 0° C. for 1 h 30, then the mixture is diluted with 100 ml of EtOAc. The solution is washed 4 times with water and once with brine. Organic layer is dried over $Na_2SO_4$, filtered, and evaporated under reduced pressure. Crude mixture is purified by flash chromatography using a silica gel column and a EtOAc/Hexane mixture as eluent. 750 mg of the title compound are obtained.
Yield: 86%.
MH+: 475.4; 477.3; 479.3 (M; M+2; M+4).

Step 7: Tert-butyl (2-(3,4-dichlorophenyl)-2-(4-(5-morpholino-1-tosyl-1H-pyrrolo[2,3-b]pyridin-3-yl)-2-oxopyridin-1(2H)-yl)ethyl)(methyl)carbamate

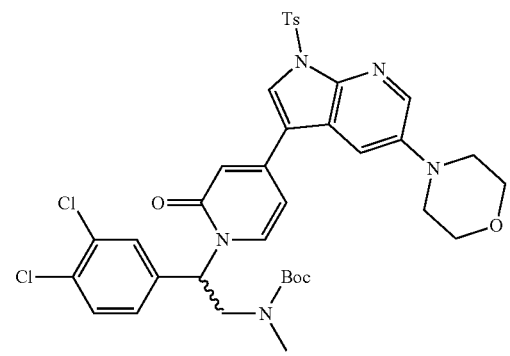 [SMILES: Cc1ccc(S(=O)(=O)n2cc(-c3ccn(C(CN(C)C(=O)OC(C)(C)C)c4ccc(Cl)c(Cl)c4)c(=O)c3)c3cc(N4CCOCC4)cnc32)cc1]

The compound is obtained by the procedure described in Example 1, Step 9, starting from 750 mg (1.57 mmol) of tert-butyl (2-(4-bromo-2-oxopyridin-1(2H)-yl)-2-(3,4-dichlorophenyl)ethyl)(methyl)carbamate (described in the previous step) instead of 4-bromo-1-(2-(dimethylamino)-1-(3-fluorophenyl)ethyl)pyridin-2(1H)-one. 1.27 g of the title compound are obtained.
Yield: Quantitative.
MH+: 753.4; 755.2 (M; M+2).

Step 8: Tert-butyl (2-(3,4-dichlorophenyl)-2-(4-(5-morpholino-1H-pyrrolo[2,3-b]pyridin-3-yl)-2-oxopyridin-1(2H)-yl)ethyl)(methyl)carbamate

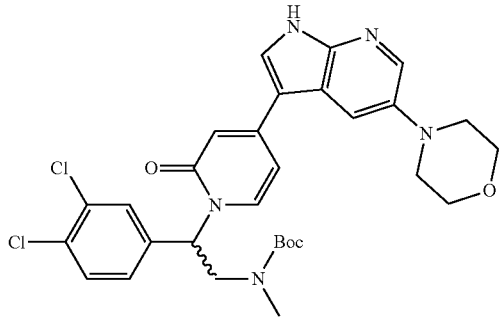 [SMILES: CN(CC(c1ccc(Cl)c(Cl)c1)n1ccc(-c2c[nH]c3ncc(N4CCOCC4)cc23)cc1=O)C(=O)OC(C)(C)C]

The compound is obtained by the procedure described in Example 9, Step 7, starting from 1.27 g (1.69 mmol) of tert-butyl (2-(3,4-dichlorophenyl)-2-(4-(5-morpholino-1-tosyl-1H-pyrrolo[2,3-b]pyridin-3-yl)-2-oxopyridin-1(2H)-yl)ethyl)(methyl)carbamate (described in the previous step) instead of 1-(1-(3-chloro-5-fluorophenyl)-2-(dimethylamino)ethyl)-4-(5-morpholino-1-tosyl-1H-pyrrolo[2,3-b]pyridin-3-yl)pyridin-2(1H)-one. 730 mg of racemate are obtained.
Yield: 72%.
MH+: 598.7; 600.5 (M; M+2).

Step 9: 1-(1-(3,4-Dichlorophenyl)-2-(methylamino)ethyl)-4-(5-morpholino-1H-pyrrolo[2,3-b]pyridin-3-yl)pyridin-2(1H)-one

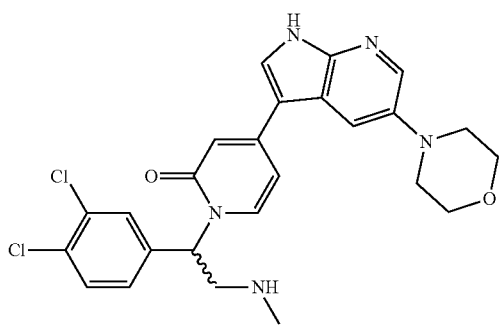 [SMILES: CNCC(c1ccc(Cl)c(Cl)c1)n1ccc(-c2c[nH]c3ncc(N4CCOCC4)cc23)cc1=O]

The compound is obtained by the procedure described in Example 27, Step 8, starting from 730 mg (1.20 mmol) of tert-butyl (2-(3,4-dichlorophenyl)-2-(4-(5-morpholino-1H-pyrrolo[2,3-b]pyridin-3-yl)-2-oxopyridin-1(2H)-yl)ethyl)(methyl)carbamate (described in the previous step) instead of tert-butyl (2-(3-chlorophenyl)-2-(4-(5-morpholino-1H-pyrrolo[2,3-b]pyridin-3-yl)-2-oxopyridin-1(2H)-yl)ethyl) carbamate. 543 mg of racemate are obtained.
Yield: 89%.
MH+: 498.6; 500.5 (M; M+2).
$^1$H NMR (DMSO-d6, 400 MHz): δ 12.08 (br s, 1H); 8.17 (d, J=2.5 Hz, 1H); 8.10 (d, J=2.6 Hz, 1H); 7.76 (d, J=7.3 Hz, 1H); 7.69 (d, J=2.5 Hz, 1H); 7.66-7.61 (m, 2H); 7.37-7.30 (m, 1H); 6.74-6.66 (m, 2H); 6.08-5.98 (m, 1H); 3.84-3.73 (m, 4H); 3.34-3.24 (m, 1H); 3.22-3.14 (m, 1H); 3.14-3.09 (m, 4H); 2.30 (s, 3H); 1.94 (br s, 1H).

Step 10: (S)-1-(1-(3,4-Dichlorophenyl)-2-(methylamino)ethyl)-4-(5-morpholino-1H-pyrrolo[2,3-b]pyridin-3-yl)pyridin-2(1H)-one

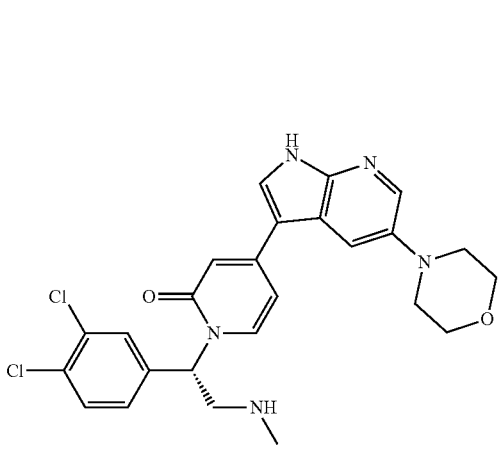

Enantiomers obtained in the previous step are separated by flash chromatography using a Chiralflash IG column and an Hexane/EtOH/DCM/0.1% TEA mixture as the mobile phase. First fraction to be eluted is the (−) (R)-enantiomer, followed by the (+) (S)-enantiomer with ee>98%. 54 mg of the title compound are obtained starting from 150 mg of racemate.
MH+: 498.6; 500.5 (M; M+2).
$^1$H NMR (DMSO-d6, 400 MHz): δ 12.08 (br s, 1H); 8.17 (d, J=2.5 Hz, 1H); 8.10 (d, J=2.6 Hz, 1H); 7.76 (d, J=7.3 Hz, 1H); 7.69 (d, J=2.5 Hz, 1H); 7.66-7.61 (m, 2H); 7.37-7.30 (m, 1H); 6.74-6.66 (m, 2H); 6.08-5.98 (m, 1H); 3.84-3.73 (m, 4H); 3.34-3.24 (m, 1H); 3.22-3.14 (m, 1H); 3.14-3.09 (m, 4H); 2.30 (s, 3H); 1.94 (br s, 1H).

The following table illustrates the chemical structures of compounds according to the invention:

TABLE 1

| Chemical structure of compounds of the invention |
|---|
| Compound No. Structures |
| 1 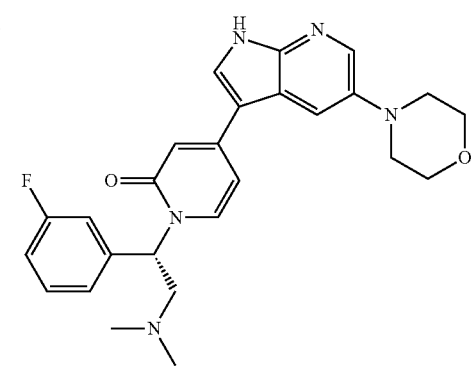 [SMILES: CN(C)C[C@H](c1cccc(F)c1)n1ccc(-c2c[nH]c3ncc(N4CCOCC4)cc23)cc1=O] |

TABLE 1-continued

Chemical structure of compounds of the invention

| Compound No. | Structures |
|---|---|
| 2 | (structure) |
| 3 | (structure) |
| 4 | (structure) |
| 5 | (structure) |
| 6 | (structure) |
| 7 | (structure) |
| 8 | (structure) |
| 9 | (structure) |

TABLE 1-continued
Chemical structure of compounds of the invention
| Compound No. | Structures |
|---|---|
| 10 | 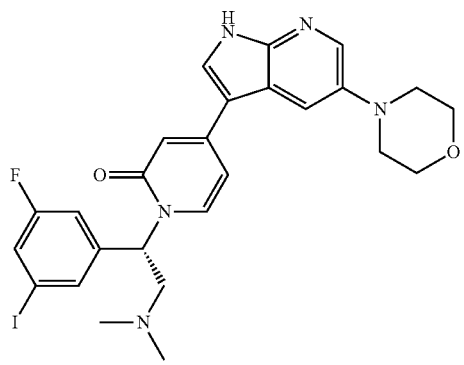 [SMILES: CN(C)C[C@H](c1cccc(I)c1)n1ccc(-c2c[nH]c3ncc(N4CCOCC4)cc23)cc1=O] |
| 11 | 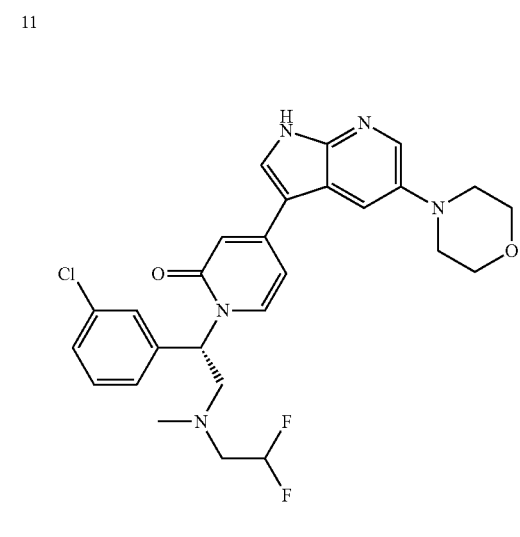 |
| 12 | 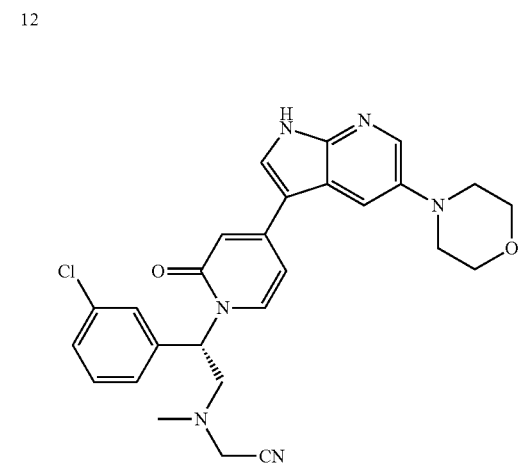 |
| 13 | 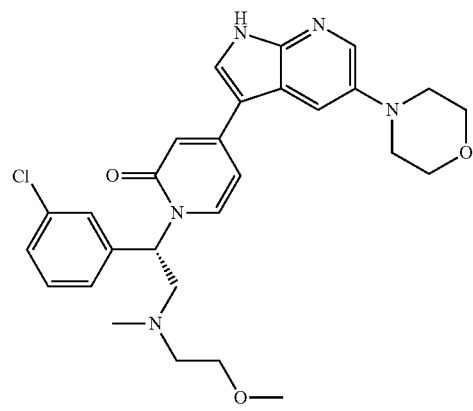 [SMILES: COCCN(C)C[C@H](c1cccc(Cl)c1)n1ccc(-c2c[nH]c3ncc(N4CCOCC4)cc23)cc1=O] |
| 14 |  |
| 15 | 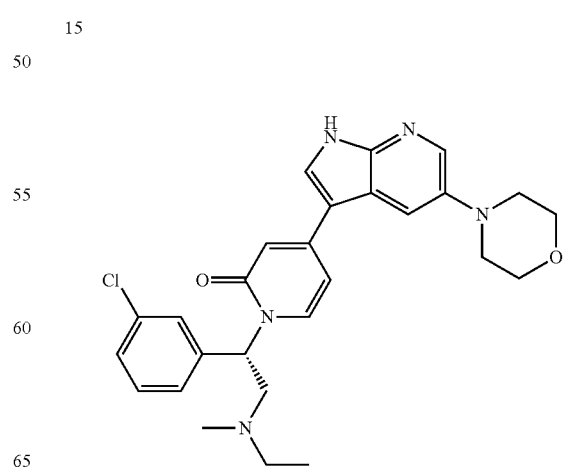 |

TABLE 1-continued

Chemical structure of compounds of the invention

| Compound No. | Structures |
|---|---|
| 16 | *(structure)* |
| 17 | *(structure)* |
| 18 | *(structure)* |
| 19 | *(structure)* |
| 20 | *(structure)* |
| 21 | *(structure)* |
| 22 | *(structure)* |
| 23 | *(structure)* |

TABLE 1-continued

Chemical structure of compounds of the invention

| Compound No. | Structures |
|---|---|
| 24 | 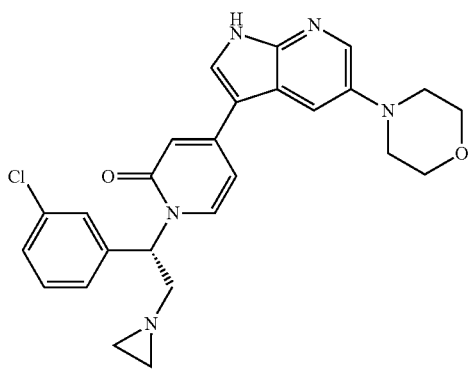 [SMILES: O=c1cc(-c2c[nH]c3ncc(N4CCOCC4)cc23)ccn1[C@H](CN1CC1)c1cccc(Cl)c1] |
| 25 | 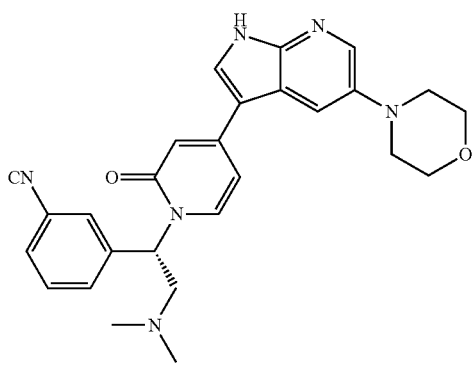 |
| 26 | 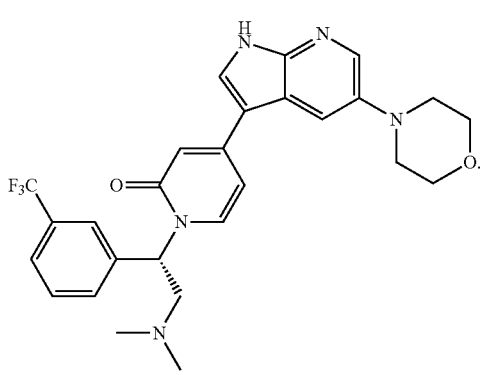 [SMILES: CN(C)C[C@H](c1cccc(C(F)(F)F)c1)n1ccc(-c2c[nH]c3ncc(N4CCOCC4)cc23)cc1=O] |

TABLE 2

Chemical structure of comparative compounds

| | |
|---|---|
| A | 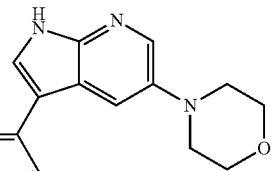 |
| | 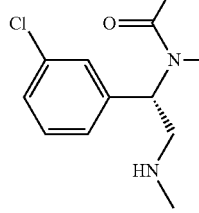 |
| B | 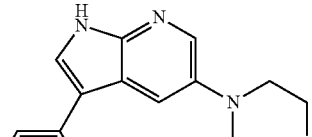 |
| | 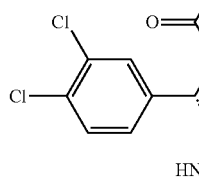 |

Comparative compounds A and B are disclosed in WO 2017/085230, but their synthesis was not described.

Comparative compounds A and B are not part of the present invention since none of $R_1$ and $R_2$ in the general formula (I) of the invention can represent a hydrogen atom.

The Examples 33 and 34 below demonstrate that the compounds of the invention are surprisingly superior to the comparative compounds A and B from the prior art.

Example 29: ERK2 (MAPK1) Enzymatic Assay

To assess the capacity of compounds to inhibit ERK2 enzymatic activity, Z'-Lyte biochemical assay from Life technologies was used according to manufacturer's instructions. Briefly, black 384-well plates containing 100 nl of 100× compound solution in 100% DMSO, 2.4 µl kinase buffer, 5 µl 2×MAPK1 (ERK2)/Ser/Thr 03 mixture and 2.5 µl 4×ATP solution were used. Plates were shaken for 30 seconds and incubated for 60 minutes at room temperature. Then, 5 µl of a 1:1024 dilution of Development Reagent A was added. Plates were shaken for 30 seconds and incubated for 60 minutes at room temperature. A plate reader was used to read fluorescence. In this assay, ERK2 enzyme was used at a concentration of 0.4 µg/ml (5.74 nM) at ATP Km (100 µM). Kinase buffer consisted of 50 mM HEPES pH 7.5, 0.01% BRIJ-35, 10 mM $MgCl_2$, 1 mM EGTA. Compounds $IC_{50}$ were determined with a 3-fold serial dilution (10 point titrations in duplicate).

ERK2 inhibitory activity of selected compounds ("ERK2 $IC_{50}$") is reported in Table 3 below:

TABLE 3

| Compounds | ERK2 $IC_{50}$ (nM) |
|---|---|
| Compound no1 (S) | 1.2 |
| Compound no2 (S) | 2.1 |
| Compound no3 (S) | 3.2 |
| Compound no4 (S) | 3.1 |
| Compound no5 (S) | 4.5 |
| Compound no6 (S) | 2.4 |
| Compound no7 (S) | 4.1 |
| Compound no8 (S) | 2.2 |
| Compound no9 (racemate) | 7.7 |
| Compound no10 (racemate) | 5.1 |
| Compound no15 (S) | 3.5 |
| Compound no17 (S) | 2.7 |
| Compound no22 (S) | 4.0 |
| Compound no23 (S) | 4.5 |

All tested compounds exhibit a capacity to inhibit ERK2 enzymatic activity.

Indeed, all the compounds have an $IC_{50}$ value lower than 10 nM and most of them have an $IC_{50}$ value lower than 5 nM.

Example 30: Cell Line Proliferation Assay

A cell line assay was used to determine the capacity of compounds to inhibit cell proliferation. A375 cells (malignant melanoma) were grown to near 80% confluence and seeded at 3000 cells per 100 µl per well in DMEM with 10% FBS in 96-well flat bottom plates. Cells were incubated for 24 hours at 37° C. under 5% $CO_2$. 100 µl compound solutions were added to cells and incubated for 72 hours at 37° C. Total volume of media was 200 µl per well. Compounds were screened in 0.15% DMSO (final) using 10 titration points in duplicate. Negative control wells consisted of vehicle only (0.15% DMSO in 10% FBS DMEM). After 72 hours of compound treatment, SDS 1% (final) was added to positive control wells for 15 minutes at 37° C. Then, medium was discarded and replaced by 100 µl per well of a MTT solution (3-[4.5-dimethylthiazol-2-yl]-2.5-diphenyltetrazolium bromide) (Sigma, Cat #M5655) at 0.5 mg/ml in 10% FBS DMEM. Cells were incubated for 4 hours at 37° C. MTT reaction was stopped and homogenized by the addition of 100 µl per well of SDS 10% 0.01M HCl. After 16 hours at 37° C., absorbance was measured at 570 nm in a Bio-Tek plate reader (PowerWave HT). Percent of proliferation inhibition was calculated using negative controls (0.15% DMSO) as 0% growth inhibition and positive controls (1% SDS) as 100% growth inhibition. $IC_{50}$ values (concentration inducing a half-maximal growth inhibition) were determined by non-linear regression analysis of the inhibition curve generated by mean replicate values (using a sigmoid dose-response with variable Hill Slope and constraining the top to a constant value of 100 and the bottom to a value between 0 and 50). Analysis was performed using GraphPad Prism software.

Cell proliferation inhibitory activity of selected compounds ("A375 $IC_{50}$") is reported in Table 4 below:

TABLE 4

| Compounds | MTT A375 $IC_{50}$ (nM) |
|---|---|
| Compound no1 (S) | 107 |
| Compound no2 (S) | 35 |

TABLE 4-continued

| Compounds | MTT A375 $IC_{50}$ (nM) |
|---|---|
| Compound no3 (S) | 132 |
| Compound no4 (S) | 72 |
| Compound no5 (S) | 77 |
| Compound no6 (S) | 42 |
| Compound no7 (S) | 53 |
| Compound no8 (S) | 64 |
| Compound no9 (S) | 188 |
| Compound no10 (S) | 116 |
| Compound no11 (S) | 229 |
| Compound no12 (S) | 7 |
| Compound no13 (S) | 262 |
| Compound no14 (S) | 420 |
| Compound no15 (S) | 51 |
| Compound no16 (S) | 162 |
| Compound no17 (S) | 103 |
| Compound no18 (S) | 371 |
| Compound no19 (S) | 303 |
| Compound no20 (S) | 825 |
| Compound no21 (S) | 199 |
| Compound no22 (S) | 77 |
| Compound no23 (S) | 8 |
| Compound no24 (S) | 96 |
| Compound no25 (S) | 156 |
| Compound no26 (S) | 15 |

All tested compounds exhibit a capacity to inhibit A375 cell proliferation.

Indeed, all the compounds have an $IC_{50}$ value lower than 1 µM and most of them have an $IC_{50}$ value lower than 500 nM.

Example 31: hERG Channel Inhibition Assay

Evaluation of hERG channel inhibition of selected compounds have been performed. Compounds were used as a 10 mM stock in DMSO before dilution in HEPES-buffered saline to 30 µM. 6-point concentration-response curves were generated using 3.16-fold serial dilutions from the top test concentration. Electrophysiological recordings were made from a Chinese Hamster Ovary cell line stably expressing the full-length ion channel. Single cell ionic currents were measured in whole-cell configuration at room temperature (21-23° C.) using a Patchliner (Nanion Technologies). The internal solution for hERG contained (mM): 120 KF, 20 KCl, 10 EGTA, 10 HEPES and was buffered to pH 7.3. The external solution (HEPES-buffered saline, HEPES-buffered saline) contained (mM): 138 NaCl, 4.5 KCl, 1.8 $CaCl_2$), 1.0 $MgCl_2$, 10 HEPES, 10 glucose, buffered to pH 7.4. Voltage protocol is given below. Currents were measured from the step and referenced to the holding current. Compounds were then incubated for 2 minutes to achieve steady state prior to addition of the next concentration.

| | |
|---|---|
| Channel | hERG |
| Holding potential (mV) | −80 |
| Step potential (mV) | +40, 2 s then −40 for 2 s |
| Frequency (Pulse applied every X seconds) | 10 |
| Cell background | CHO | hERG channel inhibition properties of selected compounds ("hERG $IC_{50}$") is reported in Table 5 below:

TABLE 5

| Compounds | hERG $IC_{50}$ (µM) |
|---|---|
| Compound no1 (S) | >30 |
| Compound no2 (S) | 10.9 |

TABLE 5-continued

| Compounds | hERG IC$_{50}$ (µM) |
|---|---|
| Compound no3 (S) | >30 |
| Compound no4 (S) | >30 |
| Compound no5 (S) | 20.5 |
| Compound no6 (S) | 11.1 |
| Compound no7 (S) | 13.3 |
| Compound no8 (S) | 9.6 |

All tested compounds exhibit a safe hERG profile with patch clamp assay.

Indeed, all the compounds have an IC$_{50}$ value higher than 9.6 µM.

Example 32: CYP 3A4 Inhibition Assay

To assess the capacity of compounds to inhibit CYP 3A4 enzymatic activity, the test compounds (0.1 µM-25 µM) were incubated with cryopreserved human hepatocytes for 10 min in the presence of the specific CYP3A4 probe substrate, midazolam. 1-Hydroxymidazolam was monitored by LC-MS/MS and a decrease in the formation of the metabolite compared to the vehicle control was used to calculate an IC$_{50}$ value.

CYP 3A4 inhibitory activity of selected compounds ("CYP 3A4 IC$_{50}$") is reported in Table 6 below:

TABLE 6

| Compounds | CYP 3A4 IC$_{50}$ (µM) |
|---|---|
| Comparative compound A (S) | 0.74 |
| Compound no1 (S) | 17.2 |
| Compound no2 (S) | 7.8 |
| Compound no3 (S) | 10.0 |
| Compound no4 (S) | 12.2 |
| Compound no5 (S) | 9.5 |
| Compound no6 (S) | 6.6 |
| Compound no7 (S) | 19.5 |
| Compound no8 (S) | 10.9 |

All tested compounds according to the invention exhibit a low inhibition of CYP 3A4. Indeed, all the compounds have an IC$_{50}$ value greater than 5 µM.

By contrast, the comparative compound A has an IC$_{50}$ value of 0.74 µM. Comparative compound A is therefore a highly potent inhibitor of CYP 3A4.

Example 33: Kinase Panel

To assess the kinase selectivity of compounds, Z'-Lyte biochemical assay, and Adapta/Lanthascreen binding assays from Life technologies were used according to manufacturer's instructions. Pourcentages of inhibition at 500 nM of test compounds were performed towards 58 kinases: ABL1, ACVR1B (ALK4), AKT2 (PKB beta), AMPK (A1/132/G3), AURKA (Aurora A), AXL, BRAF, BTK, CAMK2B (CaM-KII beta), CDK2/cyclin A, CHEK1 (CHK1), CLK1, CSNK1A1 (CK1 alpha 1), CSNK2A1 (CK2 alpha 1), DAPK3 (ZIPK), DYRK1A, EGFR (ErbB1), EPHB3, ERBB2 (HER2), FGFR2, FLT3, FRAP1 (mTOR), GSK3B (GSK3 beta), IGF1R, IKBKB (IKK beta), INSR, IRAK4, JAK2, KDR (VEGFR2), KIT, LCK, MAP2K1 (MEK1), MAPK10 (JNK3), MAPK11 (p38 beta), MAPKAPK2, MARK2, MET (cMet), NEK2, NTRK1 (TRKA), PAK2 (PAK65), PDGFRB (PDGFR beta), PDK1 Direct, PHKG2, PIK3CA/PIK3R1 (p110 alpha/p85 alpha), PIM1, PLK1, PRKACA (PKA), PRKCA (PKC alpha), PTK2 (FAK), RET, ROCK1, RPS6KA1 (RSK1), RPS6KB1 (p70S6K), SRC, STK3 (MST2), SYK, TEK (Tie2), TYRO3 (RSE). The concentration of ATP was used at apparent Km for all kinases except for MAPK10 (JNK3) which was at 100 mM and for BRAF and MAP2K1 (MEK1) which are binding assays.

The results are reported in Table 7 below:

TABLE 7

| | Kinase panel | |
|---|---|---|
| Compounds | @500 nM hits > 80% | @500 nM hits > 50% |
| Comparative compound A (S) | 15/58 | 26/58 |
| Comparative compound B (S) | 10/58 | 20/58 |
| Compound no1 (S) | 1/58 | 2/58 |
| Compound no2 (S) | 1/58 | 10/58 |
| Compound no3 (S) | 1/58 | 6/58 |
| Compound no4 (S) | 1/58 | 5/58 |
| Compound no5 (S) | 1/58 | 7/58 |
| Compound no7 (S) | 1/58 | 4/58 |
| Compound no8 (S) | 1/58 | 7/58 |

All tested compounds according to the invention exhibit a favorable kinase selectivity score in the representative kinase panel. Indeed, for each compound, only 1 kinase over 58 was inhibited with a percentage of inhibition higher than 80%, and 10 kinases at most were inhibited with a percentage of inhibition higher than 50%.

By contrast, comparative compounds A and B exhibit a poor selectivity score. Indeed, comparative compounds A and B inhibited respectively 15/58 and 10/58 kinases with a percentage of inhibition higher than 80%, and 26/58 and 20/58 kinases with a percentage of inhibition higher than 50%.

Example 34: Permeability Assay

Caco 2 cell lines were used for the in vitro transport studies and were obtained from ATCC. Cells were split every other day at a split ratio of 1:3-1:5 and grown in Dulbecco's Modified Eagle Medium (GlutaMAX I, 4,500 mg/L D-glucose, sodium pyruvate.) supplemented with 10% FBS in the presence of antibiotics. For transport studies, cells were seeded onto polycarbonate Transwell filter membranes (Millipore) at a density of 60,000 cells/well. After 24 h post seeding, changed medium and cultured for another 21 days before transport experiments. For transport studies, donor solutions were prepared by diluting the stock solutions of test compounds in transport medium (HBSS buffer with 10 mM HEPES, pH 7.4). Receiver solutions were the same HBSS buffer with 10 mM HEPES, pH 7.4. The transport of test compounds (5 µM) was measured in duplicate in two directions [apical to basolateral (A→B) and basolateral to apical (B→A)].

The permeability coefficient for membrane transport of test compounds was determined using the following equation: Papp (cm/sec)=(Vr/CO) (1/S) (dC/dt); Papp=apparent permeability, Vr=volume of medium in the receiver chamber, CO=PAR of the test drug in the receiver chamber, S=surface area of monolayer, dC/dt=drug PAR in the receiver chamber with time). Efflux Ratio was defined as: Efflux Ratio=Papp B-A/Papp A-B Bioanalysis was done on LC-MS/MS.

145

The results are reported in Table 8 below:

TABLE 8

| Compounds | Caco-2 permeability assay | |
|---|---|---|
| | Papp A-B ($10^{-6}$ cm/s) | Efflux Ratio |
| Comparative compound A (S) | 3.7 | 5.1 |
| Comparative compound B (S) | 8.3 | 5.9 |
| Compound no1 (S) | 21.2 | 3.2 |
| Compound no2 (S) | 34.9 | 0.7 |
| Compound no3 (S) | 38.2 | 1.0 |
| Compound no4 (S) | 53.9 | 0.9 |
| Compound no6 (S) | 27.9 | 1.3 |
| Compound no7 (S) | 36.9 | 1.4 |
| Compound no8 (S) | 47.4 | 0.6 |
| Compound no9 (S) | 14 | 3 |
| Compound no10 (S) | 27 | 1 |

All tested compounds according to the invention exhibit excellent Caco-2 permeability parameters.

Indeed, all the compounds have a Papp A-B value higher than $10.10^{-6}$ cm/s and most of them have a value higher than $20.10^{-6}$ cm/s. Moreover, all the compounds have an Efflux Ratio lower than 3.2, and most of them have a value lower than 2.

By contrast, comparative compounds A and B exhibit poor Caco-2 permeability parameters, with low Papp A-B values (lower than $10.10^{-6}$ cm/s) and high Efflux Ratios (higher than 3).

Example 35: PK Experiments

To determine their absolute oral bioavailability, compounds were suspended in a 0.5% CMC vehicle and administered to a group of 5-6 weeks old male BalbC mice. For intravenous injection, a single 1 mg/kg dose was injected in tail vein and blood was collected at 0.12, 0.25, 0.5, 1, 2, 4, 8 and 24 h after injection. For oral route, a single 20 mg/kg dose was administered, and blood was collected at 0.25, 0.5, 1, 2, 4, 8, 10 and 24 h after gavage. Plasma separated from blood samples was stored at −20° C. until analysis. Vials containing the study samples were retrieved and thawed to room temperature. A volume of 50 µl of sample was added to 200 µl of acetronitrile containing internal standard (tolbutamide; 25 ng/mL) and vortexed for 5 min and centrifuged at 14000 rpm for 5 min at 4° C. 200 µl of supernatant was separated and transferred to HPLC vial for analysis. For prodrug pharmacokinetics, only parent drug was dosed by HPLC.

The results are reported in Table 9 below:

TABLE 9

| | PK experiments @20 mpk PO; @1 mpk IV | | |
|---|---|---|---|
| Compounds | Oral bioavailability (%) | $C_{max}$ (ng/ml) (µM) | $T_{1/2}$ (h) |
| Compound no2 (S) | 9.3 | 641 (1.3) | 0.9 |
| Compound no4 (S) | 21.8 | 995 (1.9) | 3.07 |
| Compound no5 (S) | 9.2 | 1 731 (3.3) | 1.83 |
| Compound no6 (S) | 14.4 | 1 486 (2.6) | 1.16 |
| Compound no7 (S) | 13.7 | 1 209 (2.2) | 1.06 |
| Compound no8 (S) | 8.9 | 736 (1.3) | 1.35 |

All tested compounds according to the invention exhibit good PK parameters.

Indeed, all the compounds have an oral bioavailability upper than 8.9 which will permit to reach the target concentration of the molecule into the plasma.

The invention claimed is:

1. A compound of formula (I):

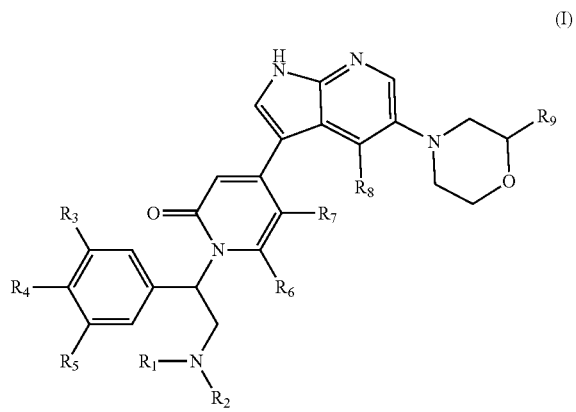

or a pharmaceutically acceptable salt thereof, wherein:

$R_1$ represents a $(C_1-C_6)$alkyl group;

$R_2$ represents a $(C_1-C_6)$alkyl group, a $(C_3-C_6)$cycloalkyl group, or a $(C_1-C_6)$alkyl group substituted by one or more radicals selected from halogen atoms, cyano group, $(C_1-C_6)$alkoxy group and $(C_3-C_6)$cycloalkyl group; or $R_1$ and $R_2$ together with a nitrogen atom to which $R_1$ and $R_2$ are bound form a 3- to 6-membered heterocyclic group; and each of $R_3$, $R_4$, $R_5$, $R_6$, $R_7$, $R_8$ and $R_9$ represent, independently of each other, a hydrogen atom, a halogen atom, a $(C_1-C_6)$alkyl group, a trifluoromethyl group or a cyano group, wherein said $(C_1-C_6)$alkyl is itself optionally substituted with a $(C_1-C_6)$alkoxy group.

2. The compound of claim 1, wherein $R_1$ represents a methyl group.

3. The compound of claim 1, wherein $R_2$ represents a $(C_1-C_6)$alkyl group.

4. The compound of claim 2, wherein both $R_1$ and $R_2$ represent a methyl group.

5. The compound of claim 1, wherein $R_5$ represents a halogen atom, a $(C_1-C_6)$alkyl group, a trifluoromethyl group or a cyano group, wherein said $(C_1-C_6)$alkyl is itself optionally substituted with a $(C_1-C_6)$alkoxy group.

6. The compound of claim 5, wherein $R_5$ represents a halogen atom.

7. The compound of claim 1, wherein $R_4$ represents a hydrogen atom or a halogen atom.

8. The compound of claim 1, wherein $R_5$ represents a hydrogen atom or a halogen atom.

9. The compound of claim 1, wherein $R_6$ represents a hydrogen atom or a $(C_1-C_6)$alkyl group.

10. The compound of claim 1, wherein $R_7$ represents a hydrogen atom or a halogen atom.

11. The compound of claim 1, wherein $R_8$ represents a hydrogen atom or a halogen atom.

12. The compound of claim 1, wherein $R_9$ represents a hydrogen atom, a halogen atom or a trifluoromethyl group.

13. The compound of claim 1, wherein the compound is selected from any one of compounds (1)-(26), as depicted in the following Table, or a pharmaceutically acceptable salt thereof:
| Compound No. | Structures |
|---|---|
| 1 | 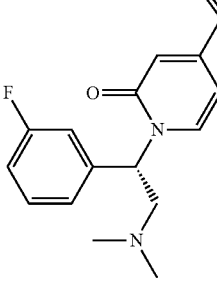 |
| 2 | 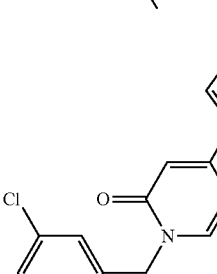 |
| 3 | 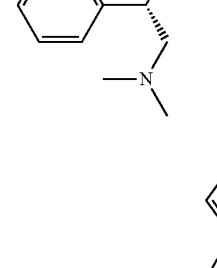 |
| 4 | 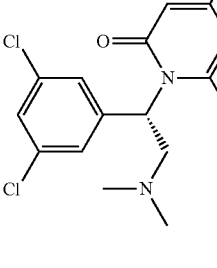 |
| 5 | 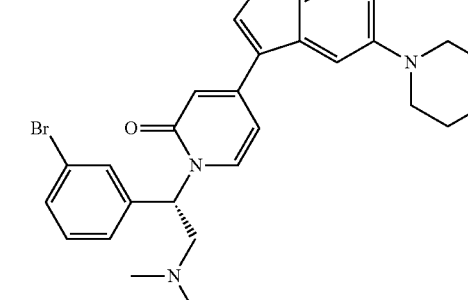 |
| 6 | 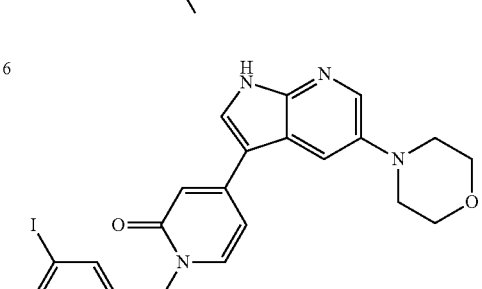 |
| 7 | 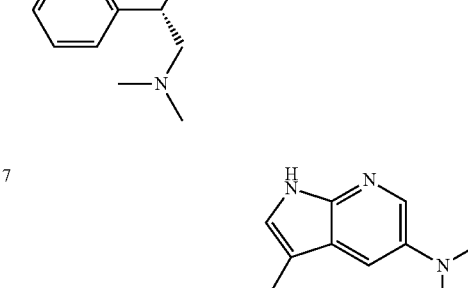 |
| 8 | 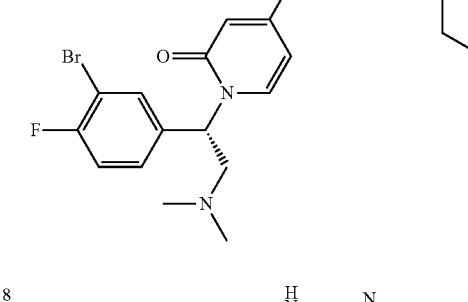 |

-continued
| Compound No. | Structures |
|---|---|
| 9 | 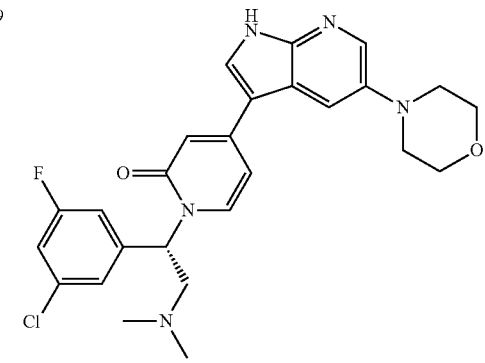 |
| 10 | 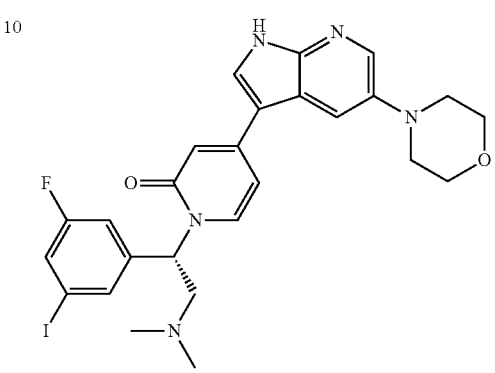 |
| 11 | 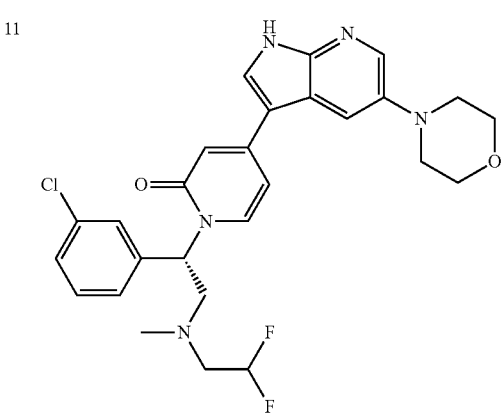 |
| 12 | 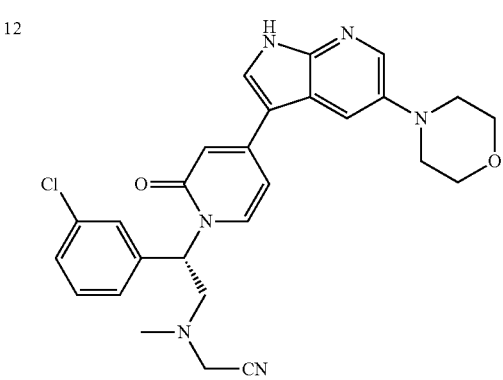 |
-continued
| Compound No. | Structures |
|---|---|
| 13 | 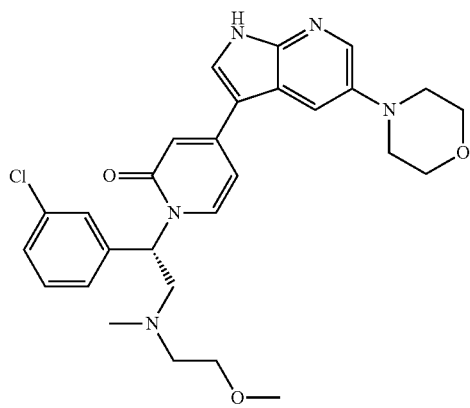 [SMILES: COCCN(C)C[C@H](c1cccc(Cl)c1)n1ccc(-c2c[nH]c3ncc(N4CCOCC4)cc23)cc1=O] |
| 14 | 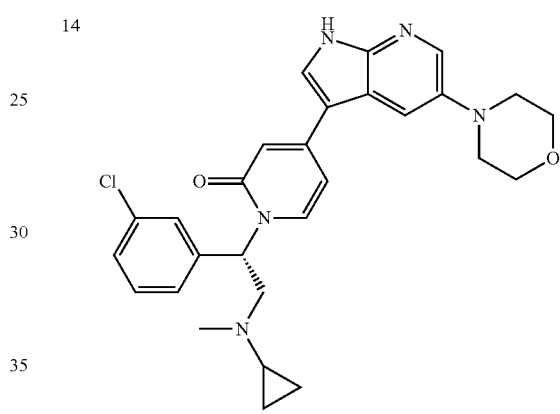 |
| 15 | 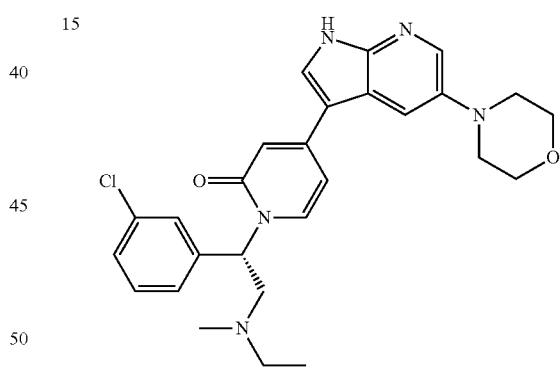 |
| 16 | 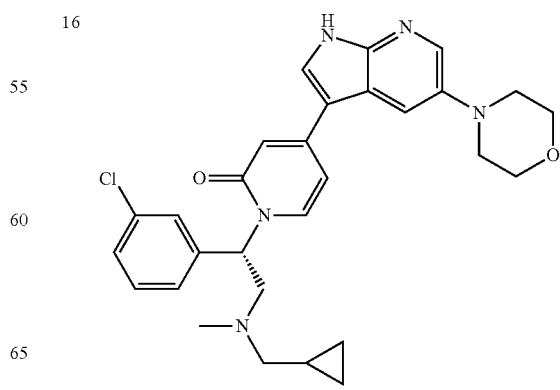 |

-continued
| Compound No. | Structures |
|---|---|
| 17 | 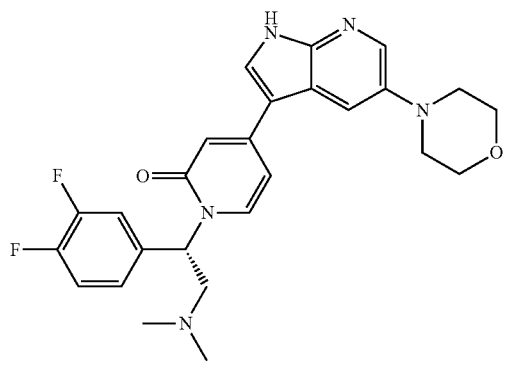 [SMILES: CN(C)C[C@H](c1ccc(F)c(F)c1)n1ccc(-c2c[nH]c3ncc(N4CCOCC4)cc23)cc1=O] |
| 18 | 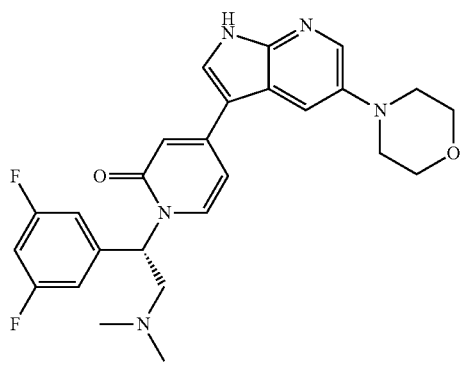 |
| 19 | 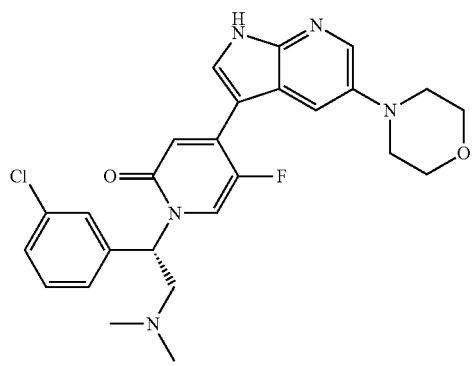 [SMILES: CN(C)C[C@H](c1cccc(Cl)c1)n1cc(F)c(-c2c[nH]c3ncc(N4CCOCC4)cc23)cc1=O] |
| 20 | 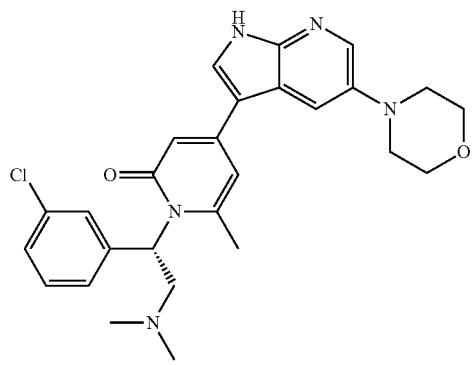 [SMILES: Cc1cc(-c2c[nH]c3ncc(N4CCOCC4)cc23)cc(=O)n1[C@H](CN(C)C)c1cccc(Cl)c1] |
-continued
| Compound No. | Structures |
|---|---|
| 21 | 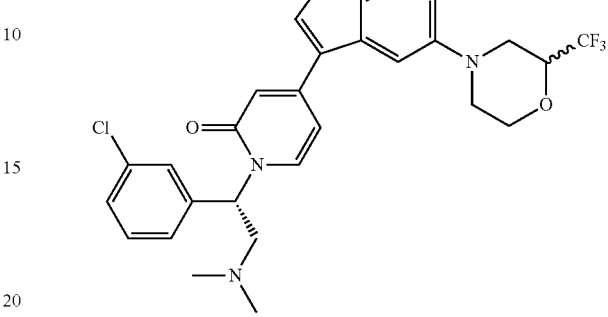 |
| 22 | 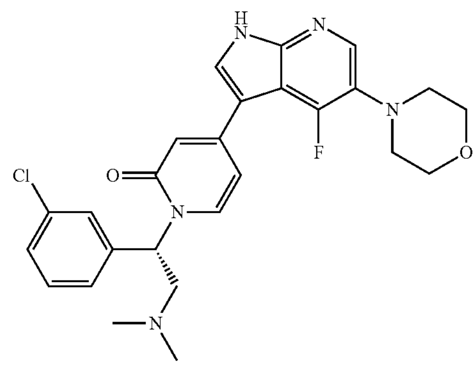 |
| 23 | 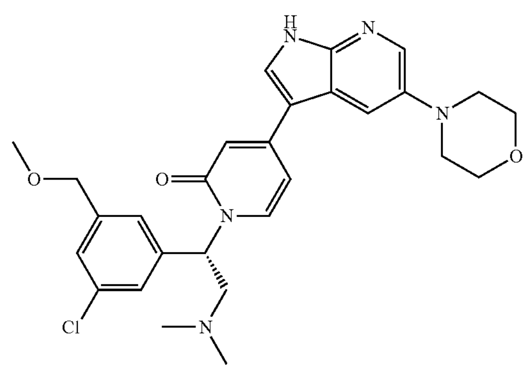 [SMILES: COCc1cc(Cl)cc([C@@H](CN(C)C)n2ccc(-c3c[nH]c4ncc(N5CCOCC5)cc34)cc2=O)c1] |
| 24 | 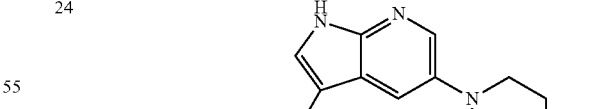 |

-continued

| Compound No. | Structures |
|---|---|
| 25 | 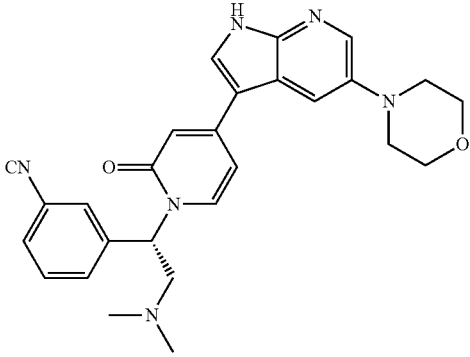 |
| 26 | 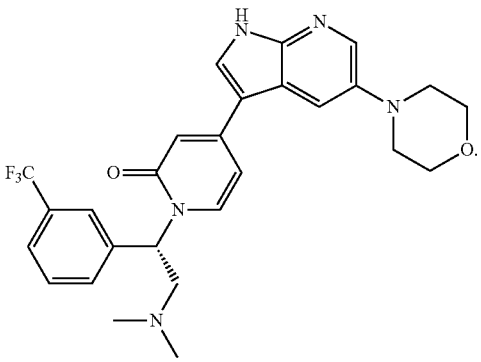 [SMILES: CN(C)C[C@H](c1cccc(C(F)(F)F)c1)n1ccc(-c2c[nH]c3ncc(N4CCOCC4)cc23)cc1=O] |

14. A method of inhibiting ERK2 kinase activity in a cell, the method comprising the step of contacting the cell with a compound selected from:
- (S)-1-(2-(dimethylamino)-1-(3-fluorophenyl)ethyl)-4-(5-morpholino-1H-pyrrolo[2,3-b]pyridin-3-yl)pyridin-2(1H)-one;
- (S)-1-(1-(3-chlorophenyl)-2-(dimethylamino)ethyl)-4-(5-morpholino-1H-pyrrolo[2,3-b]pyridin-3-yl)pyridin-2(1H)-one;
- (S)-1-(1-(3,5-dichlorophenyl)-2-(dimethylamino)ethyl)-4-(5-morpholino-1H-pyrrolo[2,3-b]pyridin-3-yl)pyridin-2(1H)-one;
- (S)-1-(1-(3,4-dichlorophenyl)-2-(dimethylamino)ethyl)-4-(5-morpholino-1H-pyrrolo[2,3-b]pyridin-3-yl)pyridin-2(1H)-one;
- (S)-1-(1-(3-bromophenyl)-2-(dimethylamino)ethyl)-4-(5-morpholino-1H-pyrrolo[2,3-b]pyridin-3-yl)pyridin-2(1H)-one;
- (S)-1-(2-(dimethylamino)-1-(3-iodophenyl)ethyl)-4-(5-morpholino-1H-pyrrolo[2,3-b]pyridin-3-yl)pyridin-2(1H)-one;
- (S)-1-(1-(3-bromo-4-fluorophenyl)-2-(dimethylamino)ethyl)-4-(5-morpholino-1H-pyrrolo[2,3-b]pyridin-3-yl)pyridin-2(1H)-one;
- (S)-1-(2-(dimethylamino)-1-(4-fluoro-3-iodophenyl)ethyl)-4-(5-morpholino-1H-pyrrolo[2,3-b]pyridin-3-yl)pyridin-2(1H)-one;
- (S)-1-(1-(3-chloro-5-fluorophenyl)-2-(dimethylamino)ethyl)-4-(5-morpholino-1H-pyrrolo[2,3-b]pyridin-3-yl)pyridin-2(1H)-one;
- (S)-1-(2-(dimethylamino)-1-(3-fluoro-5-iodophenyl)ethyl)-4-(5-morpholino-1H-pyrrolo[2,3-b]pyridin-3-yl)pyridin-2(1H)-one;
- (S)-1-(1-(3-chlorophenyl)-2-((2,2-difluoroethyl)(methyl)amino)ethyl)-4-(5-morpholino-1H-pyrrolo[2,3-b]pyridin-3-yl)pyridin-2(1H)-one;
- (S)-2-((2-(3-chlorophenyl)-2-(4-(5-morpholino-1H-pyrrolo[2,3-b]pyridin-3-yl)-2-oxopyridin-1(2H)-yl)ethyl)(methyl)amino)acetonitrile;
- (S)-1-(1-(3-chlorophenyl)-2-((2-methoxyethyl)(methyl)amino)ethyl)-4-(5-morpholino-1H-pyrrolo[2,3-b]pyridin-3-yl)pyridin-2(1H)-one;
- (S)-1-(1-(3-chlorophenyl)-2-(cyclopropyl(methyl)amino)ethyl)-4-(5-morpholino-1H-pyrrolo[2,3-b]pyridin-3-yl)pyridin-2(1H)-one;
- (S)-1-(1-(3-chlorophenyl)-2-(ethyl(methyl)amino)ethyl)-4-(5-morpholino-1H-pyrrolo[2,3-b]pyridin-3-yl)pyridin-2(1H)-one;
- (S)-1-(1-(3-chlorophenyl)-2-((cyclopropylmethyl)(methyl)amino)ethyl)-4-(5-morpholino-1H-pyrrolo[2,3-b]pyridin-3-yl)pyridin-2(1H)-one;
- (S)-1-(1-(3,4-difluorophenyl)-2-(dimethylamino)ethyl)-4-(5-morpholino-1H-pyrrolo[2,3-b]pyridin-3-yl)pyridin-2(1H)-one;
- (S)-1-(1-(3,5-difluorophenyl)-2-(dimethylamino)ethyl)-4-(5-morpholino-1H-pyrrolo[2,3-b]pyridin-3-yl)pyridin-2(1H)-one;
- (S)-1-(1-(3-chlorophenyl)-2-(dimethylamino)ethyl)-5-fluoro-4-(5-morpholino-1H-pyrrolo[2,3-b]pyridin-3-yl)pyridin-2(1H)-one;
- (S)-1-(1-(3-chlorophenyl)-2-(dimethylamino)ethyl)-6-methyl-4-(5-morpholino-1H-pyrrolo[2,3-b]pyridin-3-yl)pyridin-2(1H)-one;
- 1-((S)-1-(3-chlorophenyl)-2-(dimethylamino)ethyl)-4-(5-(2-(trifluoromethyl)morpholino)-1H-pyrrolo[2,3-b]pyridin-3-yl)pyridin-2(1H)-one;
- (S)-1-(1-(3-chlorophenyl)-2-(dimethylamino)ethyl)-4-(4-fluoro-5-morpholino-1H-pyrrolo[2,3-b]pyridin-3-yl)pyridin-2(1H)-one;
- (S)-1-(1-(3-chloro-5-(methoxymethyl)phenyl)-2-(dimethylamino)ethyl)-4-(5-morpholino-1H-pyrrolo[2,3-b]pyridin-3-yl)pyridin-2(1H)-one;
- (S)-1-(2-(aziridin-1-yl)-1-(3-chlorophenyl)ethyl)-4-(5-morpholino-1H-pyrrolo[2,3-b]pyridin-3-yl)pyridin-2(1H)-one;
- (S)-3-(2-(dimethylamino)-1-(4-(5-morpholino-1H-pyrrolo[2,3-b]pyridin-3-yl)-2-oxopyridin-1(2H)-yl)ethyl)benzonitrile; or
- (S)-1-(2-(dimethylamino)-1-(3-(trifluoromethyl)phenyl)ethyl)-4-(5-morpholino-1H-pyrrolo[2,3-b]pyridin-3-yl)pyridin-2(1H)-one, or a pharmaceutically acceptable salt thereof, in an amount sufficient to inhibit the ERK2 kinase activity.

15. The method of claim 14, further comprising treating a subject having a melanoma disease or a condition mediated by ERK kinases activity by administering to the subject an effective dose of the compound or a pharmaceutically acceptable salt thereof.

16. A pharmaceutical composition comprising a compound of any one of formulas:

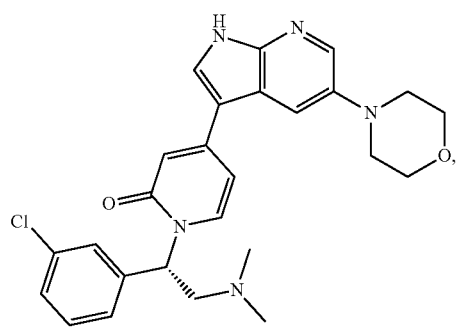

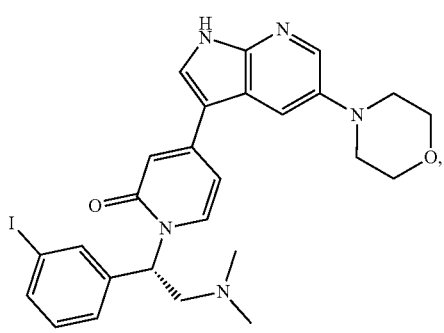

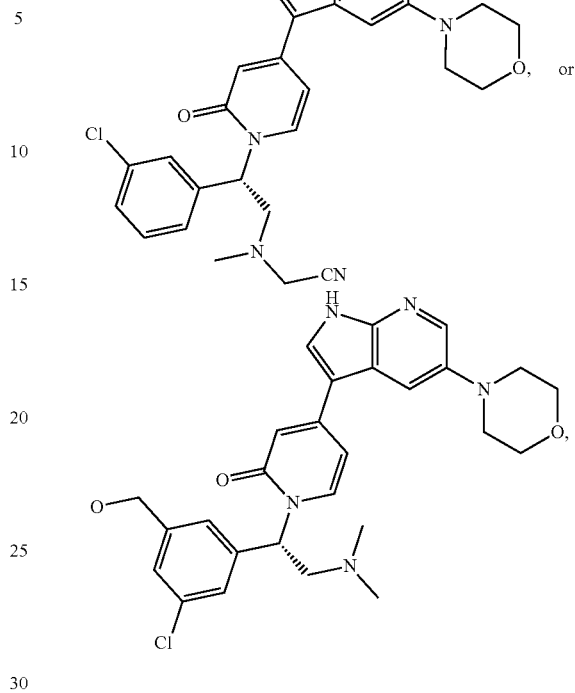

or a pharmaceutically acceptable salt thereof and a pharmaceutically acceptable excipient.

17. The pharmaceutical composition of claim 16, wherein the pharmaceutical composition is formulated for oral administration.

18. The pharmaceutical composition of claim 17, wherein the pharmaceutical composition is a tablet or a capsule.

* * * * *

UNITED STATES PATENT AND TRADEMARK OFFICE
CERTIFICATE OF CORRECTION

| | | |
|---|---|---|
| PATENT NO. | : 11,827,637 B2 | Page 1 of 1 |
| APPLICATION NO. | : 18/096996 | |
| DATED | : November 28, 2023 | |
| INVENTOR(S) | : Cédric Bories et al. | |

It is certified that error appears in the above-identified patent and that said Letters Patent is hereby corrected as shown below:

In the Claims

Column 37, Line 62, replace "at for" with --at 80° C. for--.

Signed and Sealed this
First Day of October, 2024

Katherine Kelly Vidal
Director of the United States Patent and Trademark Office